United States Patent [19]
Pedersen et al.

[11] Patent Number: 6,140,092
[45] Date of Patent: Oct. 31, 2000

[54] LACCASE MUTANTS

[75] Inventors: Anders Hjelholt Pedersen, Lyngby; Allan Svendsen, Birkerød; Palle Schneider, Ballerup; Grethe Rasmussen, Farum; Joel Cherry, Hellerup, all of Denmark

[73] Assignee: Novo Nordisk A/S, Bagsvaero, Denmark

[21] Appl. No.: 09/399,886

[22] Filed: Sep. 21, 1999

Related U.S. Application Data

[62] Division of application No. 08/993,318, Dec. 18, 1997, Pat. No. 5,998,353
[60] Provisional application No. 60/035,413, Jan. 23, 1997.

[30] Foreign Application Priority Data

Dec. 19, 1996 [DK] Denmark ................................ 1449/96
Sep. 8, 1997 [DK] Denmark ................................ 1021/97

[51] Int. Cl.⁷ .............................. C12N 9/02; C12N 15/09
[52] U.S. Cl. ............................................ 435/189; 435/440
[58] Field of Search ..................................... 435/189, 440

[56] References Cited

FOREIGN PATENT DOCUMENTS

| WO 95/07988 | 3/1995 | WIPO . |
| WO 95/33836 | 12/1995 | WIPO . |
| WO 95/33837 | 12/1995 | WIPO . |
| WO 96/00290 | 1/1996 | WIPO . |
| WO 96/06930 | 3/1996 | WIPO . |
| WO 96/23874 | 8/1996 | WIPO . |

OTHER PUBLICATIONS

Xu, F. et al. (1996) Biochimica et Biophysica Acta 1292:303–311.
Soon–ja, K. and Choi, H.T. (1995) FEMS Microbiology Letters 132:177–179.

*Primary Examiner*—Elizabeth Slobodyansky
*Attorney, Agent, or Firm*—Steven T. Zelson, Esq.; Reza Green, Esq.

[57] ABSTRACT

The present invention relates to a method of designing laccase mutants with improved stability properties, which method is based on the hitherto unknown three-dimensional structure of *Coprinus cinereus* laccase.

4 Claims, No Drawings

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
       (A) LENGTH: 539 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 1:

```
Met Phe Lys Asn Leu Leu Ser Phe Ala Leu Leu Ala Ile Ser Val Ala
1               5                  10                  15

Asn Ala Gln Ile Val Asn Ser Val Asp Thr Met Thr Leu Thr Asn Ala
            20                  25                  30

Asn Val Ser Pro Asp Gly Phe Thr Arg Ala Gly Ile Leu Val Asn Gly
        35                  40                  45

Val His Gly Pro Leu Ile Arg Gly Gly Lys Asn Asp Asn Phe Glu Leu
    50                  55                  60

Asn Val Val Asn Asp Leu Asp Asn Pro Thr Met Leu Arg Pro Thr Ser
65                  70                  75                  80

Ile His Trp His Gly Leu Phe Gln Arg Gly Thr Asn Trp Ala Asp Gly
                    85                  90                  95

Ala Asp Gly Val Asn Gln Cys Pro Ile Ser Pro Gly His Ala Phe Leu
```

```
                100                 105                 110
Tyr Lys Phe Thr Pro Ala Gly His Ala Gly Thr Phe Trp Tyr His Ser
            115                 120                 125
His Phe Gly Thr Gln Tyr Cys Asp Gly Leu Arg Gly Pro Met Val Ile
        130                 135                 140
Tyr Asp Asp Asn Asp Pro His Ala Ala Leu Tyr Asp Glu Asp Asp Glu
145                 150                 155                 160
Asn Thr Ile Ile Thr Leu Ala Asp Trp Tyr His Ile Pro Ala Pro Ser
                165                 170                 175
Ile Gln Gly Ala Ala Gln Pro Asp Ala Thr Leu Ile Asn Gly Lys Gly
            180                 185                 190
Arg Tyr Val Gly Gly Pro Ala Ala Glu Leu Ser Ile Val Asn Val Glu
        195                 200                 205
Gln Gly Lys Lys Tyr Arg Met Arg Leu Ile Ser Leu Ser Cys Asp Pro
    210                 215                 220
Asn Trp Gln Phe Ser Ile Asp Gly His Glu Leu Thr Ile Ile Glu Val
225                 230                 235                 240
Asp Gly Gln Leu Thr Glu Pro His Thr Val Asp Arg Leu Gln Ile Phe
                245                 250                 255
Thr Gly Gln Arg Tyr Ser Phe Val Leu Asp Ala Asn Gln Pro Val Asp
            260                 265                 270
Asn Tyr Trp Ile Arg Ala Gln Pro Asn Lys Gly Arg Asn Gly Leu Ala
        275                 280                 285
Gly Thr Phe Ala Asn Gly Val Asn Ser Ala Ile Leu Arg Tyr Ala Gly
    290                 295                 300
Ala Ala Asn Ala Asp Pro Thr Thr Ser Ala Asn Pro Asn Pro Ala Gln
305                 310                 315                 320
Leu Asn Glu Ala Asp Leu His Ala Leu Ile Asp Pro Ala Ala Pro Gly
                325                 330                 335
Ile Pro Thr Pro Gly Ala Ala Asp Val Asn Leu Arg Phe Gln Leu Gly
            340                 345                 350
Phe Ser Gly Gly Arg Phe Thr Ile Asn Gly Thr Ala Tyr Glu Ser Pro
        355                 360                 365
Ser Val Pro Thr Leu Leu Gln Ile Met Ser Gly Ala Gln Ser Ala Asn
    370                 375                 380
Asp Leu Leu Pro Ala Gly Ser Val Tyr Glu Leu Pro Arg Asn Gln Val
385                 390                 395                 400
Val Glu Leu Val Val Pro Ala Gly Val Leu Gly Pro His Pro Phe
                405                 410                 415
His Leu His Gly His Ala Phe Ser Val Val Arg Ser Ala Gly Ser Ser
            420                 425                 430
Thr Tyr Asn Phe Val Asn Pro Val Lys Arg Asp Val Val Ser Leu Gly
        435                 440                 445
Val Thr Gly Asp Glu Val Thr Ile Arg Phe Val Thr Asp Asn Pro Gly
    450                 455                 460
Pro Trp Phe Phe His Cys His Ile Glu Phe Leu Met Asn Gly Leu
465                 470                 475                 480
Ala Ile Val Phe Ala Glu Asp Met Ala Asn Thr Val Asp Ala Asn Asn
                485                 490                 495
Pro Pro Val Glu Trp Ala Gln Leu Cys Glu Ile Tyr Asp Asp Leu Pro
            500                 505                 510
Pro Glu Ala Thr Ser Ile Gln Thr Val Val Arg Arg Ala Glu Pro Thr
        515                 520                 525
```

Gly Phe Ser Ala Lys Phe Arg Arg Glu Gly Leu
    530                 535

(2) INFORMATION FOR SEQ ID NO: 2:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Gly Ile Gly Pro Val Ala Asp Leu Thr Ile Thr Asn Ala Ala Val Ser
1               5                   10                  15

Pro Asp Gly Phe Ser Arg Gln Ala Val Val Asn Gly Gly Thr Pro
                20                  25                  30

Gly Pro Leu Ile Thr Gly Asn Met Gly Asp Arg Phe Gln Leu Asn Val
            35                  40                  45

Ile Asp Asn Leu Thr Asn His Thr Met Leu Lys Ser Thr Ser Ile His
50                  55                  60

Trp His Gly Phe Phe Gln Lys Gly Thr Asn Trp Ala Asp Gly Pro Ala
65                  70                  75                  80

Phe Ile Asn Gln Cys Pro Ile Ser Ser Gly His Ser Phe Leu Tyr Asp
                85                  90                  95

Phe Gln Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Asn Asp Pro Ala Ala Asp Leu Tyr Asp Val Asp Asn Asp Asp Thr
130                 135                 140

Val Ile Thr Leu Val Asp Trp Tyr His Val Ala Ala Lys Leu Gly Pro
145                 150                 155                 160

Ala Phe Pro Leu Gly Ala Asp Ala Thr Leu Ile Asn Gly Lys Gly Arg
                165                 170                 175

Ser Pro Ser Thr Thr Thr Ala Asp Leu Ser Val Ile Ser Val Thr Pro
            180                 185                 190

Gly Lys Arg Tyr Arg Phe Arg Leu Val Ser Leu Ser Cys Asp Pro Asn
        195                 200                 205

Tyr Thr Phe Ser Ile Asp Gly His Asn Met Thr Ile Ile Glu Thr Asp
    210                 215                 220

Ser Ile Asn Thr Ala Pro Leu Val Val Asp Ser Ile Gln Ile Phe Ala
225                 230                 235                 240

Ala Gln Arg Tyr Ser Phe Val Leu Glu Ala Asn Gln Ala Val Asp Asn
                245                 250                 255

Tyr Trp Ile Arg Ala Asn Pro Asn Phe Gly Asn Val Gly Phe Thr Gly
                260                 265                 270

Gly Ile Asn Ser Ala Ile Leu Arg Tyr Asp Gly Ala Ala Ala Val Glu
            275                 280                 285

Pro Thr Thr Thr Gln Thr Thr Ser Thr Ala Pro Leu Asn Glu Val Asn
    290                 295                 300

Leu His Pro Leu Val Thr Thr Ala Val Pro Gly Ser Pro Val Ala Gly
305                 310                 315                 320

Gly Val Asp Leu Ala Ile Asn Met Ala Phe Asn Phe Asn Gly Thr Asn
                325                 330                 335

```
Phe Phe Ile Asn Gly Ala Ser Phe Thr Pro Pro Thr Val Pro Val Leu
                340                 345                 350

Leu Gln Ile Ile Ser Gly Ala Gln Asn Ala Gln Asp Leu Leu Pro Ser
            355                 360                 365

Gly Ser Val Tyr Ser Leu Pro Ser Asn Ala Asp Ile Glu Ile Ser Phe
        370                 375                 380

Pro Ala Thr Ala Ala Ala Pro Gly Ala Pro His Pro Phe His Leu His
385                 390                 395                 400

Gly His Ala Phe Ala Val Val Arg Ser Ala Gly Ser Thr Val Tyr Asn
                405                 410                 415

Tyr Asp Asn Pro Ile Phe Arg Asp Val Val Ser Thr Gly Thr Pro Ala
                420                 425                 430

Ala Gly Asp Asn Val Thr Ile Arg Phe Arg Thr Asp Asn Pro Gly Pro
                435                 440                 445

Trp Phe Leu His Cys His Ile Asp Phe His Leu Glu Ala Gly Phe Ala
                450                 455                 460

Val Val Phe Ala Glu Asp Ile Pro Asp Val Ala Ser Ala Asn Pro Val
465                 470                 475                 480

Pro Gln Ala Trp Ser Asp Leu Cys Pro Thr Tyr Asp Ala Leu Asp Pro
                485                 490                 495

Ser Asp Gln
```

(2) INFORMATION FOR SEQ ID NO: 3:

(i) SEQUENCE CHARACTERISTICS:
  (A) LENGTH: 499 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO: 3:

```
Ala Ile Gly Pro Val Ala Ser Leu Val Val Ala Asn Ala Pro Val Ser
1               5                   10                  15

Pro Asp Gly Phe Leu Arg Asp Ala Ile Val Val Asn Gly Val Val Pro
                20                  25                  30

Ser Pro Leu Ile Thr Gly Lys Lys Gly Asp Arg Phe Gln Leu Asn Val
            35                  40                  45

Val Asp Thr Leu Thr Asn His Ser Met Leu Lys Ser Thr Ser Ile His
        50                  55                  60

Trp His Gly Phe Phe Gln Ala Gly Thr Asn Trp Ala Glu Gly Pro Ala
65                  70                  75                  80

Phe Val Asn Gln Cys Pro Ile Ala Ser Gly His Ser Phe Leu Tyr Asp
                85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Lys Asp Pro His Ala Ser Arg Tyr Asp Val Asp Asn Glu Ser Thr
            130                 135                 140

Val Ile Thr Leu Thr Asp Trp Tyr His Thr Ala Ala Arg Leu Gly Pro
145                 150                 155                 160

Lys Phe Pro Leu Gly Ala Asp Ala Thr Leu Ile Asn Gly Leu Gly Arg
                165                 170                 175
```

```
Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
            195                 200                 205

Tyr Thr Phe Ser Ile Asp Gly His Asn Leu Thr Val Ile Glu Val Asp
            210                 215                 220

Gly Ile Asn Ser Gln Pro Leu Leu Val Asp Ser Ile Gln Ile Phe Ala
225                 230                 235                 240

Ala Gln Arg Tyr Ser Phe Val Leu Asn Ala Asn Gln Thr Val Gly Asn
            245                 250                 255

Tyr Trp Val Arg Ala Asn Pro Asn Phe Gly Thr Val Gly Phe Ala Gly
            260                 265                 270

Gly Ile Asn Ser Ala Ile Leu Arg Tyr Gln Gly Ala Pro Val Ala Glu
            275                 280                 285

Pro Thr Thr Thr Gln Thr Pro Ser Val Ile Pro Leu Ile Glu Thr Asn
            290                 295                 300

Leu His Pro Leu Ala Arg Met Pro Val Pro Gly Ser Pro Thr Pro Gly
305                 310                 315                 320

Gly Val Asp Lys Ala Leu Asn Leu Ala Phe Asn Phe Asn Gly Thr Asn
            325                 330                 335

Phe Phe Ile Asn Asn Ala Thr Phe Thr Pro Pro Thr Val Pro Val Leu
            340                 345                 350

Leu Gln Ile Leu Ser Gly Ala Gln Thr Ala Gln Asp Leu Leu Pro Ala
            355                 360                 365

Gly Ser Val Tyr Pro Leu Pro Ala His Ser Thr Ile Glu Ile Thr Leu
            370                 375                 380

Pro Ala Thr Ala Leu Ala Pro Gly Ala Pro His Pro Phe His Leu His
385                 390                 395                 400

Gly His Ala Phe Ala Val Val Arg Ser Ala Gly Ser Thr Thr Tyr Asn
            405                 410                 415

Tyr Asn Asp Pro Ile Phe Arg Asp Val Val Ser Thr Gly Thr Pro Ala
            420                 425                 430

Ala Gly Asp Asn Val Thr Ile Arg Phe Gln Thr Asp Asn Pro Gly Pro
            435                 440                 445

Trp Phe Leu His Cys His Ile Asp Phe His Leu Asp Ala Gly Phe Ala
            450                 455                 460

Ile Val Phe Ala Glu Asp Val Ala Asp Val Lys Ala Ala Asn Pro Val
465                 470                 475                 480

Pro Lys Ala Trp Ser Asp Leu Cys Pro Ile Tyr Asp Gly Leu Ser Glu
            485                 490                 495

Ala Asn Gln (2) INFORMATION FOR SEQ ID NO: 4:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Met His Thr Phe Leu Arg Ser Thr Ala Leu Val Val Ala Gly Leu Ser
1               5                   10                  15

Ala Arg Ala Leu Ala Ser Ile Gly Pro Val Thr Asp Phe His Ile Val
```

-continued

```
                20                  25                  30
Asn Ala Ala Val Ser Pro Asp Gly Phe Ser Arg Gln Ala Val Leu Ala
                35                  40                  45
Glu Gly Val Phe Pro Gly Pro Leu Ile Ala Gly Asn Lys Gly Asp Asn
 50                  55                  60
Phe Gln Ile Asn Val Ile Asp Glu Leu Thr Asn Ala Thr Met Leu Lys
 65                  70                  75                  80
Thr Thr Thr Ile His Trp His Gly Phe Phe Gln His Gly Thr Asn Trp
                85                  90                  95
Ala Asp Gly Pro Ala Phe Ile Asn Gln Cys Pro Ile Ala Ser Gly Asp
                100                 105                 110
Ser Phe Leu Tyr Asn Phe Gln Val Pro Asp Gln Ala Gly Thr Phe Trp
                115                 120                 125
Tyr His Ser His Leu Ser Thr Gln Tyr Cys Asp Gly Leu Arg Gly Pro
                130                 135                 140
Phe Val Val Tyr Asp Pro Ala Asp Pro Tyr Leu Asp Gln Tyr Asp Val
145                 150                 155                 160
Asp Asp Asp Ser Thr Val Ile Thr Leu Ala Asp Trp Tyr His Thr Ala
                165                 170                 175
Ala Arg Leu Gly Ser Pro Phe Pro Ala Ala Asp Thr Thr Leu Ile Asn
                180                 185                 190
Gly Leu Gly Arg Cys Gly Glu Ala Gly Cys Pro Val Ser Asp Leu Ala
                195                 200                 205
Val Ile Ser Val Thr Lys Gly Lys Arg Tyr Arg Phe Arg Leu Val Ser
                210                 215                 220
Ile Ser Cys Asp Ser Phe Phe Thr Phe Ser Ile Asp Gly His Ser Leu
225                 230                 235                 240
Asn Val Ile Glu Val Asp Ala Thr Asn His Gln Pro Leu Thr Val Asp
                245                 250                 255
Glu Leu Thr Ile Tyr Ala Gly Gln Arg Tyr Ser Phe Ile Leu Thr Ala
                260                 265                 270
Asp Gln Asp Val Asp Asn Tyr Trp Ile Arg Ala Asn Pro Gly Ile Gly
                275                 280                 285
Ile Thr Thr Gly Phe Ala Gly Gly Ile Asn Ser Ala Ile Leu Arg Tyr
                290                 295                 300
Asp Gly Ala Asp Val Val Glu Pro Thr Thr Thr Gln Ala Thr Ser Pro
305                 310                 315                 320
Val Val Leu Ser Glu Ser Asn Leu Ala Pro Leu Thr Asn Ala Ala Ala
                325                 330                 335
Pro Gly Leu Pro Glu Val Gly Val Asp Leu Ala Leu Asn Phe Asn
                340                 345                 350
Leu Thr Phe Asp Gly Pro Ser Leu Lys Phe Gln Ile Asn Gly Val Thr
                355                 360                 365
Phe Val Pro Pro Thr Val Pro Val Leu Leu Gln Ile Leu Ser Gly Ala
                370                 375                 380
Gln Ser Ala Ala Asp Leu Leu Pro Ser Gly Ser Val Tyr Ala Leu Pro
385                 390                 395                 400
Ser Asn Ala Thr Ile Glu Leu Ser Leu Pro Ala Gly Ala Leu Gly Gly
                405                 410                 415
Pro His Pro Phe His Leu His Gly His Thr Phe Ser Val Val Arg Pro
                420                 425                 430
Ala Gly Ser Thr Thr Tyr Asn Tyr Val Asn Pro Val Gln Arg Asp Val
                435                 440                 445
```

-continued

```
Val Ser Ile Gly Asn Thr Gly Asp Asn Val Thr Ile Arg Phe Asp Thr
    450                 455                 460

Asn Asn Pro Gly Pro Trp Phe Leu His Cys His Ile Asp Trp His Leu
465                 470                 475                 480

Glu Ala Ala Leu Pro Leu Ser Ser Leu Arg Thr Ser Leu Thr Leu Arg
                485                 490                 495

Pro Leu Thr Leu Ser Pro Arg Thr Gly Pro Thr Cys Ala Leu Ser Thr
            500                 505                 510

Thr Leu Trp Thr His Leu Ile Thr Ser Gly Phe Ala Ser Ile Ile Gln
        515                 520                 525

Trp Met Met Gly Gly Asn Gly Leu Phe Ala Pro His Ala Leu Ser Phe
    530                 535                 540

Leu Gly Ser Gln
545
```

(2) INFORMATION FOR SEQ ID NO: 5:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Met Leu Ser Ser Ile Thr Leu Leu Pro Leu Leu Ala Ala Val Ser Thr
1               5                   10                  15

Pro Ala Phe Ala Ala Val Arg Asn Tyr Lys Phe Asp Ile Lys Asn Val
            20                  25                  30

Asn Val Ala Pro Asp Gly Phe Gln Arg Ser Ile Val Ser Val Asn Gly
        35                  40                  45

Leu Val Pro Gly Thr Leu Ile Thr Ala Asn Lys Gly Asp Thr Leu Arg
50                  55                  60

Ile Asn Val Thr Asn Gln Leu Thr Asp Pro Ser Met Arg Arg Ala Thr
65                  70                  75                  80

Thr Ile His Trp His Gly Leu Phe Gln Ala Thr Thr Ala Asp Glu Asp
                85                  90                  95

Gly Pro Ala Phe Val Thr Gln Cys Pro Ile Ala Gln Asn Leu Ser Tyr
            100                 105                 110

Thr Tyr Glu Ile Pro Leu Arg Gly Gln Thr Gly Thr Met Trp Tyr His
        115                 120                 125

Ala His Leu Ala Ser Gln Tyr Val Asp Gly Leu Arg Gly Pro Leu Val
130                 135                 140

Ile Tyr Asp Pro Asn Asp Pro His Lys Ser Arg Tyr Asp Val Asp Asp
145                 150                 155                 160

Ala Ser Thr Val Val Met Leu Glu Asp Trp Tyr His Thr Pro Ala Pro
                165                 170                 175

Val Leu Glu Lys Gln Met Phe Ser Thr Asn Asn Thr Ala Leu Leu Ser
            180                 185                 190

Pro Val Pro Asp Ser Gly Leu Ile Asn Gly Lys Gly Arg Tyr Val Gly
        195                 200                 205

Gly Pro Ala Val Pro Arg Ser Val Ile Asn Val Lys Arg Gly Lys Arg
210                 215                 220

Tyr Arg Leu Arg Val Ile Asn Ala Ser Ala Ile Gly Ser Phe Thr Phe
225                 230                 235                 240
```

```
Ser Ile Glu Gly His Ser Leu Thr Val Ile Glu Ala Asp Gly Ile Leu
                245                 250                 255

His Gln Pro Leu Ala Val Asp Ser Phe Gln Ile Tyr Ala Gly Gln Arg
            260                 265                 270

Tyr Ser Val Ile Val Glu Ala Asn Gln Thr Ala Ala Asn Tyr Trp Ile
        275                 280                 285

Arg Ala Pro Met Thr Val Ala Gly Ala Gly Thr Asn Ala Asn Leu Asp
    290                 295                 300

Pro Thr Asn Val Phe Ala Val Leu His Tyr Glu Gly Ala Pro Asn Ala
305                 310                 315                 320

Glu Pro Thr Thr Glu Gln Gly Ser Ala Ile Gly Thr Ala Leu Val Glu
                325                 330                 335

Glu Asn Leu His Ala Leu Ile Asn Pro Gly Ala Pro Gly Gly Ser Ala
            340                 345                 350

Pro Ala Asp Val Ser Leu Asn Leu Ala Ile Gly Arg Ser Thr Val Asp
        355                 360                 365

Gly Ile Leu Arg Phe Thr Phe Asn Asn Ile Lys Tyr Glu Ala Pro Ser
    370                 375                 380

Leu Pro Thr Leu Leu Lys Ile Leu Ala Asn Asn Ala Ser Asn Asp Ala
385                 390                 395                 400

Asp Phe Thr Pro Asn Glu His Thr Ile Val Leu Pro His Asn Lys Val
                405                 410                 415

Ile Glu Leu Asn Ile Thr Gly Gly Ala Asp His Pro Ile His Leu His
            420                 425                 430

Gly His Val Phe Asp Ile Val Lys Ser Leu Gly Gly Thr Pro Asn Tyr
        435                 440                 445

Val Asn Pro Pro Arg Arg Asp Val Val Arg Val Gly Gly Thr Gly Val
    450                 455                 460

Val Leu Arg Phe Lys Thr Asp Asn Pro Gly Pro Trp Phe Val His Cys
465                 470                 475                 480

His Ile Asp Trp His Leu Glu Ala Gly Leu Ala Leu Val Phe Ala Glu
                485                 490                 495

Ala Pro Ser Gln Ile Arg Gln Gly Val Gln Ser Val Gln Pro Asn Asn
            500                 505                 510

Ala Trp Asn Gln Leu Cys Pro Lys Tyr Ala Ala Leu Pro Pro Asp Leu
        515                 520                 525

Gln (2) INFORMATION FOR SEQ ID NO: 6:

(i) SEQUENCE CHARACTERISTICS:
        (A) LENGTH: 599 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Ala Arg Ser Thr Thr Ser Leu Phe Ala Leu Ser Leu Val Ala Ser
1               5                   10                  15

Ala Phe Ala Arg Val Val Asp Tyr Gly Phe Asp Val Ala Asn Gly Ala
            20                  25                  30

Val Ala Pro Asp Gly Val Thr Arg Asn Ala Val Leu Val Asn Gly Arg
        35                  40                  45
```

-continued

```
Phe Pro Gly Pro Leu Ile Thr Ala Asn Lys Gly Asp Thr Leu Lys Ile
     50                  55                  60
Thr Val Arg Asn Lys Leu Ser Asp Pro Thr Met Arg Arg Ser Thr Thr
 65                  70                  75                  80
Ile His Trp His Gly Leu Leu Gln His Arg Thr Ala Glu Glu Asp Gly
                 85                  90                  95
Pro Ala Phe Val Thr Gln Cys Pro Ile Pro Pro Gln Glu Ser Tyr Thr
            100                 105                 110
Tyr Thr Met Pro Leu Gly Glu Gln Thr Gly Thr Tyr Trp Tyr His Ser
        115                 120                 125
His Leu Ser Ser Gln Tyr Val Asp Gly Leu Arg Gly Pro Ile Val Ile
    130                 135                 140
Tyr Asp Pro His Asp Pro Tyr Arg Asn Tyr Asp Val Asp Asp Glu
145                 150                 155                 160
Arg Thr Val Phe Thr Leu Ala Asp Trp Tyr His Thr Pro Ser Glu Ala
                165                 170                 175
Ile Ile Ala Thr His Asp Val Leu Lys Thr Ile Pro Asp Ser Gly Thr
            180                 185                 190
Ile Asn Gly Lys Gly Lys Tyr Asp Pro Ala Ser Ala Asn Thr Asn Asn
        195                 200                 205
Thr Thr Leu Glu Asn Leu Tyr Thr Leu Lys Val Lys Arg Gly Lys Arg
    210                 215                 220
Tyr Arg Leu Arg Ile Ile Asn Ala Ser Ala Ile Ala Ser Phe Arg Phe
225                 230                 235                 240
Gly Val Gln Gly His Lys Cys Thr Ile Ile Glu Ala Asp Gly Val Leu
                245                 250                 255
Thr Lys Pro Ile Glu Val Asp Ala Phe Asp Ile Leu Ala Gly Gln Arg
            260                 265                 270
Tyr Ser Cys Ile Leu Lys Ala Asp Gln Asp Pro Asp Ser Tyr Trp Ile
        275                 280                 285
Asn Ala Pro Ile Thr Asn Val Leu Asn Thr Asn Val Gln Ala Leu Leu
    290                 295                 300
Val Tyr Glu Asp Asp Lys Arg Pro Thr His Tyr Pro Trp Lys Pro Phe
305                 310                 315                 320
Leu Thr Trp Lys Ile Ser Asn Glu Ile Ile Gln Tyr Trp Gln His Lys
                325                 330                 335
His Gly Ser His Gly His Lys Gly Lys Gly His His His Lys Val Arg
            340                 345                 350
Ala Ile Gly Gly Val Ser Gly Leu Ser Ser Arg Val Lys Ser Arg Ala
        355                 360                 365
Ser Asp Leu Ser Lys Lys Ala Val Glu Leu Ala Ala Ala Leu Val Ala
    370                 375                 380
Gly Glu Ala Glu Leu Asp Lys Arg Gln Asn Glu Asp Asn Ser Thr Ile
385                 390                 395                 400
Val Leu Asp Glu Thr Lys Leu Ile Pro Leu Val Gln Pro Gly Ala Pro
                405                 410                 415
Gly Gly Ser Arg Pro Ala Asp Val Val Val Pro Leu Asp Phe Gly Leu
            420                 425                 430
Asn Phe Ala Asn Gly Leu Trp Thr Ile Asn Asn Val Ser Tyr Ser Pro
        435                 440                 445
Pro Asp Val Pro Thr Leu Leu Lys Ile Leu Thr Asp Lys Asp Lys Val
    450                 455                 460
Asp Ala Ser Asp Phe Thr Ala Asp Glu His Thr Tyr Ile Leu Pro Lys
```

```
                465                 470                 475                 480
Asn Gln Val Val Glu Leu His Ile Lys Gly Gln Ala Leu Gly Ile Val
                        485                 490                 495

His Pro Leu His Leu His Gly His Ala Phe Asp Val Val Gln Phe Gly
                500                 505                 510

Asp Asn Ala Pro Asn Tyr Val Asn Pro Pro Arg Arg Asp Val Val Gly
                515                 520                 525

Val Thr Asp Ala Gly Val Arg Ile Gln Phe Arg Thr Asp Asn Pro Gly
            530                 535                 540

Pro Trp Phe Leu His Cys His Ile Asp Trp His Leu Glu Glu Gly Phe
545                 550                 555                 560

Ala Met Val Phe Ala Glu Ala Pro Glu Asp Ile Lys Lys Gly Ser Gln
                565                 570                 575

Ser Val Lys Pro Asp Gly Gln Trp Lys Lys Leu Cys Glu Lys Tyr Glu
                580                 585                 590

Lys Leu Pro Glu Ala Leu Gln
        595

(2) INFORMATION FOR SEQ ID NO: 7:

(i) SEQUENCE CHARACTERISTICS:
        (A) LENGTH: 572 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Met Ala Arg Thr Thr Phe Leu Val Ser Val Ser Leu Phe Val Ser Ala
1               5                   10                  15

Val Leu Ala Arg Thr Val Glu Tyr Asn Leu Lys Ile Ser Asn Gly Lys
            20                  25                  30

Ile Ala Pro Asp Gly Val Glu Arg Asp Ala Thr Leu Val Asn Gly Gly
            35                  40                  45

Tyr Pro Gly Pro Leu Ile Phe Ala Asn Lys Gly Asp Thr Leu Lys Val
        50                  55                  60

Lys Val Gln Asn Lys Leu Thr Asn Pro Asp Met Tyr Arg Thr Thr Ser
65                  70                  75                  80

Ile His Trp His Gly Leu Leu Gln His Arg Asn Ala Asp Asp Gly
                85                  90                  95

Pro Ala Phe Val Thr Gln Cys Pro Ile Val Pro Gln Ala Ser Tyr Thr
                100                 105                 110

Tyr Thr Met Pro Leu Gly Asp Gln Thr Gly Thr Tyr Trp Tyr His Ser
            115                 120                 125

His Leu Ser Ser Gln Tyr Val Asp Gly Leu Arg Gly Pro Leu Val Ile
            130                 135                 140

Tyr Asp Pro Lys Asp Pro His Arg Arg Leu Tyr Asp Ile Asp Asp Glu
145                 150                 155                 160

Lys Thr Val Leu Ile Ile Gly Asp Trp Tyr His Thr Ser Ser Lys Ala
                165                 170                 175

Ile Leu Ala Thr Gly Asn Ile Thr Leu Gln Gln Pro Asp Ser Ala Thr
            180                 185                 190

Ile Asn Gly Lys Gly Arg Phe Asp Pro Asp Asn Thr Pro Ala Asn Pro
            195                 200                 205

Asn Thr Leu Tyr Thr Leu Lys Val Lys Arg Gly Lys Arg Tyr Arg Leu
```

```
            210                 215                 220
Arg Val Ile Asn Ser Ser Ala Ile Ala Ser Phe Arg Met Ser Ile Gln
225                 230                 235                 240

Gly His Lys Met Thr Val Ile Ala Ala Asp Gly Val Ser Thr Lys Pro
            245                 250                 255

Tyr Gln Val Asp Ser Phe Asp Ile Leu Ala Gly Gln Arg Ile Asp Ala
            260                 265                 270

Val Val Glu Ala Asn Gln Glu Pro Asp Thr Tyr Trp Ile Asn Ala Pro
            275                 280                 285

Leu Thr Asn Val Ala Asn Lys Thr Ala Gln Ala Leu Leu Ile Tyr Glu
            290                 295                 300

Asp Asp Arg Arg Pro Tyr His Pro Pro Lys Gly Pro Tyr Arg Lys Trp
305                 310                 315                 320

Ser Val Ser Glu Ala Ile Ile Lys Tyr Trp Lys His Lys His Gly Arg
            325                 330                 335

Gly Leu Leu Ser Gly His Gly Gly Leu Lys Ala Arg Met Met Glu Gly
            340                 345                 350

Ser Leu His Leu His Gly Arg Arg Asp Ile Val Lys Arg Gln Asn Glu
            355                 360                 365

Thr Thr Thr Val Val Met Asp Glu Thr Lys Leu Val Pro Leu Glu His
            370                 375                 380

Pro Gly Ala Ala Cys Gly Ser Lys Pro Ala Asp Leu Val Ile Asp Leu
385                 390                 395                 400

Thr Phe Gly Val Asn Phe Thr Thr Gly His Trp Met Ile Asn Gly Ile
            405                 410                 415

Pro His Lys Ser Pro Asp Met Pro Thr Leu Leu Lys Ile Leu Thr Asp
            420                 425                 430

Thr Asp Gly Val Thr Glu Ser Asp Phe Thr Gln Pro Glu His Thr Ile
            435                 440                 445

Ile Leu Pro Lys Asn Lys Cys Val Glu Phe Asn Ile Lys Gly Asn Ser
450                 455                 460

Gly Leu Gly Ile Val His Pro Ile His Leu His Gly His Thr Phe Asp
465                 470                 475                 480

Val Val Gln Phe Gly Asn Asn Pro Pro Asn Tyr Val Asn Pro Pro Arg
            485                 490                 495

Arg Asp Val Val Gly Ala Thr Asp Glu Gly Val Arg Phe Gln Phe Lys
            500                 505                 510

Thr Asp Asn Pro Gly Pro Trp Phe Leu His Cys His Ile Asp Trp His
            515                 520                 525

Leu Glu Glu Gly Phe Ala Met Val Phe Ala Glu Ala Pro Glu Ala Ile
            530                 535                 540

Lys Gly Gly Pro Lys Ser Val Pro Val Asp Arg Gln Trp Lys Asp Leu
545                 550                 555                 560

Cys Arg Lys Tyr Gly Ser Leu Pro Ala Gly Phe Leu
            565                 570

(2) INFORMATION FOR SEQ ID NO: 8:

(i) SEQUENCE CHARACTERISTICS:
        (A) LENGTH: 575 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO: 8:

```
Met Ala Arg Thr Thr Phe Leu Val Ser Val Ser Leu Phe Val Ser Ala
 1               5                  10                  15

Val Leu Ala Arg Thr Val Glu Tyr Gly Leu Lys Ile Ser Asp Gly Glu
             20                  25                  30

Ile Ala Pro Asp Gly Val Lys Arg Asn Ala Thr Leu Val Asn Gly Gly
             35                  40                  45

Tyr Pro Gly Pro Leu Ile Phe Ala Asn Lys Gly Asp Thr Leu Lys Val
 50                  55                  60

Lys Val Gln Asn Lys Leu Thr Asn Pro Glu Met Tyr Arg Thr Thr Ser
 65                  70                  75                  80

Ile His Trp His Gly Leu Leu Gln His Arg Asn Ala Asp Asp Asp Gly
                 85                  90                  95

Pro Ser Phe Val Thr Gln Cys Pro Ile Val Pro Arg Glu Ser Tyr Thr
                100                 105                 110

Tyr Thr Ile Pro Leu Asp Asp Gln Thr Gly Thr Tyr Trp Tyr His Ser
             115                 120                 125

His Leu Ser Ser Gln Tyr Val Asp Gly Leu Arg Gly Pro Leu Val Ile
130                 135                 140

Tyr Pro Lys Asp Pro His Arg Arg Leu Tyr Asp Val Asp Asp Glu Lys
145                 150                 155                 160

Thr Val Leu Ile Ile Gly Asp Trp Tyr His Glu Ser Ser Lys Ala Ile
                165                 170                 175

Leu Ala Ser Gly Asn Ile Thr Arg Gln Arg Pro Val Ser Ala Thr Ile
                180                 185                 190

Asn Gly Lys Gly Arg Phe Asp Pro Asp Asn Thr Pro Ala Asn Pro Asp
            195                 200                 205

Thr Leu Tyr Thr Leu Lys Val Lys Arg Gly Lys Arg Tyr Arg Leu Arg
210                 215                 220

Val Ile Asn Ser Ser Glu Ile Ala Ser Phe Arg Phe Ser Val Glu Gly
225                 230                 235                 240

His Lys Val Thr Val Ile Ala Ala Asp Gly Val Ser Thr Lys Pro Tyr
                245                 250                 255

Gln Val Asp Ala Phe Asp Ile Leu Ala Gly Gln Arg Ile Asp Cys Val
            260                 265                 270

Val Glu Ala Asn Gln Glu Pro Asp Thr Tyr Trp Ile Asn Ala Pro Leu
275                 280                 285

Thr Asn Val Pro Asn Lys Thr Ala Gln Ala Leu Leu Val Tyr Glu Glu
290                 295                 300

Asp Arg Arg Pro Tyr His Pro Lys Gly Pro Tyr Arg Lys Trp Ser
305                 310                 315                 320

Val Ser Glu Ala Ile Ile Lys Tyr Trp Asn His Lys His Lys His Gly
                325                 330                 335

Arg Gly Leu Leu Ser Gly His Gly Leu Lys Ala Arg Met Ile Glu
                340                 345                 350

Gly Ser His His Leu His Ser Arg Ser Val Val Lys Arg Gln Asn Glu
            355                 360                 365

Thr Thr Thr Val Val Met Asp Glu Ser Lys Leu Val Pro Leu Glu Tyr
370                 375                 380

Pro Gly Ala Ala Cys Gly Ser Lys Pro Ala Asp Leu Val Leu Asp Leu
385                 390                 395                 400

Thr Phe Gly Leu Asn Phe Ala Thr Gly His Trp Met Ile Asn Gly Ile
                405                 410                 415
```

```
Pro Tyr Glu Ser Pro Lys Ile Pro Thr Leu Leu Lys Ile Leu Thr Asp
                420                 425                 430

Glu Asp Gly Val Thr Glu Ser Asp Phe Thr Lys Glu Glu His Thr Val
            435                 440                 445

Ile Leu Pro Lys Asn Lys Cys Ile Glu Phe Asn Ile Lys Gly Asn Ser
        450                 455                 460

Gly Ile Pro Ile Thr His Pro Val His Leu His Gly His Thr Trp Asp
465                 470                 475                 480

Val Val Gln Phe Gly Asn Asn Pro Pro Asn Tyr Val Asn Pro Pro Arg
                485                 490                 495

Arg Asp Val Val Gly Ser Thr Asp Ala Gly Val Arg Ile Gln Phe Lys
            500                 505                 510

Thr Asp Asn Pro Gly Pro Trp Phe Leu His Cys His Ile Asp Trp His
        515                 520                 525

Leu Glu Glu Gly Phe Ala Met Val Phe Ala Glu Ala Pro Glu Ala Val
    530                 535                 540

Lys Gly Gly Pro Lys Ser Val Ala Val Asp Ser Gln Trp Glu Gly Leu
545                 550                 555                 560

Cys Gly Lys Tyr Asp Asn Trp Leu Lys Ser Asn Pro Gly Gln Leu
                565                 570                 575

(2) INFORMATION FOR SEQ ID NO: 9:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Met Lys Arg Phe Phe Ile Asn Ser Leu Leu Leu Ala Gly Leu Leu
1               5                   10                  15

Asn Ser Gly Ala Leu Ala Ala Pro Ser Thr His Pro Arg Ser Asn Pro
            20                  25                  30

Asp Ile Leu Leu Glu Arg Asp Asp His Ser Leu Thr Ser Arg Gln Gly
        35                  40                  45

Ser Cys His Ser Pro Ser Asn Arg Ala Cys Trp Cys Ser Gly Phe Asp
50                  55                  60

Ile Asn Thr Asp Tyr Glu Thr Lys Thr Pro Asn Thr Gly Val Val Arg
65                  70                  75                  80

Arg Tyr Thr Phe Asp Ile Thr Glu Val Asp Asn Arg Pro Gly Pro Asp
                85                  90                  95

Gly Val Ile Lys Glu Lys Leu Met Leu Ile Asn Asp Lys Leu Leu Gly
            100                 105                 110

Pro Thr Val Phe Ala Asn Trp Gly Asp Thr Ile Glu Val Thr Val Asn
        115                 120                 125

Asn His Leu Arg Thr Asn Gly Thr Ser Ile His Trp His Gly Leu His
    130                 135                 140

Gln Lys Gly Thr Asn Tyr His Asp Gly Ala Asn Gly Val Thr Glu Cys
145                 150                 155                 160

Pro Ile Pro Pro Gly Gly Ser Arg Val Tyr Ser Phe Arg Ala Arg Gln
                165                 170                 175

Tyr Gly Thr Ser Trp Tyr His Ser His Phe Ser Ala Gln Tyr Gly Asn
            180                 185                 190
```

```
Gly Val Ser Gly Ala Ile Gln Ile Asn Gly Pro Ala Ser Leu Pro Tyr
            195                 200                 205

Asp Ile Asp Leu Gly Val Leu Pro Leu Xaa Asp Trp Tyr Tyr Lys Ser
    210                 215                 220

Ala Asp Gln Leu Val Ile Glu Thr Leu Xaa Lys Gly Asn Ala Pro Phe
225                 230                 235                 240

Ser Asp Asn Val Leu Ile Asn Gly Thr Ala Lys His Pro Thr Thr Gly
                245                 250                 255

Glu Gly Glu Tyr Ala Ile Val Lys Leu Thr Pro Asp Lys Arg His Arg
            260                 265                 270

Leu Arg Leu Ile Asn Met Ser Val Glu Asn His Phe Gln Val Ser Leu
        275                 280                 285

Ala Lys His Thr Met Thr Val Ile Ala Ala Asp Met Val Pro Val Asn
290                 295                 300

Ala Met Thr Val Asp Ser Leu Phe Met Ala Val Gly Gln Arg Tyr Asp
305                 310                 315                 320

Val Thr Ile Asp Ala Ser Gln Ala Val Gly Asn Tyr Trp Phe Asn Ile
                325                 330                 335

Thr Phe Gly Gly Gln Gln Lys Cys Gly Phe Ser His Asn Pro Ala Pro
            340                 345                 350

Ala Ala Ile Phe Arg Tyr Glu Gly Ala Pro Asp Ala Leu Pro Thr Asp
        355                 360                 365

Pro Gly Ala Ala Pro Lys Asp His Gln Cys Leu Asp Thr Leu Asp Leu
    370                 375                 380

Ser Pro Val Val Gln Lys Asn Val Pro Val Asp Gly Phe Val Lys Glu
385                 390                 395                 400

Pro Gly Asn Thr Leu Pro Val Thr Leu His Val Asp Gln Ala Ala Ala
                405                 410                 415

Pro His Val Phe Thr Trp Lys Ile Asn Gly Ser Ala Ala Asp Val Asp
            420                 425                 430

Trp Asp Arg Pro Val Leu Glu Tyr Val Met Asn Asn Asp Leu Ser Ser
        435                 440                 445

Ile Pro Val Lys Asn Asn Ile Val Arg Val Asp Gly Val Asn Glu Trp
    450                 455                 460

Thr Tyr Trp Leu Val Glu Asn Asp Pro Glu Gly Arg Leu Ser Leu Pro
465                 470                 475                 480

His Pro Met His Leu His Gly His Asp Phe Phe Val Leu Gly Arg Ser
                485                 490                 495

Pro Asp Val Ser Pro Asp Ser Glu Thr Arg Phe Val Phe Asp Pro Ala
            500                 505                 510

Val Asp Leu Pro Arg Leu Arg Gly His Asn Pro Val Arg Arg Asp Val
        515                 520                 525

Thr Met Leu Pro Ala Arg Gly Trp Leu Leu Leu Ala Phe Arg Thr Asp
    530                 535                 540

Asn Pro Gly Ala Trp Leu Phe His Cys His Ile Ala Xaa His Val Ser
545                 550                 555                 560

Gly Gly Leu Ser Val Asp Phe Leu Glu Arg Pro Asp Glu Leu Arg Gly
                565                 570                 575

Gln Leu Thr Gly Glu Ser Lys Ala Glu Leu Glu Arg Val Cys Arg Glu
            580                 585                 590

Trp Lys Asp Trp Glu Ala Lys Ser Pro His Gly Lys Ile Asp Ser Gly
        595                 600                 605
```

```
Leu Lys Gln Arg Arg Trp Asp Ala
    610             615
```

(2) INFORMATION FOR SEQ ID NO: 10:

(i) SEQUENCE CHARACTERISTICS:
        (A) LENGTH: 573 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Gln Gln Ser Cys Asn Thr Pro Ser Asn Arg Ala Cys Trp Thr Asp Gly
1               5                   10                  15

Tyr Asp Ile Asn Thr Asp Tyr Glu Val Asp Ser Pro Asp Thr Gly Val
            20                  25                  30

Val Arg Pro Tyr Thr Leu Thr Leu Thr Glu Val Asp Asn Trp Thr Gly
        35                  40                  45

Pro Asp Gly Val Val Lys Glu Lys Val Met Leu Val Asn Asn Ser Ile
    50                  55                  60

Ile Gly Pro Thr Ile Phe Ala Asp Trp Gly Asp Thr Ile Gln Val Thr
65                  70                  75                  80

Val Ile Asn Asn Leu Glu Thr Asn Gly Thr Ser Ile His Trp His Gly
                85                  90                  95

Leu His Gln Lys Gly Thr Asn Leu His Asp Gly Ala Asn Gly Ile Thr
            100                 105                 110

Glu Cys Pro Ile Pro Pro Lys Gly Arg Lys Val Tyr Arg Phe Lys
        115                 120                 125

Ala Gln Gln Tyr Gly Thr Ser Trp Tyr His Ser His Phe Ser Ala Gln
    130                 135                 140

Tyr Gly Asn Gly Val Val Gly Ala Ile Gln Ile Asn Gly Pro Ala Ser
145                 150                 155                 160

Leu Pro Tyr Asp Thr Asp Leu Gly Val Phe Pro Ile Ser Asp Tyr Tyr
                165                 170                 175

Tyr Ser Ser Ala Asp Glu Leu Val Glu Leu Thr Lys Asn Ser Gly Ala
            180                 185                 190

Pro Phe Ser Asp Asn Val Leu Phe Asn Gly Thr Ala Lys His Pro Glu
        195                 200                 205

Thr Gly Glu Gly Glu Tyr Ala Asn Val Thr Leu Thr Pro Gly Arg Arg
    210                 215                 220

His Arg Leu Arg Leu Ile Asn Thr Ser Val Glu Asn His Phe Gln Val
225                 230                 235                 240

Ser Leu Val Asn His Thr Met Cys Ile Ile Ala Ala Asp Met Val Pro
                245                 250                 255

Val Asn Ala Met Thr Val Asp Ser Leu Phe Leu Gly Val Gly Gln Arg
            260                 265                 270

Tyr Asp Val Val Ile Glu Ala Asn Arg Thr Pro Gly Asn Tyr Trp Phe
        275                 280                 285

Asn Val Thr Phe Gly Gly Gly Leu Leu Cys Gly Gly Ser Arg Asn Pro
    290                 295                 300

Tyr Pro Ala Ala Ile Phe His Tyr Ala Gly Ala Pro Gly Gly Pro Pro
305                 310                 315                 320

Thr Asp Glu Gly Lys Ala Pro Val Asp His Asn Cys Leu Asp Leu Pro
                325                 330                 335
```

-continued

```
Asn Leu Lys Pro Val Val Ala Arg Asp Val Pro Leu Ser Gly Phe Ala
            340                 345                 350

Lys Arg Ala Asp Asn Thr Leu Asp Val Thr Leu Asp Thr Thr Gly Thr
        355                 360                 365

Pro Leu Phe Val Trp Lys Val Asn Gly Ser Ala Ile Asn Ile Asp Trp
    370                 375                 380

Gly Arg Ala Val Val Asp Tyr Val Leu Thr Gln Asn Thr Ser Phe Pro
385                 390                 395                 400

Pro Gly Tyr Asn Ile Val Glu Val Asn Gly Ala Asp Gln Trp Ser Tyr
                405                 410                 415

Trp Leu Ile Glu Asn Asp Pro Gly Ala Pro Phe Thr Leu Pro His Pro
                420                 425                 430

Met His Leu His Gly His Asp Phe Tyr Val Leu Gly Arg Ser Pro Asp
            435                 440                 445

Glu Ser Pro Ala Ser Asn Glu Arg His Val Phe Asp Pro Ala Arg Asp
        450                 455                 460

Ala Gly Leu Leu Ser Gly Ala Asn Pro Val Arg Arg Asp Val Ser Met
465                 470                 475                 480

Leu Pro Ala Phe Gly Trp Val Val Leu Ser Phe Arg Ala Asp Asn Pro
                485                 490                 495

Gly Ala Trp Leu Phe His Cys His Ile Ala Trp His Val Ser Gly Gly
            500                 505                 510

Leu Gly Val Val Tyr Leu Glu Arg Ala Asp Asp Leu Arg Gly Ala Val
            515                 520                 525

Ser Asp Ala Asp Ala Asp Asp Leu Asp Arg Leu Cys Ala Asp Trp Arg
        530                 535                 540

Arg Tyr Trp Pro Thr Asn Pro Tyr Pro Lys Ser Asp Ser Gly Leu Lys
545                 550                 555                 560

His Arg Trp Val Glu Glu Gly Glu Trp Leu Val Lys Ala
                565                 570
```

LACCASE MUTANTS

CROSS-REFERENCE TO RELATED APPLICATIONS

This application is a division of application Ser. No. 08/993,318 filed on Dec. 18, 1997, now U.S. Pat. No. 5,998,353 and claims priority of U.S. provisional application No. 60/035,413 filed Jan. 23, 1997 under 35 U.S.C. 119 and Danish application Nos. 1449/96 and 1021/97 filed Dec. 19, 1996 and Sep. 8, 1997, the contents of which are fully incorporated herein by reference.

FIELD OF THE INVENTION

The present invention relates to a method of designing laccase mutants with improved stability properties, which method is based on the hitherto unknown three-dimensional structure of laccases.

BACKGROUND OF THE INVENTION

Laccase is a polyphenol oxidase (EC 1.10.3.2) which catalyses the oxidation of a variety of inorganic and aromatic compounds, particularly phenols, with the concomitant reduction of molecular oxygen to water.

Laccase belongs to a family of blue copper-containing oxidases which includes ascorbate oxidase and the mammalian plasma protein ceruloplasmin. All these enzymes are multi-copper-containing proteins.

Because laccases are able to catalyze the oxidation of a variety of inorganic and aromatic compounds, laccases have been suggested in many potential industrial applications such as lignin modification, paper strengthening, dye transfer inhibition in detergents, phenol polymerization, hair colouring, and waste water treatment. A major problem with the use of laccases are their poor storage stability at temperatures above room temperature, especially at 40° C.

In Example 1 of the present application we have tested the stability of various laccases at 40° C., and it can be seen that after 2 weeks of storage the laccase activity is down to less than 50% of the initial value, and at low pH the laccase activity after 2 weeks is zero. For many purposes such a decrease is unacceptable, so it is the purpose of the present invention to create laccase variants with improved stability by using the information of a three-dimensional structure of a *Coprinus cinereus* laccase. No three-dimensional structural information has been available for a laccase before.

BRIEF DISCLOSURE OF THE INVENTION

The three-dimensional structure of a laccase has now been elucidated. On the basis of an analysis of said structure it is possible to identify structural parts or specific amino acid residues which from structural or functional considerations appear to be important for the stability of a laccase.

Furthermore, when comparing the three-dimensional structure of the Coprinus laccase structure with known amino acid sequences of various laccases, it has been found that some similarities exist between the sequences. The present invention is based on these findings.

Accordingly, in a first aspect the invention relates to a method of constructing a variant of a parent Coprinus laccase, which variant has laccase activity and improved stability as compared to said parent laccase, which method comprises i) analysing the three-dimensional structure of the parent Coprinus laccase to identify at least one amino acid residue or at least one structural part of the Coprinus laccase structure, which amino acid residue or structural part is believed to be of relevance for altering the stability of the parent Coprinus laccase (as evaluated on the basis of structural or functional considerations), ii) constructing a Coprinus laccase variant, which as compared to the parent Coprinus laccase, has been modified in the amino acid residue or structural part identified in i) so as to alter the stability, and, optionally, iii) testing the resulting Coprinus laccase variant with respect to stability.

In a second aspect the present invention relates to a method of constructing a variant of a parent Coprinus-like laccase, which variant has laccase activity and improved stability as compared to said parent laccase, which method comprises i) comparing the three-dimensional amino acid structure of the Coprinus laccase with an amino acid sequence of a Coprinus-like laccase, ii) identifying a part of the Coprinus-like laccase amino acid sequence which is different from the Coprinus laccase amino acid sequence and which from structural or functional considerations is contemplated to be responsible for differences in the stability of the Coprinus and Coprinus-like laccase, iii) modifying the part of the Coprinus-like laccase identified in ii) whereby a Coprinus-like laccase variant is obtained, which has an improved stability as compared to the parent Coprinus-like laccase, and optionally, iv) testing the resulting Coprinus-like laccase variant with respect to stability.

In still further aspects the invention relates to variants of a Coprinus laccase and of Coprinus-like laccases, DNA encoding such variants and methods of preparing the variants. Finally, the invention relates to the use of the variants for various industrial purposes.

DETAILED DISCLOSURE OF THE INVENTION

The Coprinus-Like Laccases

A number of laccases produced by different fungi are homologous on the amino acid level. For instance, when using the homology percent obtained from UWGCG program using the GAP program with the default parameters (penalties: gap weight=3.0, length weight=0.1; WISCONSIN PACKAGE Version 8.1-UNIX, August 1995, Genetics Computer Group, 575 Science Drive, Madison, Wis., U.S.A. 53711) the following homology was found:

*Coprinus cinereus* laccase comprising the amino acid sequence shown in SEQ ID No. 1: 100%;

*Polyporus pinsitus* (I) laccase comprising the amino acid sequence shown in SEQ ID No. 2: 74.4%;

*Polyporus pinsitus* (II) laccase comprising the amino acid sequence shown in SEQ ID No. 3: 73.8%;

*Phlebia radiata* laccase comprising the amino acid sequence shown in SEQ ID No. 4: 69.9%;

*Rhizoctonia solani* (I) laccase comprising the amino acid sequence shown in SEQ ID No. 5: 64.8%;

*Rhizoctonia solani* (II) laccase comprising the amino acid sequence shown in SEQ ID No. 6: 63.0%;

*Rhizoctonia solani* (III) laccase comprising the amino acid sequence shown in SEQ ID No. 7: 61.0%;

*Rhizoctonia solani* (IV) laccase comprising the amino acid sequence shown in SEQ ID No. 8: 59.7%;

*Scytalidium thermophilum* laccase comprising the amino acid sequence shown in SEQ ID No. 9: 57.4%;

*Myceliophthora thermophila* laccase comprising the amino acid sequence shown in SEQ ID No. 10: 56.5%.

Because of the homology found between the above mentioned laccases, they are considered to belong to the same class of laccases, namely the class of "Coprinus-like laccases".

Accordingly, in the present context, the term "Coprinus-like laccase" is intended to indicate a laccase which, on the amino acid level, displays a homology of at least 50% and less than 100% to the *Coprinus cinereus* laccase SEQ ID NO 1, or at least 55% and less than 100% to the *Coprinus cinereus* laccase SEQ ID NO 1, or at least 60% and less than 100% to the *Coprinus cinereus* laccase SEQ ID NO 1, or at least 65% and less than 100% to the *Coprinus cinereus* laccase SEQ ID NO 1, or at least 70% and less than 100% to the *Coprinus cinereus* laccase SEQ ID NO 1, or at least 75% and less than 100% to the *Coprinus cinereus* laccase SEQ ID NO 1, or at least 80% and less than 100% to the *Coprinus cinereus* laccase SEQ ID NO 1, or at least 85% and less than 100% to the *Coprinus cinereus* laccase SEQ ID NO 1, or at least 90% and less than 100% to the *Coprinus cinereus* laccase SEQ ID NO 1, or at least 95% and less than 100% to the *Coprinus cinereus* laccase SEQ ID NO 1.

In the present context, "derived from" is intended not only to indicate a laccase produced or producible by a strain of the organism in question, but also a laccase encoded by a DNA sequence isolated from such strain and produced in a host organism containing said DNA sequence. Finally, the term is intended to indicate a laccase which is encoded by a DNA sequence of synthetic and/or cDNA origin and which has the identifying characteristics of the laccase in question.

The Three-Dimensional Coprinus Laccase Structure

The Coprinus laccase which was used to elucidate the three-dimensional structure forming the basis for the present invention consists of the 539 amino acids derived from *Coprinus cinereus* laccase IFO 8371 as disclosed in sequence ID No. 1.

The obtained three-dimensional structure is believed to be representative for the structure of any Coprinus-like laccase.

The structure of the laccase was solved in accordance with the principle for X-ray crystallographic methods given in "X-Ray Structure Determination", Stout, G. K. and Jensen, L. H., John Wiley & Sons, inc. NY, 1989. The structural coordinates for the solved crystal structure of the laccase at 2.2 Å resolution using the isomorphous replacement method are given in a standard PDB format (Brookhaven Protein Data Base) in Appendix 1. It is to be understood that Appendix 1 forms part of the present application.

In Appendix 1 the amino acid residues of the enzyme are identified by three-letter amino acid code (capitalized letters).

The laccase structure is made up of three plastocyanin-like domains. These three domains all have a similar beta-barrel fold.

3 copper atoms were observed in the three-dimensional structure:

The so-called type 1 copper ion is coordinated by two histidines and one cysteine.

The so-called type 2 copper of the trinuclear centre is missing in the structure disclosed in the present application.

The so-called type 3 copper consists of two type 3 copper atoms (pair of copper atoms) bound to a total of 6 histidine ligands.

When comparing the amino acid sequence of the crystallized three-dimensional structure with *Coprinus cinereus* amino acid sequence ID No. 1 the following four differences are observed:

18 amino acids are missing from the N-terminal of the crystallized protein;
17 amino acids are missing from the C-terminal of the crystallized protein;
Q19 in sequence ID No. 1 is an A1 in the crystallized protein; and
Q243 in sequence ID No. 1 is an E225 in the crystallized protein.

Generality of Structure

Because of the homology between the Coprinus laccase and the various Coprinus-like laccases, the solved structure defined by the coordinates of Appendix 1 is believed to be representative for the structure of all Coprinus-like laccases. A model structure of Coprinus-like laccases may be built on the basis of the coordinates given in Appendix 1 adapted to the laccase in question by use of an alignment between the respective amino acid sequences.

The above identified structurally characteristic parts of the Coprinus laccase structure may be identified in other Coprinus-like laccases on the basis of a model (or solved) structure of the relevant Coprinus-like laccase or simply on the basis of an alignment between the amino acid sequence of the Coprinus-like laccase in question with that of the Coprinus laccase used herein for identifying the amino acid residues of the respective structural elements.

Furthermore, in connection with Coprinus laccase variants of the invention, which are defined by modification of specific amino acid residues of the parent Coprinus laccase, it will be understood that variants of Coprinus-like laccases modified in an equivalent position (as determined from the best possible amino acid sequence alignment between the respective sequences) are intended to be covered as well.

Methods of the Invention for Design of Novel Laccase Variants

The analysis or comparison performed in step i) of the methods of the invention may be performed by use of any suitable computer programme capable of analysing and/or comparing amino acid sequences.

The structural part which is identified in step i) of the methods of the invention may be composed of one amino acid residue. However, normally the structural part comprises more than one amino acid residue, typically constituting one of the above mentioned parts of the Coprinus structure such as one of the copper centres.

According to the invention useful laccase variants may be modified in one or more amino acid residues present within 15 Å from any copper ion, preferably variants which are modified within 10 Å from any copper ion, in particular variants which are modified within 5 Å from any copper ion.

Determination of residues within 5 Å, 10 Å and 15 Å from the copper ions in the three-dimensional structure: The coordinates from the appendix are read into INSIGHT program provided by BIOSYM technologies. The spatial coordinates are presented showing the bonds between the atoms. The copper atoms are presented as well as the water atoms. The program package contains a part which can be used for creating subsets. This part is used for creating a 5 Å, 10 Å and 15 Å subset around all Cu-ions present in the structure (the command ZONE is used). The found subsets contain all residues having an atom within 5, 10 and 15 Å from any of the Cu-ions present in the structure. All residues having an atom within this subset are compiled and written out by the LIST MOLECULE command.

The amino acid residues found in this way within a distance of 15 Å from a copper ion in the *Coprinus cinereus* laccase are the following (SEQ ID No 1 numbering):

M27, V46, G51, P52, I54, L64, L76, T79, S80, I81, H82, W83, H84, G85, L86, F87, Q88, R89, T91, N92, W93, A94,

D95, G96, A97, D98, G99, V100, N101, Q102, C103, P104, Y113, F115, H120, G122, T123, F124, W125, Y126, H127, S128, H129, F130, G131, T132, Q133, Y134, C135, D136, G137, L138, R139, G140, P141, M142, V143, I144, I164, T165, L166, A167, D168, H170, G179, A180, A181, Q182, P183, L217, I218, S219, L220, S221, C222, D223, P224, N225, W226, E239, V240, D241, G242, Q243, Q254, T255, F256, T257, G258, Q259, R260, Y261, N281, K282, E349, Q350, L351, G352, F353, S354, G356, R357, F358, T359, I360, N361, T363, A364, Y365, E366, S367, P368, P371, T372, L373, P388, S391, V392, L403, V404, V405, P406, A407, G408, V409, L410, G411, G412, P413, H414, P415, F416, H417, L418, H419, G420, H421, A422, F423, A429, K441, R442, D443, V444, V445, S446, L447, G448, V449, T450, D452, V454, I456, F458, N462, G464, P465, W466, F467, F468, H469, C470, H471, I472, E473, F474, H475, L476, M477, N478, G479, L480, A481, I482, V483, F484, A485, E486.

The amino acid residues found within a distance of 10 Å from a copper ion in the *Coprinus cinereus* laccase (SEQ ID No 1) are the following:
S80, I81, H82, W83, H84, G85, L86, D95, G96, A97, D98, V100, N101, F124, W125, Y126, H127, S128, H129, F130, G131, Y134, L138, R139, G140, I218, S219, L220, S221, C222, D223, P224, D241, F256, T257, G258, Q259, R260, K282, L351, G352, F353, F358, T359, V405, V409, L410, G411, G412, P413, H414, P415, F416, H417, L418, H419, G420, D443, V444, V445, S446, L447, G448, V454, I456, F458, W466, F467, F468, H469, C470, H471, I472, E473, F474, H475, L476, M477, N478, G479, L480, A481, I482.

The amino acid residues found within a distance of 5 Å from a copper ion in the *Coprinus cinereus* laccase (SEQ ID No 1) are the following:
H84, W125, H127, H129, G411, H414, P415, H417, H419, F467, H469, C470, H471, I472, H475, L480.

The 15 Å/10 Å/5 Å regions can be found in other laccases by comparison of the modelled structures or by taking the sequence homology numbers.

Modifications

The modification of an amino acid residue or structural part is typically accomplished by suitable modifications of a DNA sequence encoding the parent enzyme in question. The term "modified" as used in the methods according to the invention is intended to have the following meaning: When used in relation to an amino acid residue the term is intended to mean replacement of the amino acid residue in question with another amino acid residue. When used in relation to a structural part, the term is intended to mean: replacement of one or more amino acid residues of said structural part with other amino acid residues, or addition of one or more amino acid residues to said part, or deletion of one or more amino acid residues of said structural part.

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

Variants With Altered Stability

It is contemplated that it is possible to improve the stability of a parent Coprinus laccase or a parent Coprinus-like laccase, wherein said variant is the result of a mutation, i.e. one or more amino acid residues having been deleted from, replaced or added to the parent laccase, the stability test performed as described below.

Preferred positions for mutations are the following:

| MtL: | StL: | CcL: | PpL1: | PpL2: | PrL: | RsL4: | RsL1: | RsL2: | RsL3: |
|---|---|---|---|---|---|---|---|---|---|
| M433 | M483 | — | — | — | — | — | — | — | — |
| W373 | W422 | — | — | — | — | W411 | W411 | W439 | — |
| W136 | W181 | W125 | W107 | W107 | W128 | W125 | W125 | W125 | W126 |
| Y145 | Y190 | Y134 | Y116 | Y116 | Y137 | Y134 | Y134 | Y134 | Y135 |
| M480 | M530 | — | — | — | — | — | — | — | — |
| Y137 | Y182 | Y126 | Y108 | Y108 | Y129 | Y126 | Y126 | Y126 | Y127 |
| Y176 | Y221 | Y170 | Y152 | Y152 | Y137 | Y170 | Y169 | Y170 | Y171 |
| M254 | M300 | — | — | — | — | — | — | — | — |
| — | — | M75 | M57 | M57 | M78 | M75 | M75 | M75 | M76 |
| — | — | M477 | — | | | | | | |
| | | | | M328 | | | | | |
| — | M313 | — | — | | | | | | |
| W507, | | | | | | | | | | wherein
CcL: *Coprinus cinereus* laccase comprising the amino acid sequence shown in SEQ ID No. 1;
PpL1: *Polyporus pinsitus* (I) laccase comprising the amino acid sequence shown in SEQ ID No. 2;
PpL2: *Polyporus pinsitus* (II) laccase comprising the amino acid sequence shown in SEQ ID No. 3;
PrL: *Phlebia radiata* laccase comprising the amino acid sequence shown in SEQ ID No. 4;
RsL3: *Rhizoctonia solani* (I) laccase comprising the amino acid sequence shown in SEQ ID No. 5;
RsL2: *Rhizoctonia solani* (II) laccase comprising the amino acid sequence shown in SEQ ID No. 6;
RsL4: *Rhizoctonia solani* (III) laccase comprising the amino acid sequence shown in SEQ ID No. 7;
RsL1: *Rhizoctonia solani* (IV) laccase comprising the amino acid sequence shown in SEQ ID No. 8;
StL: *Scytalidium thermophilum* laccase comprising the amino acid sequence shown in SEQ ID No. 9; and
MtL: *Myceliophthora thermophila* laccase comprising the amino acid sequence shown in SEQ ID No. 10.

The above shown rows have homologous positions. (–) or ( )=not present in this laccase.

The following variants are preferred:
A variant of a parent Coprinus laccase, which comprises one or more of the following substitutions in SEQ ID No. 1:
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, P, F, W, G, S, T, C, M, N, Q, D, E, K, R, H;

Y170 A, V, L, I, P, F, W, G, S, T, C, M, N, Q, D, E, K, R, H;
M75 A, V, L, I, P, F, W, G, S, T, C, Y, N, Q, D, E, K, R, H;
M477 A, V, L, I, P, F, W, G, S, T, C, Y, N, Q, D, E, K, R, H.

In particular a variant of a parent Coprinus laccase, which comprises one or more of the following substitutions in SEQ ID No. 1:
W125 F, H;
Y134 F;
Y126 F;
Y170 F;
M75 F, V, I, L, Q;
M477 F, V, I, L, Q.

A variant of a parent *Polyporus pinsitus* (I) laccase, which comprises a mutation in a position corresponding to at least one of the following positions in SEQ ID No. 2:
W107 A, V, L, I, P, F, M, G, S, T, C, Y, N, Q, D, E, K, R, H;
Y116 A, V, L, I, P, F, W, G, S, T, C, M, N, Q, D, E, K, R, H;
Y108 A, V, L, I, P, F, W, G, S, T, C, M, N, Q, D, E, K, R, H;
Y152 A, V, L, I, P, F, W, G, S, T, C, M, N, Q, D, E, K, R, H;
M57 A, V, L, I, P, F, W, G, S, T, C, Y, N, Q, D, E, K, R, H;
M328 A, V, L, I, P, F, W, G, S, T, C, Y, N, Q, D, E, K, R, H.

In particular a variant of a parent *Polyporus pinsitus* (I) laccase, which comprises a mutation in a position corresponding to at least one of the following positions in SEQ ID No. 2:
W107 F, H;
Y116 F;
Y108 F;
Y152 F;
M57 F, V, I, L, Q;
M328 F, V, I, L, Q.

A variant of a parent *Polyporus pinsitus* (II) laccase, which comprises a mutation in a position corresponding to at least one of the following positions in SEQ ID No. 3:
W107 A, V, L, I, P, F, M, G, S, T, C, Y, N, Q, D, E, K, R, H;
Y116 A, V, L, I, P, F, W, G, S, T, C, M, N, Q, D, E, K, R, H;
Y108 A, V, L, I, P, F, W, G, S, T, C, M, N, Q, D, E, K, R, H;
Y152 A, V, L, I, P, F, W, G, S, T, C, M, N, Q, D, E, K, R, H;
M57 A, V, L, I, P, F, W, G, S, T, C, Y, N, Q, D, E, K, P, H.

In particular a variant of a parent *Polyporus pinsitus* (II) laccase, which comprises a mutation in a position corresponding to at least one of the following positions in SEQ ID No. 3:
W107 F, H;
Y116 F;
Y108 F;
Y152 F;
M57 F, V, I, L, Q.

A variant of a parent *Phlebia radiata* laccase, which comprises a mutation in a position corresponding to at least one of the following positions in SEQ ID No. 4:
W128 A, V, L, I, P, F, M, G, S, T, C, Y, N, Q, D, E, K, R, H;
Y137 A, V, L, I, P, F, W, G, S, T, C, M, N, Q, D, E, K, R, H;
Y129 A, V, L, I, P, F, W, G, S, T, C, M, N, Q, D, E, K, R, H;
Y137 A, V, L, I, P, F, W, G, S, T, C, M, N, Q, D, E, K, R, H;
M78 A, V, L, I, P, F, W, G, S, T, C, Y, N, Q, D, E, K, R, H.

In particular a variant of a parent *Phlebia radiata* laccase, which comprises a mutation in a position corresponding to at least one of the following positions in SEQ ID No. 4:
W128 F, H;
Y137 F;
Y129 F;
Y137 F;
M78 F, V, I, L, Q.

A variant of a parent *Rhizoctonia solani* (I) laccase, which comprises a mutation in a position corresponding to at least one of the following positions in SEQ ID No. 5:
W126 A, V, L, I, P, F, M, G, S, T, C, Y, N, Q, D, E, K, R, H;
Y135 A, V, L, I, P, F, W, G, S, T, C, M, N, Q, D, E, K, R, H;
Y127 A, V, L, I, P, F, W, G, S, T, C, M, N, Q, D, E, K, R, H;
Y171 A, V, L, I, P, F, W, G, S, T, C, M, N, Q, D, E, K, R, H;
M76 A, V, L, I, P, F, W, G, S, T, C, Y, N, Q, D, E, K, P, H.

In particular a variant of a parent *Rhizoctonia solani* (I) laccase, which comprises a mutation in a position corresponding to at least one of the following positions in SEQ ID No. 5:
W126 F, H;
Y135 F;
Y127 F;
Y171 F;
M76 F, V, I, L, Q.

A variant of a parent *Rhizoctonia solani* (II) laccase, which comprises a mutation in a position corresponding to at least one of the following positions in SEQ ID No. 6:
W439 A, V, L, I, P, F, M, G, S, T, C, Y, N, Q, D, E, K, R, H;
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, P, F, W, G, S, T, C, M, N, Q, D, E, K, R, H;
Y170 A, V, L, I, P, F, W, G, S, T, C, M, N, Q, D, E, K, R, H;
M75 A, V, L, I, P, F, W, G, S, T, C, Y, N, Q, D, E, K, R, H.

In particular a variant of a parent *Rhizoctonia solani* (II) laccase, which comprises a mutation in a position corresponding to at least one of the following positions in SEQ ID No. 6:
W439 F, H;
W125 F, H;
Y134 F;
Y126 F;
Y170 F;

M75 F, V, I, L, Q.

A variant of a parent *Rhizoctonia solani* (III) laccase, which comprises a mutation in a position corresponding to at least one of the following positions in SEQ ID No. 7:
W411 A, V, L, I, P, F, M, G, S, T, C, Y, N, Q, D, E, K, R, H;
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, P, F, W, G, S, T, C, M, N, Q, D, E, K, R, H;
Y170 A, V, L, I, P, F, W, G, S, T, C, M, N, Q, D, E, K, R, H;
M75 A, V, L, I, P, F, W, G, S, T, C, Y, N, Q, D, E, K, R, H.

In particular a variant of a parent *Rhizoctonia solani* (III) laccase, which comprises a mutation in a position corresponding to at least one of the following positions in SEQ ID No. 7:
W411 F, H;
W125 F, H;
Y134 F;
Y126 F;
Y170 F;
M75 F, V, I, L, Q.

A variant of a parent *Rhizoctonia solani* (IV) laccase, which comprises a mutation in a position corresponding to at least one of the following positions in SEQ ID No. 8:
W411 A, V, L, I, P, F, M, G, S, T, C, Y, N, Q, D, E, K, R, H;
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, P. F, W, G, S, T, C, M, N, Q, D, E, K, R, H;
Y170 A, V, L, I, P. F, W, G, S, T, C, M, N, Q, D, E, K, R, H;
M75 A, V, L, I, P, F, W, G, S, T, C, Y, N, Q, D, E, K, R, H.

In particular a variant of a parent *Rhizoctonia solani* (IV) laccase, which comprises a mutation in a position corresponding to at least one of the following positions in SEQ ID No. 8:
W411 F, H;
W125 F, H;
Y134 F;
Y126 F;
Y170 F;
M75 F, V, I, L, Q.

A variant of a parent *Scytalidium thermophilum* laccase, which comprises a mutation in a position corresponding to at least one of the following positions in SEQ ID No. 9:
M483 A, V, L, I, P, F, W, G, S, T, C, Y, N, Q, D, E, K, R, H;
W422 A, V, L, I, P, F, M, G, S, T, C, Y, N, Q, D, E, K, R, H;
W181 A, V, L, I, P, F, M, G, S, T, C, Y, N, Q, D, E, K, R, H;
Y190 A, V, L, I, P, F, W, G, S, T, C, M, N, Q, D, E, K, R, H;
M530 A, V, L, I, P, F, W, G, S, T, C, Y, N, Q, D, E, K, R, H;
Y182 A, V, L, I, P, F, W, G, S, T, C, M, N, Q, D, E, K, R, H;
Y221 A, V, L, I, P, F, W, G, S, T, C, M, N, Q, D, E, K, R, H;
M300 A, V, L, I, P, F, W, G, S, T, C, Y, N, Q, D, E, K, R, H;
M313 A, V, L, I, P, F, W, G, S, T, C, Y, N, Q, D, E, K, R, H.

In particular a variant of a parent *Scytalidium thermophilum* laccase, which comprises a mutation in a position corresponding to at least one of the following positions in SEQ ID No. 9:
M483 F, V, I, L, Q;
W422 F, H;
W181 F, H;
Y190 F;
M530 F, V, I, L, Q;
Y182 F;
Y221 F;
M300 F, V, I, L, Q;
M313 F, V, I, L, Q.

A variant of a parent *Myceliophthora thermophila* laccase, which comprises a mutation in a position corresponding to at least one of the following positions in SEQ ID No. 10:
M433 A, V, L, I, P, F, W, G, S, T, C, Y, N, Q, D, E, K, R, H;
W373 A, V, L, I, P, F, M, G, S, T, C, Y, N, Q, D, E, K, R, H;
W136 A, V, L, I, P, F, M, G, S, T, C, Y, N, Q, D, E, K, R, H;
Y145 A, V, L, I, P, F, W, G, S, T, C, M, N, Q, D, E, K, R, H;
M480 A, V, L, I, P, F, W, G, S, T, C, Y, N, Q, D, E, K, R, H;
Y137 A, V, L, I, P, F, W, G, S, T, C, M, N, Q, D, E, K, R, H;
Y176 A, V, L, I, P, F, W, G, S, T, C, M, N, Q, D, E, K, R, H;
M254 A, V, L, I, P, F, W, G, S, T, C, Y, N, Q, D, E, K, R, H.

In particular a variant of a parent *Myceliophthora thermophila* laccase, which comprises a mutation in a position corresponding to at least one of the following positions in SEQ ID No. 10:
M433 F, V, I, L, Q;
W373 F, H;
W136 F, H;
Y145 F;
M480 F, V, I, L, Q;
Y137 F;
Y176 F;
M254 F, V, I, L, Q.

Methods of Preparing Laccase Variants

Several methods for introducing mutations into genes are known in the art. After a brief discussion of the cloning of laccase-encoding DNA sequences, methods for generating mutations at specific sites within the laccase-encoding sequence will be discussed.

Cloning a DNA Sequence Encoding a Laccase

The DNA sequence encoding a parent laccase may be isolated from any cell or microorganism producing the laccase in question, using various methods well known in the art. First, a genomic DNA and/or cDNA library should be constructed using chromosomal DNA or messenger RNA from the organism that produces the laccase to be studied.

Then, if the amino acid sequence of the laccase is known, homologous, labelled oligonucleotide probes may be synthesized and used to identify laccase-encoding clones from a genomic library prepared from the organism in question. Alternatively, a labelled oligonucleotide probe containing sequences homologous to a known laccase gene could be used as a probe to identify laccase-encoding clones, using hybridization and washing conditions of lower stringency.

A method for identifying laccase-encoding clones involves inserting cDNA into an expression vector, such as a plasmid, transforming laccase-negative fungi with the resulting cDNA library, and then plating the transformed fungi onto agar containing a substrate for laccase, thereby allowing clones expressing the laccase to be identified.

Alternatively, the DNA sequence encoding the enzyme may be prepared synthetically by established standard methods, e.g. the phosphoroamidite method. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers.

Site-Directed Mutagenesis

Once a laccase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the laccase-encoding sequence, is created in a vector carrying the laccase gene. Then the synthetic nucleotide, bearing the desired mutation, is annealed to a homologous portion of the single-stranded DNA. The remaining gap is then filled in with T7 DNA polymerase and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into laccase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

The random mutagenesis of a DNA sequence encoding a parent laccase may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the laccase enzyme by any published technique, using e.g. PCR, LCR or any DNA polymerase and ligase.

When PCR-generated mutagenesis is used, either a chemically treated or non-treated gene encoding a parent laccase enzyme is subjected to PCR under conditions that increase the misincorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the laccase enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent laccase enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step or the screening step being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as *Aspergillus niger* or *Aspergillus oryzae*.

The mutated DNA sequence may further comprise a DNA sequence encoding functions permitting expression of the mutated DNA sequence.

Localized Random Mutagenesis

The random mutagenesis may advantageously be localized to a part of the parent laccase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently be performed by use of aa filter assay based on the following principle:

A microorganism capable of expressing the mutated laccase enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatine, polyacrylamide, starch, filter paper, cloth; or any combination of immobilizing agents.

Testing of Variants of the Invention

The storage stability of Coprinus variants or Coprinus-like variants should be investigated at 40° C. for 2 weeks at pH 5, 8 and 9.3, respectively. The stability of the parent laccase and the variants may be tested both in a liquid buffer formulation and in a lyophilized form.

According to the invention the residual activity of the variants following two weeks of incubation are then compared to the residual activity of the parent laccase, and variants with an improved stability at either pH 5, 8 or 9.3 are selected.

Laccase Activity

In the context of this invention, the laccase activity was measured using 10-(2-hydroxyethyl)-phenoxazine (HEPO) as substrate for the various laccases. HEPO was synthesized using the same procedure as described for 10-(2-hydroxyethyl)-phenothiazine, (G. Cauquil in Bulletin de la Society Chemique de France, 1960, p. 1049). In the presence of oxygen laccases (E.C. 1.10.3.2) oxidize HEPO to a HEPO radical that can be monitored photometrically at 528 nm.

The *Coprinus cinereus* laccase was measured using 0.4 mM HEPO in 50 mM sodium acetate, pH 5.0, 0.05% TWEEN-20 at 30° C. The absorbance at 528 nm was followed for 200 s and the rate calculated from the linear part of the progress curve.

The *Myceliophthora thermophila* laccase was measured using 0.4 mM HEPO in 25 mM Tris-HCl, pH 7.5, 0.05% Tween-20 at 30° C. The absorbance at 528 nm was followed for 200 s and the rate calculated from the linear part of the progress curve.

The *Polyporus pinsitus* laccase was measured using 0.4 mM HEPO in 50 mM MES-NaOH, pH 5.5. The absorbance at 528 nm was followed for 200 s and the rate calculated from the linear part of the progress curve.

Expression of Laccase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a laccase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a laccase variant of the invention, especially in a fungal host, are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the laccase variant of the invention. Termination and polyadenylation sequences may suitably be derived from the same sources as the promoter.

The vector may further comprise a DNA sequence enabling the vector to replicate in the host cell in question.

Examples of such sequences are the origins of replication of plasmids pUC19, pACYC177, pUB110, pE194, pAMB1 and pIJ702.

The vector may also comprise a selectable marker, e.g. a gene, the product of which complements a defect in the host cell, such as one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a laccase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a laccase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a fungal cell.

The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a laccase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the laccase variant of the invention. Suitable media are available from commercial suppliers or may be prepared according to published recipes (e.g. as described in catalogues of the American Type Culture Collection).

The laccase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

INDUSTRIAL APPLICATIONS

The laccase variants of this invention possesses valuable properties allowing for various industrial applications, in particular lignin modification, paper strengthening, dye transfer inhibition in detergents, phenol polymerization, hair dyeing, bleaching of textiles (in particular bleaching of denim as described in WO 96/12845 and WO 96/12846) and waste water treatment. Any detergent composition normally used for enzymes may be used, e.g., the detergent compositions disclosed in WO 95/01426.

The invention is further illustrated in the following examples, which are not intended to be in any way limiting to the scope of the invention as claimed.

EXAMPLE 1
Storage Stability of the Wild Type *Myceliophthora thermophila* and the *Polyporus pinsitus* Laccases The storage stability of the *Myceliophthora thermophila* and the *Polyporus pinsitus* laccases was tested for 2 weeks at 40° C. at pH 5, 8 and 9.3, respectively.

The laccase (1 mg/ml) was dialyzed against 0.1 M sodium acetate, pH 5, or 0.1 M Tris-maleate, pH 8, or 0.1 M Tris-maleate, pH 9.3. Following dialysis the different preparations were poured into two sets of glass vials with screw caps: one for the liquid formulation and the other one for the lyophilized form. After two weeks of incubation the enzyme activity was measured as described above and the residual activity of the enzymes was calculated in percentage using a preparation of *Myceliophthora thermophila* and *Polyporus pinsitus* kept at 4° C. as references. The results are given below in Table 1 and 2.

TABLE 1

Storage stability of *Myceliophthora thermophila*

| pH | Liquid formulation Residual activity (%) | Lyophilized form Residual activity (%) |
|---|---|---|
| 5.0 | <5 | <5 |
| 8.0 | <5 | <5 |
| 9.3 | 35 | 30 |

TABLE 2

Storage stability of *Polyporus pinsitus*

| pH | Liquid formulation Residual activity (%) | Lyophilized form Residual activity (%) |
|---|---|---|
| 5.0 | <5 | n.d. |
| 8.0 | 35 | n.d. |
| 9.3 | n.d* | n.d. |

*not determined

EXAMPLE 2
Homology Building of the *Polyporus pinsitus* 3D-Structure

Using sequence homology of *Coprinus cinereus* (CcL) to other sequences, e.g., *Polyporus pinsitus*, Coprinus-like 3 D-structures can be found.

In comparison with the *Coprinus cinereus*, used for elucidating the structure, *Polyporus pinsitus* differs in a number of residues. The model may be built using the HOMOLOGY program from BIOSYM. The program substitutes the amino acids in the *Coprinus cinereus* with amino acids from *Polyporus pinsitus* in the homologous positions defined in the program as structurally conserved regions (SCR). The residues in between are built using the LOOP option with GENERATE. Using these steps a crude model may be obtained which gives information of spatial interactions.

The structure can be refined using the method described in the HOMOLOGY package.

EXAMPLE 3

Storage Stability of *Myceliophthora thermophila* Variants

Laccase Activity

In this Example the *Myceliophthora thermophila* laccase variants were measured using 0.4 mM HEPO in 0.1 M Tris-maleate, pH 7.5, 0.05% TWEEN-20 at 30° C. The absorbance at 528 nm was followed for 200 s and the rate calculated from the linear part of the progress curve.

The storage stability of the *Myceliophthora thermophila* variants were tested for 4 weeks at 40° C. at pH 5, 7, and 9.3, respectively. The laccase (1 mg/ml) was dialyzed against 0.1 M Tris-maleate, pH 5 or 0.1 M Tris-maleate, pH 7 or 0.1 M Tris-maleate, pH 9.3. Following dialysis the different preparations were poured into two set of glass vials with screw caps: one for the liquid formulation and the other set of glasses for lyophilization. Following two and four weeks of incubation the enzyme activity was measured as described above and the residual activity of the variants were calculated in percentage using a preparation kept at 4° C. as reference.

TABLE 3

Storage stability of *Myceliophthora thermophila* variants, lyophilized formulation

|  | Residual activity, pH 5 | | Residual activity, pH 7 | | Residual activity, pH 9.2 | |
| --- | --- | --- | --- | --- | --- | --- |
|  | 2 weeks | 4 weeks | 2 weeks | 4 weeks | 2 weeks | 4 weeks |
| wt | 18 | 18 | 55 | 36 | 59 | 38 |
| W136F | <5 | <5 | 76 | 64 | 88 | 77 |
| Y137F | 12 | <5 | 58 | 41 | 64 | 49 |
| Y145F | 1215 | <5 | 53 | 20 | 45 | 51 |
| W373F | 14 | 14 | 33 | 19 | 51 | 36 |
| M433I | 7 | <5 | 57 | 43 | 74 | 35 |

TABLE 3-continued

Storage stability of *Myceliophthora thermophila* variants, lyophilized formulation

|  | Residual activity, pH 5 | | Residual activity, pH 7 | | Residual activity, pH 9.2 | |
| --- | --- | --- | --- | --- | --- | --- |
|  | 2 weeks | 4 weeks | 2 weeks | 4 weeks | 2 weeks | 4 weeks |
| M480L | 33 | 18 | 65 | 32 | 72 | 52 |
| W507F | 18 | <5 | 72 | 51 | 68 | 71 |

In lyophilized form none of the tested variants have improved stability at pH 5. At pH 7 and pH 9.2 both W136F and W507F have increased stability. At pH 9.2 M480L is also better than wt.

TABLE 4

Storage stability of *Myceliophthora thermophila* variants, liquid formulation

|  | Residual activity, 5, 2 weeks | Residual pH activity, pH 7, 2 weeks | Residual activity, pH 9.2, 2 weeks |
| --- | --- | --- | --- |
| wt | <5 | 5 | 20 |
| W136F | 5 | 28 | 55 |
| Y137F | <5 | <5 | <5 |
| Y145F | <5 | <5 | <5 |
| W373F | <5 | 40 | <5 |
| M433I | 8 | 40 | 65 |
| M480L | <5 | <5 | 15 |
| W507F | <5 | <5 | 22 |

Also in the liquid formulation none of the tested variants have improved stability at pH 5. At pH 7 and pH 9.2 both W136F and M433I has increased stability. At pH7 W373F has better stability than wt but the variant looses the stability completely at pH 9.2.

Of the tested variants only W136F has increased stability in both formulations.

APPENDIX 1

```
SEQRES  1 A  504  GLN ILE VAL ASN SER VAL ASP THR MET THR LEU THR ASN

SEQRES  2 A  504  ALA ASN VAL SER PRO ASP GLY PHE THR ARG ALA GLY ILE

SEQRES  3 A  504  LEU VAL ASN GLY VAL HIS GLY PRO LEU ILE ARG GLY GLY

SEQRES  4 A  504  LYS ASN ASP ASN PHE GLU LEU ASN VAL VAL ASN ASP LEU

SEQRES  5 A  504  ASP ASN PRO THR MET LEU ARG PRO THR SER ILE HIS TRP

SEQRES  6 A  504  HIS GLY LEU PHE GLN ARG GLY THR ASN TRP ALA ASN GLY

SEQRES  7 A  504  ALA ASP GLY VAL ASN GLN CYS PRO ILE SER PRO GLY HIS

SEQRES  8 A  504  ALA PHE LEU TYR LYS PHE THR PRO ALA GLY HIS ALA GLY

SEQRES  9 A  504  THR PHE TRP TYR HIS SER HIS PHE GLY THR GLN TYR CYS

SEQRES 10 A  504  ASP GLY LEU ARG GLY PRO MET VAL ILE TYR ASP ASP ASN

SEQRES 11 A  504  ASP PRO HIS ALA ALA LEU TYR ASP GLU ASP GLU ASN
```

APPENDIX 1-continued

```
SEQRES  12 A  504   THR ILE ILE THR LEU ALA ASP TRP TYR HIS ILE PRO ALA
SEQRES  13 A  504   PRO SER ILE GLN GLY ALA ALA GLN PRO ASP ALA THR LEU
SEQRES  14 A  504   ILE ASN GLY LYS GLY ARG TYR VAL GLY GLY PRO ALA ALA
SEQRES  15 A  504   GLU LEU SER ILE VAL ASN VAL GLU GLN GLY LYS LYS TYR
SEQRES  16 A  504   ARG MET ARG LEU ILE SER LEU SER CYS ASP PRO ASN TRP
SEQRES  17 A  504   GLN PHE SER ILE ASP GLY HIS GLU LEU THR ILE ILE GLU
SEQRES  18 A  504   VAL ASP GLY ASN LEU THR GLU PRO HIS THR VAL ASP ARG
SEQRES  19 A  504   LEU GLN ILE PHE THR GLY GLN ARG TYR SER PHE VAL LEU
SEQRES  20 A  504   ASP ALA ASN GLN PRO VAL ASP ASN TYR TRP ILE ARG ALA
SEQRES  21 A  504   GLN PRO ASN LYS GLY ARG ASN GLY LEU ALA GLY THR PHE
SEQRES  22 A  504   ALA ASN GLY VAL ASN SER ALA ILE LEU ARG TYR ALA GLY
SEQRES  23 A  504   ALA ALA ASN ALA ASP PRO THR THR SER ALA ASN PRO ASN
SEQRES  24 A  504   PRO ALA GLN LEU ASN GLU ALA ASP LEU HIS ALA LEU ILE
SEQRES  25 A  504   ASP PRO ALA ALA PRO GLY ILE PRO THR PRO GLY ALA ALA
SEQRES  26 A  504   ASN VAL ASN LEU ARG PHE GLN LEU GLY PHE SER GLY GLY
SEQRES  27 A  504   ARG PHE THR ILE ASN GLY THR ALA TYR GLU SER PRO SER
SEQRES  28 A  504   VAL PRO THR LEU LEU GLN ILE MET SER GLY ALA GLN SER
SEQRES  29 A  504   ALA ASN ASP LEU LEU PRO ALA GLY SER VAL TYR GLU LEU
SEQRES  30 A  504   PRO ARG ASN GLN VAL VAL GLU LEU VAL VAL PRO ALA GLY
SEQRES  31 A  504   VAL LEU GLY GLY PRO HIS PRO PHE HIS LEU HIS GLY HIS
SEQRES  32 A  504   ALA PHE SER VAL VAL ARG SER ALA GLY SER SER THR TYR
SEQRES  33 A  504   ASN PHE VAL ASN PRO VAL LYS ARG ASP VAL VAL SER LEU
SEQRES  34 A  504   GLY VAL THR GLY ASP GLU VAL THR ILE ARG PHE VAL THR
SEQRES  35 A  504   ASP ASN PRO GLY PRO TRP PHE PHE HIS CYS HIS ILE GLU
SEQRES  36 A  504   PHE HIS LEU MET ASN GLY LEU ALA ILE VAL PHE ALA GLU
SEQRES  37 A  504   ASP MET ALA ASN THR VAL ASP ALA ASN ASN PRO PRO VAL
SEQRES  38 A  504   GLU TRP ALA GLN LEU CYS GLU ILE TYR ASP ASP LEU PRO
SEQRES  39 A  504   PRO GLU ALA THR SER ILE GLN THR VAL VAL
SSBOND   1 CYS    85  CYS   487
SSBOND   2 CYS   117  CYS   204
CRYST  45.390  85.720  143.070  90.00  90.00  90.00  P212121
SCALE1      0.02203  0.00000  0.00000     0.00000
SCALE2      0.00000  0.01167  0.00000     0.00000
SCALE3      0.00000  0.00000  0.00699     0.00000
ATOM       1 N   ALA A   1 0  18.748  34.495   5.326  1.00  36.36
ATOM       2 CA  ALA A   1 0  19.554  35.757   5.185  1.00  35.87
ATOM       3 C   ALA A   1 0  19.785  36.380   6.558  1.00  34.53
ATOM       4 O   ALA A   1 0  19.248  35.884   7.577  1.00  35.40
ATOM       5 CB  ALA A   1 0  19.050  36.675   4.107  1.00  36.65
```

APPENDIX 1-continued

| | | | | | | | | | | |
|---|---|---|---|---|---|---|---|---|---|---|
| ATOM | 6 | N | ILE | A | 2 0 | 20.844 | 37.201 | 6.659 | 1.00 | 31.00 |
| ATOM | 7 | CA | ILE | A | 2 0 | 21.310 | 37.654 | 7.963 | 1.00 | 27.71 |
| ATOM | 8 | C | ILE | A | 2 0 | 21.368 | 39.165 | 8.117 | 1.00 | 25.19 |
| ATOM | 9 | O | ILE | A | 2 0 | 21.789 | 39.861 | 7.192 | 1.00 | 23.77 |
| ATOM | 10 | CB | ILE | A | 2 0 | 22.744 | 37.107 | 8.206 | 1.00 | 28.28 |
| ATOM | 11 | CG1 | ILE | A | 2 0 | 22.790 | 35.590 | 8.022 | 1.00 | 28.54 |
| ATOM | 12 | CG2 | ILE | A | 2 0 | 23.285 | 37.557 | 9.554 | 1.00 | 27.91 |
| ATOM | 13 | CD1 | ILE | A | 2 0 | 23.334 | 34.738 | 9.130 | 1.00 | 29.32 |
| ATOM | 14 | N | VAL | A | 3 0 | 20.986 | 39.659 | 9.283 | 1.00 | 22.31 |
| ATOM | 15 | CA | VAL | A | 3 0 | 21.093 | 41.092 | 9.540 | 1.00 | 22.78 |
| ATOM | 16 | C | VAL | A | 3 0 | 22.246 | 41.297 | 10.524 | 1.00 | 22.62 |
| ATOM | 17 | O | VAL | A | 3 0 | 22.460 | 40.556 | 11.467 | 1.00 | 21.74 |
| ATOM | 18 | CB | VAL | A | 3 0 | 19.801 | 41.849 | 9.799 | 1.00 | 23.54 |
| ATOM | 19 | CG1 | VAL | A | 3 0 | 18.537 | 40.985 | 9.684 | 1.00 | 21.30 |
| ATOM | 20 | CG2 | VAL | A | 3 0 | 19.760 | 42.709 | 11.055 | 1.00 | 21.32 |
| ATOM | 21 | N | ASN | A | 4 0 | 23.122 | 42.261 | 10.209 | 1.00 | 23.39 |
| ATOM | 22 | CA | ASN | A | 4 0 | 24.303 | 42.520 | 11.021 | 1.00 | 23.45 |
| ATOM | 23 | C | ASN | A | 4 0 | 24.002 | 43.517 | 12.126 | 1.00 | 24.44 |
| ATOM | 24 | O | ASN | A | 4 0 | 22.928 | 44.122 | 12.160 | 1.00 | 23.05 |
| ATOM | 25 | CB | ASN | A | 4 0 | 25.477 | 42.965 | 10.149 | 1.00 | 24.77 |
| ATOM | 26 | CG | ASN | A | 4 0 | 25.726 | 41.991 | 9.021 | 1.00 | 26.62 |
| ATOM | 27 | OD1 | ASN | A | 4 0 | 25.668 | 42.388 | 7.849 | 1.00 | 30.29 |
| ATOM | 28 | ND2 | ASN | A | 4 0 | 25.923 | 40.719 | 9.324 | 1.00 | 27.59 |
| ATOM | 29 | N | SER | A | 5 0 | 24.960 | 43.707 | 13.040 | 1.00 | 24.28 |
| ATOM | 30 | CA | SER | A | 5 0 | 24.702 | 44.636 | 14.143 | 1.00 | 25.77 |
| ATOM | 31 | C | SER | A | 5 0 | 24.595 | 46.090 | 13.701 | 1.00 | 24.41 |
| ATOM | 32 | O | SER | A | 5 0 | 23.973 | 46.862 | 14.452 | 1.00 | 23.55 |
| ATOM | 33 | CB | SER | A | 5 0 | 25.741 | 44.405 | 15.240 | 1.00 | 26.18 |
| ATOM | 34 | OG | SER | A | 5 0 | 26.976 | 44.750 | 14.641 | 1.00 | 27.89 |
| ATOM | 35 | N | VAL | A | 6 0 | 25.104 | 46.517 | 12.539 | 1.00 | 24.01 |
| ATOM | 36 | CA | VAL | A | 6 0 | 24.770 | 47.863 | 12.096 | 1.00 | 25.06 |
| ATOM | 37 | C | VAL | A | 6 0 | 24.131 | 47.617 | 10.731 | 1.00 | 25.57 |
| ATOM | 38 | O | VAL | A | 6 0 | 24.778 | 47.030 | 9.874 | 1.00 | 28.07 |
| ATOM | 39 | CB | VAL | A | 6 0 | 25.722 | 49.032 | 12.155 | 1.00 | 26.65 |
| ATOM | 40 | CG1 | VAL | A | 6 0 | 26.937 | 48.759 | 13.025 | 1.00 | 26.73 |
| ATOM | 41 | CG2 | VAL | A | 6 0 | 26.098 | 49.614 | 10.801 | 1.00 | 25.50 |
| ATOM | 42 | N | ASP | A | 7 0 | 22.848 | 47.952 | 10.605 | 1.00 | 23.82 |
| ATOM | 43 | CA | ASP | A | 7 0 | 22.173 | 47.543 | 9.369 | 1.00 | 24.07 |
| ATOM | 44 | C | ASP | A | 7 0 | 20.794 | 48.170 | 9.276 | 1.00 | 23.66 |
| ATOM | 45 | O | ASP | A | 7 0 | 20.342 | 48.845 | 10.204 | 1.00 | 23.47 |

APPENDIX 1-continued

| | | | | | | | | | |
|---|---|---|---|---|---|---|---|---|---|
| ATOM | 46 | CB | ASP A | 7 | 0 | 21.996 | 46.012 | 9.444 | 1.00 23.43 |
| ATOM | 47 | CG | ASP A | 7 | 0 | 22.017 | 45.317 | 8.111 | 1.00 23.78 |
| ATOM | 48 | OD1 | ASP A | 7 | 0 | 21.805 | 45.937 | 7.055 | 1.00 23.74 |
| ATOM | 49 | OD2 | ASP A | 7 | 0 | 22.255 | 44.089 | 8.099 | 1.00 24.62 |
| ATOM | 50 | N | THR A | 8 | 0 | 20.155 | 47.881 | 8.158 | 1.00 23.88 |
| ATOM | 51 | CA | THR A | 8 | 0 | 18.799 | 48.359 | 7.928 | 1.00 24.45 |
| ATOM | 52 | C | THR A | 8 | 0 | 17.813 | 47.189 | 7.950 | 1.00 22.49 |
| ATOM | 53 | O | THR A | 8 | 0 | 18.143 | 46.142 | 7.377 | 1.00 22.56 |
| ATOM | 54 | CB | THR A | 8 | 0 | 18.694 | 49.108 | 6.579 | 1.00 25.75 |
| ATOM | 55 | OG1 | THR A | 8 | 0 | 19.573 | 50.242 | 6.719 | 1.00 28.53 |
| ATOM | 56 | CG2 | THR A | 8 | 0 | 17.295 | 49.656 | 6.339 | 1.00 25.55 |
| ATOM | 57 | N | MET A | 9 | 0 | 16.677 | 47.364 | 8.602 | 1.00 19.10 |
| ATOM | 58 | CA | MET A | 9 | 0 | 15.650 | 46.311 | 8.616 | 1.00 20.47 |
| ATOM | 59 | C | MET A | 9 | 0 | 14.392 | 46.863 | 7.925 | 1.00 21.97 |
| ATOM | 60 | O | MET A | 9 | 0 | 13.638 | 47.638 | 8.544 | 1.00 19.49 |
| ATOM | 61 | CB | MET A | 9 | 0 | 15.308 | 45.871 | 10.022 | 1.00 20.49 |
| ATOM | 62 | CG | MET A | 9 | 0 | 16.351 | 44.982 | 10.682 | 1.00 22.11 |
| ATOM | 63 | SD | MET A | 9 | 0 | 16.192 | 44.917 | 12.482 | 1.00 24.71 |
| ATOM | 64 | CE | MET A | 9 | 0 | 14.640 | 44.024 | 12.635 | 1.00 22.61 |
| ATOM | 65 | N | THR A | 10 | 0 | 14.246 | 46.516 | 6.641 | 1.00 21.81 |
| ATOM | 66 | CA | THR A | 10 | 0 | 13.073 | 47.064 | 5.926 | 1.00 23.43 |
| ATOM | 67 | C | THR A | 10 | 0 | 11.912 | 46.081 | 6.046 | 1.00 22.90 |
| ATOM | 68 | O | THR A | 10 | 0 | 12.056 | 44.890 | 5.719 | 1.00 23.55 |
| ATOM | 69 | CB | TRR A | 10 | 0 | 13.390 | 47.384 | 4.459 | 1.00 24.69 |
| ATOM | 70 | OG1 | THR A | 10 | 0 | 14.533 | 48.261 | 4.456 | 1.00 26.08 |
| ATOM | 71 | CG2 | THR A | 10 | 0 | 12.216 | 48.028 | 3.742 | 1.00 23.95 |
| ATOM | 72 | N | LEU A | 11 | 0 | 10.820 | 46.600 | 6.583 | 1.00 21.13 |
| ATOM | 73 | CA | LEU A | 11 | 0 | 9.615 | 45.836 | 6.846 | 1.00 21.10 |
| ATOM | 74 | C | LEU A | 11 | 0 | 8.607 | 45.957 | 5.709 | 1.00 24.58 |
| ATOM | 75 | O | LEU A | 11 | 0 | 8.124 | 47.056 | 5.358 | 1.00 23.89 |
| ATOM | 76 | CB | LEU A | 11 | 0 | 9.045 | 46.411 | 8.129 | 1.00 21.29 |
| ATOM | 77 | CG | LEU A | 11 | 0 | 9.474 | 45.955 | 9.508 | 1.00 22.26 |
| ATOM | 78 | CD1 | LEU A | 11 | 0 | 10.952 | 45.742 | 9.692 | 1.00 22.42 |
| ATOM | 79 | CD2 | LEU A | 11 | 0 | 8.978 | 46.931 | 10.583 | 1.00 22.75 |
| ATOM | 80 | N | THR A | 12 | 0 | 8.272 | 44.836 | 5.057 | 1.00 24.01 |
| ATOM | 81 | CA | THR A | 12 | 0 | 7.302 | 44.851 | 3.980 | 1.00 24.33 |
| ATOM | 82 | C | THR A | 12 | 0 | 6.322 | 43.677 | 4.123 | 1.00 25.34 |
| ATOM | 83 | O | THR A | 12 | 0 | 6.480 | 42.740 | 4.913 | 1.00 25.62 |
| ATOM | 84 | CB | THR A | 12 | 0 | 7.882 | 44.776 | 2.560 | 1.00 25.12 |

APPENDIX 1-continued

| ATOM | 85 | OG1 | THR A | 12 | 0 | 8.575 | 43.548 | 2.377 | 1.00 | 24.05 |
|---|---|---|---|---|---|---|---|---|---|---|
| ATOM | 86 | CG2 | THR A | 12 | 0 | 8.847 | 45.905 | 2.217 | 1.00 | 25.26 |
| ATOM | 87 | N | ASN A | 13 | 0 | 5.261 | 43.760 | 3.335 | 1.00 | 24.09 |
| ATOM | 88 | CA | ASN A | 13 | 0 | 4.232 | 42.722 | 3.299 | 1.00 | 22.87 |
| ATOM | 89 | C | ASN A | 13 | 0 | 4.422 | 41.954 | 1.989 | 1.00 | 22.13 |
| ATOM | 90 | O | ASN A | 13 | 0 | 4.809 | 42.600 | 1.023 | 1.00 | 22.32 |
| ATOM | 91 | CB | ASN A | 13 | 0 | 2.852 | 43.355 | 3.311 | 1.00 | 21.58 |
| ATOM | 92 | CG | ASN A | 13 | 0 | 2.526 | 44.060 | 4.607 | 1.00 | 22.50 |
| ATOM | 93 | OD1 | ASN A | 13 | 0 | 2.187 | 45.245 | 4.648 | 1.00 | 22.20 |
| ATOM | 94 | ND2 | ASN A | 13 | 0 | 2.615 | 43.306 | 5.705 | 1.00 | 21.81 |
| ATOM | 95 | N | ALA A | 14 | 0 | 4.218 | 40.655 | 1.985 | 1.00 | 21.00 |
| ATOM | 96 | CA | ALA A | 14 | 0 | 4.270 | 39.869 | 0.762 | 1.00 | 21.93 |
| ATOM | 97 | C | ALA A | 14 | 0 | 3.571 | 38.533 | 1.078 | 1.00 | 20.77 |
| ATOM | 98 | O | ALA A | 14 | 0 | 3.292 | 38.309 | 2.259 | 1.00 | 20.45 |
| ATOM | 99 | CB | ALA A | 14 | 0 | 5.676 | 39.618 | 0.248 | 1.00 | 23.72 |
| ATOM | 100 | N | ASN A | 15 | 0 | 3.366 | 37.695 | 0.072 | 1.00 | 18.88 |
| ATOM | 101 | CA | ASN A | 15 | 0 | 2.748 | 36.412 | 0.337 | 1.00 | 19.67 |
| ATOM | 102 | C | ASN A | 15 | 0 | 3.798 | 35.457 | 0.873 | 1.00 | 19.19 |
| ATOM | 103 | O | ASN A | 15 | 0 | 4.891 | 35.474 | 0.338 | 1.00 | 19.57 |
| ATOM | 104 | CB | ASN A | 15 | 0 | 2.114 | 35.721 | −0.875 | 1.00 | 21.13 |
| ATOM | 105 | CG | ASN A | 15 | 0 | 0.839 | 36.457 | −1.284 | 1.00 | 21.15 |
| ATOM | 106 | OD1 | ASN A | 15 | 0 | 0.343 | 37.207 | −0.472 | 1.00 | 20.87 |
| ATOM | 107 | ND2 | ASN A | 15 | 0 | 0.379 | 36.284 | −2.501 | 1.00 | 20.00 |
| ATOM | 108 | N | VAL A | 16 | 0 | 3.358 | 34.614 | 1.772 | 1.00 | 19.11 |
| ATOM | 109 | CA | VAL A | 16 | 0 | 4.322 | 33.628 | 2.342 | 1.00 | 18.90 |
| ATOM | 110 | C | VAL A | 16 | 0 | 3.626 | 32.293 | 2.345 | 1.00 | 19.25 |
| ATOM | 111 | O | VAL A | 16 | 0 | 2.386 | 32.281 | 2.406 | 1.00 | 16.71 |
| ATOM | 112 | CB1 | VAL A | 16 | 0 | 4.612 | 34.317 | 3.691 | 1.00 | 19.95 |
| ATOM | 113 | CG1 | VAL A | 16 | 0 | 3.990 | 33.749 | 4.937 | 1.00 | 18.58 |
| ATOM | 114 | CG2 | VAL A | 16 | 0 | 6.091 | 34.603 | 3.814 | 1.00 | 21.38 |
| ATOM | 115 | N | SER A | 17 | 0 | 4.312 | 31.157 | 2.303 | 1.00 | 18.57 |
| ATOM | 116 | CA | SER A | 17 | 0 | 3.678 | 29.869 | 2.410 | 1.00 | 20.90 |
| ATOM | 117 | C | SER A | 17 | 0 | 4.608 | 28.866 | 3.065 | 1.00 | 21.12 |
| ATOM | 118 | O | SER A | 17 | 0 | 5.106 | 27.939 | 2.448 | 1.00 | 21.24 |
| ATOM | 119 | CB | SER A | 17 | 0 | 3.186 | 29.285 | 1.080 | 1.00 | 23.95 |
| ATOM | 120 | OG | SER A | 17 | 0 | 4.204 | 29.399 | 0.125 | 1.00 | 26.79 |
| ATOM | 121 | N | PRO A | 18 | 0 | 4.834 | 29.051 | 4.358 | 1.00 | 20.78 |
| ATOM | 122 | CA | PRO A | 18 | 0 | 5.703 | 28.216 | 5.141 | 1.00 | 20.02 |
| ATOM | 123 | C | PRO A | 18 | 0 | 5.197 | 26.793 | 5.376 | 1.00 | 19.74 |
| ATOM | 124 | O | PRO A | 18 | 0 | 5.978 | 25.920 | 5.753 | 1.00 | 17.97 |

APPENDIX 1-continued

| | | | | | | | | | |
|---|---|---|---|---|---|---|---|---|---|
| ATOM | 125 | CB | PRO A | 18 | 0 | 5.889 | 28.954 | 6.481 | 1.00 19.27 |
| ATOM | 126 | CG | PRO A | 18 | 0 | 4.701 | 29.832 | 6.536 | 1.00 21.41 |
| ATOM | 127 | CD | PRO A | 18 | 0 | 4.249 | 30.153 | 5.128 | 1.00 20.70 |
| ATOM | 128 | N | ASP A | 19 | 0 | 3.899 | 26.534 | 5.241 | 1.00 18.82 |
| ATOM | 129 | CA | ASP A | 19 | 0 | 3.323 | 25.227 | 5.475 | 1.00 16.87 |
| ATOM | 130 | C | ASP A | 19 | 0 | 2.548 | 24.823 | 4.237 | 1 00 17.28 |
| ATOM | 131 | O | ASP A | 19 | 0 | 1.713 | 23.929 | 4.337 | 1.00 17.84 |
| ATOM | 132 | CB | ASP A | 19 | 0 | 2.419 | 25.207 | 6.701 | 1.00 16.54 |
| ATOM | 133 | CG | ASP A | 19 | 0 | 1.192 | 26.120 | 6.596 | 1.00 16.67 |
| ATOM | 134 | OD1 | ASP A | 19 | 0 | 1.032 | 26.935 | 5.654 | 1.00 14.17 |
| ATOM | 135 | OD2 | ASP A | 19 | 0 | 0.360 | 26.045 | 7.529 | 1.00 14.56 |
| ATOM | 136 | N | GLY A | 20 | 0 | 2.782 | 25.469 | 3.100 | 1.00 17.87 |
| ATOM | 137 | CA | GLY A | 20 | 0 | 2.079 | 25.091 | 1.890 | 1.00 19.40 |
| ATOM | 138 | C | GLY A | 20 | 0 | 0.732 | 25.789 | 1.699 | 1.00 22.52 |
| ATOM | 139 | O | GLY A | 20 | 0 | 0.158 | 25.619 | 0.628 | 1.00 22.87 |
| ATOM | 140 | N | PHE A | 21 | 0 | 0.240 | 26.587 | 2.631 | 1.00 21.35 |
| ATOM | 141 | CA | PHE A | 21 | 0 | -0.913 | 27.443 | 2.534 | 1.00 20.39 |
| ATOM | 142 | C | PHE A | 21 | 0 | -0.348 | 28.855 | 2.322 | 1.00 21.23 |
| ATOM | 143 | O | PHE A | 21 | 0 | 0.475 | 29.316 | 3.122 | 1.00 21.26 |
| ATOM | 144 | CB | PHE A | 21 | 0 | -1.742 | 27.472 | 3.814 | 1.00 20.80 |
| ATOM | 145 | CG | PHE A | 21 | 0 | -3.059 | 28.180 | 3.695 | 1.00 21.91 |
| ATOM | 146 | CD1 | PHE A | 21 | 0 | -3.171 | 29.527 | 3.963 | 1.00 22.49 |
| ATOM | 147 | CD2 | PHE A | 21 | 0 | -4.207 | 27.470 | 3.327 | 1.00 22.51 |
| ATOM | 148 | CE1 | PHE A | 21 | 0 | -4.370 | 30.207 | 3.845 | 1.00 22.27 |
| ATOM | 149 | CE2 | PHE A | 21 | 0 | -5.419 | 28.128 | 3.203 | 1.00 22.79 |
| ATOM | 150 | CZ | PHE A | 21 | 0 | -5.498 | 29.497 | 3.474 | 1.00 23.34 |
| ATOM | 151 | N | THR A | 22 | 0 | -0.638 | 29.514 | 1.225 | 1.00 20.20 |
| ATOM | 152 | CA | THR A | 22 | 0 | -0.143 | 30.850 | 0.977 | 1.00 21.36 |
| ATOM | 153 | C | THR A | 22 | 0 | -1.083 | 31.939 | 1.488 | 1.00 21.79 |
| ATOM | 154 | O | THR A | 22 | 0 | -2.271 | 31.952 | 1.162 | 1.00 21.19 |
| ATOM | 155 | CB | THR A | 22 | 0 | 0.045 | 31.012 | -0.553 | 1.00 21.46 |
| ATOM | 156 | OG1 | THR A | 22 | 0 | 0.838 | 29.881 | -0.934 | 1.00 20.09 |
| ATOM | 157 | CG2 | THR A | 22 | 0 | 0.693 | 32.353 | -0.891 | 1.00 20.94 |
| ATOM | 158 | N | ARG A | 23 | 0 | -0.562 | 32.871 | 2.257 | 1.00 20.80 |
| ATOM | 159 | CA | ARG A | 23 | 0 | -1.230 | 34.008 | 2.844 | 1.00 20.78 |
| ATOM | 160 | C | ARG A | 23 | 0 | -0.257 | 35.189 | 2.960 | 1.00 21.15 |
| ATOM | 161 | O | ARG A | 23 | 0 | 0.954 | 35.018 | 2.740 | 1.00 20.42 |
| ATOM | 162 | CB | ARG A | 23 | 0 | -1.874 | 33.685 | 4.172 | 1.00 20.47 |
| ATOM | 163 | CG | ARG A | 23 | 0 | -0.964 | 33.152 | 5.295 | 1.00 21.52 |

APPENDIX 1-continued

| ATOM | 164 | CD  | ARG A | 23 0 | -0.552 | 34.357 | 6.113  | 1.00 | 22.75 |
| ---- | --- | --- | ----- | ---- | ------ | ------ | ------ | ---- | ----- |
| ATOM | 165 | NE  | ARG A | 23 0 | -0.905 | 34.419 | 7.477  | 1.00 | 21.60 |
| ATOM | 166 | CZ  | ARG A | 23 0 | -0.870 | 35.283 | 8.464  | 1.00 | 19.89 |
| ATOM | 167 | NH1 | ARG A | 23 0 | -0.526 | 36.565 | 8.453  | 1.00 | 20.19 |
| ATOM | 168 | NH2 | ARG A | 23 0 | -1.249 | 34.744 | 9.610  | 1.00 | 18.64 |
| ATOM | 169 | N   | ALA A | 24 0 | -0.784 | 36.389 | 3.199  | 1.00 | 20.05 |
| ATOM | 170 | CA  | ALA A | 24 0 | 0.140  | 37.541 | 3.243  | 1.00 | 22.03 |
| ATOM | 171 | C   | ALA A | 24 0 | 0.786  | 37.561 | 4.635  | 1.00 | 21.09 |
| ATOM | 172 | O   | ALA A | 24 0 | 0.200  | 37.124 | 5.637  | 1.00 | 21.16 |
| ATOM | 173 | CB  | ALA A | 24 0 | -0.578 | 38.836 | 2.902  | 1.00 | 22.98 |
| ATOM | 174 | N   | GLY A | 25 0 | 2.042  | 37.984 | 4.683  | 1.00 | 20.28 |
| ATOM | 175 | CA  | GLY A | 25 0 | 2.786  | 37.993 | 5.950  | 1.00 | 20.29 |
| ATOM | 176 | C   | GLY A | 25 0 | 3.649  | 39.254 | 5.979  | 1.00 | 21.38 |
| ATOM | 177 | O   | GLY A | 25 0 | 3.465  | 40.229 | 5.238  | 1.00 | 21.06 |
| ATOM | 178 | N   | ILE A | 26 0 | 4.604  | 39.221 | 6.897  | 1.00 | 20.33 |
| ATOM | 179 | CA  | ILE A | 26 0 | 5.475  | 40.365 | 7.145  | 1.00 | 20.64 |
| ATOM | 180 | C   | ILE A | 26 0 | 6.903  | 39.886 | 6.932  | 1.00 | 20.00 |
| ATOM | 181 | O   | ILE A | 26 0 | 7.247  | 38.851 | 7.485  | 1.00 | 21.34 |
| ATOM | 182 | CB  | ILE A | 26 0 | 5.278  | 40.933 | 8.564  | 1.00 | 20.38 |
| ATOM | 183 | CG  | ILE A | 26 0 | 3.883  | 41.536 | 8.667  | 1.00 | 20.72 |
| ATOM | 184 | CG2 | ILE A | 26 0 | 6.333  | 42.007 | 8.821  | 1.00 | 22.34 |
| ATOM | 185 | CD1 | ILE A | 26 0 | 3.310  | 41.822 | 10.024 | 1.00 | 20.76 |
| ATOM | 186 | N   | LEU A | 27 0 | 7.644  | 40.551 | 6.079  | 1.00 | 19.10 |
| ATOM | 187 | CA  | LEU A | 27 0 | 9.005  | 40.168 | 5.739  | 1.00 | 19.67 |
| ATOM | 188 | C   | LEU A | 27 0 | 9.964  | 41.226 | 6.280  | 1.00 | 19.85 |
| ATOM | 189 | O   | LEU A | 27 0 | 9.591  | 42.407 | 6.356  | 1.00 | 19.19 |
| ATOM | 190 | CB  | LEU A | 27 0 | 9.138  | 40.172 | 4.219  | 1.00 | 20.26 |
| ATOM | 191 | CG  | LEU A | 27 0 | 9.046  | 38.883 | 3.415  | 1 00 | 22.65 |
| ATOM | 192 | CD1 | LEU A | 27 0 | 8.127  | 37.835 | 3.989  | 1.00 | 21.10 |
| ATOM | 193 | CD2 | LEU A | 27 0 | 8.738  | 39.198 | 1.963  | 1.00 | 22.01 |
| ATOM | 194 | N   | VAL A | 28 0 | 11.162 | 40.804 | 6.630  | 1.00 | 18.03 |
| ATOM | 195 | CA  | VAL A | 28 0 | 12.199 | 41.723 | 7.088  | 1.00 | 17.24 |
| ATOM | 196 | C   | VAL A | 28 0 | 13.289 | 41.573 | 6.040  | 1.00 | 18.99 |
| ATOM | 197 | O   | VAL A | 28 0 | 13.791 | 40.453 | 5.863  | 1.00 | 20.36 |
| ATOM | 198 | CB  | VAL A | 28 0 | 12.762 | 41.415 | 8.491  | 1.00 | 16.50 |
| ATOM | 199 | CG1 | VAL A | 28 0 | 13.899 | 42.361 | 8.845  | 1.00 | 15.41 |
| ATOM | 200 | CG2 | VAL A | 28 0 | 11.681 | 41.517 | 9.558  | 1.00 | 15.42 |
| ATOM | 201 | N   | ASN A | 29 0 | 13.575 | 42.601 | 5.256  | 1.00 | 20.78 |
| ATOM | 202 | CA  | ASN A | 29 0 | 14.567 | 42.579 | 4.198  | 1.00 | 20.46 |
| ATOM | 203 | C   | ASN A | 29 0 | 14.316 | 41.435 | 3.226  | 1.00 | 23.05 |

APPENDIX 1-continued

| ATOM | 204 | O   | ASN | A | 29 | 0 | 15.247 | 40.675 | 2.880  | 1.00 | 23.62 |
|------|-----|-----|-----|---|----|---|--------|--------|--------|------|-------|
| ATOM | 205 | CB  | ASN | A | 29 | 0 | 15.982 | 42.446 | 4.764  | 1.00 | 21.06 |
| ATOM | 206 | CG  | ASN | A | 29 | 0 | 16.475 | 43.654 | 5.522  | 1.00 | 22.44 |
| ATOM | 207 | OD1 | ASN | A | 29 | 0 | 15.870 | 44.722 | 5.434  | 1.00 | 23.47 |
| ATOM | 208 | ND2 | ASN | A | 29 | 0 | 17.560 | 43.507 | 6.288  | 1.00 | 22.23 |
| ATOM | 209 | N   | GLY | A | 30 | 0 | 13.053 | 41.215 | 2.878  | 1.00 | 23.18 |
| ATOM | 210 | CA  | GLY | A | 30 | 0 | 12.662 | 40.181 | 1.922  | 1.00 | 23.36 |
| ATOM | 211 | C   | GLY | A | 30 | 0 | 12.723 | 38.757 | 2.436  | 1.00 | 23.85 |
| ATOM | 212 | O   | GLY | A | 30 | 0 | 12.707 | 37.814 | 1.633  | 1.00 | 25.17 |
| ATOM | 213 | N   | VAL | A | 31 | 0 | 12.832 | 38.585 | 3.755  | 1.00 | 21.85 |
| ATOM | 214 | CA  | VAL | A | 31 | 0 | 12.999 | 37.276 | 4.352  | 1.00 | 20.55 |
| ATOM | 215 | C   | VAL | A | 31 | 0 | 12.031 | 37.190 | 5.548  | 1.00 | 19.91 |
| ATOM | 216 | O   | VAL | A | 31 | 0 | 11.796 | 38.172 | 6.269  | 1.00 | 17.50 |
| ATOM | 217 | CB  | VAL | A | 31 | 0 | 14.436 | 37.020 | 4.856  | 1.00 | 21.36 |
| ATOM | 218 | CG1 | VAL | A | 31 | 0 | 14.556 | 35.709 | 5.626  | 1.00 | 20.79 |
| ATOM | 219 | CG2 | VAL | A | 31 | 0 | 15.495 | 37.005 | 3.757  | 1.00 | 21.84 |
| ATOM | 220 | N   | HIS | A | 32 | 0 | 11.489 | 35.984 | 5.698  | 1.00 | 17.05 |
| ATOM | 221 | CA  | HIS | A | 32 | 0 | 10.592 | 35.729 | 6.797  | 1.00 | 18.61 |
| ATOM | 222 | C   | HIS | A | 32 | 0 | 11.417 | 35.499 | 8.050  | 1.00 | 17.67 |
| ATOM | 223 | O   | HIS | A | 32 | 0 | 11.873 | 34.385 | 8.216  | 1.00 | 18.72 |
| ATOM | 224 | CB  | HIS | A | 32 | 0 | 9.676  | 34.543 | 6.493  | 1.00 | 21.00 |
| ATOM | 225 | CG  | HIS | A | 32 | 0 | 8.639  | 34.208 | 7.517  | 1.00 | 23.80 |
| ATOM | 226 | ND1 | HIS | A | 32 | 0 | 7.744  | 33.174 | 7.332  | 1.00 | 25.14 |
| ATOM | 227 | CD2 | HIS | A | 32 | 0 | 8.331  | 34.720 | 8.735  | 1.00 | 25.32 |
| ATOM | 228 | CE1 | HIS | A | 32 | 0 | 6.942  | 33.061 | 8.385  | 1.00 | 25.36 |
| ATOM | 229 | NE2 | HIS | A | 32 | 0 | 7.271  | 33.986 | 9.260  | 1.00 | 26.23 |
| ATOM | 230 | N   | GLY | A | 33 | 0 | 11.522 | 36.446 | 8.960  | 1.00 | 16.23 |
| ATOM | 231 | CA  | GLY | A | 33 | 0 | 12.276 | 36.252 | 10.198 | 1.00 | 16.97 |
| ATOM | 232 | C   | GLY | A | 33 | 0 | 13.740 | 35.869 | 10.083 | 1.00 | 15.54 |
| ATOM | 233 | O   | GLY | A | 33 | 0 | 14.228 | 34.885 | 10.609 | 1.00 | 15.13 |
| ATOM | 234 | N   | PRO | A | 34 | 0 | 14.555 | 36.734 | 9.475  | 1.00 | 15.75 |
| ATOM | 235 | CA  | PRO | A | 34 | 0 | 16.012 | 36.561 | 9.359  | 1.00 | 14.70 |
| ATOM | 236 | C   | PRO | A | 34 | 0 | 16.734 | 36.660 | 10.701 | 1.00 | 14.02 |
| ATOM | 237 | O   | PRO | A | 34 | 0 | 16.241 | 37.252 | 11.673 | 1.00 | 10.44 |
| ATOM | 238 | CB  | PRO | A | 34 | 0 | 16.491 | 37.699 | 8.435  | 1.00 | 14.40 |
| ATOM | 239 | CG  | PRO | A | 34 | 0 | 15.441 | 38.742 | 8.783  | 1.00 | 15.11 |
| ATOM | 240 | CD  | PRO | A | 34 | 0 | 14.113 | 38.005 | 8.905  | 1.00 | 13.69 |
| ATOM | 241 | N   | LEU | A | 35 | 0 | 17.925 | 36.049 | 10.767 | 1.00 | 13.60 |
| ATOM | 242 | CA  | LEU | A | 35 | 0 | 18.748 | 36.022 | 11.963 | 1.00 | 14.35 |

APPENDIX 1-continued

| | | | | | | | | | | |
|---|---|---|---|---|---|---|---|---|---|---|
| ATOM | 243 | C | LEU | A | 35 | 0 | 19.462 | 37.359 | 12.161 | 1.00 16.25 |
| ATOM | 244 | O | LEU | A | 35 | 0 | 20.015 | 37.902 | 11.210 | 1.00 14.10 |
| ATOM | 245 | CB | LEU | A | 35 | 0 | 19.834 | 34.916 | 11.862 | 1.00 15.33 |
| ATOM | 246 | CG | LEU | A | 35 | 0 | 20.958 | 34.943 | 12.911 | 1.00 17.74 |
| ATOM | 247 | CD1 | LEU | A | 35 | 0 | 20.486 | 34.698 | 14.348 | 1.00 16.30 |
| ATOM | 248 | CD2 | LEU | A | 35 | 0 | 22.052 | 33.934 | 12.575 | 1.00 16.60 |
| ATOM | 249 | N | ILE | A | 36 | 0 | 19.471 | 37.855 | 13.384 | 1.00 16.71 |
| ATOM | 250 | CA | ILE | A | 36 | 0 | 20.265 | 39.027 | 13.738 | 1.00 16.66 |
| ATOM | 251 | C | ILE | A | 36 | 0 | 21.403 | 38.487 | 14.620 | 1.00 17.92 |
| ATOM | 252 | O | ILE | A | 36 | 0 | 21.183 | 37.732 | 15.573 | 1.00 17.20 |
| ATOM | 253 | CB | ILE | A | 36 | 0 | 19.560 | 40.129 | 14.533 | 1.00 16.60 |
| ATOM | 254 | CG1 | ILE | A | 36 | 0 | 18.389 | 40.771 | 13.771 | 1.00 16.09 |
| ATOM | 255 | CG2 | ILE | A | 36 | 0 | 20.565 | 41.226 | 14.917 | 1.00 17.67 |
| ATOM | 256 | CD1 | ILE | A | 36 | 0 | 17.590 | 41.754 | 14.629 | 1.00 15.88 |
| ATOM | 257 | N | ARG | A | 37 | 0 | 22.647 | 38.829 | 14.288 | 1 00 18.72 |
| ATOM | 258 | CA | ARG | A | 37 | 0 | 23.754 | 38.315 | 15.091 | 1.00 19.94 |
| ATOM | 259 | C | ARG | A | 37 | 0 | 24.839 | 39.369 | 15.280 | 1.00 20.08 |
| ATOM | 260 | O | ARG | A | 37 | 0 | 24.979 | 40.249 | 14.450 | 1.00 20.52 |
| ATOM | 261 | CB | ARG | A | 37 | 0 | 24.395 | 37.077 | 14.465 | 1.00 21.72 |
| ATOM | 262 | CG | ARG | A | 37 | 0 | 25.102 | 37.393 | 13.171 | 1.00 24.46 |
| ATOM | 263 | CD | ARG | A | 37 | 0 | 26.113 | 36.339 | 12.762 | 1.00 26.90 |
| ATOM | 264 | NE | ARG | A | 37 | 0 | 26.584 | 36.571 | 11.381 | 1.00 29.30 |
| ATOM | 265 | CZ | ARG | A | 37 | 0 | 26.838 | 35.571 | 10.528 | 1.00 31.29 |
| ATOM | 266 | NH1 | ARG | A | 37 | 0 | 26.711 | 34.283 | 10.851 | 1.00 31.37 |
| ATOM | 267 | NR2 | ARG | A | 37 | 0 | 27.252 | 35.827 | 9.291 | 1.00 31.66 |
| ATOM | 268 | N | GLY | A | 38 | 0 | 25.587 | 39.223 | 16.361 | 1.00 20.22 |
| ATOM | 269 | CA | GLY | A | 38 | 0 | 26.716 | 40.121 | 16.611 | 1.00 18.98 |
| ATOM | 270 | C | GLY | A | 38 | 0 | 27.533 | 39.545 | 17.765 | 1.00 18.08 |
| ATOM | 271 | O | GLY | A | 38 | 0 | 27.259 | 38.421 | 18.225 | 1.00 15.92 |
| ATOM | 272 | N | GLY | A | 39 | 0 | 28.436 | 40.412 | 18.238 | 1.00 17.65 |
| ATOM | 273 | CA | GLY | A | 39 | 0 | 29.322 | 40.026 | 19.351 | 1.00 16.23 |
| ATOM | 274 | C | GLY | A | 39 | 0 | 28.861 | 40.774 | 20.592 | 1.00 17.21 |
| ATOM | 275 | O | GLY | A | 39 | 0 | 28.157 | 41.784 | 20.489 | 1.00 17.27 |
| ATOM | 276 | N | LYS | A | 40 | 0 | 29.276 | 40.328 | 21.764 | 1.00 16.58 |
| ATOM | 277 | CA | LYS | A | 40 | 0 | 28.839 | 40.805 | 23.057 | 1.00 18.03 |
| ATOM | 278 | C | LYS | A | 40 | 0 | 29.185 | 42.267 | 23.348 | 1.00 20.44 |
| ATOM | 279 | O | LYS | A | 40 | 0 | 28.562 | 42.878 | 24.221 | 1.00 19.42 |
| ATOM | 280 | CB | LYS | A | 40 | 0 | 29.394 | 39.933 | 24.185 | 1.00 16.74 |
| ATOM | 284 | CG | LYS | A | 40 | 0 | 30.892 | 39.997 | 24.370 | 1.00 17.98 |
| ATOM | 282 | CD | LYS | A | 40 | 0 | 31.333 | 39.170 | 25.569 | 1.00 20.66 |

APPENDIX 1-continued

| ATOM | 283 | CE  | LYS A | 40 | 0 | 32.809 | 38.768 | 25.493 | 1.00 | 21.70 |
| ATOM | 284 | NZ  | LYS A | 40 | 0 | 33.227 | 38.111 | 26.757 | 1.00 | 23.11 |
| ATOM | 285 | N   | ASN A | 41 | 0 | 30.181 | 42.780 | 22.645 | 1.00 | 21.43 |
| ATOM | 286 | CA  | ASN A | 41 | 0 | 30.536 | 44.171 | 22.840 | 1.00 | 25.14 |
| ATOM | 287 | C   | ASN A | 41 | 0 | 30.092 | 44.976 | 21.644 | 1.00 | 24.05 |
| ATOM | 288 | O   | ASN A | 41 | 0 | 30.409 | 46.161 | 21.655 | 1.00 | 25.66 |
| ATOM | 289 | CB  | ASN A | 41 | 0 | 32.052 | 44.326 | 23.111 | 1.00 | 27.02 |
| ATOM | 290 | CG  | ASN A | 41 | 0 | 32.434 | 43.606 | 24.404 | 1.00 | 29.76 |
| ATOM | 291 | OD1 | ASN A | 41 | 0 | 33.398 | 42.832 | 24.431 | 1.00 | 31.54 |
| ATOM | 292 | ND2 | ASN A | 41 | 0 | 31.663 | 43.825 | 25.473 | 1.00 | 30.13 |
| ATOM | 293 | N   | ASP A | 42 | 0 | 29.424 | 44.447 | 20.631 | 1.00 | 23.80 |
| ATOM | 294 | CA  | ASP A | 42 | 0 | 29.073 | 45.325 | 19.506 | 1.00 | 24.12 |
| ATOM | 295 | C   | ASP A | 42 | 0 | 28.169 | 46.484 | 19.891 | 1.00 | 24.24 |
| ATOM | 296 | O   | ASP A | 42 | 0 | 27.420 | 46.428 | 20.872 | 1.00 | 22.42 |
| ATOM | 297 | CB  | ASP A | 42 | 0 | 28.388 | 44.528 | 18.392 | 1.00 | 26.65 |
| ATOM | 298 | CG  | ASP A | 42 | 0 | 29.404 | 43.599 | 17.773 | 1.00 | 28.94 |
| ATOM | 299 | OD1 | ASP A | 42 | 0 | 30.603 | 43.754 | 18.056 | 1.00 | 31.45 |
| ATOM | 300 | OD2 | ASP A | 42 | 0 | 29.026 | 42.708 | 17.009 | 1.00 | 31.69 |
| ATOM | 301 | N   | ASN A | 43 | 0 | 28.258 | 47.547 | 19.090 | 1.00 | 24.72 |
| ATOM | 302 | CA  | ASN A | 43 | 0 | 27.316 | 48.660 | 19.255 | 1.00 | 26.50 |
| ATOM | 303 | C   | ASN A | 43 | 0 | 26.293 | 48.430 | 18.128 | 1.00 | 26.23 |
| ATOM | 304 | O   | ASN A | 43 | 0 | 26.723 | 48.420 | 16.979 | 1.00 | 25.02 |
| ATOM | 305 | CB  | ASN A | 43 | 0 | 27.934 | 50.047 | 19.128 | 1.00 | 28.45 |
| ATOM | 306 | CG  | ASN A | 43 | 0 | 28.858 | 50.244 | 20.323 | 1.00 | 31.09 |
| ATOM | 307 | OD1 | ASN A | 43 | 0 | 30.041 | 50.502 | 20.106 | 1.00 | 33.11 |
| ATOM | 308 | ND2 | ASN A | 43 | 0 | 28.364 | 50.055 | 21.531 | 1.00 | 31.18 |
| ATOM | 309 | N   | PHE A | 44 | 0 | 25.039 | 48.155 | 18.468 | 1.00 | 24.63 |
| ATOM | 310 | CA  | PHE A | 44 | 0 | 24.083 | 47.897 | 17.393 | 1.00 | 23.28 |
| ATOM | 311 | C   | PHE A | 44 | 0 | 23.450 | 49.191 | 16.916 | 1.00 | 22.36 |
| ATOM | 312 | O   | PHE A | 44 | 0 | 23.024 | 50.008 | 17.735 | 1.00 | 21.07 |
| ATOM | 313 | CB  | PHE A | 44 | 0 | 22.959 | 46.965 | 17.853 | 1.00 | 22.04 |
| ATOM | 314 | CG  | PHE A | 44 | 0 | 23.376 | 45.525 | 17.955 | 1.00 | 22.96 |
| ATOM | 315 | CD1 | PHE A | 44 | 0 | 22.779 | 44.562 | 17.153 | 1.00 | 23.91 |
| ATOM | 316 | CD2 | PHE A | 44 | 0 | 24.330 | 45.120 | 18.869 | 1.00 | 22.03 |
| ATOM | 317 | CE1 | PHE A | 44 | 0 | 23.131 | 43.230 | 17.253 | 1.00 | 24.42 |
| ATOM | 318 | CE2 | PHE A | 44 | 0 | 24.689 | 43.797 | 18.974 | 1 00 | 23.25 |
| ATOM | 319 | CZ  | PHE A | 44 | 0 | 24.995 | 42.837 | 18.168 | 1.00 | 24.02 |
| ATOM | 320 | N   | GLU A | 45 | 0 | 23.350 | 49.343 | 15.604 | 1.00 | 22.78 |
| ATOM | 321 | CA  | GLU A | 45 | 0 | 22.611 | 50.482 | 15.054 | 1.00 | 24.47 |

APPENDIX 1-continued

| ATOM | 322 | C | GLU | A | 45 | 0 | 21.619 | 49.884 | 14.055 | 1.00 | 23.79 |
|------|-----|------|-----|---|----|---|--------|--------|--------|------|-------|
| ATOM | 323 | O | GLU | A | 45 | 0 | 22.017 | 49.587 | 12.924 | 1.00 | 24.40 |
| ATOM | 324 | CB | GLU | A | 45 | 0 | 23.543 | 51.473 | 14.368 | 1.00 | 27.07 |
| ATOM | 325 | CG | GLU | A | 45 | 0 | 24.474 | 52.130 | 15.374 | 1.00 | 31.60 |
| ATOM | 326 | CD | GLU | A | 45 | 0 | 25.380 | 53.179 | 14.772 | 1.00 | 33.90 |
| ATOM | 327 | OE1 | GLU | A | 45 | 0 | 25.354 | 53.438 | 13.559 | 1.00 | 35.62 |
| ATOM | 328 | OE2 | GLU | A | 45 | 0 | 26.155 | 53.748 | 15.565 | 1.00 | 36.42 |
| ATOM | 329 | N | LEU | A | 46 | 0 | 20.369 | 49.684 | 14.465 | 1.00 | 22.18 |
| ATOM | 330 | CA | LEU | A | 46 | 0 | 19.419 | 49.044 | 13.556 | 1.00 | 21.22 |
| ATOM | 331 | C | LEU | A | 46 | 0 | 18.348 | 50.001 | 13.077 | 1.00 | 21.27 |
| ATOM | 332 | O | LEU | A | 46 | 0 | 17.464 | 50.429 | 13.812 | 1.00 | 21.60 |
| ATOM | 333 | CB | LEU | A | 46 | 0 | 18.837 | 47.811 | 14.262 | 1.00 | 20.72 |
| ATOM | 334 | CG | LEU | A | 46 | 0 | 19.827 | 46.658 | 14.403 | 1.00 | 21.28 |
| ATOM | 335 | CD1 | LEU | A | 46 | 0 | 19.334 | 45.621 | 15.397 | 1.00 | 20.83 |
| ATOM | 336 | CD2 | LEU | A | 46 | 0 | 20.148 | 46.034 | 13.052 | 1.00 | 18.33 |
| ATOM | 337 | N | ASN | A | 47 | 0 | 18.438 | 50.403 | 11.823 | 1.00 | 21.09 |
| ATOM | 338 | CA | ASN | A | 47 | 0 | 17.498 | 51.344 | 11.252 | 1.00 | 22.37 |
| ATOM | 339 | C | ASN | A | 47 | 0 | 16.273 | 50.558 | 10.803 | 1.00 | 22.18 |
| ATOM | 340 | O | ASN | A | 47 | 0 | 16.390 | 49.810 | 9.847 | 1.00 | 23.41 |
| ATOM | 341 | CB | ASN | A | 47 | 0 | 18.131 | 52.104 | 10.066 | 1.00 | 24.01 |
| ATOM | 342 | CG | ASN | A | 47 | 0 | 17.226 | 53.243 | 9.615 | 1.00 | 25.54 |
| ATOM | 343 | OD1 | ASN | A | 47 | 0 | 16.443 | 53.772 | 10.413 | 1.00 | 26.53 |
| ATOM | 344 | ND2 | ASN | A | 47 | 0 | 17.332 | 53.612 | 8.346 | 1.00 | 26.01 |
| ATOM | 345 | N | VAL | A | 48 | 0 | 15.147 | 50.692 | 11.475 | 1.00 | 22.04 |
| ATOM | 346 | CA | VAL | A | 48 | 0 | 13.918 | 49.995 | 11.140 | 1.00 | 21.99 |
| ATOM | 347 | C | VAL | A | 48 | 0 | 13.026 | 50.879 | 10.269 | 1.00 | 21.82 |
| ATOM | 348 | O | VAL | A | 48 | 0 | 12.532 | 51.910 | 10.699 | 1.00 | 20.61 |
| ATOM | 349 | CB | VAL | A | 48 | 0 | 13.176 | 49.579 | 12.430 | 1.00 | 22.64 |
| ATOM | 350 | CG1 | VAL | A | 48 | 0 | 11.819 | 48.931 | 12.148 | 1.00 | 21.99 |
| ATOM | 351 | CG2 | VAL | A | 48 | 0 | 14.098 | 48.631 | 13.216 | 1.00 | 21.68 |
| ATOM | 352 | N | VAL | A | 49 | 0 | 12.931 | 50.512 | 9.009 | 1.00 | 21.79 |
| ATOM | 353 | CA | VAL | A | 49 | 0 | 12.164 | 51.167 | 7.966 | 1.00 | 21.34 |
| ATOM | 354 | C | VAL | A | 49 | 0 | 10.816 | 50.460 | 7.795 | 1.00 | 21.12 |
| ATOM | 355 | O | VAL | A | 49 | 0 | 10.703 | 49.308 | 7.365 | 1.00 | 19.76 |
| ATOM | 356 | CB | VAL | A | 49 | 0 | 12.983 | 51.189 | 6.665 | 1.00 | 22.02 |
| ATOM | 357 | CG1 | VAL | A | 49 | 0 | 12.267 | 51.913 | 5.519 | 1.00 | 21.70 |
| ATOM | 358 | CG2 | VAL | A | 49 | 0 | 14.312 | 51.933 | 6.906 | 1.00 | 21.47 |
| ATOM | 359 | N | ASN | A | 50 | 0 | 9.767 | 51.112 | 8.257 | 1.00 | 20.26 |
| ATOM | 360 | CA | ASN | A | 50 | 0 | 8.424 | 50.611 | 8.215 | 1.00 | 22.70 |
| ATOM | 361 | C | ASN | A | 50 | 0 | 7.751 | 50.899 | 6.869 | 1.00 | 25.99 |

APPENDIX 1-continued

| ATOM | 362 | O | ASN | A | 50 | 0 | 7.043 | 51.925 | 6.735 | 1.00 | 27.06 |
|------|-----|-----|-----|---|----|---|-------|--------|-------|------|-------|
| ATOM | 363 | CB | ASN | A | 50 | 0 | 7.549 | 51.230 | 9.318 | 1.00 | 21.92 |
| ATOM | 364 | CG | ASN | A | 50 | 0 | 6.198 | 50.569 | 9.471 | 1.00 | 22.44 |
| ATOM | 365 | OD1 | ASN | A | 50 | 0 | 5.818 | 49.801 | 8.572 | 1.00 | 24.19 |
| ATOM | 366 | ND2 | ASN | A | 50 | 0 | 5.435 | 50.833 | 10.526 | 1.00 | 20.19 |
| ATOM | 367 | N | ASP | A | 51 | 0 | 7.915 | 49.959 | 5.926 | 1.00 | 26.42 |
| ATOM | 368 | CA | ASP | A | 51 | 0 | 7.208 | 50.071 | 4.641 | 1.00 | 26.35 |
| ATOM | 369 | C | ASP | A | 51 | 0 | 5.951 | 49.200 | 4.600 | 1.00 | 24.86 |
| ATOM | 370 | O | ASP | A | 51 | 0 | 5.542 | 48.810 | 3.511 | 1.00 | 25.19 |
| ATOM | 371 | CB | ASP | A | 51 | 0 | 8.126 | 49.698 | 3.481 | 1.00 | 26.75 |
| ATOM | 372 | CG | ASP | A | 51 | 0 | 9.152 | 50.761 | 3.158 | 1.00 | 29.77 |
| ATOM | 373 | OD1 | ASP | A | 51 | 0 | 8.944 | 51.904 | 3.617 | 1.00 | 31.03 |
| ATOM | 374 | OD2 | ASP | A | 51 | 0 | 10.166 | 50.509 | 2.465 | 1.00 | 30.42 |
| ATOM | 375 | N | LEU | A | 52 | 0 | 5.332 | 48.801 | 5.700 | 1.00 | 25.05 |
| ATOM | 376 | CA | LEU | A | 52 | 0 | 4.172 | 47.911 | 5.640 | 1.00 | 25.44 |
| ATOM | 377 | C | LEU | A | 52 | 0 | 2.934 | 48.624 | 5.094 | 1.00 | 26.65 |
| ATOM | 378 | O | LEU | A | 52 | 0 | 2.553 | 49.696 | 5.586 | 1.00 | 24.56 |
| ATOM | 379 | CB | LEU | A | 52 | 0 | 3.837 | 47.374 | 7.029 | 1.00 | 24.19 |
| ATOM | 380 | CG | LEU | A | 52 | 0 | 4.896 | 46.503 | 7.699 | 1.00 | 24.60 |
| ATOM | 381 | CD1 | LEU | A | 52 | 0 | 4.611 | 46.424 | 9.196 | 1.00 | 24.05 |
| ATOM | 382 | CD2 | LEU | A | 52 | 0 | 4.891 | 45.119 | 7.061 | 1.00 | 23.49 |
| ATOM | 383 | N | ASP | A | 53 | 0 | 2.242 | 47.980 | 4.169 | 1.00 | 28.79 |
| ATOM | 384 | CA | ASP | A | 53 | 0 | 1.049 | 48.602 | 3.581 | 1.00 | 29.91 |
| ATOM | 385 | C | ASP | A | 53 | 0 | -0.135 | 47.658 | 3.492 | 1.00 | 29.90 |
| ATOM | 386 | O | ASP | A | 53 | 0 | -1.152 | 48.082 | 2.951 | 1.00 | 30.40 |
| ATOM | 387 | CB | ASP | A | 53 | 0 | 1.367 | 49.190 | 2.197 | 1.00 | 29.26 |
| ATOM | 388 | CG | ASP | A | 53 | 0 | 1.838 | 48.140 | 1.218 | 1.00 | 31.28 |
| ATOM | 389 | OD1 | ASP | A | 53 | 0 | 1.865 | 46.926 | 1.540 | 1.00 | 31.64 |
| ATOM | 390 | OD2 | ASP | A | 53 | 0 | 2.233 | 48.474 | 0.074 | 1.00 | 32.42 |
| ATOM | 391 | N | ASN | A | 54 | 0 | -0.060 | 46.437 | 4.014 | 1.00 | 29.44 |
| ATOM | 392 | CA | ASN | A | 54 | 0 | -1.237 | 45.554 | 3.983 | 1.00 | 26.89 |
| ATOM | 393 | C | ASN | A | 54 | 0 | -2.089 | 45.832 | 5.192 | 1.00 | 27.37 |
| ATOM | 394 | O | ASN | A | 54 | 0 | -1.772 | 45.528 | 6.350 | 1.00 | 27.99 |
| ATOM | 395 | CB | ASN | A | 54 | 0 | -0.831 | 44.095 | 3.913 | 1.00 | 25.11 |
| ATOM | 396 | CG | ASN | A | 54 | 0 | -1.978 | 43.141 | 3.690 | 1.00 | 24.20 |
| ATOM | 397 | OD1 | ASN | A | 54 | 0 | -1.874 | 42.344 | 2.746 | 1.00 | 25.13 |
| ATOM | 398 | ND2 | ASN | A | 54 | 0 | -3.030 | 43.182 | 4.481 | 1.00 | 23.26 |
| ATOM | 399 | N | PRO | A | 55 | 0 | -3.337 | 46.256 | 4.961 | 1.00 | 28.44 |
| ATOM | 400 | C | PRO | A | 55 | 0 | -4.286 | 46.589 | 6.014 | 1.00 | 26.57 |

APPENDIX 1-continued

| ATOM | 401 | C | PRO | A | 55 | 0 | -4.909 | 45.414 | 6.723 | 1.00 | 27.10 |
| ATOM | 402 | O | PRO | A | 55 | 0 | -5.671 | 45.624 | 7.687 | 1.00 | 26.05 |
| ATOM | 403 | CB | PRO | A | 55 | 0 | -5.368 | 47.465 | 5.334 | 1.00 | 28.18 |
| ATOM | 404 | CG | PRO | A | 55 | 0 | -5.249 | 47.049 | 3.899 | 1.00 | 27.50 |
| ATOM | 405 | CD | PRO | A | 55 | 0 | -3.844 | 46.564 | 3.625 | 1.00 | 27.56 |
| ATOM | 406 | N | THR | A | 56 | 0 | -4.603 | 44.160 | 6.345 | 1.00 | 25.55 |
| ATOM | 407 | CA | THR | A | 56 | 0 | -5.214 | 43.024 | 7.065 | 1.00 | 25.52 |
| ATOM | 408 | C | THR | A | 56 | 0 | -4.446 | 42.647 | 8.326 | 1.00 | 24.87 |
| ATOM | 409 | O | THR | A | 56 | 0 | -4.766 | 41.764 | 9.115 | 1.00 | 23.97 |
| ATOM | 410 | CB | THR | A | 56 | 0 | -5.393 | 41.807 | 6.154 | 1.00 | 25.10 |
| ATOM | 411 | OG1 | THR | A | 56 | 0 | -4.100 | 41.345 | 5.763 | 1.00 | 24.26 |
| ATOM | 412 | CG2 | THR | A | 56 | 0 | -6.178 | 42.123 | 4.861 | 1.00 | 25.63 |
| ATOM | 413 | N | MET | A | 57 | 0 | -3.317 | 43.311 | 8.558 | 1.00 | 26.01 |
| ATOM | 414 | CA | MET | A | 57 | 0 | -2.553 | 43.099 | 9.801 | 1.00 | 26.57 |
| ATOM | 415 | C | MET | A | 57 | 0 | -2.026 | 44.475 | 10.201 | 1.00 | 25.88 |
| ATOM | 416 | O | MET | A | 57 | 0 | -2.026 | 45.416 | 9.397 | 1.00 | 25.18 |
| ATOM | 417 | CB | MET | A | 57 | 0 | -1.561 | 41.939 | 9.698 | 1.00 | 25.42 |
| ATOM | 418 | CG | MET | A | 57 | 0 | -0.639 | 41.868 | 8.554 | 1.00 | 24.37 |
| ATOM | 419 | SD | MET | A | 57 | 0 | -0.034 | 40.288 | 7.916 | 1.00 | 22.34 |
| ATOM | 420 | CE | MET | A | 57 | 0 | -0.275 | 40.640 | 6.167 | 1.00 | 19.23 |
| ATOM | 421 | N | LEU | A | 58 | 0 | -1.694 | 44.601 | 11.476 | 1.00 | 25.98 |
| ATOM | 422 | CA | LEU | A | 58 | 0 | -1.180 | 45.850 | 12.036 | 1.00 | 25.57 |
| ATOM | 423 | C | LEU | A | 58 | 0 | -0.053 | 46.425 | 11.195 | 1.00 | 24.52 |
| ATOM | 424 | O | LEU | A | 58 | 0 | 0.824 | 45.739 | 10.638 | 1.00 | 23.63 |
| ATOM | 425 | CB | LEU | A | 58 | 0 | -0.757 | 45.535 | 13.463 | 1.00 | 26.67 |
| ATOM | 426 | CG | LEU | A | 58 | 0 | -1.628 | 45.817 | 14.657 | 1.00 | 28.97 |
| ATOM | 427 | CD1 | LEU | A | 58 | 0 | -3.107 | 45.995 | 14.312 | 1.00 | 30.99 |
| ATOM | 428 | CD2 | LEU | A | 58 | 0 | -1.488 | 44.756 | 15.736 | 1.00 | 28.36 |
| ATOM | 429 | N | ARG | A | 59 | 0 | -0.078 | 47.741 | 11.030 | 1.00 | 24.96 |
| ATOM | 430 | CA | ARG | A | 59 | 0 | 0.918 | 48.434 | 10.231 | 1.00 | 26.92 |
| ATOM | 431 | C | ARG | A | 59 | 0 | 1.932 | 49.229 | 11.014 | 1.00 | 26.31 |
| ATOM | 432 | O | ARG | A | 59 | 0 | 3.120 | 49.198 | 10.699 | 1.00 | 28.82 |
| ATOM | 433 | CB | ARG | A | 59 | 0 | 0.260 | 49.277 | 9.132 | 1.00 | 28.35 |
| ATOM | 434 | CG | ARG | A | 59 | 0 | -0.252 | 48.385 | 7.986 | 1.00 | 29.50 |
| ATOM | 435 | CD | ARG | A | 59 | 0 | -0.986 | 49.274 | 6.996 | 1.00 | 30.33 |
| ATOM | 436 | NE | ARG | A | 59 | 0 | -2.333 | 49.604 | 7.459 | 1.00 | 32.26 |
| ATOM | 437 | CZ | ARG | A | 59 | 0 | -3.121 | 50.525 | 6.883 | 1.00 | 33.24 |
| ATOM | 438 | NH1 | ARG | A | 59 | 0 | -2.679 | 51.233 | 5.845 | 1.00 | 32.27 |
| ATOM | 439 | NH2 | ARG | A | 59 | 0 | -4.340 | 50.712 | 7.389 | 1.00 | 32.65 |
| ATOM | 440 | N | PRO | A | 60 | 0 | 1.542 | 49.961 | 12.020 | 1.00 | 26.30 |

APPENDIX 1-continued

| ATOM | 441 | CA  | PRO A | 60 | 0 | 2.460  | 50.669 | 12.916 | 1.00 | 26.19 |
| ---- | --- | --- | ----- | -- | - | ------ | ------ | ------ | ---- | ----- |
| ATOM | 442 | C   | PRO A | 60 | 0 | 3.312  | 49.591 | 13.595 | 1.00 | 25.29 |
| ATOM | 443 | O   | PRO A | 60 | 0 | 2.879  | 48.432 | 13.668 | 1.00 | 24.63 |
| ATOM | 444 | CB  | PRO A | 60 | 0 | 1.623  | 51.464 | 13.925 | 1.00 | 25.93 |
| ATOM | 445 | CG  | PRO A | 60 | 0 | 0.235  | 51.357 | 13.325 | 1.00 | 26.19 |
| ATOM | 446 | CD  | PRO A | 60 | 0 | 0.165  | 50.073 | 12.508 | 1.00 | 26.23 |
| ATOM | 447 | N   | THR A | 61 | 0 | 4.544  | 49.932 | 13.976 | 1.00 | 24.60 |
| ATOM | 448 | CA  | THR A | 61 | 0 | 5.365  | 48.871 | 14.587 | 1.00 | 23.49 |
| ATOM | 449 | C   | THR A | 61 | 0 | 6.204  | 49.400 | 15.743 | 1.00 | 22.83 |
| ATOM | 450 | O   | THR A | 61 | 0 | 6.390  | 50.601 | 15.921 | 1.00 | 20.77 |
| ATOM | 451 | CB  | THR A | 61 | 0 | 6.245  | 48.170 | 13.535 | 1.00 | 22.69 |
| ATOM | 452 | OG1 | THR A | 61 | 0 | 6.668  | 46.918 | 14.096 | 1.00 | 23.55 |
| ATOM | 453 | CG2 | THR A | 61 | 0 | 7.444  | 48.976 | 13.119 | 1.00 | 20.92 |
| ATOM | 454 | N   | SER A | 62 | 0 | 6.702  | 48.449 | 16.507 | 1.00 | 22.38 |
| ATOM | 455 | CA  | SER A | 62 | 0 | 7.599  | 48.672 | 17.633 | 1.00 | 22.47 |
| ATOM | 456 | C   | SER A | 62 | 0 | 8.381  | 47.380 | 17.893 | 1.00 | 22.12 |
| ATOM | 457 | O   | SER A | 62 | 0 | 7.763  | 46.331 | 18.124 | 1.00 | 20.53 |
| ATOM | 458 | CB  | SER A | 62 | 0 | 6.784  | 49.033 | 18.882 | 1.00 | 22.02 |
| ATOM | 459 | OG  | SER A | 62 | 0 | 7.666  | 49.570 | 19.832 | 1.00 | 21.19 |
| ATOM | 460 | N   | ILE A | 63 | 0 | 9.716  | 47.451 | 17.806 | 1.00 | 21.17 |
| ATOM | 461 | CA  | ILE A | 63 | 0 | 10.513 | 46.240 | 17.960 | 1.00 | 18.32 |
| ATOM | 462 | C   | ILE A | 63 | 0 | 11.095 | 46.034 | 19.354 | 1.00 | 18.28 |
| ATOM | 463 | O   | ILE A | 63 | 0 | 11.832 | 46.909 | 19.826 | 1.00 | 19.63 |
| ATOM | 464 | CB  | ILE A | 63 | 0 | 11.642 | 46.234 | 16.924 | 1.00 | 16.68 |
| ATOM | 465 | CG1 | ILE A | 63 | 0 | 11.166 | 46.509 | 15.508 | 1.00 | 18.51 |
| ATOM | 466 | CG2 | ILE A | 63 | 0 | 12.319 | 44.848 | 16.906 | 1.00 | 16.78 |
| ATOM | 467 | CD1 | ILE A | 63 | 0 | 10.055 | 45.625 | 14.994 | 1.00 | 18.25 |
| ATOM | 468 | N   | HIS A | 64 | 0 | 10.880 | 44.890 | 19.985 | 1.00 | 15.18 |
| ATOM | 469 | CA  | HIS A | 64 | 0 | 11.478 | 44.539 | 21.261 | 1.00 | 15.51 |
| ATOM | 470 | C   | HIS A | 64 | 0 | 12.648 | 43.559 | 21.029 | 1.00 | 16.73 |
| ATOM | 471 | O   | HIS A | 64 | 0 | 12.491 | 42.591 | 20.279 | 1.00 | 16.85 |
| ATOM | 472 | CB  | HIS A | 64 | 0 | 10.512 | 43.912 | 22.239 | 1.00 | 14.37 |
| ATOM | 473 | CG  | HIS A | 64 | 0 | 11.033 | 43.420 | 23.546 | 1.00 | 14.47 |
| ATOM | 474 | ND1 | HIS A | 64 | 0 | 11.763 | 44.191 | 24.410 | 1.00 | 12.89 |
| ATOM | 475 | CD2 | HIS A | 64 | 0 | 10.883 | 42.223 | 24.193 | 1.00 | 14.85 |
| ATOM | 476 | CE1 | HIS A | 64 | 0 | 12.067 | 43.518 | 25.498 | 1.00 | 11.53 |
| ATOM | 477 | NE2 | HIS A | 64 | 0 | 11.547 | 42.325 | 25.423 | 1.00 | 13.63 |
| ATOM | 478 | N   | TRP A | 65 | 0 | 13.761 | 43.781 | 21.723 | 1.00 | 14.37 |
| ATOM | 479 | CA  | TRP A | 65 | 0 | 14.966 | 42.926 | 21.577 | 1.00 | 13.92 |

APPENDIX 1-continued

| ATOM | 480 | C   | TRP | A | 65 | 0 | 14.987 | 42.084 | 22.840 | 1.00 | 13.50 |
| ATOM | 481 | O   | TRP | A | 65 | 0 | 15.482 | 42.538 | 23.901 | 1.00 | 12.84 |
| ATOM | 482 | CB  | TRP | A | 65 | 0 | 16.189 | 43.825 | 21.371 | 1.00 | 13.50 |
| ATOM | 483 | CG  | TRP | A | 65 | 0 | 15.890 | 45.020 | 20.492 | 1.00 | 13.19 |
| ATOM | 484 | CD1 | TRP | A | 65 | 0 | 15.453 | 46.247 | 20.913 | 1.00 | 12.42 |
| ATOM | 485 | CD2 | TRP | A | 65 | 0 | 15.908 | 45.087 | 19.068 | 1.00 | 13.61 |
| ATOM | 486 | NE1 | TRP | A | 65 | 0 | 15.234 | 47.067 | 19.862 | 1.00 | 11.49 |
| ATOM | 487 | CE2 | TRP | A | 65 | 0 | 15.511 | 46.390 | 18.710 | 1.00 | 13.77 |
| ATOM | 488 | CE3 | TRP | A | 65 | 0 | 16.251 | 44.174 | 18.061 | 1.00 | 14.35 |
| ATOM | 489 | CZ2 | TRP | A | 65 | 0 | 15.439 | 46.815 | 17.378 | 1.00 | 14.99 |
| ATOM | 490 | CZ3 | TRP | A | 65 | 0 | 16.169 | 44.572 | 16.735 | 1.00 | 13.99 |
| ATOM | 491 | CH2 | TRP | A | 65 | 0 | 15.756 | 45.869 | 16.411 | 1.00 | 15.82 |
| ATOM | 492 | N   | HIS | A | 66 | 0 | 14.295 | 40.941 | 22.747 | 1.00 | 10.39 |
| ATOM | 493 | CA  | HIS | A | 66 | 0 | 13.939 | 40.200 | 23.966 | 1.00 | 12.00 |
| ATOM | 494 | C   | HIS | A | 66 | 0 | 15.158 | 39.653 | 24.698 | 1.00 | 11.34 |
| ATOM | 495 | O   | HIS | A | 66 | 0 | 15.889 | 38.859 | 24.130 | 1.00 | 11.51 |
| ATOM | 496 | CB  | HIS | A | 66 | 0 | 12.923 | 39.069 | 23.629 | 1.00 | 10.76 |
| ATOM | 497 | CG  | HIS | A | 66 | 0 | 12.418 | 38.308 | 24.808 | 1.00 | 11.26 |
| ATOM | 498 | ND1 | HIS | A | 66 | 0 | 11.106 | 38.085 | 25.092 | 1.00 | 13.10 |
| ATOM | 499 | CD2 | HIS | A | 66 | 0 | 13.050 | 37.676 | 25.824 | 1.00 | 13.49 |
| ATOM | 500 | CE1 | HIS | A | 66 | 0 | 10.919 | 37.407 | 26.191 | 1.00 | 12.50 |
| ATOM | 501 | NE2 | HIS | A | 66 | 0 | 12.116 | 37.146 | 26.683 | 1.00 | 13.71 |
| ATOM | 502 | N   | GLY | A | 67 | 0 | 15.345 | 39.971 | 25.948 | 1.00 | 12.84 |
| ATOM | 503 | CA  | GLY | A | 67 | 0 | 16.492 | 39.469 | 26.719 | 1.00 | 13.36 |
| ATOM | 504 | C   | GLY | A | 67 | 0 | 17.596 | 40.500 | 26.914 | 1.00 | 13.11 |
| ATOM | 505 | O   | GLY | A | 67 | 0 | 18.435 | 40.289 | 27.788 | 1.00 | 13.36 |
| ATOM | 506 | N   | LEU | A | 68 | 0 | 17.641 | 41.558 | 26.131 | 1.00 | 12.89 |
| ATOM | 507 | CA  | LEU | A | 68 | 0 | 18.659 | 42.598 | 26.300 | 1.00 | 15.22 |
| ATOM | 508 | C   | LEU | A | 68 | 0 | 18.235 | 43.501 | 27.448 | 1.00 | 16.14 |
| ATOM | 509 | O   | LEU | A | 68 | 0 | 17.029 | 43.842 | 27.505 | 1.00 | 16.50 |
| ATOM | 510 | CB  | LEU | A | 68 | 0 | 18.929 | 43.320 | 24.988 | 1.00 | 15.98 |
| ATOM | 511 | CG  | LEU | A | 68 | 0 | 20.002 | 42.638 | 24.114 | 1.00 | 19.57 |
| ATOM | 512 | CD1 | LEU | A | 68 | 0 | 19.719 | 41.185 | 23.809 | 1.00 | 20.39 |
| ATOM | 513 | CD2 | LEU | A | 68 | 0 | 20.188 | 43.316 | 22.758 | 1.00 | 19.59 |
| ATOM | 514 | N   | PHE | A | 69 | 0 | 19.125 | 43.848 | 28.386 | 1.00 | 13.24 |
| ATOM | 515 | CA  | PHE | A | 69 | 0 | 18.700 | 44.657 | 29.526 | 1.00 | 13.85 |
| ATOM | 516 | C   | PHE | A | 69 | 0 | 18.499 | 46.128 | 29.205 | 1.00 | 14.34 |
| ATOM | 517 | O   | PHE | A | 69 | 0 | 17.806 | 46.879 | 29.895 | 1.00 | 15.02 |
| ATOM | 518 | CB  | PHE | A | 69 | 0 | 19.770 | 44.579 | 30.637 | 1.00 | 16.02 |
| ATOM | 519 | CG  | PHE | A | 69 | 0 | 20.112 | 43.187 | 31.072 | 1.00 | 16.45 |

APPENDIX 1-continued

| ATOM | 520 | CD1 | PHE | A | 69 | 0 | 19.172 | 42.162 | 31.026 | 1.00 | 16.68 |
|------|-----|-----|-----|---|----|---|--------|--------|--------|------|-------|
| ATOM | 521 | CD2 | PHE | A | 69 | 0 | 21.381 | 42.927 | 31.578 | 1.00 | 16.78 |
| ATOM | 522 | CE1 | PHE | A | 69 | 0 | 19.504 | 40.883 | 31.448 | 1.00 | 18.86 |
| ATOM | 523 | CE2 | PHE | A | 69 | 0 | 21.717 | 41.652 | 32.001 | 1.00 | 17.34 |
| ATOM | 524 | CZ  | PHE | A | 69 | 0 | 20.782 | 40.628 | 31.932 | 1.00 | 18.09 |
| ATOM | 525 | N   | GLN | A | 70 | 0 | 19.081 | 46.611 | 28.130 | 1.00 | 12.22 |
| ATOM | 526 | CA  | GLN | A | 70 | 0 | 18.919 | 47.990 | 27.708 | 1.00 | 15.20 |
| ATOM | 527 | C   | GLN | A | 70 | 0 | 19.242 | 49.004 | 28.799 | 1.00 | 16.76 |
| ATOM | 528 | O   | GLN | A | 70 | 0 | 18.555 | 50.016 | 28.919 | 1.00 | 16.08 |
| ATOM | 529 | CB  | GLN | A | 70 | 0 | 17.488 | 48.115 | 27.232 | 1.00 | 15.52 |
| ATOM | 530 | CG  | GLN | A | 70 | 0 | 17.168 | 47.303 | 26.003 | 1.00 | 17.37 |
| ATOM | 531 | CD  | GLN | A | 70 | 0 | 17.781 | 47.744 | 24.709 | 1.00 | 17.70 |
| ATOM | 532 | OE1 | GLN | A | 70 | 0 | 17.557 | 47.090 | 23.676 | 1.00 | 21.63 |
| ATOM | 533 | NE2 | GLN | A | 70 | 0 | 18.549 | 48.805 | 24.620 | 1.00 | 16.79 |
| ATOM | 534 | N   | ARG | A | 71 | 0 | 20.338 | 48.804 | 29.518 | 1.00 | 16.49 |
| ATOM | 535 | CA  | ARG | A | 71 | 0 | 20.765 | 49.712 | 30.588 | 1.00 | 18.41 |
| ATOM | 536 | C   | ARG | A | 71 | 0 | 21.239 | 51.011 | 29.970 | 1.00 | 16.23 |
| ATOM | 537 | O   | ARG | A | 71 | 0 | 22.059 | 50.998 | 29.027 | 1.00 | 14.48 |
| ATOM | 538 | CB  | ARG | A | 71 | 0 | 21.827 | 48.942 | 31.382 | 1.00 | 22.65 |
| ATOM | 539 | CG  | ARG | A | 71 | 0 | 22.273 | 49.589 | 32.671 | 1.00 | 29.50 |
| ATOM | 540 | CD  | ARG | A | 71 | 0 | 23.286 | 48.756 | 33.457 | 1.00 | 32.92 |
| ATOM | 541 | NE  | ARG | A | 71 | 0 | 22.712 | 47.550 | 34.035 | 1.00 | 38.11 |
| ATOM | 542 | CZ  | ARG | A | 71 | 0 | 22.551 | 46.358 | 33.452 | 1.00 | 40.14 |
| ATOM | 543 | NH1 | ARG | A | 71 | 0 | 22.939 | 46.138 | 32.190 | 1.00 | 41.23 |
| ATOM | 544 | NH2 | ARG | A | 71 | 0 | 22.022 | 45.333 | 34.130 | 1.00 | 40.89 |
| ATOM | 545 | N   | GLY | A | 72 | 0 | 20.613 | 52.145 | 30.311 | 1.00 | 14.82 |
| ATOM | 546 | CA  | GLY | A | 72 | 0 | 20.981 | 53.414 | 29.676 | 1.00 | 14.51 |
| ATOM | 547 | C   | GLY | A | 72 | 0 | 20.268 | 53.606 | 28.338 | 1.00 | 15.55 |
| ATOM | 548 | O   | GLY | A | 72 | 0 | 20.401 | 54.706 | 27.777 | 1.00 | 16.32 |
| ATOM | 549 | N   | THR | A | 73 | 0 | 19.503 | 52.651 | 27.804 | 1.00 | 12.12 |
| ATOM | 550 | CA  | THR | A | 73 | 0 | 18.857 | 52.781 | 26.516 | 1.00 | 12.50 |
| ATOM | 551 | C   | THR | A | 73 | 0 | 17.418 | 52.252 | 26.621 | 1.00 | 13.98 |
| ATOM | 552 | O   | THR | A | 73 | 0 | 16.890 | 51.534 | 25.776 | 1.00 | 13.81 |
| ATOM | 553 | CB  | THR | A | 73 | 0 | 19.577 | 52.086 | 25.346 | 1.00 | 12.21 |
| ATOM | 554 | QG1 | THR | A | 73 | 0 | 19.854 | 50.711 | 25.666 | 1.00 | 12.83 |
| ATOM | 555 | CG2 | THR | A | 73 | 0 | 20.944 | 52.711 | 25.000 | 1.00 |  9.81 |
| ATOM | 556 | N   | ASN | A | 74 | 0 | 16.744 | 52.617 | 27.708 | 1.00 | 12.97 |
| ATOM | 557 | CA  | ASN | A | 74 | 0 | 15.354 | 52.273 | 27.951 | 1.00 | 14.93 |
| ATOM | 558 | C   | ASN | A | 74 | 0 | 14.469 | 52.718 | 26.784 | 1.00 | 15.92 |

APPENDIX 1-continued

| ATOM | 559 | O | ASN | A | 74 | 0 | 13.501 | 52.030 | 26.455 | 1.00 | 16.56 |
|------|-----|-----|-----|---|----|---|--------|--------|--------|------|-------|
| ATOM | 560 | CB | ASN | A | 74 | 0 | 14.851 | 52.821 | 29.271 | 1.00 | 13.06 |
| ATOM | 561 | CG | ASN | A | 74 | 0 | 13.385 | 52.519 | 29.556 | 1.00 | 15.47 |
| ATOM | 562 | OD1 | ASN | A | 74 | 0 | 12.557 | 53.250 | 29.021 | 1.00 | 13.99 |
| ATOM | 563 | ND2 | ASN | A | 74 | 0 | 13.063 | 51.500 | 30.367 | 1.00 | 13.91 |
| ATOM | 564 | N | TRP | A | 75 | 0 | 14.806 | 53.765 | 26.041 | 1.00 | 16.16 |
| ATOM | 565 | CA | TRP | A | 75 | 0 | 14.036 | 54.262 | 24.917 | 1.00 | 16.49 |
| ATOM | 566 | C | TRP | A | 75 | 0 | 14.050 | 53.345 | 23.701 | 1.00 | 17.29 |
| ATOM | 567 | O | TRP | A | 75 | 0 | 13.235 | 53.529 | 22.776 | 1.00 | 16.34 |
| ATOM | 568 | CB | TRP | A | 75 | 0 | 14.516 | 55.657 | 24.509 | 1.00 | 15.90 |
| ATOM | 569 | CG | TRP | A | 75 | 0 | 15.990 | 55.705 | 24.207 | 1.00 | 16.04 |
| ATOM | 570 | CD1 | TRP | A | 75 | 0 | 17.011 | 55.972 | 25.072 | 1.00 | 14.90 |
| ATOM | 571 | CD2 | TRP | A | 75 | 0 | 16.584 | 55.475 | 22.916 | 1.00 | 15.94 |
| ATOM | 572 | NE1 | TRP | A | 75 | 0 | 18.210 | 55.917 | 24.384 | 1.00 | 15.89 |
| ATOM | 573 | CE2 | TRP | A | 75 | 0 | 17.977 | 55.624 | 23.076 | 1.00 | 15.80 |
| ATOM | 574 | CE3 | TRP | A | 75 | 0 | 16.060 | 55.171 | 21.656 | 1 | 00 | 14.88 |
| ATOM | 575 | CZ2 | TRP | A | 75 | 0 | 18.867 | 55.459 | 22.016 | 1.00 | 17.60 |
| ATOM | 576 | CZ3 | TRP | A | 75 | 0 | 16.928 | 55.025 | 20.603 | 1.00 | 16.64 |
| ATOM | 577 | CH2 | TRP | A | 75 | 0 | 18.321 | 55.153 | 20.785 | 1.00 | 18.16 |
| ATOM | 578 | N | ALA | A | 76 | 0 | 14.962 | 52.372 | 23.675 | 1.00 | 15.12 |
| ATOM | 579 | CA | ALA | A | 76 | 0 | 15.075 | 51.430 | 22.578 | 1.00 | 14.61 |
| ATOM | 580 | C | ALA | A | 76 | 0 | 14.569 | 50.047 | 22.971 | 1.00 | 13.98 |
| ATOM | 581 | O | ALA | A | 76 | 0 | 14.617 | 49.132 | 22.159 | 1.00 | 14.20 |
| ATOM | 582 | CB | ALA | A | 76 | 0 | 16.554 | 51.354 | 22.157 | 1.00 | 13.68 |
| ATOM | 583 | N | ASP | A | 77 | 0 | 13.941 | 49.885 | 24.121 | 1.00 | 14.47 |
| ATOM | 584 | CA | ASP | A | 77 | 0 | 13.409 | 48.605 | 24.586 | 1.00 | 14.23 |
| ATOM | 585 | C | ASP | A | 77 | 0 | 12.198 | 48.167 | 23.762 | 1.00 | 15.04 |
| ATOM | 586 | O | ASP | A | 77 | 0 | 11.982 | 46.946 | 23.638 | 1.00 | 13.78 |
| ATOM | 587 | CB | ASP | A | 77 | 0 | 13.112 | 48.567 | 26.072 | 1.00 | 13.41 |
| ATOM | 588 | CG | ASP | A | 77 | 0 | 12.945 | 47.155 | 26.612 | 1.00 | 14.93 |
| ATOM | 589 | OD1 | ASP | A | 77 | 0 | 11.943 | 46.986 | 27.345 | 1.00 | 15.07 |
| ATOM | 590 | OD2 | ASP | A | 77 | 0 | 13.744 | 46.217 | 26.334 | 1.00 | 13.73 |
| ATOM | 591 | N | GLY | A | 78 | 0 | 11.458 | 49.095 | 23.160 | 1.00 | 13.63 |
| ATOM | 592 | CA | GLY | A | 78 | 0 | 10.442 | 48.686 | 22.210 | 1.00 | 14.96 |
| ATOM | 593 | C | GLY | A | 78 | 0 | 9.040 | 48.309 | 22.631 | 1.00 | 16.75 |
| ATOM | 594 | O | GLY | A | 78 | 0 | 8.276 | 47.865 | 21.755 | 1.00 | 16.49 |
| ATOM | 595 | N | ALA | A | 79 | 0 | 8.631 | 48.436 | 23.886 | 1.00 | 15.34 |
| ATOM | 596 | CA | ALA | A | 79 | 0 | 7.252 | 48.176 | 24.270 | 1.00 | 14.70 |
| ATOM | 597 | C | ALA | A | 79 | 0 | 6.490 | 49.495 | 24.084 | 1.00 | 17.51 |
| ATOM | 598 | O | ALA | A | 79 | 0 | 6.690 | 50.486 | 24.807 | 1.00 | 17.05 |

APPENDIX 1-continued

| ATOM | 599 | CB | ALA A | 79 | 0 | 7.145 | 47.701 | 25.708 | 1.00 | 14.78 |
|---|---|---|---|---|---|---|---|---|---|---|
| ATOM | 600 | N | ASP A | 80 | 0 | 5.641 | 49.536 | 23.053 | 1.00 | 18.56 |
| ATOM | 601 | CA | ASP A | 80 | 0 | 4.859 | 50.741 | 22.798 | 1.00 | 19.52 |
| ATOM | 602 | C | ASP A | 80 | 0 | 3.959 | 50.963 | 24.010 | 1.00 | 17.61 |
| ATOM | 603 | O | ASP A | 80 | 0 | 3.530 | 49.999 | 24.664 | 1.00 | 16.72 |
| ATOM | 604 | CB | ASP A | 80 | 0 | 4.044 | 50.714 | 21.510 | 1.00 | 24.02 |
| ATOM | 605 | CG | ASP A | 80 | 0 | 3.003 | 49.607 | 21.549 | 1.00 | 28.13 |
| ATOM | 606 | OD1 | ASP A | 80 | 0 | 3.410 | 48.417 | 21.541 | 1.00 | 30.66 |
| ATOM | 607 | OD2 | ASP A | 80 | 0 | 1.803 | 49.959 | 21.603 | 1.00 | 30.61 |
| ATOM | 608 | N | GLY A | 81 | 0 | 3.776 | 52.242 | 24.337 | 1.00 | 15.85 |
| ATOM | 609 | CA | GLY A | 81 | 0 | 2.991 | 52.566 | 25.532 | 1.00 | 16.27 |
| ATOM | 610 | C | GLY A | 81 | 0 | 3.846 | 52.615 | 26.784 | 1.00 | 18.72 |
| ATOM | 611 | O | GLY A | 81 | 0 | 3.405 | 52.983 | 27.890 | 1.00 | 20.61 |
| ATOM | 612 | N | VAL A | 82 | 0 | 5.108 | 52.173 | 26.725 | 1.00 | 19.11 |
| ATOM | 613 | CA | VAL A | 82 | 0 | 5.978 | 52.119 | 27.890 | 1.00 | 19.14 |
| ATOM | 614 | C | VAL A | 82 | 0 | 7.288 | 52.851 | 27.590 | 1.00 | 18.41 |
| ATOM | 615 | O | VAL A | 82 | 0 | 7.594 | 53.839 | 28.242 | 1.00 | 16.79 |
| ATOM | 616 | CB | VAL A | 82 | 0 | 6.266 | 50.697 | 28.390 | 1.00 | 19.82 |
| ATOM | 617 | CG1 | VAL A | 82 | 0 | 7.059 | 50.741 | 29.710 | 1.00 | 21.37 |
| ATOM | 618 | CG2 | VAL A | 82 | 0 | 4.995 | 49.894 | 28.640 | 1.00 | 19.27 |
| ATOM | 619 | N | ASN A | 83 | 0 | 7.982 | 52.408 | 26.551 | 1.00 | 17.90 |
| ATOM | 620 | CA | ASN A | 83 | 0 | 9.271 | 52.926 | 26.147 | 1.00 | 16.94 |
| ATOM | 621 | C | ASN A | 83 | 0 | 9.226 | 53.778 | 24.886 | 1.00 | 18.32 |
| ATOM | 622 | O | ASN A | 83 | 0 | 10.175 | 54.551 | 24.634 | 1.00 | 20.58 |
| ATOM | 623 | CB | ASN A | 83 | 0 | 10.249 | 51.747 | 25.937 | 1.00 | 15.23 |
| ATOM | 624 | CG | ASN A | 83 | 0 | 10.112 | 50.745 | 27.063 | 1.00 | 16.00 |
| ATOM | 625 | OD1 | ASN A | 83 | 0 | 9.493 | 49.676 | 26.879 | 1.00 | 14.98 |
| ATOM | 626 | ND2 | ASN A | 83 | 0 | 10.583 | 51.131 | 28.249 | 1.00 | 13.17 |
| ATOM | 627 | N | GLN A | 84 | 0 | 8.183 | 53.668 | 24.066 | 1.00 | 16.40 |
| ATOM | 628 | CA | GLN A | 84 | 0 | 8.080 | 54.464 | 22.867 | 1.00 | 16.34 |
| ATOM | 629 | C | GLN A | 84 | 0 | 6.658 | 54.465 | 22.309 | 1.00 | 17.95 |
| ATOM | 630 | O | GLN A | 84 | 0 | 5.816 | 53.679 | 22.728 | 1.00 | 17.69 |
| ATOM | 631 | CB | GLN A | 84 | 0 | 8.995 | 53.953 | 21.754 | 1.00 | 17.98 |
| ATOM | 632 | CG | GLN A | 84 | 0 | 8.456 | 52.654 | 21.127 | 1.00 | 16.63 |
| ATOM | 633 | CD | GLN A | 84 | 0 | 9.272 | 52.225 | 19.938 | 1.00 | 18.17 |
| ATOM | 634 | OE1 | GLN A | 84 | 0 | 8.994 | 52.601 | 18.792 | 1.00 | 20.91 |
| ATOM | 635 | NE2 | GLN A | 84 | 0 | 10.279 | 51.385 | 20.096 | 1.00 | 18.70 |
| ATOM | 636 | N | CYS A | 85 | 0 | 6.419 | 55.350 | 21.365 | 1.00 | 18.60 |
| ATOM | 637 | CA | CYS A | 85 | 0 | 5.140 | 55.344 | 20.622 | 1.00 | 20.25 |

APPENDIX 1-continued

| ATOM | 638 | C   | CYS | A | 85 | 0 | 5.512  | 54.555 | 19.375 | 1.00 | 19.55 |
|------|-----|-----|-----|---|----|---|--------|--------|--------|------|-------|
| ATOM | 639 | O   | CYS | A | 85 | 0 | 6.690  | 54.546 | 18.995 | 1.00 | 18.92 |
| ATOM | 640 | CB  | CYS | A | 85 | 0 | 4.772  | 56.786 | 20.228 | 1.00 | 22.20 |
| ATOM | 641 | SG  | CYS | A | 85 | 0 | 3.899  | 57.783 | 21.481 | 1.00 | 24.65 |
| ATOM | 642 | N   | PRO | A | 86 | 0 | 4.589  | 53.951 | 18.674 | 1.00 | 21.19 |
| ATOM | 643 | CA  | PRO | A | 86 | 0 | 4.869  | 53.152 | 17.498 | 1.00 | 20.78 |
| ATOM | 644 | C   | PRO | A | 86 | 0 | 5.560  | 53.930 | 16.394 | 1.00 | 21.46 |
| ATOM | 645 | O   | PRO | A | 86 | 0 | 5.453  | 55.137 | 16.298 | 1.00 | 23.08 |
| ATOM | 646 | CB  | PRO | A | 86 | 0 | 3.530  | 52.555 | 17.028 | 1.00 | 19.94 |
| ATOM | 647 | CG  | PRO | A | 86 | 0 | 2.667  | 52.720 | 18.252 | 1.00 | 19.59 |
| ATOM | 648 | CD  | PRO | A | 86 | 0 | 3.174  | 53.872 | 19.062 | 1.00 | 20.46 |
| ATOM | 649 | N   | ILE | A | 87 | 0 | 6.318  | 53.259 | 15.550 | 1.00 | 20.95 |
| ATOM | 650 | CA  | ILE | A | 87 | 0 | 6.907  | 53.773 | 14.337 | 1.00 | 22.43 |
| ATOM | 651 | C   | ILE | A | 87 | 0 | 5.768  | 53.641 | 13.292 | 1.00 | 22.80 |
| ATOM | 652 | O   | ILE | A | 87 | 0 | 5.148  | 52.562 | 13.228 | 1.00 | 21.61 |
| ATOM | 653 | CB  | ILE | A | 87 | 0 | 8.105  | 52.954 | 13.844 | 1.00 | 21.99 |
| ATOM | 654 | CG1 | ILE | A | 87 | 0 | 9.130  | 52.696 | 14.944 | 1.00 | 24.18 |
| ATOM | 655 | CG2 | ILE | A | 87 | 0 | 8.773  | 53.656 | 12.674 | 1.00 | 22.91 |
| ATOM | 656 | CD1 | ILE | A | 87 | 0 | 10.256 | 51.776 | 14.514 | 1.00 | 23.87 |
| ATOM | 657 | N   | SER | A | 88 | 0 | 5.464  | 54.702 | 12.570 | 1.00 | 22.64 |
| ATOM | 658 | CA  | SER | A | 88 | 0 | 4.338  | 54.709 | 11.647 | 1.00 | 22.85 |
| ATOM | 659 | C   | SER | A | 88 | 0 | 4.751  | 54.268 | 10.249 | 1.00 | 23.35 |
| ATOM | 660 | O   | SER | A | 88 | 0 | 5.870  | 54.489 | 9.764  | 1.00 | 23.30 |
| ATOM | 661 | CB  | SER | A | 88 | 0 | 3.767  | 56.137 | 11.518 | 1.00 | 24.00 |
| ATOM | 662 | OG  | SER | A | 88 | 0 | 3.379  | 56.770 | 12.720 | 1.00 | 23.93 |
| ATOM | 663 | N   | PRO | A | 89 | 0 | 3.778  | 53.752 | 9.514  | 1.00 | 23.60 |
| ATOM | 664 | CA  | PRO | A | 89 | 0 | 3.955  | 53.382 | 8.116  | 1.00 | 25.19 |
| ATOM | 665 | C   | PRO | A | 89 | 0 | 4.579  | 54.556 | 7.361  | 1.00 | 26.58 |
| ATOM | 666 | O   | PRO | A | 89 | 0 | 4.177  | 55.699 | 7.585  | 1.00 | 26.66 |
| ATOM | 667 | CB  | PRO | A | 89 | 0 | 2.566  | 53.065 | 7.555  | 1.00 | 23.59 |
| ATOM | 668 | CG  | PRO | A | 89 | 0 | 1.740  | 52.856 | 8.798  | 1.00 | 22.37 |
| ATOM | 669 | CD  | PRO | A | 89 | 0 | 2.415  | 53.513 | 9.970  | 1.00 | 23.25 |
| ATOM | 670 | N   | GLY | A | 90 | 0 | 5.588  | 54.311 | 6.550  | 1.00 | 27.73 |
| ATOM | 671 | CA  | GLY | A | 90 | 0 | 6.223  | 55.338 | 5.748  | 1.00 | 30.55 |
| ATOM | 672 | C   | GLY | A | 90 | 0 | 7.384  | 56.032 | 6.438  | 1.00 | 32.38 |
| ATOM | 673 | O   | GLY | A | 90 | 0 | 8.050  | 56.894 | 5.879  | 1.00 | 32.53 |
| ATOM | 674 | N   | HIS | A | 91 | 0 | 7.639  | 55.693 | 7.702  | 1.00 | 32.77 |
| ATOM | 675 | CA  | HIS | A | 91 | 0 | 8.691  | 56.283 | 8.494  | 1.00 | 32.55 |
| ATOM | 676 | C   | HIS | A | 91 | 0 | 9.649  | 55.179 | 8.982  | 1.00 | 32.36 |
| ATOM | 677 | O   | HIS | A | 91 | 0 | 9.381  | 53.972 | 8.961  | 1.00 | 31.30 |

APPENDIX 1-continued

```
ATOM    678  CB   HIS A   91   0      8.118 57.016  9.722 1.00 33.75
ATOM    679  CG   HIS A   91   0      7.147 58.073  9.295 1.00 34.64
ATOM    680  ND1  HIS A   91   0      7.519 59.381  9.072 1.00 34.41
ATOM    681  CD2  HIS A   91   0      5.822 57.977  9.002 1.00 34.89
ATOM    682  CE1  HIS A   91   0      6.450 60.050  8.679 1.00 34.87
ATOM    683  NE2  HIS A   91   0      5.410 59.233  8.628 1.00 35.14
ATOM    684  N    ALA A   92   0     10.786 55.668  9.437 1.00 29.57
ATOM    685  CA   ALA A   92   0     11.895 54.898  9.937 1.00 27.71
ATOM    686  C    ALA A   92   0     12.316 55.347 11.337 1.00 27.41
ATOM    687  O    ALA A   92   0     12.076 56.484 11.741 1.00 26.12
ATOM    688  CB   ALA A   92   0     13.051 55.057  8.967 1.00 25.23
ATOM    689  N    PHE A   93   0     12.931 54.418 12.081 1.00 26.87
ATOM    690  CA   PHE A   93   0     13.441 54.760 13.405 1.00 25.87
ATOM    691  C    PHE A   93   0     14.746 54.008 13.632 1.00 25.21
ATOM    692  O    PHE A   93   0     14.797 52.810 13.347 1.00 25.80
ATOM    693  CB   PHE A   93   0     12.457 54.456 14.526 1.00 25.30
ATOM    694  CG   PHE A   93   0     12.964 54.955 15.847 1.00 25.41
ATOM    695  CD1  PHE A   93   0     13.154 56.309 16.061 1.00 25.36
ATOM    696  CD2  PHE A   93   0     13.276 54.057 16.853 1.00 25.31
ATOM    697  CE1  PHE A   93   0     13.637 56.753 17.285 1.00 26.54
ATOM    698  CE2  PHE A   93   0     13.754 54.503 18.078 1.00 25.39
ATOM    699  CZ   PHE A   93   0     13.935 55.857 18.302 1.00 25.01
ATOM    700  N    LEU A   94   0     15.756 54.699 14.136 1.00 23.39
ATOM    701  CA   LEU A   94   0     17.046 54.058 14.361 1.00 23.35
ATOM    702  C    LEU A   94   0     17.191 53.611 15.804 1.00 23.22
ATOM    703  O    LEU A   94   0     17.261 54.431 16.714 1.00 23.47
ATOM    704  CB   LEU A   94   0     18.186 54.994 13.943 1.00 24.96
ATOM    705  CG   LEU A   94   0     19.630 54.555 14.170 1.00 26.28
ATOM    706  CD1  LEU A   94   0     19.979 53.313 13.352 1.00 25.99
ATOM    707  CD2  LEU A   94   0     20.627 55.678 13.887 1.00 26.06
ATOM    708  N    TYR A   95   0     17.261 52.293 16.023 1.00 21.81
ATOM    709  CA   TYR A   95   0     17.481 51.780 17.379 1.00 19.72
ATOM    710  C    TYR A   95   0     18.991 51.663 17.585 1.00 20.90
ATOM    711  O    TYR A   95   0     19.690 51.248 16.656 1.00 20.74
ATOM    712  CB   TYR A   95   0     16.831 50.448 17.609 1.00 17.86
ATOM    713  CG   TYR A   95   0     15.329 50.411 17.691 1.00 16.35
ATOM    714  CD1  TYR A   95   0     14.541 50.288 16.535 1.00 16.89
ATOM    715  CD2  TYR A   95   0     14.701 50.442 18.911 1.00 15.71
ATOM    716  CE1  TYR A   95   0     13.157 50.205 16.621 1.00 17.21
```

APPENDIX 1-continued

| ATOM | 717 | CE2 | TYR A | 95 | 0 | 13.325 | 50.362 | 19.033 | 1.00 | 16.25 |
| --- | --- | --- | --- | --- | --- | --- | --- | --- | --- | --- |
| ATOM | 718 | CZ | TYR A | 95 | 0 | 12.568 | 50.266 | 17.874 | 1.00 | 17.97 |
| ATOM | 719 | OH | TYR A | 95 | 0 | 11.205 | 50.189 | 18.001 | 1.00 | 18.61 |
| ATOM | 720 | N | LYS A | 96 | 0 | 19.475 | 52.105 | 18.752 | 1.00 | 20.56 |
| ATOM | 721 | CA | LYS A | 96 | 0 | 20.917 | 52.058 | 18.975 | 1.00 | 21.77 |
| ATOM | 722 | C | LYS A | 96 | 0 | 21.139 | 51.519 | 20.386 | 1.00 | 20.91 |
| ATOM | 723 | O | LYS A | 96 | 0 | 20.558 | 52.122 | 21.286 | 1.00 | 21.98 |
| ATOM | 724 | CB | LYS A | 96 | 0 | 21.565 | 53.427 | 18.960 | 1.00 | 22.89 |
| ATOM | 725 | CG | LYS A | 96 | 0 | 21.857 | 54.046 | 17.609 | 1.00 | 26.39 |
| ATOM | 726 | CD | LYS A | 96 | 0 | 22.749 | 55.251 | 17.923 | 1.00 | 30.80 |
| ATOM | 727 | CE | LYS A | 96 | 0 | 22.732 | 56.348 | 16.884 | 1.00 | 32.90 |
| ATOM | 728 | NZ | LYS A | 96 | 0 | 23.767 | 57.378 | 17.277 | 1.00 | 36.06 |
| ATOM | 729 | N | PHE A | 97 | 0 | 21.871 | 50.437 | 20.520 | 1.00 | 18.14 |
| ATOM | 730 | CA | PHE A | 97 | 0 | 22.062 | 49.863 | 21.854 | 1.00 | 18.19 |
| ATOM | 731 | C | PHE A | 97 | 0 | 23.276 | 48.928 | 21.805 | 1 00 | 16.76 |
| ATOM | 732 | O | PHE A | 97 | 0 | 23.870 | 48.700 | 20.747 | 1.00 | 14.19 |
| ATOM | 733 | CB | PHE A | 97 | 0 | 20.816 | 49.067 | 22.307 | 1.00 | 17.34 |
| ATOM | 734 | CG | PHE A | 97 | 0 | 20.379 | 48.026 | 21.304 | 1.00 | 17.56 |
| ATOM | 735 | CD1 | PHE A | 97 | 0 | 20.873 | 46.732 | 21.348 | 1 00 | 16.27 |
| ATOM | 736 | CD2 | PHE A | 97 | 0 | 19.451 | 48.343 | 20.326 | 1.00 | 18.65 |
| ATOM | 737 | CE1 | PHE A | 97 | 0 | 20.476 | 45.801 | 20.398 | 1.00 | 17.76 |
| ATOM | 738 | CE2 | PHE A | 97 | 0 | 19.026 | 47.408 | 19.386 | 1.00 | 18.64 |
| ATOM | 739 | CZ | PHE A | 97 | 0 | 19.546 | 46.120 | 19.416 | 1.00 | 17.55 |
| ATOM | 740 | N | THR A | 98 | 0 | 23.552 | 48.348 | 22.971 | 1.00 | 17.45 |
| ATOM | 741 | CA | THR A | 98 | 0 | 24.644 | 47.359 | 22.992 | 1.00 | 17.00 |
| ATOM | 742 | C | THR A | 98 | 0 | 24.304 | 46.333 | 24.042 | 1.00 | 16.63 |
| ATOM | 743 | O | THR A | 98 | 0 | 23.725 | 46.631 | 25.090 | 1.00 | 15.86 |
| ATOM | 744 | CB | THR A | 98 | 0 | 26.028 | 47.990 | 23.256 | 1.00 | 17.53 |
| ATOM | 745 | OG1 | THR A | 98 | 0 | 27.017 | 46.924 | 23.372 | 1.00 | 19.01 |
| ATOM | 746 | CG2 | THR A | 98 | 0 | 26.088 | 48.807 | 24.525 | 1.00 | 14.85 |
| ATOM | 747 | N | PRO A | 99 | 0 | 24.740 | 45.097 | 23.831 | 1.00 | 15.98 |
| ATOM | 748 | CA | PRO A | 99 | 0 | 24.601 | 44.019 | 24.787 | 1.00 | 15.11 |
| ATOM | 749 | C | PRO A | 99 | 0 | 25.445 | 44.270 | 26.020 | 1.00 | 15.99 |
| ATOM | 750 | O | PRO A | 99 | 0 | 25.260 | 43.633 | 27.064 | 1.00 | 15.94 |
| ATOM | 751 | CB | PRO A | 99 | 0 | 25.025 | 42.717 | 24.098 | 1.00 | 15.83 |
| ATOM | 752 | CG | PRO A | 99 | 0 | 25.042 | 43.140 | 22.644 | 1.00 | 17.12 |
| ATOM | 753 | CD | PRO A | 99 | 0 | 25.362 | 44.627 | 22.601 | 1.00 | 15.68 |
| ATOM | 754 | N | ALA A | 100 | 0 | 26.452 | 45.149 | 25.932 | 1.00 | 17.29 |
| ATOM | 755 | CA | ALA A | 100 | 0 | 27.316 | 45.501 | 27.050 | 1.00 | 16.88 |
| ATOM | 756 | C | ALA A | 100 | 0 | 27.919 | 44.293 | 27.754 | 1.00 | 16.16 |

APPENDIX 1-continued

| ATOM | 757 | O   | ALA | A | 100 | 0 | 27.779 | 44.187 | 28.977 | 1.00 | 18.13 |
| ---- | --- | --- | --- | - | --- | - | ------ | ------ | ------ | ---- | ----- |
| ATOM | 758 | CB  | ALA | A | 100 | 0 | 26.498 | 46.292 | 28.084 | 1.00 | 14.96 |
| ATOM | 759 | N   | GLY | A | 101 | 0 | 28.474 | 43.360 | 27.033 | 1.00 | 16.41 |
| ATOM | 760 | CA  | GLY | A | 101 | 0 | 29.063 | 42.172 | 27.599 | 1.00 | 17.49 |
| ATOM | 761 | C   | GLY | A | 101 | 0 | 28.130 | 40.994 | 27.769 | 1.00 | 16.15 |
| ATOM | 762 | O   | GLY | A | 101 | 0 | 28.593 | 39.930 | 28.137 | 1.00 | 16.57 |
| ATOM | 763 | N   | HIS | A | 102 | 0 | 26.838 | 41.120 | 27.521 | 1.00 | 17.58 |
| ATOM | 764 | CA  | HIS | A | 102 | 0 | 25.858 | 40.058 | 27.804 | 1.00 | 15.77 |
| ATOM | 765 | C   | HIS | A | 102 | 0 | 25.707 | 39.165 | 26.600 | 1.00 | 15.28 |
| ATOM | 766 | O   | HIS | A | 102 | 0 | 25.087 | 39.641 | 25.662 | 1.00 | 17.64 |
| ATOM | 767 | CB  | HIS | A | 102 | 0 | 24.498 | 40.666 | 28.186 | 1.00 | 17.95 |
| ATOM | 768 | CG  | HIS | A | 102 | 0 | 23.432 | 39.661 | 28.493 | 1.00 | 20.00 |
| ATOM | 769 | ND1 | HIS | A | 102 | 0 | 22.099 | 40.005 | 28.547 | 1.00 | 20.59 |
| ATOM | 770 | CD2 | HIS | A | 102 | 0 | 23.475 | 38.323 | 28.772 | 1.00 | 20.09 |
| ATOM | 771 | CE1 | HIS | A | 102 | 0 | 21.398 | 38.937 | 28.866 | 1.00 | 20.77 |
| ATOM | 772 | NE2 | HIS | A | 102 | 0 | 22.201 | 37.896 | 29.016 | 1.00 | 20.56 |
| ATOM | 773 | N   | ALA | A | 103 | 0 | 26.277 | 37.958 | 26.584 | 1.00 | 13.32 |
| ATOM | 774 | CA  | ALA | A | 103 | 0 | 26.141 | 37.127 | 25.415 | 1.00 | 13.99 |
| ATOM | 775 | C   | ALA | A | 103 | 0 | 24.974 | 36.156 | 25.649 | 1.00 | 13.43 |
| ATOM | 776 | O   | ALA | A | 103 | 0 | 24.571 | 35.905 | 26.784 | 1.00 | 11.81 |
| ATOM | 777 | CB  | ALA | A | 103 | 0 | 27.418 | 36.329 | 25.151 | 1.00 | 16.36 |
| ATOM | 778 | N   | GLY | A | 104 | 0 | 24.459 | 35.610 | 24.554 | 1.00 | 12.38 |
| ATOM | 779 | CA  | GLY | A | 104 | 0 | 23.381 | 34.632 | 24.778 | 1.00 | 12.85 |
| ATOM | 780 | C   | GLY | A | 104 | 0 | 22.480 | 34.451 | 23.581 | 1.00 | 11.06 |
| ATOM | 781 | O   | GLY | A | 104 | 0 | 22.674 | 35.057 | 22.515 | 1.00 | 10.91 |
| ATOM | 782 | N   | THR | A | 105 | 0 | 21.442 | 33.650 | 23.794 | 1.00 | 10.14 |
| ATOM | 783 | CA  | THR | A | 105 | 0 | 20.490 | 33.394 | 22.704 | 1.00 | 10.04 |
| ATOM | 784 | C   | THR | A | 105 | 0 | 19.238 | 34.236 | 22.989 | 1.00 | 9.52  |
| ATOM | 785 | O   | THR | A | 105 | 0 | 18.738 | 34.194 | 24.125 | 1.00 | 7.52  |
| ATOM | 786 | CB  | THR | A | 105 | 0 | 20.114 | 31.913 | 22.665 | 1.00 | 12.67 |
| ATOM | 787 | OG1 | THR | A | 105 | 0 | 21.273 | 31.075 | 22.593 | 1.00 | 13.47 |
| ATOM | 788 | CG2 | THR | A | 105 | 0 | 19.187 | 31.684 | 21.468 | 1.00 | 12.75 |
| ATOM | 789 | N   | PHE | A | 106 | 0 | 18.842 | 35.065 | 22.044 | 1.00 | 7.76  |
| ATOM | 790 | CA  | PHE | A | 106 | 0 | 17.731 | 35.992 | 22.243 | 1.00 | 10.15 |
| ATOM | 791 | C   | PHE | A | 106 | 0 | 16.756 | 35.910 | 21.068 | 1.00 | 8.42  |
| ATOM | 792 | O   | PHE | A | 106 | 0 | 16.941 | 35.083 | 20.166 | 1.00 | 8.33  |
| ATOM | 793 | CB  | PHE | A | 106 | 0 | 18.283 | 37.460 | 22.369 | 1.00 | 10.19 |
| ATOM | 794 | CG  | PHE | A | 106 | 0 | 19.291 | 37.577 | 23.506 | 1.00 | 12.95 |
| ATOM | 795 | CD1 | PHE | A | 106 | 0 | 18.905 | 37.443 | 24.815 | 1.00 | 11.44 |

APPENDIX 1-continued

| ATOM | 796 | CD2 | PHE | A | 106 | 0 | 20.654 | 37.775 | 23.230 | 1.00 | 12.37 |
| --- | --- | --- | --- | --- | --- | --- | --- | --- | --- | --- | --- |
| ATOM | 797 | CE1 | PHE | A | 106 | 0 | 19.855 | 37.531 | 25.822 | 1.00 | 14.20 |
| ATOM | 798 | CE2 | PHE | A | 106 | 0 | 21.574 | 37.857 | 24.273 | 1.00 | 11.56 |
| ATOM | 799 | CZ | PHE | A | 106 | 0 | 21.202 | 37.733 | 25.599 | 1.00 | 9.45 |
| ATOM | 800 | N | TRP | A | 107 | 0 | 15.869 | 36.887 | 20.917 | 1.00 | 6.61 |
| ATOM | 801 | CA | TRP | A | 107 | 0 | 15.062 | 36.977 | 19.713 | 1.00 | 10.20 |
| ATOM | 802 | C | TRP | A | 107 | 0 | 14.511 | 38.398 | 19.625 | 1.00 | 10.63 |
| ATOM | 803 | O | TRP | A | 107 | 0 | 14.463 | 39.036 | 20.657 | 1.00 | 13.71 |
| ATOM | 804 | CB | TRP | A | 107 | 0 | 13.928 | 35.966 | 19.636 | 1.00 | 7.49 |
| ATOM | 805 | CG | TRP | A | 107 | 0 | 12.945 | 35.916 | 20.755 | 1.00 | 9.41 |
| ATOM | 806 | CD1 | TRP | A | 107 | 0 | 13.136 | 35.804 | 22.106 | 1.00 | 10.53 |
| ATOM | 807 | CD2 | TRP | A | 107 | 0 | 11.509 | 36.004 | 20.581 | 1.00 | 9.17 |
| ATOM | 808 | NE1 | TRP | A | 107 | 0 | 11.929 | 35.784 | 22.768 | 1.00 | 10.63 |
| ATOM | 809 | CE2 | TRP | A | 107 | 0 | 10.924 | 35.926 | 21.842 | 1.00 | 9.90 |
| ATOM | 810 | CE3 | TRP | A | 107 | 0 | 10.698 | 36.144 | 19.444 | 1.00 | 8.77 |
| ATOM | 811 | CZ2 | TRP | A | 107 | 0 | 9.538 | 35.947 | 22.025 | 1.00 | 10.01 |
| ATOM | 812 | CZ3 | TRP | A | 107 | 0 | 9.336 | 36.167 | 19.613 | 1.00 | 8.60 |
| ATOM | 813 | CH2 | TRP | A | 107 | 0 | 8.774 | 36.061 | 20.890 | 1.00 | 10.09 |
| ATOM | 814 | N | TYR | A | 108 | 0 | 14.117 | 38.847 | 18.464 | 1.00 | 10.72 |
| ATOM | 815 | CA | TYR | A | 108 | 0 | 13.498 | 40.148 | 18.302 | 1.00 | 12.19 |
| ATOM | 816 | C | TYR | A | 108 | 0 | 12.030 | 39.869 | 17.875 | 1.00 | 13.62 |
| ATOM | 817 | O | TYR | A | 108 | 0 | 11.752 | 38.837 | 17.245 | 1.00 | 13.85 |
| ATOM | 818 | CB | TYR | A | 108 | 0 | 14.182 | 40.994 | 17.259 | 1.00 | 11.05 |
| ATOM | 819 | CG | TYR | A | 108 | 0 | 14.176 | 40.413 | 15.857 | 1.00 | 13.89 |
| ATOM | 820 | CD1 | TYR | A | 108 | 0 | 15.087 | 39.464 | 15.423 | 1.00 | 12.99 |
| ATOM | 821 | CD2 | TYR | A | 108 | 0 | 13.257 | 40.897 | 14.920 | 1.00 | 14.94 |
| ATOM | 822 | CE1 | TYR | A | 108 | 0 | 15.064 | 38.979 | 14.130 | 1.00 | 13.64 |
| ATOM | 823 | CE2 | TYR | A | 108 | 0 | 13.216 | 40.409 | 13.624 | 1.00 | 15.34 |
| ATOM | 824 | CZ | TYR | A | 108 | 0 | 14.123 | 39.443 | 13.236 | 1.00 | 14.99 |
| ATOM | 825 | OR | TYR | A | 108 | 0 | 14.063 | 38.960 | 11.946 | 1.00 | 16.68 |
| ATOM | 826 | N | HIS | A | 109 | 0 | 11.123 | 40.752 | 18.254 | 1.00 | 12.81 |
| ATOM | 827 | CA | HIS | A | 109 | 0 | 9.735 | 40.630 | 17.826 | 1.00 | 14.92 |
| ATOM | 828 | C | HIS | A | 109 | 0 | 9.057 | 41.988 | 17.991 | 1.00 | 15.96 |
| ATOM | 829 | O | HIS | A | 109 | 0 | 9.392 | 42.800 | 18.875 | 1.00 | 15.67 |
| ATOM | 830 | CB | HIS | A | 109 | 0 | 8.903 | 39.566 | 18.550 | 1.00 | 12.30 |
| ATOM | 831 | CG | HIS | A | 109 | 0 | 8.804 | 39.727 | 20.036 | 1.00 | 12.30 |
| ATOM | 832 | ND1 | HIS | A | 109 | 0 | 7.788 | 40.429 | 20.666 | 1.00 | 9.89 |
| ATOM | 833 | CD2 | HIS | A | 109 | 0 | 9.614 | 39.264 | 21.034 | 1.00 | 10.76 |
| ATOM | 834 | CE1 | HIS | A | 109 | 0 | 7.982 | 40.379 | 21.971 | 1.00 | 8.49 |
| ATOM | 835 | NE2 | HIS | A | 109 | 0 | 9.086 | 39.679 | 22.224 | 1.00 | 7.92 |

APPENDIX 1-continued

```
ATOM    836  N    SER A  110  0     8.070  42.203  17.122  1.00  16.26
ATOM    837  CA   SER A  110  0     7.244  43.404  17.300  1.00  14.55
ATOM    838  C    SER A  110  0     6.548  43.283  18.646  1.00  13.56
ATOM    839  O    SER A  110  0     6.219  42.191  19.140  1.00  13.54
ATOM    840  CB   SER A  110  0     6.219  43.543  16.159  1.00  16.69
ATOM    841  OG   SER A  110  0     5.212  44.481  16.508  1.00  15.32
ATOM    842  N    HIS A  111  0     6.396  44.395  19.359  1.00  14.60
ATOM    843  CA   HIS A  111  0     5.724  44.397  20.645  1.00  16.23
ATOM    844  C    HIS A  111  0     4.349  45.070  20.478  1.00  18.61
ATOM    845  O    HIS A  111  0     3.713  45.391  21.473  1.00  21.72
ATOM    846  CB   HIS A  111  0     6.478  45.166  21.721  1.00  14.37
ATOM    847  CG   HIS A  111  0     6.392  44.519  23.077  1.00  15.33
ATOM    848  ND1  HIS A  111  0     5.341  44.660  23.947  1.00  14.55
ATOM    849  CD2  HIS A  111  0     7.265  43.676  23.680  1.00  14.72
ATOM    850  CE1  HIS A  111  0     5.589  43.936  25.040  1.00  16.29
ATOM    851  NE2  HIS A  111  0     6.773  43.326  24.920  1.00  15.35
ATOM    852  N    PHE A  112  0     3.950  45.382  19.258  1.00  18.67
ATOM    853  CA   PHE A  112  0     2.725  46.139  19.037  1.00  19.61
ATOM    854  C    PHE A  112  0     1.540  45.219  18.777  1.00  19.06
ATOM    855  O    PHE A  112  0     1.521  44.630  17.707  1.00  17.50
ATOM    856  CB   PHE A  112  0     2.971  47.113  17.875  1.00  21.16
ATOM    857  CG   PHE A  112  0     1.798  48.019  17.611  1.00  23.12
ATOM    858  CD1  PHE A  112  0     1.456  49.007  18.509  1.00  24.59
ATOM    859  CD2  PHE A  112  0     1.034  47.886  16.466  1.00  24.82
ATOM    860  CE1  PHE A  112  0     0.387  49.852  18.312  1.00  24.29
ATOM    861  CE2  PHE A  112  0    -0.063  48.714  16.243  1.00  25.87
ATOM    862  CZ   PHE A  112  0    -0.378  49.698  17.161  1.00  25.17
ATOM    863  N    GLY A  113  0     0.599  45.092  19.707  1.00  18.05
ATOM    864  CA   GLY A  113  0    -0.554  44.236  19.433  1.00  19.69
ATOM    865  C    GLY A  113  0    -0.085  42.819  19.096  1.00  22.25
ATOM    866  O    GLY A  113  0     0.937  42.333  19.593  1.00  20.55
ATOM    867  N    THR A  114  0    -0.817  42.173  18.186  1.00  20.91
ATOM    868  CA   THR A  114  0    -0.493  40.816  17.749  1.00  20.85
ATOM    869  C    THR A  114  0     0.296  40.774  16.471  1.00  18.04
ATOM    870  O    THR A  114  0     0.243  39.783  15.743  1.00  18.26
ATOM    871  CB   THR A  114  0    -1.847  40.095  17.487  1.00  23.93
ATOM    872  OG1  THR A  114  0    -2.609  40.910  16.554  1.00  25.68
ATOM    873  CG2  THR A  114  0    -2.571  39.928  18.792  1.00  23.72
ATOM    874  N    GLN A  115  0     1.023  41.819  16.095  1.00  17.04
```

APPENDIX 1-continued

| ATOM | 875 | CA | GLN A | 115 | 0 | 1.792 | 41.842 | 14.853 | 1.00 | 16.88 |
|---|---|---|---|---|---|---|---|---|---|---|
| ATOM | 876 | C | GLN A | 115 | 0 | 2.881 | 40.775 | 14.744 | 1.00 | 17.94 |
| ATOM | 877 | O | GLN A | 115 | 0 | 3.203 | 40.263 | 13.649 | 1.00 | 17.18 |
| ATOM | 878 | CB | GLN A | 115 | 0 | 2.391 | 43.244 | 14.757 | 1.00 | 17.55 |
| ATOM | 879 | CG | GLN A | 115 | 0 | 3.026 | 43.601 | 13.418 | 1.00 | 17.65 |
| ATOM | 880 | CD | GLN A | 115 | 0 | 3.558 | 45.024 | 13.418 | 1.00 | 17.73 |
| ATOM | 881 | OE1 | GLN A | 115 | 0 | 3.257 | 45.782 | 12.482 | 1.00 | 19.19 |
| ATOM | 882 | NE2 | GLN A | 115 | 0 | 4.334 | 45.421 | 14.422 | 1.00 | 14.70 |
| ATOM | 883 | N | TYR A | 116 | 0 | 3.515 | 40.416 | 15.881 | 1.00 | 16.32 |
| ATOM | 884 | CA | TYR A | 116 | 0 | 4.561 | 39.386 | 15.859 | 1.00 | 15.92 |
| ATOM | 885 | C | TYR A | 116 | 0 | 3.935 | 38.042 | 15.479 | 1.00 | 17.17 |
| ATOM | 886 | O | TYR A | 116 | 0 | 4.584 | 37.258 | 14.786 | 1.00 | 16.70 |
| ATOM | 887 | CB | TYR A | 116 | 0 | 5.411 | 39.312 | 17.096 | 1.00 | 13.45 |
| ATOM | 888 | CG | TYR A | 116 | 0 | 5.209 | 38.487 | 18.314 | 1.00 | 10.97 |
| ATOM | 889 | CD1 | TYR A | 116 | 0 | 5.581 | 37.146 | 18.394 | 1.00 | 11.02 |
| ATOM | 890 | CD2 | TYR A | 116 | 0 | 4.665 | 39.052 | 19.460 | 1.00 | 12.18 |
| ATOM | 891 | CE1 | TYR A | 116 | 0 | 5.364 | 36.399 | 19.532 | 1.00 | 10.02 |
| ATOM | 892 | CE2 | TYR A | 116 | 0 | 4.491 | 38.345 | 20.642 | 1.00 | 12.25 |
| ATOM | 893 | CZ | TYR A | 116 | 0 | 4.838 | 36.996 | 20.649 | 1.00 | 11.73 |
| ATOM | 894 | OH | TYR A | 116 | 0 | 4.642 | 36.295 | 21.821 | 1.00 | 12.72 |
| ATOM | 895 | N | CYS A | 117 | 0 | 2.654 | 37.829 | 15.842 | 1.00 | 17.70 |
| ATOM | 896 | CA | CYS A | 117 | 0 | 1.965 | 36.617 | 15.424 | 1.00 | 18.01 |
| ATOM | 897 | C | CYS A | 117 | 0 | 1.883 | 36.496 | 13.911 | 1.00 | 17.55 |
| ATOM | 898 | O | CYS A | 117 | 0 | 1.796 | 35.352 | 13.450 | 1.00 | 17.50 |
| ATOM | 899 | CB | CYS A | 117 | 0 | 0.565 | 36.528 | 16.042 | 1.00 | 17.90 |
| ATOM | 900 | SG | CYS A | 117 | 0 | 0.463 | 36.895 | 17.810 | 1.00 | 19.72 |
| ATOM | 901 | N | ASP A | 118 | 0 | 2.001 | 37.568 | 13.136 | 1.00 | 15.51 |
| ATOM | 902 | CA | ASP A | 118 | 0 | 1.953 | 37.509 | 11.696 | 1.00 | 17.74 |
| ATOM | 903 | C | ASP A | 118 | 0 | 3.341 | 37.445 | 11.061 | 1.00 | 18.72 |
| ATOM | 904 | O | ASP A | 118 | 0 | 3.494 | 37.770 | 9.865 | 1.00 | 17.47 |
| ATOM | 905 | CB | ASP A | 118 | 0 | 1.142 | 38.696 | 11.131 | 1.00 | 18.61 |
| ATOM | 906 | CG | ASP A | 118 | 0 | -0.356 | 38.448 | 11.378 | 1.00 | 21.44 |
| ATOM | 907 | OD1 | ASP A | 118 | 0 | -0.826 | 37.331 | 11.082 | 1.00 | 21.55 |
| ATOM | 908 | OD2 | ASP A | 118 | 0 | -1.064 | 39.333 | 11.885 | 1.00 | 21.54 |
| ATOM | 909 | N | GLY A | 119 | 0 | 4.355 | 37.095 | 11.882 | 1.00 | 18.19 |
| ATOM | 910 | CA | GLY A | 119 | 0 | 5.671 | 36.889 | 11.313 | 1.00 | 19.00 |
| ATOM | 911 | C | GLY A | 119 | 0 | 6.751 | 37.898 | 11.590 | 1.00 | 19.79 |
| ATOM | 912 | O | GLY A | 119 | 0 | 7.909 | 37.640 | 11.213 | 1.00 | 19.97 |
| ATOM | 913 | N | LEU A | 120 | 0 | 6.445 | 39.011 | 12.280 | 1.00 | 18.24 |
| ATOM | 914 | CA | LEU A | 120 | 0 | 7.484 | 39.991 | 12.569 | 1.00 | 16.08 |

APPENDIX 1-continued

| | | | | | | | | | | |
|---|---|---|---|---|---|---|---|---|---|---|
| ATOM | 915 | C | LEU | A | 120 | 0 | 8.210 | 39.565 | 13.848 | 1.00 16.53 |
| ATOM | 916 | O | LEU | A | 120 | 0 | 7.933 | 40.051 | 14.939 | 1.00 15.31 |
| ATOM | 917 | CB | LEU | A | 120 | 0 | 6.918 | 41.389 | 12.654 | 1.00 16.22 |
| ATOM | 918 | CG | LEU | A | 120 | 0 | 7.916 | 42.540 | 12.830 | 1.00 17.73 |
| ATOM | 919 | CD1 | LEU | A | 120 | 0 | 9.188 | 42.293 | 12.043 | 1.00 17.73 |
| ATOM | 920 | CD2 | LEU | A | 120 | 0 | 7.302 | 43.880 | 12.448 | 1.00 16.66 |
| ATOM | 921 | N | ARG | A | 121 | 0 | 9.144 | 38.622 | 13.682 | 1.00 14.23 |
| ATOM | 922 | CA | ARG | A | 121 | 0 | 9.859 | 37.985 | 14.773 | 1.00 14.19 |
| ATOM | 923 | C | ARG | A | 121 | 0 | 11.007 | 37.152 | 14.159 | 1.00 14.09 |
| ATOM | 924 | O | ARG | A | 121 | 0 | 10.936 | 36.787 | 12.978 | 1.00 13.72 |
| ATOM | 925 | CB | ARG | A | 121 | 0 | 8.934 | 37.061 | 15.581 | 1.00 12.30 |
| ATOM | 926 | CG | ARG | A | 121 | 0 | 8.253 | 35.999 | 14.728 | 1.00 12.44 |
| ATOM | 927 | CD | ARG | A | 121 | 0 | 7.303 | 35.098 | 15.518 | 1.00 11.94 |
| ATOM | 928 | NE | ARG | A | 121 | 0 | 6.507 | 34.269 | 14.604 | 1.00 12.92 |
| ATOM | 929 | CZ | ARG | A | 121 | 0 | 5.413 | 33.570 | 14.933 | 1.00 10.55 |
| ATOM | 930 | NH1 | ARG | A | 121 | 0 | 4.897 | 33.483 | 16.137 | 1.00 8.12 |
| ATOM | 931 | NH2 | ARG | A | 121 | 0 | 4.803 | 32.946 | 13.930 | 1.00 10.40 |
| ATOM | 932 | N | GLY | A | 122 | 0 | 12.045 | 36.848 | 14.937 | 1.00 12.29 |
| ATOM | 933 | CA | GLY | A | 122 | 0 | 13.162 | 36.078 | 14.364 | 1.00 11.42 |
| ATOM | 934 | C | GLY | A | 122 | 0 | 14.185 | 35.918 | 15.486 | 1.00 12.42 |
| ATOM | 935 | O | GLY | A | 122 | 0 | 14.095 | 36.604 | 16.509 | 1.00 11.47 |
| ATOM | 936 | N | PRO | A | 123 | 0 | 15.164 | 35.075 | 15.246 | 1.00 11.82 |
| ATOM | 937 | CA | PRO | A | 123 | 0 | 16.226 | 34.778 | 16.190 | 1.00 12.81 |
| ATOM | 938 | C | PRO | A | 123 | 0 | 17.288 | 35.857 | 16.258 | 1.00 12.41 |
| ATOM | 939 | O | PRO | A | 123 | 0 | 17.565 | 36.580 | 15.302 | 1.00 12.03 |
| ATOM | 940 | CB | PRO | A | 123 | 0 | 16.833 | 33.416 | 15.713 | 1.00 12.34 |
| ATOM | 941 | CG | PRO | A | 123 | 0 | 16.567 | 33.494 | 14.223 | 1.00 12.19 |
| ATOM | 942 | CD | PRO | A | 123 | 0 | 15.283 | 34.289 | 14.021 | 1.00 11.35 |
| ATOM | 943 | N | MET | A | 124 | 0 | 17.903 | 36.027 | 17.431 | 1.00 14.30 |
| ATOM | 944 | CA | MET | A | 124 | 0 | 18.959 | 37.024 | 17.628 | 1.00 14.19 |
| ATOM | 945 | C | MET | A | 124 | 0 | 2D.040 | 36.414 | 18.528 | 1.00 15.37 |
| ATOM | 946 | O | MET | A | 124 | 0 | 19.788 | 36.067 | 19.690 | 1.00 15.41 |
| ATOM | 947 | CB | MET | A | 124 | 0 | 18.411 | 38.290 | 18.242 | 1.00 15.94 |
| ATOM | 948 | CG | MET | A | 124 | 0 | 19.464 | 39.345 | 18.604 | 1.00 19.30 |
| ATOM | 949 | SD | MET | A | 124 | 0 | 18.646 | 40.875 | 19.164 | 1.00 21.94 |
| ATOM | 950 | CE | MET | A | 124 | 0 | 19.918 | 42.061 | 18.729 | 1.00 23.64 |
| ATOM | 951 | N | VAL | A | 125 | 0 | 21.212 | 36.178 | 17.939 | 1.00 13.74 |
| ATOM | 952 | CA | VAL | A | 125 | 0 | 22.282 | 35.479 | 18.658 | 1.00 13.87 |
| ATOM | 953 | C | VAL | A | 125 | 0 | 23.478 | 36.390 | 18.872 | 1.00 13.68 |

APPENDIX 1-continued

| ATOM | 954 | O | VAL A | 125 | 0 | 24.004 | 36.976 | 17.945 | 1.00 | 14.01 |
|------|-----|-----|-------|-----|---|--------|--------|--------|------|-------|
| ATOM | 955 | CB | VAL A | 125 | 0 | 22.672 | 34.139 | 18.005 | 1.00 | 12.58 |
| ATOM | 956 | CG1 | VAL A | 125 | 0 | 23.787 | 33.383 | 18.749 | 1.00 | 11.23 |
| ATOM | 957 | CG2 | VAL A | 125 | 0 | 21.448 | 33.212 | 18.033 | 1.00 | 12.14 |
| ATOM | 958 | N | ILE A | 126 | 0 | 23.860 | 36.535 | 20.135 | 1.00 | 14.48 |
| ATOM | 959 | CA | ILE A | 126 | 0 | 25.016 | 37.295 | 20.557 | 1.0D | 14.53 |
| ATOM | 960 | C | ILE A | 126 | 0 | 26.131 | 36.348 | 21.054 | 1.00 | 13.58 |
| ATOM | 961 | O | ILE A | 126 | 0 | 26.061 | 35.791 | 22.154 | 1.00 | 12.93 |
| ATOM | 962 | CB | ILE A | 126 | 0 | 24.649 | 38.295 | 21.662 | 1.00 | 14.95 |
| ATOM | 963 | CG1 | ILE A | 126 | 0 | 23.563 | 39.302 | 21.254 | 1.00 | 15.29 |
| ATOM | 964 | CG2 | ILE A | 126 | 0 | 25.901 | 39.014 | 22.174 | 1.00 | 14.24 |
| ATOM | 965 | CD1 | ILE A | 126 | 0 | 23.703 | 39.905 | 19.896 | 1.00 | 15.84 |
| ATOM | 966 | N | TYR A | 127 | 0 | 27.142 | 36.146 | 20.236 | 1.00 | 13.66 |
| ATOM | 967 | CA | TYR A | 127 | 0 | 28.278 | 35.258 | 20.529 | 1.00 | 14.62 |
| ATOM | 968 | C | TYR A | 127 | 0 | 29.328 | 35.778 | 21.507 | 1.00 | 15.97 |
| ATOM | 969 | O | TYR A | 127 | 0 | 29.626 | 36.977 | 21.669 | 1.00 | 15.27 |
| ATOM | 970 | CB | TYR A | 127 | 0 | 28.965 | 34.939 | 19.176 | 1.00 | 14.97 |
| ATOM | 971 | CG | TYR A | 127 | 0 | 28.057 | 34.136 | 18.272 | 1.00 | 16.10 |
| ATOM | 972 | CD1 | TYR A | 127 | 0 | 27.823 | 32.782 | 18.496 | 1.00 | 14.96 |
| ATOM | 973 | CD2 | TYR A | 127 | 0 | 27.428 | 34.753 | 17.177 | 1.00 | 16.64 |
| ATOM | 974 | CE1 | TYR A | 127 | 0 | 26.995 | 32.057 | 17.650 | 1.00 | 16.16 |
| ATOM | 975 | CE2 | TYR A | 127 | 0 | 26.576 | 34.039 | 16.356 | 1.00 | 17.32 |
| ATOM | 976 | CZ | TYR A | 127 | 0 | 26.374 | 32.692 | 16.592 | 1.00 | 18.16 |
| ATOM | 977 | OH | TYR A | 127 | 0 | 25.540 | 31.971 | 15.756 | 1.00 | 20.32 |
| ATOM | 978 | N | ASP A | 128 | 0 | 29.892 | 34.895 | 22.312 | 1.00 | 14.36 |
| ATOM | 979 | CA | ASP A | 128 | 0 | 30.825 | 35.269 | 23.365 | 1.00 | 16.80 |
| ATOM | 980 | C | ASP A | 128 | 0 | 32.222 | 34.863 | 22.939 | 1.00 | 20.11 |
| ATOM | 981 | O | ASP A | 128 | 0 | 32.508 | 33.656 | 22.777 | 1.00 | 21.41 |
| ATOM | 982 | CB | ASP A | 128 | 0 | 30.398 | 34.568 | 24.649 | 1.00 | 16.65 |
| ATOM | 983 | CG | ASP A | 128 | 0 | 31.136 | 35.055 | 25.874 | 1.00 | 18.36 |
| ATOM | 984 | OD1 | ASP A | 128 | 0 | 32.194 | 35.708 | 25.750 | 1.00 | 18.72 |
| ATOM | 985 | OD2 | ASP A | 128 | 0 | 30.710 | 34.819 | 27.024 | 1.00 | 20.03 |
| ATOM | 986 | N | ASP A | 129 | 0 | 33.148 | 35.798 | 22.771 | 1.00 | 22.30 |
| ATOM | 987 | CA | ASP A | 129 | 0 | 34.511 | 35.389 | 22.377 | 1.00 | 24.39 |
| ATOM | 988 | C | ASP A | 129 | 0 | 35.282 | 34.740 | 23.509 | 1.00 | 22.47 |
| ATOM | 989 | O | ASP A | 129 | 0 | 36.275 | 34.096 | 23.209 | 1.00 | 23.18 |
| ATOM | 990 | CB | ASP A | 129 | 0 | 35.298 | 36.490 | 21.707 | 1.00 | 28.46 |
| ATOM | 991 | CG | ASP A | 129 | 0 | 35.372 | 37.764 | 22.516 | 1.00 | 31.10 |
| ATOM | 992 | OD1 | ASP A | 129 | 0 | 35.254 | 37.652 | 23.747 | 1.00 | 32.87 |
| ATOM | 993 | OD2 | ASP A | 129 | 0 | 35.553 | 38.824 | 21.891 | 1.00 | 34.70 |

APPENDIX 1-continued

| ATOM | 994 | N | ASN A | 130 | 0 | 34.829 | 34.684 | 24.736 | 1.00 | 21.92 |
| --- | --- | --- | --- | --- | --- | --- | --- | --- | --- | --- |
| ATOM | 995 | CA | ASN A | 130 | 0 | 35.368 | 34.015 | 25.874 | 1.00 | 23.74 |
| ATOM | 996 | C | ASN A | 130 | 0 | 34.382 | 32.976 | 26.417 | 1.00 | 23.02 |
| ATOM | 997 | O | ASN A | 130 | 0 | 34.352 | 32.684 | 27.616 | 1.00 | 20.14 |
| ATOM | 998 | CB | ASN A | 130 | 0 | 35.686 | 35.002 | 27.028 | 1.00 | 26.41 |
| ATOM | 999 | CG | ASN A | 130 | 0 | 36.583 | 36.127 | 26.550 | 1.00 | 30.99 |
| ATOM | 1000 | OD1 | ASN A | 130 | 0 | 36.187 | 37.309 | 26.486 | 1.00 | 33.20 |
| ATOM | 1001 | ND2 | ASN A | 130 | 0 | 37.818 | 35.769 | 26.175 | 1.00 | 30.96 |
| ATOM | 1002 | N | ASP A | 131 | 0 | 33.533 | 32.401 | 25.561 | 1.00 | 23.32 |
| ATOM | 1003 | CA | ASP A | 131 | 0 | 32.476 | 31.543 | 26.127 | 1.00 | 21.63 |
| ATOM | 1004 | C | ASP A | 131 | 0 | 33.010 | 30.514 | 27.103 | 1.00 | 19.56 |
| ATOM | 1005 | O | ASP A | 131 | 0 | 33.704 | 29.569 | 26.766 | 1.00 | 19.71 |
| ATOM | 1006 | CB | ASP A | 131 | 0 | 31.594 | 30.877 | 25.063 | 1.00 | 22.97 |
| ATOM | 1007 | CG | ASP A | 131 | 0 | 30.220 | 30.487 | 25.591 | 1.00 | 24.48 |
| ATOM | 1008 | OD1 | ASP A | 131 | 0 | 30.181 | 29.525 | 26.397 | 1.00 | 26.42 |
| ATOM | 1009 | OD2 | ASP A | 131 | 0 | 29.166 | 31.051 | 25.212 | 1.00 | 22.66 |
| ATOM | 1010 | N | PRO A | 132 | 0 | 32.491 | 30.548 | 28.315 | 1.00 | 18.77 |
| ATOM | 1011 | CA | PRO A | 132 | 0 | 32.759 | 29.611 | 29.381 | 1.00 | 19.41 |
| ATOM | 1012 | C | PRO A | 132 | 0 | 32.523 | 28.141 | 29.031 | 1.00 | 20.89 |
| ATOM | 1013 | O | PRO A | 132 | 0 | 33.112 | 27.250 | 29.672 | 1.00 | 19.99 |
| ATOM | 1014 | CB | PRO A | 132 | 0 | 31.799 | 29.990 | 30.531 | 1.00 | 18.42 |
| ATOM | 1015 | CG | PRO A | 132 | 0 | 31.589 | 31.470 | 30.263 | 1.00 | 16.87 |
| ATOM | 1016 | CD | PRO A | 132 | 0 | 31.645 | 31.673 | 28.778 | 1.00 | 16.73 |
| ATOM | 1017 | N | HIS A | 133 | 0 | 31.668 | 27.836 | 28.063 | 1.00 | 19.47 |
| ATOM | 1018 | CA | HIS A | 133 | 0 | 31.331 | 26.465 | 27.700 | 1.00 | 18.79 |
| ATOM | 1019 | C | HIS A | 133 | 0 | 31.887 | 26.014 | 26.372 | 1.00 | 19.35 |
| ATOM | 1020 | O | HIS A | 133 | 0 | 31.503 | 24.954 | 25.826 | 1.00 | 18.60 |
| ATOM | 1021 | CB | HIS A | 133 | 0 | 29.789 | 26.428 | 27.536 | 1.00 | 18.91 |
| ATOM | 1022 | CG | HIS A | 133 | 0 | 29.065 | 26.242 | 28.815 | 1.00 | 18.13 |
| ATOM | 1023 | ND1 | HIS A | 133 | 0 | 29.566 | 25.551 | 29.877 | 1.00 | 19.52 |
| ATOM | 1024 | CD2 | HIS A | 133 | 0 | 27.817 | 26.625 | 29.183 | 1.00 | 19.38 |
| ATOM | 1025 | CE1 | HIS A | 133 | 0 | 28.679 | 25.530 | 30.855 | 1.00 | 20.08 |
| ATOM | 1026 | NE2 | HIS A | 133 | 0 | 27.587 | 26.180 | 30.457 | 1.00 | 19.60 |
| ATOM | 1027 | N | ALA A | 134 | 0 | 32.840 | 26.801 | 25.852 | 1.00 | 19.40 |
| ATOM | 1028 | CA | ALA A | 134 | 0 | 33.413 | 26.465 | 24.552 | 1.00 | 21.88 |
| ATOM | 1029 | C | ALA A | 134 | 0 | 34.080 | 25.107 | 24.525 | 1.00 | 21.69 |
| ATOM | 1030 | O | ALA A | 134 | 0 | 34.120 | 24.514 | 23.439 | 1.00 | 21.61 |
| ATOM | 1031 | CB | ALA A | 134 | 0 | 34.418 | 27.548 | 24.128 | 1.00 | 22.55 |
| ATOM | 1032 | N | ALA A | 135 | 0 | 34.582 | 24.527 | 25.622 | 1.00 | 21.96 |

APPENDIX 1-continued

| ATOM | 1033 | CA  | ALA | A | 135 | 0 | 35.178 | 23.192 | 25.483 | 1.00 | 23.53 |
|------|------|-----|-----|---|-----|---|--------|--------|--------|------|-------|
| ATOM | 1034 | C   | ALA | A | 135 | 0 | 34.144 | 22.096 | 25.232 | 1.00 | 24.47 |
| ATOM | 1035 | O   | ALA | A | 135 | 0 | 34.488 | 20.936 | 24.989 | 1.00 | 24.77 |
| ATOM | 1036 | CB  | ALA | A | 135 | 0 | 35.910 | 22.820 | 26.776 | 1.00 | 21.92 |
| ATOM | 1037 | N   | LEU | A | 136 | 0 | 32.862 | 22.375 | 25.457 | 1.00 | 24.95 |
| ATOM | 1038 | CA  | LEU | A | 136 | 0 | 31.800 | 21.376 | 25.404 | 1.00 | 23.15 |
| ATOM | 1039 | C   | LEU | A | 136 | 0 | 31.284 | 21.076 | 24.016 | 1.00 | 20.31 |
| ATOM | 1040 | O   | LEU | A | 136 | 0 | 30.609 | 20.054 | 23.924 | 1.00 | 19.62 |
| ATOM | 1041 | CB  | LEU | A | 136 | 0 | 30.665 | 21.845 | 26.318 | 1.00 | 24.43 |
| ATOM | 1042 | CG  | LEU | A | 136 | 0 | 30.501 | 21.211 | 27.686 | 1.00 | 27.55 |
| ATOM | 1043 | CD1 | LEU | A | 136 | 0 | 31.803 | 20.721 | 28.285 | 1.00 | 25.75 |
| ATOM | 1044 | CD2 | LEU | A | 136 | 0 | 29.747 | 22.129 | 28.644 | 1.00 | 26.92 |
| ATOM | 1045 | N   | TYR | A | 137 | 0 | 31.565 | 21.888 | 22.998 | 1.00 | 17.05 |
| ATOM | 1046 | CA  | TYR | A | 137 | 0 | 31.085 | 21.612 | 21.662 | 1.00 | 16.65 |
| ATOM | 1047 | C   | TYR | A | 137 | 0 | 32.076 | 22.054 | 20.599 | 1.00 | 17.99 |
| ATOM | 1048 | O   | TYR | A | 137 | 0 | 32.965 | 22.891 | 20.794 | 1.00 | 18.69 |
| ATOM | 1049 | CB  | TYR | A | 137 | 0 | 29.724 | 22.319 | 21.402 | 1.00 | 16.73 |
| ATOM | 1050 | CG  | TYR | A | 137 | 0 | 29.711 | 23.760 | 21.857 | 1.00 | 16.24 |
| ATOM | 1051 | CD1 | TYR | A | 137 | 0 | 29.302 | 24.108 | 23.150 | 1.00 | 16.00 |
| ATOM | 1052 | CD2 | TYR | A | 137 | 0 | 30.159 | 24.754 | 21.001 | 1.00 | 14.76 |
| ATOM | 1053 | CE1 | TYR | A | 137 | 0 | 29.355 | 25.448 | 23.551 | 1.00 | 15.32 |
| ATOM | 1054 | CE2 | TYR | A | 137 | 0 | 30.165 | 26.081 | 21.396 | 1.00 | 15.52 |
| ATOM | 1055 | CZ  | TYR | A | 137 | 0 | 29.759 | 26.410 | 22.675 | 1.00 | 15.61 |
| ATOM | 1056 | OH  | TYR | A | 137 | 0 | 29.782 | 27.731 | 23.055 | 1.00 | 17.56 |
| ATOM | 1057 | N   | ASP | A | 138 | 0 | 31.903 | 21.549 | 19.393 | 1.00 | 19.04 |
| ATOM | 1058 | CA  | ASP | A | 138 | 0 | 32.733 | 21.859 | 18.253 | 1.00 | 20.02 |
| ATOM | 1059 | C   | ASP | A | 138 | 0 | 32.139 | 22.933 | 17.364 | 1.00 | 21.05 |
| ATOM | 1060 | O   | ASP | A | 138 | 0 | 32.911 | 23.553 | 16.631 | 1.00 | 21.98 |
| ATOM | 1061 | CB  | ASP | A | 138 | 0 | 32.836 | 20.628 | 17.315 | 1.00 | 20.66 |
| ATOM | 1062 | CG  | ASP | A | 138 | 0 | 33.355 | 19.455 | 18.089 | 1.00 | 22.79 |
| AT0M | 1063 | OD1 | ASP | A | 138 | 0 | 32.744 | 18.404 | 18.318 | 1.00 | 24.88 |
| ATOM | 1064 | OD2 | ASP | A | 138 | 0 | 34.481 | 19.675 | 18.581 | 1.00 | 25.34 |
| ATOM | 1065 | N   | GLU | A | 139 | 0 | 30.825 | 22.957 | 17.184 | 1.00 | 19.73 |
| ATOM | 1066 | CA  | GLU | A | 139 | 0 | 30.223 | 23.865 | 16.213 | 1.00 | 21.27 |
| ATOM | 1067 | C   | GLU | A | 139 | 0 | 29.086 | 24.668 | 16.825 | 1.00 | 18.97 |
| ATOM | 1068 | O   | GLU | A | 139 | 0 | 28.306 | 24.143 | 17.608 | 1.00 | 16.95 |
| ATOM | 1069 | CB  | GLU | A | 139 | 0 | 29.617 | 23.164 | 15.000 | 1.00 | 24.71 |
| ATOM | 1070 | CG  | GLU | A | 139 | 0 | 30.509 | 22.149 | 14.311 | 1.00 | 30.89 |
| ATOM | 1071 | CD  | GLU | A | 139 | 0 | 31.633 | 22.868 | 13.587 | 1.00 | 34.42 |
| ATOM | 1072 | OE1 | GLU | A | 139 | 0 | 31.340 | 23.869 | 12.898 | 1.00 | 36.87 |

APPENDIX 1-continued

| ATOM | 1073 | OE2 | GLU A | 139 | 0 | 32.794 | 22.457 | 13.705 | 1.00 | 37.60 |
| --- | --- | --- | --- | --- | --- | --- | --- | --- | --- | --- |
| ATOM | 1074 | N | ASP A | 140 | 0 | 29.057 | 25.933 | 16.408 | 1.00 | 19.38 |
| ATOM | 1075 | CA | ASP A | 140 | 0 | 28.026 | 26.847 | 16.912 | 1.00 | 17.89 |
| ATOM | 1076 | C | ASP A | 140 | 0 | 27.858 | 27.901 | 15.837 | 1.00 | 18.87 |
| ATOM | 1077 | O | ASP A | 140 | 0 | 28.705 | 28.780 | 15.768 | 1.00 | 21.31 |
| ATOM | 1078 | CB | ASP A | 140 | 0 | 28.438 | 27.399 | 18.268 | 1.00 | 16.26 |
| ATOM | 1079 | CG | ASP A | 140 | 0 | 27.445 | 28.399 | 18.858 | 1.00 | 16.73 |
| ATOM | 1080 | OD1 | ASP A | 140 | 0 | 27.854 | 29.143 | 19.781 | 1.00 | 14.86 |
| ATOM | 1081 | OD2 | ASP A | 140 | 0 | 26.287 | 28.446 | 18.401 | 1.00 | 13.82 |
| ATOM | 1082 | N | ASP A | 141 | 0 | 26.862 | 27.844 | 14.972 | 1.00 | 17.34 |
| ATOM | 1083 | CA | ASP A | 141 | 0 | 26.750 | 28.859 | 13.937 | 1.00 | 19.52 |
| ATOM | 1084 | C | ASP A | 141 | 0 | 25.301 | 29.031 | 13.520 | 1.00 | 19.33 |
| ATOM | 1085 | O | ASP A | 141 | 0 | 24.342 | 28.513 | 14.115 | 1.00 | 17.91 |
| ATOM | 1086 | CB | ASP A | 141 | 0 | 27.681 | 28.509 | 12.772 | 1.00 | 21.66 |
| ATOM | 1087 | CG | ASP A | 141 | 0 | 27.384 | 27.151 | 12.193 | 1.00 | 24.87 |
| ATOM | 1088 | OD1 | ASP A | 141 | 0 | 28.280 | 26.521 | 11.567 | 1.00 | 28.90 |
| ATOM | 1089 | OD2 | ASP A | 141 | 0 | 26.271 | 26.604 | 12.302 | 1.00 | 25.89 |
| ATOM | 1090 | N | GLU A | 142 | 0 | 25.102 | 29.688 | 12.387 | 1.00 | 19.21 |
| ATOM | 1091 | CA | GLU A | 142 | 0 | 23.775 | 29.945 | 11.880 | 1.00 | 20.84 |
| ATOM | 1092 | C | GLU A | 142 | 0 | 23.052 | 28.636 | 11.592 | 1.00 | 19.95 |
| ATOM | 1093 | O | GLU A | 142 | 0 | 21.844 | 28.656 | 11.665 | 1.00 | 18.73 |
| ATOM | 1094 | CB | GLU A | 142 | 0 | 23.771 | 30.894 | 10.699 | 1.00 | 23.40 |
| ATOM | 1095 | CG | GLU A | 142 | 0 | 24.295 | 30.301 | 9.407 | 1.00 | 27.22 |
| ATOM | 1096 | CD | GLU A | 142 | 0 | 25.718 | 30.826 | 9.221 | 1.00 | 32.36 |
| ATOM | 1097 | OE1 | GLU A | 142 | 0 | 26.513 | 30.920 | 10.206 | 1.00 | 31.87 |
| ATOM | 1098 | OE2 | GLU A | 142 | 0 | 25.968 | 31.136 | 8.023 | 1.00 | 35.76 |
| ATOM | 1099 | N | ASN A | 143 | 0 | 23.723 | 27.508 | 11.378 | 1.00 | 20.40 |
| ATOM | 1100 | CA | ASN A | 143 | 0 | 23.105 | 26.227 | 11.151 | 1.00 | 19.61 |
| ATOM | 1101 | C | ASN A | 143 | 0 | 22.785 | 25.468 | 12.421 | 1.00 | 18.35 |
| ATOM | 1102 | O | ASN A | 143 | 0 | 22.317 | 24.337 | 12.325 | 1.00 | 15.65 |
| ATOM | 1103 | CB | ASN A | 143 | 0 | 24.024 | 25.401 | 10.229 | 1.00 | 23.57 |
| ATOM | 1104 | CG | ASN A | 143 | 0 | 24.133 | 26.067 | 8.857 | 1.00 | 26.63 |
| ATOM | 1105 | OD1 | ASN A | 143 | 0 | 25.220 | 26.376 | 8.356 | 1.00 | 29.89 |
| ATOM | 1106 | ND2 | ASN A | 143 | 0 | 23.049 | 26.342 | 8.175 | 1.00 | 25.46 |
| ATOM | 1107 | N | THR A | 144 | 0 | 23.067 | 25.974 | 13.632 | 1.00 | 16.76 |
| ATOM | 1108 | CA | THR A | 144 | 0 | 22.678 | 25.257 | 14.825 | 1.00 | 15.40 |
| ATOM | 1109 | C | THR A | 144 | 0 | 21.556 | 25.976 | 15.577 | 1.00 | 15.58 |
| ATOM | 1110 | O | THR A | 144 | 0 | 21.361 | 25.776 | 16.789 | 1.00 | 17.88 |
| ATOM | 1111 | CB | THR A | 144 | 0 | 23.848 | 25.018 | 15.785 | 1.00 | 16.43 |

APPENDIX 1-continued

| ATOM | 1112 | OG1 | THR | A | 144 | 0 | 24.296 | 26.270 | 16.297 | 1.00 | 14.82 |
|------|------|-----|-----|---|-----|---|--------|--------|--------|------|-------|
| ATOM | 1113 | CG2 | THR | A | 144 | 0 | 24.935 | 24.215 | 15.104 | 1.00 | 15.98 |
| ATOM | 1114 | N | ILE | A | 145 | 0 | 20.821 | 26.834 | 14.898 | 1.00 | 13.92 |
| ATOM | 1115 | CA | ILE | A | 145 | 0 | 19.697 | 27.550 | 15.500 | 1.00 | 14.31 |
| ATOM | 1116 | C | ILE | A | 145 | 0 | 18.392 | 26.835 | 15.139 | 1.00 | 13.84 |
| ATOM | 1117 | O | ILE | A | 145 | 0 | 18.127 | 26.478 | 13.996 | 1.00 | 12.32 |
| ATOM | 1118 | CB | ILE | A | 145 | 0 | 19.641 | 29.016 | 15.011 | 1.00 | 15.15 |
| ATOM | 1119 | CG1 | ILE | A | 145 | 0 | 20.881 | 29.726 | 15.608 | 1.00 | 16.27 |
| ATOM | 1120 | CG2 | ILE | A | 145 | 0 | 18.346 | 29.736 | 15.375 | 1.00 | 13.14 |
| ATOM | 1121 | CD1 | ILE | A | 145 | 0 | 21.256 | 31.006 | 14.892 | 1.00 | 16.72 |
| ATOM | 1122 | N | ILE | A | 146 | 0 | 17.550 | 26.644 | 16.141 | 1.00 | 13.54 |
| ATOM | 1123 | CA | ILE | A | 146 | 0 | 16.263 | 25.983 | 15.926 | 1.00 | 13.70 |
| ATOM | 1124 | C | ILE | A | 146 | 0 | 15.167 | 26.899 | 16.494 | 1.00 | 12.67 |
| ATOM | 1125 | O | ILE | A | 146 | 0 | 15.155 | 27.082 | 17.714 | 1.00 | 10.09 |
| ATOM | 1126 | CB | ILE | A | 146 | 0 | 16.183 | 24.580 | 16.553 | 1.00 | 15.97 |
| ATOM | 1127 | CG1 | ILE | A | 146 | 0 | 17.280 | 23.621 | 16.012 | 1.00 | 17.29 |
| ATOM | 1128 | CG2 | ILE | A | 146 | 0 | 14.831 | 23.937 | 16.207 | 1.00 | 14.52 |
| ATOM | 1129 | CD1 | ILE | A | 146 | 0 | 17.359 | 22.340 | 16.832 | 1.00 | 18.45 |
| ATOM | 1130 | N | THR | A | 147 | 0 | 14.360 | 27.507 | 15.610 | 1.00 | 10.81 |
| ATOM | 1131 | CA | THR | A | 147 | 0 | 13.240 | 28.310 | 16.102 | 1.00 | 12.54 |
| ATOM | 1132 | C | THR | A | 147 | 0 | 11.912 | 27.526 | 15.988 | 1.00 | 13.55 |
| ATOM | 1133 | O | THR | A | 147 | 0 | 11.655 | 26.724 | 15.076 | 1.00 | 12.65 |
| ATOM | 1134 | CB | THR | A | 147 | 0 | 13.078 | 29.642 | 15.351 | 1.00 | 12.37 |
| ATOM | 1135 | OG1 | THR | A | 147 | 0 | 12.728 | 29.311 | 14.005 | 1.00 | 10.17 |
| ATOM | 1136 | CG2 | THR | A | 147 | 0 | 14.381 | 30.479 | 15.402 | 1.00 | 11.93 |
| ATOM | 1137 | N | LEU | A | 148 | 0 | 11.062 | 27.715 | 16.972 | 1.00 | 12.48 |
| ATOM | 1138 | CA | LEU | A | 148 | 0 | 9.719 | 27.171 | 17.039 | 1.00 | 13.90 |
| ATOM | 1139 | C | LEU | A | 148 | 0 | 8.719 | 28.350 | 16.916 | 1.00 | 15.44 |
| ATOM | 1140 | O | LEU | A | 148 | 0 | 8.860 | 29.383 | 17.579 | 1.00 | 15.28 |
| ATOM | 1141 | CB | LEU | A | 148 | 0 | 9.501 | 26.419 | 18.340 | 1.00 | 12.83 |
| ATOM | 1142 | CG | LEU | A | 148 | 0 | 10.502 | 25.293 | 18.669 | 1.00 | 12.45 |
| ATOM | 1143 | CD1 | LEU | A | 148 | 0 | 10.154 | 24.669 | 19.997 | 1.00 | 11.49 |
| ATOM | 1144 | CD2 | LEU | A | 148 | 0 | 10.552 | 24.203 | 17.597 | 1.00 | 11.82 |
| ATOM | 1145 | N | ALA | A | 149 | 0 | 7.726 | 28.241 | 16.053 | 1.00 | 14.08 |
| ATOM | 1146 | CA | ALA | A | 149 | 0 | 6.725 | 29.256 | 15.825 | 1.00 | 15.37 |
| ATOM | 1147 | C | ALA | A | 149 | 0 | 5.336 | 28.658 | 15.521 | 1.00 | 16.78 |
| ATOM | 1148 | O | ALA | A | 149 | 0 | 5.198 | 27.637 | 14.841 | 1.00 | 15.78 |
| ATOM | 1149 | CB | ALA | A | 149 | 0 | 7.068 | 30.127 | 14.628 | 1.00 | 13.22 |
| ATOM | 1150 | N | ASP | A | 150 | 0 | 4.337 | 29.344 | 16.065 | 1.00 | 16.39 |
| ATOM | 1151 | CA | ASP | A | 150 | 0 | 2.941 | 28.995 | 15.864 | 1.00 | 15.96 |

APPENDIX 1-continued

| ATOM | 1152 | C | ASP A | 150 | 0 | 2.515 | 29.758 | 14.624 | 1.00 | 16.53 |
|---|---|---|---|---|---|---|---|---|---|---|
| ATOM | 1153 | O | ASP A | 150 | 0 | 2.960 | 30.905 | 14.483 | 1.00 | 18.17 |
| ATOM | 1154 | CB | ASP A | 150 | 0 | 2.066 | 29.440 | 17.027 | 1.00 | 16.78 |
| ATOM | 1155 | CG | ASP A | 150 | 0 | 2.345 | 30.836 | 17.561 | 1.00 | 18.15 |
| ATOM | 1156 | OD1 | ASP A | 150 | 0 | 3.410 | 31.472 | 17.347 | 1.00 | 16.29 |
| ATOM | 1157 | OD2 | ASP A | 150 | 0 | 1.414 | 31.311 | 18.264 | 1.00 | 17.83 |
| ATOM | 1158 | N | TRP A | 151 | 0 | 1.776 | 29.157 | 13.726 | 1.00 | 15.62 |
| ATOM | 1159 | CA | TRP A | 151 | 0 | 1.366 | 29.828 | 12.499 | 1.00 | 14.37 |
| ATOM | 1160 | C | TRP A | 151 | 0 | -0.140 | 29.688 | 12.226 | 1.00 | 14.78 |
| ATOM | 1161 | O | TRP A | 151 | 0 | -0.679 | 28.607 | 12.425 | 1.00 | 13.41 |
| ATOM | 1162 | CB | TRP A | 151 | 0 | 2.229 | 29.239 | 11.373 | 1.00 | 13.56 |
| ATOM | 1163 | CG | TRP A | 151 | 0 | 2.046 | 30.004 | 10.097 | 1.00 | 13.31 |
| ATOM | 1164 | CD1 | TRP A | 151 | 0 | 1.385 | 29.545 | 8.991 | 1.00 | 13.60 |
| ATOM | 1165 | CD2 | TRP A | 151 | 0 | 2.484 | 31.316 | 9.806 | 1.00 | 15.46 |
| ATOM | 1166 | NE1 | TRP A | 151 | 0 | 1.412 | 30.497 | 8.017 | 1.00 | 14.49 |
| ATOM | 1167 | CE2 | TRP A | 151 | 0 | 2.061 | 31.605 | 8.473 | 1.00 | 15.53 |
| ATOM | 1168 | CE3 | TRP A | 151 | 0 | 3.189 | 32.294 | 10.522 | 1.00 | 16.28 |
| ATOM | 1169 | CZ2 | TRP A | 151 | 0 | 2.306 | 32.822 | 7.846 | 1.00 | 16.57 |
| ATOM | 1170 | CZ3 | TRP A | 151 | 0 | 3.436 | 33.505 | 9.881 | 1.00 | 18.22 |
| ATOM | 1171 | CH2 | TRP A | 151 | 0 | 3.003 | 33.766 | 8.560 | 1.00 | 18.00 |
| ATOM | 1172 | N | TYR A | 152 | 0 | -0.818 | 30.745 | 11.812 | 1.00 | 15.59 |
| ATOM | 1173 | CA | TYR A | 152 | 0 | -2.266 | 30.813 | 11.614 | 1.00 | 17.47 |
| ATOM | 1174 | C | TYR A | 152 | 0 | -2.556 | 31.086 | 10.149 | 1.00 | 18.79 |
| ATOM | 1175 | O | TYR A | 152 | 0 | -1.830 | 31.856 | 9.521 | 1.00 | 19.15 |
| ATOM | 1176 | CB | TYR A | 152 | 0 | -2.981 | 31.930 | 12.434 | 1.00 | 16.37 |
| ATOM | 1177 | CG | TYR A | 152 | 0 | -2.539 | 31.776 | 13.887 | 1.00 | 16.24 |
| ATOM | 1178 | CD1 | TYR A | 152 | 0 | -1.313 | 32.303 | 14.318 | 1.00 | 15.22 |
| ATOM | 1179 | CD2 | TYR A | 152 | 0 | -3.267 | 30.998 | 14.767 | 1.00 | 15.29 |
| ATOM | 1180 | CE1 | TYR A | 152 | 0 | -0.889 | 32.135 | 15.626 | 1.00 | 14.67 |
| ATOM | 1181 | CE2 | TYR A | 152 | 0 | -2.831 | 30.799 | 16.054 | 1.00 | 16.52 |
| ATOM | 1182 | CZ | TYR A | 152 | 0 | -1.632 | 31.369 | 16.474 | 1.00 | 16.12 |
| ATOM | 1183 | OH | TYR A | 152 | 0 | -1.219 | 31.139 | 17.771 | 1.00 | 16.36 |
| ATOM | 1184 | N | HIS A | 153 | 0 | -3.590 | 30.445 | 9.599 | 1.00 | 20.39 |
| ATOM | 118S | CA | HIS A | 153 | 0 | -3.899 | 30.683 | 8.181 | 1.00 | 21.90 |
| ATOM | 1186 | C | HIS A | 153 | 0 | -4.642 | 31.988 | 7.952 | 1.00 | 21.94 |
| ATOM | 1187 | O | HIS A | 153 | 0 | -4.750 | 32.386 | 6.784 | 1.00 | 22.32 |
| ATOM | 1188 | CB | HIS A | 153 | 0 | -4.592 | 29.483 | 7.549 | 1.00 | 22.29 |
| ATOM | 1189 | CG | HIS A | 153 | 0 | -3.651 | 28.319 | 7.385 | 1.00 | 24.52 |
| ATOM | 1190 | ND1 | HIS A | 153 | 0 | -4.071 | 27.022 | 7.258 | 1.00 | 24.25 |

APPENDIX 1-continued

```
ATOM   1191  CD2  HIS A  153  0   -2.286  28.274   7.338  1.00  23.32
ATOM   1192  CE1  HIS A  153  0   -3.034  26.220   7.124  1.00  24.15
ATOM   1193  NE2  HIS A  153  0   -1.956  26.965   7.178  1.00  24.30
ATOM   1194  N    ILE A  154  0   -5.084  32.718   8.972  1.00  21.86
ATOM   1195  CA   ILE A  154  0   -5.611  34.046   8.686  1.00  24.39
ATOM   1196  C    ILE A  154  0   -4.904  35.051   9.597  1.00  22.15
ATOM   1197  O    ILE A  154  0   -4.517  34.732  10.698  1.00  20.15
ATOM   1198  CB   ILE A  154  0   -7.120  34.281   8.693  1.00  26.43
ATOM   1199  CG1  ILE A  154  0   -7.682  34.498  10.099  1.00  27.66
ATOM   1200  CG2  ILE A  154  0   -7.947  33.251   7.928  1.00  26.60
ATOM   1201  CD1  ILE A  154  0   -7.312  33.468  11.125  1.00  28.86
ATOM   1202  N    PRO A  155  0   -4.723  36.255   9.105  1.00  23.79
ATOM   1203  CA   PRO A  155  0   -4.108  37.361   9.816  1.00  23.66
ATOM   1204  C    PRO A  155  0   -4.604  37.435  11.252  1.00  24.59
ATOM   1205  O    PRO A  155  0   -5.814  37.317  11.539  1.00  24.53
ATOM   1206  CB   PRO A  155  0   -4.546  38.634   9.077  1.00  24.20
ATOM   1207  CG   PRO A  155  0   -4.990  38.162   7.733  1.00  23.40
ATOM   1208  CD   PRO A  155  0   -5.207  36.672   7.776  1.00  23.41
ATOM   1209  N    ALA A  156  0   -3.704  37.776  12.178  1.00  24.03
ATOM   1210  CA   ALA A  156  0   -4.066  37.806  13.588  1.00  25.45
ATOM   1211  C    ALA A  156  0   -5.262  38.667  13.992  1.00  24.85
ATOM   1212  O    ALA A  156  0   -6.083  38.217  14.798  1.00  22.79
ATOM   1213  CB   ALA A  156  0   -2.866  38.045  14.492  1.00  24.30
ATOM   1214  N    PRO A  157  0   -5.393  39.873  13.518  1.00  25.98
ATOM   1215  CA   PRO A  157  0   -6.521  40.741  13.807  1.00  28.77
ATOM   1216  C    PRO A  157  0   -7.840  40.092  13.406  1.00  30.78
ATOM   1217  O    PRO A  157  0   -8.798  40.416  14.105  1.00  34.62
ATOM   1218  CB   PRO A  157  0   -6.324  42.071  13.068  1.00  26.56
ATOM   1219  CG   PRO A  157  0   -4.859  42.013  12.762  1.00  25.98
ATOM   1220  CD   PRO A  157  0   -4.480  40.547  12.585  1.00  25.96
ATOM   1221  N    SER A  158  0   -7.950  39.207  12.430  1.00  30.95
ATOM   1222  CA   SER A  158  0   -9.174  38.549  12.047  1.00  31.32
ATOM   1223  C    SER A  158  0   -9.450  37.288  12.851  1.00  33.61
ATOM   1224  O    SER A  158  0  -10.472  36.633  12.575  1.00  34.71
ATOM   1225  CB   SER A  158  0   -9.176  38.118  10.577  1.00  30.14
ATOM   1226  OG   SER A  158  0   -8.942  39.187   9.665  1.00  31.20
ATOM   1227  N    ILE A  159  0   -8.588  36.875  13.773  1.00  34.23
ATOM   1228  CA   ILE A  159  0   -8.918  35.642  14.491  1.00  36.40
ATOM   1229  C    ILE A  159  0  -10.189  35.896  15.309  1.00  39.20
ATOM   1230  O    ILE A  159  0  -10.294  36.875  16.046  1.00  39.00
```

APPENDIX 1-continued

```
ATOM   1231  CB   ILE A  159  0   -7.769  35.121  15.360  1.00  35.56
ATOM   1232  CG1  ILE A  159  0   -6.713  34.408  14.485  1.00  35.58
ATOM   1233  CG2  ILE A  159  0   -8.262  34.184  16.452  1.00  34.97
ATOM   1234  CD1  ILE A  159  0   -5.388  34.268  15.212  1.00  34.91
ATOM   1235  N    GLN A  160  0  -11.137  34.969  15.196  1.00  41.53
ATOM   1236  CA   GLN A  160  0  -12.398  35.056  15.946  1.00  42.57
ATOM   1237  C    GLN A  160  0  -12.466  33.914  16.949  1.00  40.51
ATOM   1238  O    GLN A  160  0  -12.308  32.741  16.585  1.00  41.96
ATOM   1239  CB   GLN A  160  0  -13.542  35.062  14.937  1.00  45.52
ATOM   1240  CG   GLN A  160  0  -14.814  34.319  15.267  1.00  48.48
ATOM   1241  CD   GLN A  160  0  -15.570  33.799  14.055  1.00  50.12
ATOM   1242  OE1  GLN A  160  0  -16.204  32.737  14.118  1.00  50.77
ATOM   1243  NE2  GLN A  160  0  -15.504  34.520  12.940  1.00  51.22
ATOM   1244  N    GLY A  161  0  -12.667  34.191  18.225  1.00  37.10
ATOM   1245  CA   GLY A  161  0  -12.722  33.112  19.208  1.00  34.91
ATOM   1246  C    GLY A  161  0  -11.305  32.826  19.696  1.00  34.13
ATOM   1247  O    GLY A  161  0  -10.412  33.648  19.451  1.00  32.40
ATOM   1248  N    ALA A  162  0  -11.158  31.738  20.433  1.00  33.01
ATOM   1249  CA   ALA A  162  0   -9.864  31.355  20.988  1.00  32.39
ATOM   1250  C    ALA A  162  0   -8.927  30.902  19.880  1.00  31.53
ATOM   1251  O    ALA A  162  0   -9.285  30.132  19.013  1.00  30.73
ATOM   1252  CB   ALA A  162  0  -10.058  30.263  22.010  1.00  34.12
ATOM   1253  N    ALA A  163  0   -7.731  31.475  19.851  1.00  32.06
ATOM   1254  CA   ALA A  163  0   -6.740  31.202  18.814  1.00  30.85
ATOM   1255  C    ALA A  163  0   -6.219  29.774  18.897  1.00  29.40
ATOM   1256  O    ALA A  163  0   -5.967  29.223  19.965  1.00  30.49
ATOM   1257  CB   ALA A  163  0   -5.607  32.217  18.911  1.00  30.29
ATOM   1258  N    GLN A  164  0   -6.101  29.130  17.754  1.00  28.69
ATOM   1259  CA   GLN A  164  0   -5.616  27.769  17.612  1.00  28.24
ATOM   1260  C    GLN A  164  0   -4.720  27.744  16.370  1.00  25.02
ATOM   1261  O    GLN A  164  0   -5.157  28.046  15.260  1.00  23.64
ATOM   1262  CB   GLN A  164  0   -6.732  26.756  17.361  1.00  31.99
ATOM   1263  CG   GLN A  164  0   -7.885  26.640  18.319  1.00  36.24
ATOM   1264  CD   GLN A  164  0   -7.535  25.809  19.540  1.00  40.95
ATOM   1265  OE1  GLN A  164  0   -7.863  26.166  20.684  1.00  43.34
ATOM   1266  NE2  GLN A  164  0   -6.864  24.672  19.328  1.00  41.86
ATOM   1267  N    PRO A  165  0   -3.446  27.406  16.549  1.00  22.68
ATOM   1268  CA   PRO A  165  0   -2.501  27.360  15.463  1.00  20.43
ATOM   1269  C    PRO A  165  0   -2.856  26.294  14.429  1.00  18.89
```

APPENDIX 1-continued

| ATOM | 1270 | O | PRO | A | 165 | 0 | -3.286 | 25.176 | 14.715 | 1.00 | 18.00 |
|------|------|-----|-----|---|-----|---|--------|--------|--------|------|-------|
| ATOM | 1271 | CB | PRO | A | 165 | 0 | -1.126 | 27.075 | 16.088 | 1.00 | 20.83 |
| ATOM | 1272 | CG | PRO | A | 165 | 0 | -1.476 | 26.651 | 17.479 | 1.00 | 22.05 |
| ATOM | 1273 | CD | PRO | A | 165 | 0 | -2.873 | 27.081 | 17.851 | 1.00 | 21.57 |
| ATOM | 1274 | N | ASP | A | 166 | 0 | -2.667 | 26.608 | 13.169 | 1.00 | 17.50 |
| ATOM | 1275 | CA | ASP | A | 166 | 0 | -2.829 | 25.677 | 12.059 | 1.00 | 19.82 |
| ATOM | 1276 | C | ASP | A | 166 | 0 | -1.591 | 24.788 | 11.930 | 1.00 | 19.47 |
| ATOM | 1277 | O | ASP | A | 166 | 0 | -1.692 | 23.649 | 11.506 | 1.00 | 19.38 |
| ATOM | 1278 | CB | ASP | A | 166 | 0 | -3.005 | 26.413 | 10.727 | 1.00 | 19.75 |
| ATOM | 1279 | CG | ASP | A | 166 | 0 | -4.347 | 27.162 | 10.728 | 1.00 | 21.69 |
| ATOM | 1280 | OD1 | ASP | A | 166 | 0 | -5.376 | 26.480 | 10.593 | 1.00 | 22.24 |
| ATOM | 1281 | OD2 | ASP | A | 166 | 0 | -4.384 | 28.392 | 10.885 | 1.00 | 22.13 |
| ATOM | 1282 | N | ALA | A | 167 | 0 | -0.435 | 25.386 | 12.231 | 1.00 | 18.54 |
| ATOM | 1283 | CA | ALA | A | 167 | 0 | 0.806 | 24.614 | 12.142 | 1.00 | 18.74 |
| ATOM | 1284 | C | ALA | A | 167 | 0 | 1.867 | 25.056 | 13.148 | 1.00 | 17.69 |
| ATOM | 1285 | O | ALA | A | 167 | 0 | 1.874 | 26.147 | 13.715 | 1.00 | 15.83 |
| ATOM | 1286 | CB | ALA | A | 167 | 0 | 1.387 | 24.767 | 10.735 | 1.00 | 17.32 |
| ATOM | 1287 | N | THR | A | 168 | 0 | 2.826 | 24.166 | 13.335 | 1.00 | 18.40 |
| ATOM | 1288 | CA | THR | A | 168 | 0 | 4.087 | 24.402 | 14.027 | 1.00 | 14.85 |
| ATOM | 1289 | C | THR | A | 168 | 0 | 5.180 | 24.553 | 12.955 | 1.00 | 15.24 |
| ATOM | 1290 | O | THR | A | 168 | 0 | 5.402 | 23.737 | 12.071 | 1.00 | 12.99 |
| ATOM | 1291 | CB | THR | A | 168 | 0 | 4.530 | 23.235 | 14.900 | 1.00 | 14.31 |
| ATOM | 1292 | OG1 | THR | A | 168 | 0 | 3.558 | 23.068 | 15.920 | 1.00 | 12.30 |
| ATOM | 1293 | CG2 | THR | A | 168 | 0 | 5.921 | 23.516 | 15.524 | 1.00 | 13.60 |
| ATOM | 1294 | N | LEU | A | 169 | 0 | 5.867 | 25.686 | 12.973 | 1.00 | 16.69 |
| ATOM | 1295 | CA | LEU | A | 169 | 0 | 6.976 | 26.002 | 12.071 | 1.00 | 14.74 |
| ATOM | 1296 | C | LEU | A | 169 | 0 | 8.285 | 25.747 | 12.833 | 1.00 | 14.34 |
| ATOM | 1297 | O | LEU | A | 169 | 0 | 8.497 | 26.259 | 13.942 | 1.00 | 12.34 |
| ATOM | 1298 | CB | LEU | A | 169 | 0 | 6.890 | 27.471 | 11.652 | 1.00 | 14.90 |
| ATOM | 1299 | CG | LEU | A | 169 | 0 | 6.071 | 27.845 | 10.428 | 1.00 | 17.83 |
| ATOM | 1300 | CD1 | LEU | A | 169 | 0 | 4.978 | 26.825 | 10.133 | 1.00 | 15.89 |
| ATOM | 1301 | CD2 | LEU | A | 169 | 0 | 5.500 | 29.254 | 10.443 | 1.00 | 16.43 |
| ATOM | 1302 | N | ILE | A | 170 | 0 | 9.141 | 24.923 | 12.255 | 1.00 | 14.06 |
| ATOM | 1303 | CA | ILE | A | 170 | 0 | 10.472 | 24.659 | 12.819 | 1.00 | 14.01 |
| ATOM | 1304 | C | ILE | A | 170 | 0 | 11.397 | 25.312 | 11.784 | 1.00 | 15.19 |
| ATOM | 1305 | O | ILE | A | 170 | 0 | 11.307 | 25.009 | 10.585 | 1.00 | 14.73 |
| ATOM | 1306 | CB | ILE | A | 170 | 0 | 10.807 | 23.179 | 13.025 | 1.00 | 14.75 |
| ATOM | 1307 | CG1 | ILE | A | 170 | 0 | 9.849 | 22.605 | 14.069 | 1.00 | 13.74 |
| ATOM | 1308 | CG2 | ILE | A | 170 | 0 | 12.268 | 22.983 | 13.468 | 1.00 | 13.47 |
| ATOM | 1309 | CD1 | ILE | A | 170 | 0 | 9.915 | 21.134 | 14.385 | 1.00 | 15.26 |

APPENDIX 1-continued

| ATOM | 1310 | N   | ASN | A | 171 | 0 | 12.166 | 26.317 | 12.208 | 1.00 | 13.13 |
| ATOM | 1311 | CA  | ASN | A | 171 | 0 | 12.992 | 27.042 | 11.250 | 1.00 | 13.74 |
| ATOM | 1312 | C   | ASN | A | 171 | 0 | 12.163 | 27.517 | 10.083 | 1.00 | 13.71 |
| ATOM | 1313 | O   | ASN | A | 171 | 0 | 12.562 | 27.381 | 8.921  | 1.00 | 13.20 |
| ATOM | 1314 | CB  | ASN | A | 171 | 0 | 14.220 | 26.209 | 10.793 | 1.00 | 14.42 |
| ATOM | 1315 | CG  | ASN | A | 171 | 0 | 15.236 | 26.157 | 11.940 | 1.00 | 16.29 |
| ATOM | 1316 | OD1 | ASN | A | 171 | 0 | 15.123 | 26.983 | 12.875 | 1.00 | 16.78 |
| ATOM | 1317 | ND2 | ASN | A | 171 | 0 | 16.203 | 25.259 | 11.964 | 1.00 | 14.32 |
| ATOM | 1318 | N   | GLY | A | 172 | 0 | 10.967 | 28.074 | 10.337 | 1.00 | 14.17 |
| ATOM | 1319 | CA  | GLY | A | 172 | 0 | 10.157 | 28.619 | 9.270  | 1.00 | 11.74 |
| ATOM | 1320 | C   | GLY | A | 172 | 0 | 9.387  | 27.636 | 8.433  | 1.00 | 14.40 |
| ATOM | 1321 | O   | GLY | A | 172 | 0 | 8.783  | 28.064 | 7.441  | 1.00 | 15.60 |
| ATOM | 1322 | N   | LYS | A | 173 | 0 | 9.430  | 26.319 | 8.669  | 1.00 | 13.84 |
| ATOM | 1323 | CA  | LYS | A | 173 | 0 | 8.777  | 25.363 | 7.794  | 1.00 | 13.67 |
| ATOM | 1324 | C   | LYS | A | 173 | 0 | 8.038  | 24.303 | 8.589  | 1.00 | 13.59 |
| ATOM | 1325 | O   | LYS | A | 173 | 0 | 8.445  | 24.027 | 9.723  | 1.00 | 11.70 |
| ATOM | 1326 | CB  | LYS | A | 173 | 0 | 9.775  | 24.645 | 6.875  | 1.00 | 17.03 |
| ATOM | 1327 | CG  | LYS | A | 173 | 0 | 10.704 | 25.577 | 6.118  | 1.00 | 17.63 |
| ATOM | 1328 | CD  | LYS | A | 173 | 0 | 11.508 | 24.796 | 5.094  | 1.00 | 20.84 |
| ATOM | 1329 | CE  | LYS | A | 173 | 0 | 12.213 | 25.821 | 4.198  | 1.00 | 22.63 |
| ATOM | 1330 | NZ  | LYS | A | 173 | 0 | 13.304 | 25.087 | 3.499  | 1.00 | 28.08 |
| ATOM | 1331 | N   | GLY | A | 174 | 0 | 6.922  | 23.821 | 8.014  | 1.00 | 12.28 |
| ATOM | 1332 | CA  | GLY | A | 174 | 0 | 6.178  | 22.768 | 8.753  | 1.00 | 11.45 |
| ATOM | 1333 | C   | GLY | A | 174 | 0 | 4.958  | 22.409 | 7.896  | 1.00 | 13.55 |
| ATOM | 1334 | O   | GLY | A | 174 | 0 | 4.823  | 22.877 | 6.760  | 1.00 | 13.37 |
| ATOM | 1335 | N   | ARG | A | 175 | 0 | 4.042  | 21.619 | 8.432  | 1.00 | 14.54 |
| ATOM | 1336 | CA  | ARG | A | 175 | 0 | 2.859  | 21.201 | 7.687  | 1.00 | 16.62 |
| ATOM | 1337 | C   | ARG | A | 175 | 0 | 1.598  | 21.336 | 8.541  | 1.00 | 17.67 |
| ATOM | 1338 | O   | ARG | A | 175 | 0 | 1.727  | 21.264 | 9.769  | 1.00 | 18.41 |
| ATOM | 1339 | CB  | ARG | A | 175 | 0 | 2.985  | 19.718 | 7.292  | 1.00 | 16.05 |
| ATOM | 1340 | CG  | ARG | A | 175 | 0 | 3.894  | 19.472 | 6.116  | 1.00 | 16.55 |
| ATOM | 1341 | CD  | ARG | A | 175 | 0 | 4.358  | 18.009 | 6.108  | 1.00 | 17.70 |
| ATOM | 1342 | NE  | ARG | A | 175 | 0 | 5.421  | 17.861 | 5.097  | 1.00 | 17.74 |
| ATOM | 1343 | CZ  | ARG | A | 175 | 0 | 5.971  | 16.667 | 4.792  | 1.00 | 17.63 |
| ATOM | 1344 | NH1 | ARG | A | 175 | 0 | 6.918  | 16.665 | 3.866  | 1.00 | 17.25 |
| ATOM | 1345 | NH2 | ARG | A | 175 | 0 | 5.594  | 15.538 | 5.375  | 1.00 | 14.80 |
| ATOM | 1346 | N   | TYR | A | 176 | 0 | 0.429  | 21.438 | 7.908  | 1.00 | 18.08 |
| ATOM | 1347 | CA  | TYR | A | 176 | 0 | -0.800 | 21.481 | 8.746  | 1.00 | 18.67 |
| ATOM | 1348 | C   | TYR | A | 176 | 0 | -1.613 | 20.200 | 8.509  | 1.00 | 18.24 |

APPENDIX 1-continued

| ATOM | 1349 | O   | TYR | A | 176 | 0 | -1.417 | 19.534 | 7.483  | 1.00 | 17.67 |
|------|------|-----|-----|---|-----|---|--------|--------|--------|------|-------|
| ATOM | 1350 | CB  | TYR | A | 176 | 0 | -1.635 | 22.709 | 8.462  | 1.00 | 17.21 |
| ATOM | 1351 | CG  | TYR | A | 176 | 0 | -2.102 | 22.931 | 7.053  | 1.00 | 16.36 |
| ATOM | 1352 | CD1 | TYR | A | 176 | 0 | -1.246 | 23.433 | 6.089  | 1.00 | 14.84 |
| ATOM | 1353 | CD2 | TYR | A | 176 | 0 | -3.441 | 22.676 | 6.677  | 1.00 | 17.26 |
| ATOM | 1354 | CE1 | TYR | A | 176 | 0 | -1.640 | 23.686 | 4.796  | 1.00 | 16.01 |
| ATOM | 1355 | CE2 | TYR | A | 176 | 0 | -3.862 | 22.908 | 5.361  | 1.00 | 16.65 |
| ATOM | 1356 | CZ  | TYR | A | 176 | 0 | -2.967 | 23.407 | 4.432  | 1.00 | 17.65 |
| ATOM | 1357 | OH  | TYR | A | 176 | 0 | -3.347 | 23.678 | 3.131  | 1.00 | 17.81 |
| ATOM | 1358 | N   | VAL | A | 177 | 0 | -2.427 | 19.815 | 9.464  | 1.00 | 18.46 |
| ATOM | 1359 | CA  | VAL | A | 177 | 0 | -3.200 | 18.571 | 9.303  | 1.00 | 21.18 |
| ATOM | 1360 | C   | VAL | A | 177 | 0 | -4.090 | 18.639 | 8.073  | 1.00 | 21.50 |
| ATOM | 1361 | O   | VAL | A | 177 | 0 | -4.788 | 19.620 | 7.858  | 1.00 | 21.85 |
| ATOM | 1362 | CB  | VAL | A | 177 | 0 | -4.072 | 18.306 | 10.532 | 1.00 | 22.29 |
| ATOM | 1363 | CG1 | VAL | A | 177 | 0 | -4.802 | 16.974 | 10.370 | 1.00 | 21.70 |
| ATOM | 1364 | CG2 | VAL | A | 177 | 0 | -3.205 | 18.289 | 11.784 | 1.00 | 22.43 |
| ATOM | 1365 | N   | GLY | A | 178 | 0 | -3.989 | 17.707 | 7.142  | 1.00 | 21.84 |
| ATOM | 1366 | CA  | GLY | A | 178 | 0 | -4.761 | 17.742 | 5.918  | 1.00 | 20.35 |
| ATOM | 1367 | C   | GLY | A | 178 | 0 | -4.047 | 18.602 | 4.900  | 1.00 | 22.84 |
| ATOM | 1368 | O   | GLY | A | 178 | 0 | -4.576 | 18.673 | 3.774  | 1.00 | 23.86 |
| ATOM | 1369 | N   | GLY | A | 179 | 0 | -2.887 | 19.220 | 5.210  | 1.00 | 21.49 |
| ATOM | 1370 | CA  | GLY | A | 179 | 0 | -2.291 | 20.060 | 4.149  | 1.00 | 19.94 |
| ATOM | 1371 | C   | GLY | A | 179 | 0 | -1.389 | 19.250 | 3.242  | 1.00 | 18.86 |
| ATOM | 1372 | O   | GLY | A | 179 | 0 | -1.192 | 18.052 | 3.399  | 1.00 | 19.35 |
| ATOM | 1373 | N   | PRO | A | 180 | 0 | -0.800 | 19.905 | 2.268  | 1.00 | 19.42 |
| ATOM | 1374 | CA  | PRO | A | 180 | 0 | 0.150  | 19.328 | 1.335  | 1.00 | 19.92 |
| ATOM | 1375 | C   | PRO | A | 180 | 0 | 1.430  | 18.922 | 2.041  | 1.00 | 20.56 |
| ATOM | 1376 | O   | PRO | A | 180 | 0 | 1.731  | 19.399 | 3.145  | 1.00 | 20.66 |
| ATOM | 1377 | CB  | PRO | A | 180 | 0 | 0.503  | 20.399 | 0.298  | 1.00 | 19.52 |
| ATOM | 1378 | CG  | PRO | A | 180 | 0 | -0.144 | 21.639 | 0.829  | 1.00 | 19.70 |
| ATOM | 1379 | CD  | PRO | A | 180 | 0 | -0.930 | 21.356 | 2.081  | 1.00 | 19.79 |
| ATOM | 1380 | N   | ALA | A | 181 | 0 | 2.213  | 18.059 | 1.403  | 1.00 | 21.19 |
| ATOM | 1381 | CA  | ALA | A | 181 | 0 | 3.489  | 17.644 | 2.007  | 1.00 | 23.04 |
| ATOM | 1382 | C   | ALA | A | 181 | 0 | 4.548  | 18.723 | 1.772  | 1.00 | 21.24 |
| ATOM | 1383 | O   | ALA | A | 181 | 0 | 5.465  | 18.522 | 0.986  | 1.00 | 23.93 |
| ATOM | 1384 | CB  | ALA | A | 181 | 0 | 3.928  | 16.305 | 1.435  | 1.00 | 21.73 |
| ATOM | 1385 | N   | ALA | A | 182 | 0 | 4.398  | 19.905 | 2.315  | 1.00 | 19.30 |
| ATOM | 1386 | CA  | ALA | A | 182 | 0 | 5.357  | 20.987 | 2.183  | 1.00 | 18.39 |
| ATOM | 1387 | C   | ALA | A | 182 | 0 | 6.706  | 20.549 | 2.791  | 1.00 | 17.36 |
| ATOM | 1388 | O   | ALA | A | 182 | 0 | 6.858  | 19.712 | 3.701  | 1.00 | 16.16 |

APPENDIX 1-continued

| | | | | | | | | | | |
|---|---|---|---|---|---|---|---|---|---|---|
| ATOM | 1389 | CB | ALA | A | 182 | 0 | 4.826 | 22.209 | 2.932 | 1.00 17.68 |
| ATOM | 1390 | N | GLU | A | 183 | 0 | 7.739 | 21.103 | 2.210 | 1.00 18.23 |
| ATOM | 1391 | CA | GLU | A | 183 | 0 | 9.134 | 20.882 | 2.599 | 1.00 20.90 |
| ATOM | 1392 | C | GLU | A | 183 | 0 | 9.381 | 21.078 | 4.093 | 1.00 18.87 |
| ATOM | 1393 | O | GLU | A | 183 | 0 | 8.976 | 22.073 | 4.699 | 1.00 17.80 |
| ATOM | 1394 | CB | GLU | A | 183 | 0 | 9.990 | 21.875 | 1.820 | 1.00 25.16 |
| ATOM | 1395 | CG | GLU | A | 183 | 0 | 11.508 | 21.760 | 1.962 | 1.00 31.31 |
| ATOM | 1396 | CD | GLU | A | 183 | 0 | 12.075 | 22.803 | 0.998 | 1.00 34.38 |
| ATOM | 1397 | OE1 | GLU | A | 183 | 0 | 11.901 | 22.609 | -0.229 | 1.00 36.88 |
| ATOM | 1398 | OE2 | GLU | A | 183 | 0 | 12.619 | 23.809 | 1.484 | 1.00 36.18 |
| ATOM | 1399 | N | LEU | A | 184 | 0 | 10.010 | 20.093 | 4.691 | 1.00 17.33 |
| ATOM | 1400 | CA | LEU | A | 184 | 0 | 10.388 | 20.155 | 6.098 | 1.00 18.77 |
| ATOM | 1401 | C | LEU | A | 184 | 0 | 11.780 | 20.743 | 6.255 | 1.00 19.44 |
| ATOM | 1402 | O | LEU | A | 184 | 0 | 12.582 | 20.687 | 5.314 | 1 00 20.95 |
| ATOM | 1403 | CB | LEU | A | 184 | 0 | 10.331 | 18.735 | 6.673 | 1.00 18.11 |
| ATOM | 1404 | CG | LEU | A | 184 | 0 | 8.915 | 18.125 | 6.577 | 1.00 19.10 |
| ATOM | 1405 | CD1 | LEU | A | 184 | 0 | 8.887 | 16.734 | 7.178 | 1.00 18.87 |
| ATOM | 1406 | CD2 | LEU | A | 184 | 0 | 7.868 | 19.026 | 7.229 | 1.00 18.69 |
| ATOM | 1407 | N | SER | A | 185 | 0 | 12.054 | 21.342 | 7.398 | 1.00 18.46 |
| ATOM | 1408 | CA | SER | A | 185 | 0 | 13.366 | 21.883 | 7.699 | 1.00 17.73 |
| ATOM | 1409 | C | SER | A | 185 | 0 | 14.298 | 20.699 | 8.018 | 1.00 16.95 |
| ATOM | 1410 | O | SER | A | 185 | 0 | 13.883 | 19.710 | 8.629 | 1.00 15.84 |
| ATOM | 1411 | CB | SER | A | 185 | 0 | 13.303 | 22.786 | 8.934 | 1.00 17.34 |
| ATOM | 1412 | OG | SER | A | 185 | 0 | 12.846 | 24.073 | 8.560 | 1.00 18.09 |
| ATOM | 1413 | N | ILE | A | 186 | 0 | 15.533 | 20.845 | 7.587 | 1.00 16.43 |
| ATOM | 1414 | CA | ILE | A | 186 | 0 | 16.595 | 19.858 | 7.821 | 1.00 16.85 |
| ATOM | 1415 | C | ILE | A | 186 | 0 | 17.725 | 20.491 | 8.626 | 1.00 15.86 |
| ATOM | 1416 | O | ILE | A | 186 | 0 | 18.178 | 21.605 | 8.387 | 1.00 11.67 |
| ATOM | 1417 | CB | ILE | A | 186 | 0 | 17.193 | 19.390 | 6.471 | 1.00 18.77 |
| ATOM | 1418 | CG1 | ILE | A | 186 | 0 | 16.048 | 18.895 | 5.557 | 1.00 19.78 |
| ATOM | 1419 | CG2 | ILE | A | 186 | 0 | 18.167 | 18.241 | 6.697 | 1.00 18.53 |
| ATOM | 1420 | CD1 | ILE | A | 186 | 0 | 16.464 | 18.731 | 4.110 | 1.00 22.35 |
| ATOM | 1421 | N | VAL | A | 187 | 0 | 18.114 | 19.840 | 9.703 | 1.00 16.18 |
| ATOM | 1422 | CA | VAL | A | 187 | 0 | 19.243 | 20.287 | 10.505 | 1.00 16.63 |
| ATOM | 1423 | C | VAL | A | 187 | 0 | 20.362 | 19.239 | 10.231 | 1.00 17.36 |
| ATOM | 1424 | O | VAL | A | 187 | 0 | 20.158 | 18.046 | 10.505 | 1.00 15.19 |
| ATOM | 1425 | CB | VAL | A | 187 | 0 | 18.928 | 20.323 | 11.984 | 1.00 16.68 |
| ATOM | 1426 | CG1 | VAL | A | 187 | 0 | 20.198 | 20.622 | 12.796 | 1.00 16.82 |
| ATOM | 1427 | CG2 | VAL | A | 187 | 0 | 17.874 | 21.375 | 12.275 | 1.00 17.07 |

APPENDIX 1-continued

| ATOM | 1428 | N | ASN A | 188 | 0 | 21.449 | 19.695 | 9.634 | 1.00 | 16.45 |
|------|------|-----|-------|-----|---|--------|--------|--------|------|-------|
| ATOM | 1429 | CA | ASN A | 188 | 0 | 22.528 | 18.766 | 9.272 | 1.00 | 19.84 |
| ATOM | 1430 | C | ASN A | 188 | 0 | 23.598 | 18.597 | 10.349 | 1.00 | 19.41 |
| ATOM | 1431 | O | ASN A | 188 | 0 | 24.051 | 19.618 | 10.862 | 1.00 | 21.31 |
| ATOM | 1432 | CB | ASN A | 188 | 0 | 23.209 | 19.246 | 7.976 | 1.00 | 18.78 |
| ATOM | 1433 | CG | ASN A | 188 | 0 | 22.249 | 19.186 | 6.797 | 1.00 | 20.77 |
| ATOM | 1434 | OD1 | ASN A | 188 | 0 | 21.734 | 20.201 | 6.305 | 1.00 | 21.70 |
| ATOM | 1435 | ND2 | ASN A | 188 | 0 | 21.995 | 17.985 | 6.286 | 1.00 | 20.52 |
| ATOM | 1436 | N | VAL A | 189 | 0 | 24.024 | 17.389 | 10.681 | 1.00 | 17.35 |
| ATOM | 1437 | CA | VAL A | 189 | 0 | 25.098 | 17.164 | 11.617 | 1.00 | 17.93 |
| ATOM | 1438 | C | VAL A | 189 | 0 | 26.091 | 16.135 | 11.046 | 1.00 | 19.82 |
| ATOM | 1439 | O | VAL A | 189 | 0 | 25.773 | 15.392 | 10.109 | 1.00 | 18.90 |
| ATOM | 1440 | CB | VAL A | 189 | 0 | 24.660 | 16.684 | 13.009 | 1.00 | 18.43 |
| ATOM | 1441 | CG1 | VAL A | 189 | 0 | 23.931 | 17.796 | 13.766 | 1.00 | 18.89 |
| ATOM | 1442 | CG2 | VAL A | 189 | 0 | 23.760 | 15.449 | 12.965 | 1.00 | 15.94 |
| ATOM | 1443 | N | GLU A | 190 | 0 | 27.242 | 15.993 | 11.688 | 1.00 | 21.48 |
| ATOM | 1444 | CA | GLU A | 190 | 0 | 28.220 | 14.972 | 11.274 | 1.00 | 24.63 |
| ATOM | 1445 | C | GLU A | 190 | 0 | 28.514 | 14.065 | 12.469 | 1.00 | 23.06 |
| ATOM | 1446 | O | GLU A | 190 | 0 | 28.797 | 14.650 | 13.522 | 1.00 | 21.04 |
| ATOM | 1447 | CB | GLU A | 190 | 0 | 29.569 | 15.551 | 10.860 | 1.00 | 26.79 |
| ATOM | 1448 | CG | GLU A | 190 | 0 | 29.571 | 16.355 | 9.567 | 1.00 | 32.24 |
| ATOM | 1449 | CD | GLU A | 190 | 0 | 30.951 | 16.990 | 9.351 | 1.00 | 34.67 |
| ATOM | 1450 | OE1 | GLU A | 190 | 0 | 31.927 | 16.199 | 9.305 | 1.00 | 35.41 |
| ATOM | 1451 | OE2 | GLU A | 190 | 0 | 30.999 | 18.236 | 9.264 | 1.00 | 35.78 |
| ATOM | 1452 | N | GLN A | 191 | 0 | 28.490 | 12.752 | 12.256 | 1.00 | 21.94 |
| ATOM | 1453 | CA | GLN A | 191 | 0 | 28.768 | 11.824 | 13.357 | 1.00 | 21.92 |
| ATOM | 1454 | C | GLN A | 191 | 0 | 30.121 | 12.151 | 13.984 | 1.00 | 22.68 |
| ATOM | 1455 | O | GLN A | 191 | 0 | 31.052 | 12.516 | 13.251 | 1.00 | 23.08 |
| ATOM | 1456 | CB | GLN A | 191 | 0 | 28.797 | 10.400 | 12.820 | 1.00 | 22.01 |
| ATOM | 1457 | CG | GLN A | 191 | 0 | 28.795 | 9.347 | 13.917 | 1.00 | 23.87 |
| ATOM | 1458 | CD | GLN A | 191 | 0 | 28.846 | 7.966 | 13.259 | 1.00 | 26.64 |
| ATOM | 1459 | OE1 | GLN A | 191 | 0 | 29.745 | 7.761 | 12.427 | 1.00 | 28.86 |
| ATOM | 1460 | NE2 | GLN A | 191 | 0 | 27.909 | 7.080 | 13.563 | 1.00 | 26.40 |
| ATOM | 1461 | N | GLY A | 192 | 0 | 30.224 | 12.119 | 15.290 | 1.00 | 21.84 |
| ATOM | 1462 | CA | GLY A | 192 | 0 | 31.418 | 12.469 | 15.996 | 1.00 | 22.91 |
| ATOM | 1463 | C | GLY A | 192 | 0 | 31.564 | 13.910 | 16.446 | 1.00 | 23.87 |
| ATOM | 1464 | O | GLY A | 192 | 0 | 32.394 | 14.174 | 17.322 | 1.00 | 25.80 |
| ATOM | 1465 | N | LYS A | 193 | 0 | 30.839 | 14.867 | 15.922 | 1.00 | 23.54 |
| ATOM | 1466 | CA | LYS A | 193 | 0 | 30.899 | 16.259 | 16.362 | 1.00 | 22.84 |
| ATOM | 1467 | C | LYS A | 193 | 0 | 29.840 | 16.584 | 17.404 | 1.00 | 21.67 |

APPENDIX 1-continued

| | | | | | | | | | | |
|---|---|---|---|---|---|---|---|---|---|---|
| ATOM | 1468 | O | LYS | A | 193 | 0 | 28.826 | 15.882 | 17.538 | 1.00 20.99 |
| ATOM | 1469 | CB | LYS | A | 193 | 0 | 30.682 | 17.155 | 15.143 | 1.00 24.53 |
| ATOM | 1470 | CG | LYS | A | 193 | 0 | 31.900 | 17.149 | 14.217 | 1.00 27.82 |
| ATOM | 1471 | CD | LYS | A | 193 | 0 | 31.739 | 18.261 | 13.199 | 1.00 30.02 |
| ATOM | 1472 | CE | LYS | A | 193 | 0 | 33.060 | 19.001 | 12.990 | 1.00 31.93 |
| ATOM | 1473 | NZ | LYS | A | 193 | 0 | 33.392 | 18.906 | 11.540 | 1.00 33.14 |
| ATOM | 1474 | N | LYS | A | 194 | 0 | 30.067 | 17.626 | 18.169 | 1.00 19.25 |
| ATOM | 1475 | CA | LYS | A | 194 | 0 | 29.168 | 18.115 | 19.187 | 1.00 19.49 |
| ATOM | 1476 | C | LYS | A | 194 | 0 | 28.722 | 19.523 | 18.780 | 1.00 19.40 |
| ATOM | 1477 | O | LYS | A | 194 | 0 | 29.512 | 20.285 | 18.235 | 1.00 19.29 |
| ATOM | 1478 | CB | LYS | A | 194 | 0 | 29.771 | 18.115 | 20.576 | 1.00 21.88 |
| ATOM | 1479 | CG | LYS | A | 194 | 0 | 30.338 | 16.748 | 20.999 | 1.00 25.59 |
| ATOM | 1480 | CD | LYS | A | 194 | 0 | 31.054 | 16.902 | 22.331 | 1.00 29.48 |
| ATOM | 1481 | CE | LYS | A | 194 | 0 | 31.455 | 15.582 | 22.970 | 1.00 33.58 |
| ATOM | 1482 | NZ | LYS | A | 194 | 0 | 30.363 | 15.049 | 23.868 | 1.00 35.93 |
| ATOM | 1483 | N | TYR | A | 195 | 0 | 27.418 | 19.818 | 18.910 | 1.00 16.92 |
| ATOM | 1484 | CA | TYR | A | 195 | 0 | 26.858 | 21.068 | 18.431 | 1.00 15.60 |
| ATOM | 1485 | C | TYR | A | 195 | 0 | 26.143 | 21.838 | 19.530 | 1.00 14.20 |
| ATOM | 1486 | O | TYR | A | 195 | 0 | 25.394 | 21.232 | 20.295 | 1.00 13.75 |
| ATOM | 1487 | CB | TYR | A | 195 | 0 | 25.814 | 20.880 | 17.300 | 1.00 16.13 |
| ATOM | 1488 | CG | TYR | A | 195 | 0 | 26.424 | 20.225 | 16.066 | 1.00 15.41 |
| ATOM | 1489 | CD1 | TYR | A | 195 | 0 | 26.663 | 18.851 | 16.091 | 1.00 15.91 |
| ATOM | 1490 | CD2 | TYR | A | 195 | 0 | 26.786 | 20.942 | 14.945 | 1.00 14.73 |
| ATOM | 1491 | CE1 | TYR | A | 195 | 0 | 27.244 | 18.204 | 15.010 | 1.00 16.55 |
| ATOM | 1492 | CE2 | TYR | A | 195 | 0 | 27.331 | 20.312 | 13.839 | 1.00 15.60 |
| ATOM | 1493 | CZ | TYR | A | 195 | 0 | 27.570 | 18.947 | 13.888 | 1.00 16.18 |
| ATOM | 1494 | OH | TYR | A | 195 | 0 | 28.144 | 18.287 | 12.831 | 1.00 15.64 |
| ATOM | 1495 | N | ARG | A | 196 | 0 | 26.366 | 23.136 | 19.561 | 1.00 12.74 |
| ATOM | 1496 | CA | ARG | A | 196 | 0 | 25.619 | 23.980 | 20.482 | 1.00 13.63 |
| ATOM | 1497 | C | ARG | A | 196 | 0 | 24.343 | 24.369 | 19.711 | 1.00 13.86 |
| ATOM | 1498 | O | ARG | A | 196 | 0 | 24.343 | 25.218 | 18.802 | 1.00 13.81 |
| ATOM | 1499 | CB | ARG | A | 196 | 0 | 26.379 | 25.187 | 20.991 | 1.00 13.96 |
| ATOM | 1500 | CG | ARG | A | 196 | 0 | 25.520 | 26.162 | 21.796 | 1.00 14.22 |
| ATOM | 1501 | CD | ARG | A | 196 | 0 | 26.337 | 27.238 | 22.438 | 1.00 15.27 |
| ATOM | 1502 | NE | ARG | A | 196 | 0 | 25.649 | 28.138 | 23.319 | 1.00 17.38 |
| ATOM | 1503 | CZ | ARG | A | 196 | 0 | 26.203 | 29.034 | 24.140 | 1.00 18.86 |
| ATOM | 1504 | NH1 | ARG | A | 196 | 0 | 27.540 | 29.141 | 24.217 | 1.00 16.30 |
| ATOM | 1505 | NH2 | ARG | A | 196 | 0 | 25.377 | 29.788 | 24.869 | 1.00 16.73 |
| ATOM | 1506 | N | MET | A | 197 | 0 | 23.266 | 23.624 | 20.002 | 1.00 13.86 |

APPENDIX 1-continued

| ATOM | 1507 | CA  | MET | A | 197 | 0 | 21.980 | 23.932 | 19.340 | 1.00 | 12.98 |
|------|------|-----|-----|---|-----|---|--------|--------|--------|------|-------|
| ATOM | 1508 | C   | MET | A | 197 | 0 | 21.293 | 25.055 | 20.127 | 1.00 | 12.50 |
| ATOM | 1509 | O   | MET | A | 197 | 0 | 21.285 | 24.997 | 21.359 | 1.00 | 13.93 |
| ATOM | 1510 | CB  | MET | A | 197 | 0 | 21.118 | 22.693 | 19.266 | 1.00 | 12.50 |
| ATOM | 1511 | CG  | MET | A | 197 | 0 | 21.762 | 21.567 | 18.447 | 1.00 | 13.94 |
| ATOM | 1512 | SD  | MET | A | 197 | 0 | 21.860 | 22.033 | 16.735 | 1.00 | 16.62 |
| ATOM | 1513 | CE  | MET | A | 197 | 0 | 22.157 | 20.467 | 15.927 | 1.00 | 16.37 |
| ATOM | 1514 | N   | ARG | A | 198 | 0 | 20.768 | 26.064 | 19.450 | 1.00 | 11.00 |
| ATOM | 1515 | CA  | ARG | A | 198 | 0 | 20.131 | 27.191 | 20.137 | 1.00 | 11.83 |
| ATOM | 1516 | C   | ARG | A | 198 | 0 | 18.624 | 27.130 | 19.868 | 1.00 | 12.36 |
| ATOM | 1517 | O   | ARG | A | 198 | 0 | 18.145 | 27.304 | 18.731 | 1.00 | 10.03 |
| ATOM | 1518 | CB  | ARG | A | 198 | 0 | 20.804 | 28.460 | 19.629 | 1.00 | 13.98 |
| ATOM | 1519 | CG  | ARG | A | 198 | 0 | 22.282 | 28.567 | 20.065 | 1.00 | 16.25 |
| ATOM | 1520 | CD  | ARG | A | 198 | 0 | 22.932 | 29.863 | 19.626 | 1.00 | 16.68 |
| ATOM | 1521 | NE  | ARG | A | 198 | 0 | 24.350 | 29.957 | 20.042 | 1.00 | 16.91 |
| ATOM | 1522 | CZ  | ARG | A | 198 | 0 | 24.812 | 30.691 | 21.055 | 1.00 | 15.76 |
| ATOM | 1523 | NH1 | ARG | A | 198 | 0 | 24.031 | 31.456 | 21.820 | 1.00 | 13.44 |
| ATOM | 1524 | NH2 | ARG | A | 198 | 0 | 26.123 | 30.721 | 21.316 | 1.00 | 15.41 |
| ATOM | 1525 | N   | LEU | A | 199 | 0 | 17.871 | 26.807 | 20.908 | 1.00 | 10.44 |
| ATOM | 1526 | CA  | LEU | A | 199 | 0 | 16.426 | 26.568 | 20.708 | 1.00 | 10.69 |
| ATOM | 1527 | C   | LEU | A | 199 | 0 | 15.598 | 27.772 | 21.169 | 1.00 | 10.07 |
| ATOM | 1528 | O   | LEU | A | 199 | 0 | 15.682 | 28.216 | 22.317 | 1.00 | 10.07 |
| ATOM | 1529 | CB  | LEU | A | 199 | 0 | 16.003 | 25.317 | 21.491 | 1.00 | 8.67  |
| ATOM | 1530 | CG  | LEU | A | 199 | 0 | 14.499 | 24.942 | 21.391 | 1.00 | 10.33 |
| ATOM | 1531 | CD1 | LEU | A | 199 | 0 | 14.193 | 24.333 | 20.023 | 1.00 | 8.13  |
| ATOM | 1532 | CD2 | LEU | A | 199 | 0 | 14.170 | 23.907 | 22.485 | 1.00 | 9.10  |
| ATOM | 1533 | N   | ILE | A | 200 | 0 | 14.857 | 28.370 | 20.242 | 1.00 | 10.46 |
| ATOM | 1534 | CA  | ILE | A | 200 | 0 | 14.104 | 29.572 | 20.585 | 1.00 | 11.72 |
| ATOM | 1535 | C   | ILE | A | 200 | 0 | 12.627 | 29.428 | 20.310 | 1.00 | 13.84 |
| ATOM | 1536 | O   | ILE | A | 200 | 0 | 12.254 | 29.059 | 19.192 | 1.00 | 13.22 |
| ATOM | 1537 | CB  | ILE | A | 200 | 0 | 14.628 | 30.755 | 19.735 | 1.00 | 12.89 |
| ATOM | 1538 | CG1 | ILE | A | 200 | 0 | 16.165 | 30.899 | 19.824 | 1.00 | 12.38 |
| ATOM | 1539 | CG2 | ILE | A | 200 | 0 | 13.998 | 32.091 | 20.065 | 1.00 | 13.13 |
| ATOM | 1540 | CD1 | ILE | A | 200 | 0 | 16.811 | 31.634 | 18.671 | 1.00 | 12.54 |
| ATOM | 1541 | N   | SER | A | 201 | 0 | 11.829 | 29.825 | 21.312 | 1.00 | 14.64 |
| ATOM | 1542 | CA  | SER | A | 201 | 0 | 10.379 | 29.849 | 21.023 | 1.00 | 13.89 |
| ATOM | 1543 | C   | SER | A | 201 | 0 | 10.018 | 31.280 | 20.608 | 1.00 | 11.10 |
| ATOM | 1544 | O   | SER | A | 201 | 0 | 10.250 | 32.261 | 21.320 | 1.00 | 8.85  |
| ATOM | 1545 | CB  | SER | A | 201 | 0 | 9.539  | 29.367 | 22.202 | 1.00 | 13.01 |
| ATOM | 1546 | OG  | SER | A | 201 | 0 | 8.313  | 30.047 | 22.207 | 1.00 | 12.19 |

APPENDIX 1-continued

```
ATOM   1547  N    LEU A  202  0    9.428 31.376 19.438 1.00  9.64
ATOM   1548  CA   LEU A  202  0    8.959 32.637 18.881 1.00  9.06
ATOM   1549  C    LEU A  202  0    7.415 32.740 19.046 1.00 10.40
ATOM   1550  O    LEU A  202  0    6.802 33.528 18.351 1.00  9.36
ATOM   1551  CB   LEU A  202  0    9.239 32.618 17.379 1.00  9.09
ATOM   1552  CG   LEU A  202  0   10.691 32.451 16.888 1.00 10.90
ATOM   1553  CD1  LEU A  202  0   10.637 32.470 15.367 1.00 10.05
ATOM   1554  CD2  LEU A  202  0   11.617 33.559 17.414 1.00  8.56
ATOM   1555  N    SER A  203  0    6.821 31.942 19.892 1.00  9.59
ATOM   1556  CA   SER A  203  0    5.414 31.756 20.017 1.00 15.31
ATOM   1557  C    SER A  203  0    4.624 32.960 20.544 1.00 16.67
ATOM   1558  O    SER A  203  0    4.964 33.676 21.483 1.00 16.42
ATOM   1559  CB   SER A  203  0    5.130 30.505 20.867 1.00 15.21
ATOM   1560  OG   SER A  203  0    3.742 30.240 21.004 1.00 17.14
ATOM   1561  N    CYS A  204  0    3.428 33.051 19.984 1.00 17.18
ATOM   1562  CA   CYS A  204  0    2.442 34.018 20.470 1.00 18.43
ATOM   1563  C    CYS A  204  0    1.599 33.316 21.522 1.00 17.02
ATOM   1564  O    CYS A  204  0    0.867 34.039 22.200 1.00 17.27
ATOM   1565  CB   CYS A  204  0    1.524 34.508 19.334 1.00 18.60
ATOM   1566  SG   CYS A  204  0    2.135 36.038 18.612 1.00 20.23
ATOM   1567  N    ASP A  205  0    1.687 31.989 21.665 1.00 16.38
ATOM   1568  CA   ASP A  205  0    0.776 31.392 22.683 1.00 12.26
ATOM   1569  C    ASP A  205  0    1.123 30.002 23.087 1.00 11.34
ATOM   1570  O    ASP A  205  0    1.432 29.687 24.255 1.00 11.40
ATOM   1571  CB   ASP A  205  0   -0.622 31.516 22.076 1.00 14.87
ATOM   1572  CG   ASP A  205  0   -1.729 30.881 22.892 1.00 16.61
ATOM   1573  OD1  ASP A  205  0   -2.884 30.999 22.433 1.00 18.48
ATOM   1574  OD2  ASP A  205  0   -1.534 30.263 23.966 1.00 17.48
ATOM   1575  N    PRO A  206  0    1.036 29.030 22.205 1.00 11.79
ATOM   1576  CA   PRO A  206  0    1.313 27.639 22.542 1.00 11.91
ATOM   1577  C    PRO A  206  0    2.739 27.411 23.045 1.00 14.01
ATOM   1578  O    PRO A  206  0    3.676 28.135 22.661 1.00 14.38
ATOM   1579  CB   PRO A  206  0    1.124 26.816 21.262 1.00 11.87
ATOM   1580  CG   PRO A  206  0    1.112 27.893 20.191 1.00 12.83
ATOM   1581  CD   PRO A  206  0    0.749 29.241 20.766 1.00 11.09
ATOM   1582  N    ASN A  207  0    2.888 26.439 23.911 1.00 13.06
ATOM   1583  CA   ASN A  207  0    4.128 25.919 24.429 1.00 15.01
ATOM   1584  C    ASN A  207  0    4.332 24.591 23.677 1.00 15.84
ATOM   1585  O    ASN A  207  0    3.376 24.095 23.038 1.00 16.22
```

APPENDIX 1-continued

```
ATOM   1586  CB   ASN A  207  0      4.144  25.682  25.933  1.00  15.12
ATOM   1587  CG   ASN A  207  0      3.054  24.708  26.395  1.00  19.36
ATOM   1588  OD1  ASN A  207  0      2.062  25.161  27.014  1.00  19.36
ATOM   1589  ND2  ASN A  207  0      3.174  23.408  26.203  1.00  16.49
ATOM   1590  N    TRP A  208  0      5.557  24.077  23.634  1.00  14.46
ATOM   1591  CA   TRP A  208  0      5.827  22.865  22.892  1.00  12.04
ATOM   1592  C    TRP A  208  0      6.638  21.921  23.783  1.00  13.85
ATOM   1593  O    TRP A  208  0      7.482  22.385  24.558  1.00  13.02
ATOM   1594  CB   TRP A  208  0      6.654  23.136  21.628  1.00  11.91
ATOM   1595  CG   TRP A  208  0      5.951  23.769  20.465  1.00  11.27
ATOM   1596  CD1  TRP A  208  0      5.149  23.164  19.561  1.00  10.33
ATOM   1597  CD2  TRP A  208  0      5.988  25.158  20.092  1.00  10.29
ATOM   1598  NE1  TRP A  208  0      4.698  24.078  18.625  1.00  10.91
ATOM   1599  CE2  TRP A  208  0      5.201  25.313  18.954  1.00   9.64
ATOM   1600  CE3  TRP A  208  0      6.634  26.294  20.625  1.00  10.25
ATOM   1601  CZ2  TRP A  208  0      5.011  26.553  18.344  1.00   8.53
ATOM   1602  CZ3  TRP A  208  0      6.494  27.514  20.019  1.00  10.02
ATOM   1603  CH2  TRP A  208  0      5.668  27.633  18.881  1.00  11.79
ATOM   1604  N    GLN A  209  0      6.420  20.620  23.580  1.00  13.82
ATOM   1605  CA   GLN A  209  0      7.240  19.588  24.192  1.00  13.83
ATOM   1606  C    GLN A  209  0      8.251  19.281  23.075  1.00  13.07
ATOM   1607  O    GLN A  209  0      7.848  18.968  21.948  1.00  14.18
ATOM   1608  CB   GLN A  209  0      6.441  18.319  24.487  1.00  15.65
ATOM   1609  CG   GLN A  209  0      5.449  18.481  25.649  1.00  17.26
ATOM   1610  CD   GLN A  209  0      6.177  18.514  26.975  1.00  18.17
ATOM   1611  OE1  GLN A  209  0      7.414  18.471  27.002  1.00  20.00
ATOM   1612  NE2  GLN A  209  0      5.462  18.570  28.085  1.00  16.89
ATOM   1613  N    PHE A  210  0      9.538  19.461  23.351  1.00  11.26
ATOM   1614  CA   PHE A  210  0     10.526  19.329  22.287  1.00  10.01
ATOM   1615  C    PHE A  210  0     11.457  18.153  22.585  1.00   9.18
ATOM   1616  O    PHE A  210  0     11.894  17.999  23.732  1.00  10.07
ATOM   1617  CB   PHE A  210  0     11.370  20.629  22.292  1.00  10.86
ATOM   1618  CG   PHE A  210  0     12.489  20.581  21.292  1.00   9.63
ATOM   1619  CD1  PHE A  210  0     13.760  20.179  21.674  1.00   9.95
ATOM   1620  CD2  PHE A  210  0     12.251  20.922  19.984  1.00   8.54
ATOM   1621  CE1  PHE A  210  0     14.778  20.150  20.738  1.00   9.23
ATOM   1622  CE2  PHE A  210  0     13.243  20.862  19.023  1.00   7.93
ATOM   1623  CZ   PHE A  210  0     14.520  20.491  19.426  1.00   8.71
ATOM   1624  N    SER A  211  0     11.741  17.384  21.545  1.00   8.62
ATOM   1625  CA   SER A  211  0     12.645  16.255  21.716  1.00  10.71
```

APPENDIX 1-continued

| ATOM | 1626 | C   | SER A | 211 | 0 | 13.142 | 15.844 | 20.347 | 1.00 | 11.36 |
| --- | --- | --- | --- | --- | --- | --- | --- | --- | --- | --- |
| ATOM | 1627 | O   | SER A | 211 | 0 | 12.661 | 16.323 | 19.315 | 1.00 | 9.99 |
| ATOM | 1628 | CB  | SER A | 211 | 0 | 11.970 | 15.070 | 22.427 | 1.00 | 10.56 |
| ATOM | 1629 | OG  | SER A | 211 | 0 | 10.899 | 14.731 | 21.513 | 1.00 | 12.92 |
| ATOM | 1630 | N   | ILE A | 212 | 0 | 14.268 | 15.122 | 20.390 | 1.00 | 13.67 |
| ATOM | 1631 | CA  | ILE A | 212 | 0 | 14.883 | 14.680 | 19.131 | 1.00 | 14.79 |
| ATOM | 1632 | C   | ILE A | 212 | 0 | 15.013 | 13.166 | 19.220 | 1.00 | 15.44 |
| ATOM | 1633 | O   | ILE A | 212 | 0 | 15.624 | 12.689 | 20.177 | 1.00 | 15.98 |
| ATOM | 1634 | CB  | ILE A | 212 | 0 | 16.255 | 15.341 | 18.887 | 1.00 | 17.04 |
| ATOM | 1635 | CG1 | ILE A | 212 | 0 | 16.082 | 16.859 | 18.756 | 1.00 | 15.64 |
| ATOM | 1636 | CG2 | ILE A | 212 | 0 | 16.935 | 14.722 | 17.648 | 1.00 | 15.24 |
| ATOM | 1637 | CD1 | ILE A | 212 | 0 | 17.352 | 17.648 | 18.553 | 1.00 | 16.57 |
| ATOM | 1638 | N   | ASP A | 213 | 0 | 14.453 | 12.418 | 18.281 | 1.00 | 15.53 |
| ATOM | 1639 | CA  | ASP A | 213 | 0 | 14.549 | 10.952 | 18.401 | 1.00 | 16.50 |
| ATOM | 1640 | C   | ASP A | 213 | 0 | 16.004 | 10.469 | 18.541 | 1.00 | 16.69 |
| ATOM | 1641 | O   | ASP A | 213 | 0 | 16.948 | 10.902 | 17.851 | 1.00 | 14.36 |
| ATOM | 1642 | CB  | ASP A | 213 | 0 | 13.884 | 10.359 | 17.173 | 1.00 | 17.15 |
| ATOM | 1643 | CG  | ASP A | 213 | 0 | 12.369 | 10.467 | 17.144 | 1.00 | 18.12 |
| ATOM | 1644 | OD1 | ASP A | 213 | 0 | 11.751 | 10.995 | 18.092 | 1.00 | 16.90 |
| ATOM | 1645 | OD2 | ASP A | 213 | 0 | 11.801 | 9.990 | 16.129 | 1.00 | 17.35 |
| ATOM | 1646 | N   | GLY A | 214 | 0 | 16.198 | 9.559 | 19.477 | 1.00 | 15.76 |
| ATOM | 1647 | CA  | GLY A | 214 | 0 | 17.457 | 8.900 | 19.747 | 1.00 | 17.22 |
| ATOM | 1648 | C   | GLY A | 214 | 0 | 18.548 | 9.757 | 20.368 | 1.00 | 18.54 |
| ATOM | 1649 | O   | GLY A | 214 | 0 | 19.680 | 9.277 | 20.404 | 1.00 | 18.20 |
| ATOM | 1650 | N   | HIS A | 215 | 0 | 18.341 | 11.024 | 20.738 | 1.00 | 18.17 |
| ATOM | 1651 | CA  | HIS A | 215 | 0 | 19.422 | 11.88b | 21.229 | 1.00 | 17.59 |
| ATOM | 1652 | C   | HIS A | 215 | 0 | 19.096 | 12.505 | 22.577 | 1.00 | 17.92 |
| ATOM | 1653 | O   | HIS A | 215 | 0 | 17.917 | 12.696 | 22.898 | 1.00 | 20.45 |
| ATOM | 1654 | CB  | HIS A | 215 | 0 | 19.705 | 13.008 | 20.221 | 1.00 | 15.73 |
| ATOM | 1655 | CG  | HIS A | 215 | 0 | 20.309 | 12.543 | 18.936 | 1.00 | 16.90 |
| ATOM | 1656 | ND1 | HIS A | 215 | 0 | 19.589 | 11.864 | 17.963 | 1.00 | 17.35 |
| ATOM | 1657 | CD2 | HIS A | 215 | 0 | 21.574 | 12.658 | 18.444 | 1.00 | 16.15 |
| ATOM | 1658 | CE1 | HIS A | 215 | 0 | 20.376 | 11.576 | 16.933 | 1.00 | 17.63 |
| ATOM | 1659 | NE2 | HIS A | 215 | 0 | 21.599 | 12.046 | 17.216 | 1.00 | 17.73 |
| ATOM | 1660 | N   | GLU A | 216 | 0 | 20.104 | 12.815 | 23.382 | 1.00 | 17.22 |
| ATOM | 1661 | CA  | GLU A | 216 | 0 | 19.876 | 13.479 | 24.665 | 1.00 | 15.86 |
| ATOM | 1662 | C   | GLU A | 216 | 0 | 20.070 | 14.976 | 24.456 | 1.00 | 15.61 |
| ATOM | 1663 | O   | GLU A | 216 | 0 | 20.684 | 15.386 | 23.453 | 1.00 | 14.96 |
| ATOM | 1664 | CB  | GLU A | 216 | 0 | 20.817 | 12.901 | 25.694 | 1.00 | 15.38 |

APPENDIX 1-continued

| ATOM | 1665 | CG  | GLU A | 216 | 0 | 20.440 | 11.520 | 26.166 | 1.00 | 16.53 |
| ATOM | 1666 | CD  | GLU A | 216 | 0 | 21.242 | 11.058 | 27.357 | 1.00 | 17.23 |
| ATOM | 1667 | OE1 | GLU A | 216 | 0 | 22.378 | 10.619 | 27.129 | 1.00 | 20.31 |
| ATOM | 1668 | OE2 | GLU A | 216 | 0 | 20.813 | 11.119 | 28.519 | 1.00 | 16.06 |
| ATOM | 1669 | N   | LEU A | 217 | 0 | 19.623 | 15.792 | 25.394 | 1.00 | 14.64 |
| ATOM | 1670 | CA  | LEU A | 217 | 0 | 19.738 | 17.243 | 25.251 | 1.00 | 14.91 |
| ATOM | 1671 | C   | LEU A | 217 | 0 | 20.512 | 17.792 | 26.446 | 1.00 | 14.71 |
| ATOM | 1672 | O   | LEU A | 217 | 0 | 19.950 | 17.734 | 27.539 | 1.00 | 15.67 |
| ATOM | 1673 | CB  | LEU A | 217 | 0 | 18.362 | 17.931 | 25.229 | 1.00 | 14.75 |
| ATOM | 1674 | CG  | LEU A | 217 | 0 | 17.276 | 17.349 | 24.306 | 1.00 | 15.40 |
| ATOM | 1675 | CD1 | LEU A | 217 | 0 | 15.939 | 18.075 | 24.505 | 1.00 | 15.08 |
| ATOM | 1676 | CD2 | LEU A | 217 | 0 | 17.723 | 17.453 | 22.849 | 1.00 | 15.22 |
| ATOM | 1677 | N   | THR A | 218 | 0 | 21.732 | 18.278 | 26.229 | 1.00 | 13.65 |
| ATOM | 1678 | CA  | THR A | 218 | 0 | 22.507 | 18.714 | 27.402 | 1.00 | 13.26 |
| ATOM | 1679 | C   | THR A | 218 | 0 | 22.427 | 20.232 | 27.505 | 1.00 | 13.27 |
| ATOM | 1680 | O   | THR A | 218 | 0 | 23.142 | 20.955 | 26.805 | 1.00 | 12.91 |
| ATOM | 1681 | CB  | THR A | 218 | 0 | 23.955 | 18.216 | 27.304 | 1.00 | 12.08 |
| ATOM | 1682 | OG1 | THR A | 218 | 0 | 23.935 | 16.782 | 27.331 | 1.00 | 15.48 |
| ATOM | 1683 | CG2 | THR A | 218 | 0 | 24.767 | 18.721 | 28.470 | 1.00 | 11.46 |
| ATOM | 1684 | N   | ILE A | 219 | 0 | 21.522 | 20.649 | 28.385 | 1.00 | 13.30 |
| ATOM | 1685 | CA  | ILE A | 219 | 0 | 21.259 | 22.068 | 28.547 | 1.00 | 14.53 |
| ATOM | 1686 | C   | ILE A | 219 | 0 | 22.420 | 22.818 | 29.180 | 1.00 | 12.72 |
| ATOM | 1687 | O   | ILE A | 219 | 0 | 22.795 | 22.492 | 30.292 | 1.00 | 13.08 |
| ATOM | 1688 | CB  | ILE A | 219 | 0 | 19.930 | 22.268 | 29.323 | 1.00 | 14.74 |
| ATOM | 1689 | CG1 | ILE A | 219 | 0 | 18.761 | 21.699 | 28.441 | 1.00 | 17.33 |
| ATOM | 1690 | CG2 | ILE A | 219 | 0 | 19.666 | 23.717 | 29.656 | 1.00 | 13.40 |
| ATOM | 1691 | CD1 | ILE A | 219 | 0 | 17.597 | 21.481 | 29.412 | 1.00 | 19.42 |
| ATOM | 1692 | N   | ILE A | 220 | 0 | 22.898 | 23.869 | 28.510 | 1.00 | 12.55 |
| ATOM | 1693 | CA  | ILE A | 220 | 0 | 23.994 | 24.696 | 29.019 | 1.00 | 13.25 |
| ATOM | 1694 | C   | ILE A | 220 | 0 | 23.686 | 26.193 | 29.085 | 1.00 | 15.11 |
| ATOM | 1695 | O   | ILE A | 220 | 0 | 24.477 | 27.001 | 29.618 | 1.00 | 14.73 |
| ATOM | 1696 | CB  | ILE A | 220 | 0 | 25.239 | 24.507 | 28.125 | 1.00 | 11.80 |
| ATOM | 1697 | CG1 | ILE A | 220 | 0 | 24.954 | 24.871 | 26.671 | 1.00 | 10.93 |
| ATOM | 1698 | CG2 | ILE A | 220 | 0 | 25.770 | 23.072 | 28.291 | 1.00 |  9.59 |
| ATOM | 1699 | CD1 | ILE A | 220 | 0 | 26.249 | 25.231 | 25.928 | 1.00 | 12.07 |
| ATOM | 1700 | N   | GLU A | 221 | 0 | 22.490 | 26.573 | 28.597 | 1.00 | 13.30 |
| ATOM | 1701 | CA  | GLU A | 221 | 0 | 22.048 | 27.951 | 28.624 | 1.00 | 12.96 |
| ATOM | 1702 | C   | GLU A | 221 | 0 | 20.522 | 28.066 | 28.727 | 1.00 | 13.77 |
| ATOM | 1703 | O   | GLU A | 221 | 0 | 19.799 | 27.301 | 28.068 | 1.00 | 14.06 |
| ATOM | 1704 | CB  | GLU A | 221 | 0 | 22.436 | 28.666 | 27.318 | 1.00 | 12.73 |

APPENDIX 1-continued

| ATOM | 1705 | CG  | GLU A | 221 | 0 | 22.280 | 30.178 | 27.325 | 1.00 | 12.94 |
| ATOM | 1706 | CD  | GLU A | 221 | 0 | 22.018 | 30.783 | 25.969 | 1.00 | 13.84 |
| ATOM | 1707 | OE1 | GLU A | 221 | 0 | 22.345 | 30.269 | 24.887 | 1.00 | 12.66 |
| ATOM | 1708 | OE2 | GLU A | 221 | 0 | 21.386 | 31.862 | 25.936 | 1.00 | 14.80 |
| ATOM | 1709 | N   | VAL A | 222 | 0 | 20.062 | 29.091 | 29.434 | 1.00 | 13.89 |
| ATOM | 1710 | CA  | VAL A | 222 | 0 | 18.632 | 29.350 | 29.534 | 1.00 | 14.13 |
| ATOM | 1711 | C   | VAL A | 222 | 0 | 18.409 | 30.853 | 29.493 | 1.00 | 13.87 |
| ATOM | 1712 | O   | VAL A | 222 | 0 | 18.900 | 31.657 | 30.300 | 1.00 | 11.55 |
| ATOM | 1713 | CB  | VAL A | 222 | 0 | 18.003 | 28.649 | 30.737 | 1.00 | 16.86 |
| ATOM | 1714 | CG1 | VAL A | 222 | 0 | 18.730 | 28.941 | 32.017 | 1.00 | 19.16 |
| ATOM | 1715 | CG2 | VAL A | 222 | 0 | 16.575 | 29.120 | 31.033 | 1.00 | 18.45 |
| ATOM | 1716 | N   | ASP A | 223 | 0 | 17.631 | 31.267 | 28.481 | 1.00 | 11.69 |
| ATOM | 1717 | CA  | ASP A | 223 | 0 | 17.245 | 32.673 | 28.386 | 1.00 | 13.60 |
| ATOM | 1718 | C   | ASP A | 223 | 0 | 18.472 | 33.598 | 28.548 | 1.00 | 14.44 |
| ATOM | 1719 | O   | ASP A | 223 | 0 | 18.423 | 34.552 | 29.336 | 1.00 | 12.75 |
| ATOM | 1720 | CB  | ASP A | 223 | 0 | 16.161 | 33.033 | 29.417 | 1.00 | 12.59 |
| ATOM | 1721 | CG  | ASP A | 223 | 0 | 14.845 | 32.279 | 29.364 | 1.00 | 14.64 |
| ATOM | 1722 | OD1 | ASP A | 223 | 0 | 14.697 | 31.397 | 28.493 | 1.00 | 13.34 |
| ATOM | 1723 | OD2 | ASP A | 223 | 0 | 13.858 | 32.463 | 30.156 | 1.00 | 13.85 |
| ATOM | 1724 | N   | GLY A | 224 | 0 | 19.544 | 33.372 | 27.767 | 1.00 | 13.49 |
| ATOM | 1725 | CA  | GLY A | 224 | 0 | 20.728 | 34.213 | 27.770 | 1.00 | 12.85 |
| ATOM | 1726 | C   | GLY A | 224 | 0 | 21.562 | 34.112 | 29.049 | 1.00 | 13.00 |
| ATOM | 1727 | O   | GLY A | 224 | 0 | 22.326 | 35.040 | 29.317 | 1.00 | 13.97 |
| ATOM | 1728 | N   | GLU A | 225 | 0 | 21.370 | 33.105 | 29.875 | 1.00 | 11.78 |
| ATOM | 1729 | CA  | GLU A | 225 | 0 | 22.068 | 32.888 | 31.114 | 1.00 | 14.97 |
| ATOM | 1730 | C   | GLU A | 225 | 0 | 22.609 | 31.447 | 31.106 | 1.00 | 16.73 |
| ATOM | 1731 | O   | GLU A | 225 | 0 | 21.858 | 30.498 | 30.849 | 1.00 | 15.88 |
| ATOM | 1732 | CB  | GLU A | 225 | 0 | 21.174 | 33.062 | 32.358 | 1.00 | 16.54 |
| ATOM | 1733 | CG  | GLU A | 225 | 0 | 20.509 | 34.424 | 32.534 | 1.00 | 16.30 |
| ATOM | 1734 | CD  | GLU A | 225 | 0 | 21.492 | 35.546 | 32.823 | 1.00 | 17.57 |
| ATOM | 1735 | OE1 | GLU A | 225 | 0 | 22.450 | 35.254 | 33.561 | 1.00 | 18.76 |
| ATOM | 1736 | OE2 | GLU A | 225 | 0 | 21.360 | 36.711 | 32.360 | 1.00 | 17.77 |
| ATOM | 1737 | N   | LEU A | 226 | 0 | 23.922 | 31.285 | 31.324 | 1.00 | 16.90 |
| ATOM | 1738 | CA  | LEU A | 226 | 0 | 24.526 | 29.955 | 31.318 | 1.00 | 15.50 |
| ATOM | 1739 | C   | LEU A | 226 | 0 | 24.183 | 29.127 | 32.540 | 1.00 | 15.04 |
| ATOM | 1740 | O   | LEU A | 226 | 0 | 24.002 | 29.648 | 33.652 | 1.00 | 15.17 |
| ATOM | 1741 | CB  | LEU A | 226 | 0 | 26.062 | 30.008 | 31.216 | 1.00 | 15.36 |
| ATOM | 1742 | CG  | LEU A | 226 | 0 | 26.567 | 30.741 | 29.958 | 1.00 | 17.95 |
| ATOM | 1743 | CD1 | LEU A | 226 | 0 | 28.076 | 30.876 | 29.979 | 1.00 | 18.77 |

APPENDIX 1-continued

| ATOM | 1744 | CD2 | LEU A | 226 | 0 | 26.111 | 30.029 | 28.687 | 1.00 | 17.36 |
| ATOM | 1745 | N | THR A | 227 | 0 | 24.119 | 27.799 | 32.332 | 1.00 | 13.62 |
| ATOM | 1746 | CK | THR A | 227 | 0 | 23.848 | 26.930 | 33.479 | 1.00 | 13.72 |
| ATOM | 1747 | C | THR A | 227 | 0 | 24.936 | 25.851 | 33.528 | 1.00 | 14.30 |
| ATOM | 1748 | O | THR A | 227 | 0 | 25.732 | 25.629 | 32.592 | 1.00 | 14.28 |
| ATOM | 1749 | CB | THR A | 227 | 0 | 22.478 | 26.217 | 33.352 | 1.00 | 14.35 |
| ATOM | 1750 | OG1 | THR A | 227 | 0 | 22.506 | 25.385 | 32.178 | 1.00 | 13.68 |
| ATOM | 1751 | CG2 | THR A | 227 | 0 | 21.284 | 27.161 | 33.180 | 1.00 | 12.29 |
| ATOM | 1752 | N | GLU A | 228 | 0 | 24.960 | 25.136 | 34.625 | 1.00 | 14.73 |
| ATOM | 1753 | CA | GLU A | 228 | 0 | 25.765 | 23.907 | 34.714 | 1.00 | 17.32 |
| ATOM | 1754 | C | GLU A | 228 | 0 | 25.110 | 22.971 | 33.680 | 1.00 | 17.30 |
| ATOM | 1755 | O | GLU A | 228 | 0 | 23.917 | 23.035 | 33.472 | 1.00 | 16.97 |
| ATOM | 1756 | CB | GLU A | 228 | 0 | 25.617 | 23.315 | 36.114 | 1.00 | 16.58 |
| ATOM | 1757 | CG | GLU A | 228 | 0 | 26.493 | 23.979 | 37.186 | 1.00 | 18.10 |
| ATOM | 1758 | CD | GLU A | 228 | 0 | 26.236 | 23.458 | 38.575 | 1.00 | 20.92 |
| ATOM | 1759 | OE1 | GLU A | 228 | 0 | 25.469 | 22.470 | 38.755 | 1.00 | 23.38 |
| ATOM | 1760 | OE2 | GLU A | 228 | 0 | 26.769 | 23.997 | 39.564 | 1.00 | 21.26 |
| ATOM | 1761 | N | PRO A | 229 | 0 | 25.867 | 22.158 | 32.984 | 1.00 | 16.91 |
| ATOM | 1762 | CA | PRO A | 229 | 0 | 25.369 | 21.207 | 31.992 | 1.00 | 16.37 |
| ATOM | 1763 | C | PRO A | 229 | 0 | 24.351 | 20.275 | 32.599 | 1.00 | 16.24 |
| ATOM | 1764 | O | PRO A | 229 | 0 | 24.624 | 19.652 | 33.619 | 1.00 | 15.76 |
| ATOM | 1765 | CB | PRO A | 229 | 0 | 26.612 | 20.469 | 31.419 | 1.00 | 15.97 |
| ATOM | 1766 | CG | PRO A | 229 | 0 | 27.701 | 21.509 | 31.741 | 1.00 | 15.92 |
| ATOM | 1767 | CD | PRO A | 229 | 0 | 27.337 | 22.141 | 33.083 | 1.00 | 14.86 |
| ATOM | 1768 | N | HIS A | 230 | 0 | 23.140 | 20.164 | 32.038 | 1.00 | 15.58 |
| ATOM | 1769 | CA | HIS A | 230 | 0 | 22.090 | 19.325 | 32.618 | 1.00 | 15.01 |
| ATOM | 1770 | C | HIS A | 230 | 0 | 21.354 | 18.610 | 31.488 | 1.00 | 13.55 |
| ATOM | 1771 | O | HIS A | 230 | 0 | 20.756 | 19.192 | 30.590 | 1.00 | 13.47 |
| ATOM | 1772 | CB | HIS A | 230 | 0 | 21.172 | 20.164 | 33.510 | 1.00 | 15.89 |
| ATOM | 1773 | CG | HIS A | 230 | 0 | 20.045 | 19.341 | 34.064 | 1.00 | 18.32 |
| ATOM | 1774 | ND1 | HIS A | 230 | 0 | 20.252 | 18.347 | 35.004 | 1.00 | 18.14 |
| ATOM | 1775 | CD2 | HIS A | 230 | 0 | 18.713 | 19.328 | 33.791 | 1.00 | 17.75 |
| ATOM | 1776 | CE1 | HIS A | 230 | 0 | 19.121 | 17.768 | 35.310 | 1.00 | 16.33 |
| ATOM | 1777 | NE2 | HIS A | 230 | 0 | 18.173 | 18.344 | 34.609 | 1.00 | 17.85 |
| ATOM | 1778 | N | THR A | 231 | 0 | 21.496 | 17.304 | 31.458 | 1.00 | 12.94 |
| ATOM | 1779 | CA | THR A | 231 | 0 | 20.995 | 16.474 | 30.346 | 1.00 | 14.15 |
| ATOM | 1780 | C | THR A | 231 | 0 | 19.620 | 15.890 | 30.547 | 1.00 | 13.41 |
| ATOM | 1781 | O | THR A | 231 | 0 | 19.293 | 15.401 | 31.616 | 1.00 | 14.89 |
| ATOM | 1782 | CB | THR A | 231 | 0 | 22.040 | 15.364 | 30.060 | 1.00 | 13.73 |
| ATOM | 1783 | OG1 | THR A | 231 | 0 | 23.3t4 | 16.023 | 29.852 | 1.00 | 14.77 |

APPENDIX 1-continued

```
ATOM   1784  CG2  THR A  231  0   21.655  14.600  28.818  1.00  13.06
ATOM   1785  N    VAL A  232  0   18.776  15.954  29.549  1.00  12.86
ATOM   1786  CA   VAL A  232  0   17.374  15.505  29.665  1.00  13.44
ATOM   1787  C    VAL A  232  0   16.999  14.966  28.319  1.00  14.96
ATOM   1788  O    VAL A  232  0   17.790  15.258  27.390  1.00  14.12
ATOM   1789  CB   VAL A  232  0   16.771  16.910  30.000  1.00  17.41
ATOM   1790  CG1  VAL A  232  0   16.075  17.587  28.856  1.00  14.66
ATOM   1791  CG2  VAL A  232  0   16.158  16.935  31.371  1.00  15.66
ATOM   1792  N    ASP A  233  0   15.874  14.277  28.153  1.00  14.01
ATOM   1793  CA   ASP A  233  0   15.405  13.803  26.874  1.00  14.73
ATOM   1794  C    ASP A  233  0   14.353  14.718  26.245  1.00  14.74
ATOM   1795  O    ASP A  233  0   14.187  14.731  25.027  1.00  13.41
ATOM   1796  CB   ASP A  233  0   14.640  12.465  27.046  1.00  16.54
ATOM   1797  CG   ASP A  233  0   15.637  11.417  27.536  1.00  19.27
ATOM   1798  OD1  ASP A  233  0   16.543  11.145  26.732  1.00  20.98
ATOM   1799  OD2  ASP A  233  0   15.536  10.945  28.667  1.00  19.27
ATOM   1800  N    ARG A  234  0   13.595  15.386  27.122  1.00  13.79
ATOM   1801  CA   ARG A  234  0   12.514  16.199  26.598  1.00  16.36
ATOM   1802  C    ARG A  234  0   12.258  17.426  27.472  1.00  15.17
ATOM   1803  O    ARG A  234  0   12.418  17.390  28.686  1.00  13.96
ATOM   1804  CB   ARG A  234  0   11.265  15.330  26.482  1.00  19.23
ATOM   1805  CG   ARG A  234  0   10.104  16.036  25.788  1.00  22.25
ATOM   1806  CD   ARG A  234  0    8.981  15.023  25.506  1.00  24.68
ATOM   1807  NE   ARG A  234  0    8.157  14.983  26.705  1.00  28.27
ATOM   1808  CZ   ARG A  234  0    6.845  14.828  26.719  1.00  28.66
ATOM   1809  NH1  ARG A  234  0    6.291  14.833  27.909  1.00  30.08
ATOM   1810  NH2  ARG A  234  0    6.191  14.662  25.587  1.00  30.24
ATOM   1811  N    LEU A  235  0   11.874  18.524  26.816  1.00  13.90
ATOM   1812  CA   LEU A  235  0   11.619  19.742  27.607  1.00  13.15
ATOM   1813  C    LEU A  235  0   10.390  20.430  27.041  1.00  11.49
ATOM   1814  O    LEU A  235  0   10.025  20.304  25.873  1.00  11.08
ATOM   1815  CB   LEU A  235  0   12.825  20.630  27.695  1.00  14.39
ATOM   1816  CG   LEU A  235  0   13.459  21.645  26.801  1.00  17.19
ATOM   1817  CD1  LEU A  235  0   14.795  21.218  26.197  1.00  16.98
ATOM   1818  CD2  LEU A  235  0   12.556  22.219  25.685  1.00  18.24
ATOM   1819  N    GLN A  236  0    9.769  21.152  27.949  1.00  12.74
ATOM   1820  CA   GLN A  236  0    8.576  21.944  27.616  1.00  13.45
ATOM   1821  C    GLN A  236  0    9.005  23.390  27.459  1.00  12.21
ATOM   1822  O    GLN A  236  0    9.606  23.939  28.406  1.00  13.90
```

APPENDIX 1-continued

```
ATOM   1823 CB  GLN A 236 0      7.525 21.770 28.741 1.00 12.06
ATOM   1824 CG  GLN A 236 0      6.197 22.276 28.238 1.00 14.12
ATOM   1525 CD  GLN A 236 0      5.025 22.108 29.205 1.00 13.35
ATOM   1826 OE1 GLN A 236 0      3.893 22.215 28.721 1.00 15.61
ATOM   1827 NE2 GLN A 236 0      5.226 21.912 30.463 1.00 12.00
ATOM   1828 N   ILE A 237 0      8.748 24.011 26.311 1.00 12.17
ATOM   1829 CA  ILE A 237 0      9.213 25.390 26.156 1.00 12.41
ATOM   1830 C   ILE A 237 0      8.061 26.376 25.953 1.00 13.14
ATOM   1831 O   ILE A 237 0      7.283 26.310 24.990 1.00 13.64
ATOM   1832 CB  ILE A 237 0     10.255 25.437 25.022 1.00 11.03
ATOM   1833 CG1 ILE A 237 0     10.947 26.793 24.960 1.00 11.84
ATOM   1834 CG2 ILE A 237 0      9.615 25.056 23.662 1.00 10.02
ATOM   1835 CD1 ILE A 237 0     12.041 26.953 23.902 1.00 11.23
ATOM   1836 N   PHE A 238 0      8.037 27.414 26.765 1.00 12.53
ATOM   1537 CA  PHE A 238 0      6.979 25.431 26.714 1.00 13.23
ATOM   1838 C   PHE A 238 0      7.382 29.683 25.957 1.00 13.99
ATOM   1839 O   PHE A 238 0      8.530 29.848 25.545 1.00 13.87
ATOM   1840 CB  PHE A 238 0      6.592 25.548 25.145 1.00 12.72
ATOM   1841 CG  PHE A 238 0      6.176 27.691 28.993 1.00 14.51
ATOM   1842 CD1 PHE A 238 0      7.095 26.957 29.710 1.00 14.84
ATOM   1843 CD2 PHE A 238 0      4.836 27.314 29.078 1.00 15.50
ATOM   1544 CE1 PHE A 238 0      6.748 25.882 30.497 1.00 13.57
ATOM   1845 CE2 PHE A 238 0      4.465 26.236 29.862 1.00 14.62
ATOM   1846 CZ  PHE A 238 0      5.423 25.525 30.568 1.00 15.15
ATOM   1847 N   THR A 239 0      6.388 30.494 25.604 1.00 14.16
ATOM   1545 CA  THR A 239 0      6.543 31.678 24.806 1.00 13.44
ATOM   1549 C   THR A 239 0      7.532 32.453 25.106 1.00 11.74
ATOM   1850 O   THR A 239 0      8.012 32.950 26.215 1.00 10.47
ATOM   1851 CB  THR A 239 0      5.381 32.695 24.978 1.00 15.55
ATOM   1852 OG1 THR A 239 0      5.258 33.008 26.359 1.00 17.88
ATOM   1853 CG2 THR A 239 0      4.055 32.131 24.478 1.00 16.75
ATOM   1854 N   GLY A 240 0      8.672 32.593 24.078 1.00  7.94
ATOM   1855 CA  GLY A 240 0      9.877 33.348 24.193 1.00 10.08
ATOM   1856 C   GLY A 240 0     11.039 32.865 25.041 1.00 11.34
ATOM   1857 O   GLY A 240 0     11.977 33.650 25.216 1.00 11.02
ATOM   1858 N   GLN A 241 0     10.990 31.646 25.592 1.00  9.73
ATOM   1859 CA  GLN A 241 0     12.067 31.090 26.364 1.00  9.59
ATOM   1860 C   GLN A 241 0     13.114 30.587 25.342 1.00 10.56
ATOM   1861 O   GLN A 241 0     12.823 30.467 24.126 1.00  8.44
ATOM   1862 CB  GLN A 241 0     11.604 29.965 27.285 1.00 10.57
```

APPENDIX 1-continued

| | | | | | | | | | | |
|---|---|---|---|---|---|---|---|---|---|---|
| ATOM | 1863 | CG | GLN A | 241 | 0 | 10.820 | 30.363 | 28.523 | 1.00 | 10.54 |
| ATOM | 1864 | CD | GLN A | 241 | 0 | 10.341 | 29.190 | 29.341 | 1.00 | 12.22 |
| ATOM | 1865 | OE1 | GLN A | 241 | 0 | 10.118 | 28.077 | 28.815 | 1.00 | 13.21 |
| ATOM | 1866 | NE2 | GLN A | 241 | 0 | 10.220 | 29.466 | 30.639 | 1.00 | 11.74 |
| ATOM | 1867 | N | ARG A | 242 | 0 | 14.372 | 30.492 | 25.774 | 1.00 | 9.00 |
| ATOM | 1868 | CA | ARG A | 242 | 0 | 15.388 | 29.992 | 24.834 | 1.00 | 11.01 |
| ATOM | 1869 | C | ARG A | 242 | 0 | 16.210 | 28.966 | 25.609 | 1.00 | 11.30 |
| ATOM | 1870 | O | ARG A | 242 | 0 | 16.292 | 29.133 | 26.816 | 1.00 | 9.51 |
| ATOM | 1871 | CB | ARG A | 242 | 0 | 16.324 | 31.043 | 24.265 | 1.00 | 12.77 |
| ATOM | 1872 | CG | ARG A | 242 | 0 | 15.694 | 32.128 | 23.364 | 1.00 | 12.52 |
| ATOM | 1873 | CD | ARG A | 242 | 0 | 15.066 | 33.249 | 24.138 | 1.00 | 10.81 |
| ATOM | 1874 | NE | ARG A | 242 | 0 | 15.957 | 34.126 | 24.892 | 1.00 | 10.80 |
| ATOM | 1875 | CZ | ARG A | 242 | 0 | 15.630 | 34.761 | 26.002 | 1.00 | 11.36 |
| ATOM | 1876 | NH1 | ARG A | 242 | 0 | 16.486 | 35.548 | 26.648 | 1.00 | 7.98 |
| ATOM | 1871 | NH2 | ARG A | 242 | 0 | 14.365 | 34.589 | 26.489 | 1.00 | 12.78 |
| ATOM | 1878 | N | TYR A | 243 | 0 | 16.717 | 27.934 | 24.942 | 1.00 | 11.61 |
| ATOM | 1879 | CA | TYR A | 243 | 0 | 17.631 | 27.009 | 25.610 | 1.00 | 12.54 |
| ATOM | 1880 | C | TYR A | 243 | 0 | 18.819 | 26.762 | 24.650 | 1.00 | 14.46 |
| ATOM | 1881 | O | TYR A | 243 | 0 | 18.568 | 26.656 | 23.435 | 1.00 | 16.11 |
| ATOM | 1882 | CB | TYR A | 243 | 0 | 17.015 | 25.638 | 25.934 | 1.00 | 11.09 |
| ATOM | 1883 | CG | TYR A | 243 | 0 | 16.007 | 25.667 | 27.054 | 1.00 | 12.11 |
| ATOM | 1884 | CD1 | TYR A | 243 | 0 | 14.641 | 25.825 | 26.843 | 1.00 | 12.88 |
| ATOM | 1885 | CD2 | TYR A | 243 | 0 | 16.440 | 25.575 | 28.371 | 1.00 | 12.11 |
| ATOM | 1886 | CE1 | TYR A | 243 | 0 | 13.748 | 25.869 | 27.915 | 1.00 | 12.71 |
| ATOM | 1887 | CE2 | TYR A | 243 | 0 | 15.560 | 25.582 | 29.436 | 1.00 | 12.50 |
| ATOM | 1888 | CZ | TYR A | 243 | 0 | 14.205 | 25.738 | 29.188 | 1.00 | 12.29 |
| ATOM | 1889 | OH | TYR A | 243 | 0 | 13.379 | 25.789 | 30.286 | 1.00 | 13.65 |
| ATOM | 1890 | N | SER A | 244 | 0 | 20.059 | 26.734 | 25.144 | 1.00 | 12.78 |
| ATOM | 1891 | CA | SER A | 244 | 0 | 21.117 | 26.212 | 24.268 | 1.00 | 13.22 |
| ATOM | 1892 | C | SER A | 244 | 0 | 21.333 | 24.779 | 24.814 | 1.00 | 11.06 |
| ATOM | 1893 | O | SER A | 244 | 0 | 21.377 | 24.604 | 26.018 | 1.00 | 11.27 |
| ATOM | 1894 | CB | SER A | 244 | 0 | 22.485 | 26.907 | 24.308 | 1.00 | 14.46 |
| ATOM | 1895 | OG | SER A | 244 | 0 | 22.551 | 28.029 | 23.463 | 1.00 | 13.59 |
| ATOM | 1896 | N | PHE A | 245 | 0 | 21.484 | 23.780 | 23.983 | 1.00 | 11.89 |
| ATOM | 1897 | CA | PHE A | 245 | 0 | 21.772 | 22.437 | 24.452 | 1.00 | 13.14 |
| ATOM | 1898 | C | PHE A | 245 | 0 | 22.867 | 21.857 | 23.546 | 1.00 | 12.32 |
| ATOM | 1899 | O | PHE A | 245 | 0 | 22.890 | 22.128 | 22.354 | 1.00 | 11.11 |
| ATOM | 1900 | CB | PHE A | 245 | 0 | 20.554 | 21.495 | 24.526 | 1.00 | 11.40 |
| ATOM | 1901 | CG | PHE A | 245 | 0 | 19.915 | 21.236 | 23.195 | 1.00 | 11.98 |

APPENDIX 1-continued

```
ATOM   1902  CD1  PHE A  245  0   18.815  21.993  22.813  1.00  13.38
ATOM   1903  CD2  PHE A  245  0   20.349  20.236  22.351  1.00  11.45
ATOM   1904  CE1  PHE A  245  0   18.216  21.773  21.588  1.00  12.84
ATOM   1905  CE2  PHE A  245  0   19.759  20.000  21.129  1.00  11.48
ATOM   1906  CZ   PHE A  245  0   18.705  20.796  20.743  1.00  12.65
ATOM   1907  N    VAL A  246  0   23.742  21.073  24.169  1.00  13.51
ATOM   1908  CA   VAL A  246  0   24.775  20.427  23.341  1.00  13.37
ATOM   1909  C    VAL A  246  0   24.096  19.177  22.783  1.00  12.47
ATOM   1910  O    VAL A  246  0   23.505  18.425  23.540  1.00  11.41
ATOM   1911  CB   VAL A  246  0   25.990  19.984  24.190  1.00  14.96
ATOM   1912  CG1  VAL A  246  0   26.995  19.186  23.364  1.00  13.75
ATOM   1913  CG2  VAL A  246  0   26.681  21.165  24.841  1.00  15.92
ATOM   1914  N    LEU A  247  0   24.160  18.996  21.490  1.00  12.97
ATOM   1915  CA   LEU A  247  0   23.766  17.833  20.785  1.00  14.32
ATOM   1916  C    LEU A  247  0   25.071  17.077  20.395  1.00  14.22
ATOM   1917  O    LEU A  247  0   25.954  17.529  19.664  1.00  12.45
ATOM   1918  CB   LEU A  247  0   22.980  18.109  19.505  1.00  16.00
ATOM   1919  CG   LEU A  247  0   22.514  16.786  18.835  1.00  16.80
ATOM   1920  CD1  LEU A  247  0   21.266  16.306  19.513  1.00  18.30
ATOM   1921  CD2  LEU A  247  0   22.207  16.988  17.373  1.00  18.70
ATOM   1922  N    ASP A  248  0   25.144  15.886  20.926  1.00  13.56
ATOM   1923  CA   ASP A  248  0   26.278  14.980  20.727  1.00  16.65
ATOM   1924  C    ASP A  248  0   25.916  14.072  19.581  1.00  16.18
ATOM   1925  O    ASP A  248  0   25.095  13.166  19.813  1.00  17.60
ATOM   1926  CB   ASP A  248  0   26.536  14.229  22.036  1.00  17.83
ATOM   1927  CG   ASP A  248  0   27.798  13.359  22.024  1.00  21.77
ATOM   1928  OD1  ASP A  248  0   28.231  12.967  23.140  1.00  24.11
ATOM   1929  OD2  ASP A  248  0   28.345  13.060  20.950  1.00  21.25
ATOM   1930  N    ALA A  249  0   26.414  14.277  18.369  1.00  15.85
ATOM   1931  CA   ALA A  249  0   25.982  13.416  17.255  1.00  17.99
ATOM   1932  C    ALA A  249  0   26.698  12.049  17.306  1.00  20.21
ATOM   1933  O    ALA A  249  0   27.569  11.766  16.485  1.00  19.11
ATOM   1934  CB   ALA A  249  0   26.165  14.126  15.930  1.00  14.57
ATOM   1935  N    ASN A  250  0   26.273  11.223  18.253  1.00  21.66
ATOM   1936  CA   ASN A  250  0   26.861   9.961  18.581  1.00  25.53
ATOM   1937  C    ASN A  250  0   26.061   8.721  18.202  1.00  27.30
ATOM   1938  O    ASN A  250  0   26.344   7.645  18.756  1.00  29.42
ATOM   1939  CB   ASN A  250  0   27.108   9.912  20.104  1.00  25.83
ATOM   1940  CG   ASN A  250  0   25.888   9.968  20.978  1.00  28.76
ATOM   1941  OD1  ASN A  250  0   24.757  10.156  20.527  1.00  29.90
```

APPENDIX 1-continued

| | | | | | | | | | | |
|---|---|---|---|---|---|---|---|---|---|---|
| ATOM | 1942 | ND2 | ASN A | 250 | 0 | 26.042 | 9.826 | 22.306 | 1.00 | 29.52 |
| ATOM | 1943 | N | GLN A | 251 | 0 | 25.089 | 8.841 | 17.302 | 1.00 | 26.74 |
| ATOM | 1944 | CA | GLN A | 251 | 0 | 24.239 | 7.712 | 16.934 | 1.00 | 23.48 |
| ATOM | 1945 | C | GLN A | 251 | 0 | 24.583 | 7.311 | 15.510 | 1.00 | 21.73 |
| ATOM | 1946 | O | GLN A | 251 | 0 | 25.333 | 8.009 | 14.843 | 1.00 | 19.39 |
| ATOM | 1947 | CB | GLN A | 251 | 0 | 22.757 | 8.104 | 17.022 | 1.00 | 24.79 |
| ATOM | 1948 | CG | GLN A | 251 | 0 | 22.333 | 8.701 | 18.360 | 1.00 | 25.14 |
| ATOM | 1949 | CD | GLN A | 251 | 0 | 22.430 | 7.693 | 19.480 | 1.00 | 26.76 |
| ATOM | 1950 | OE1 | GLN A | 251 | 0 | 21.762 | 6.654 | 19.405 | 1.00 | 28.78 |
| ATOM | 1951 | NE2 | GLN A | 251 | 0 | 23.202 | 7.986 | 20.514 | 1.00 | 26.02 |
| ATOM | 1952 | N | PRO A | 252 | 0 | 24.058 | 6.177 | 15.076 | 1.00 | 20.53 |
| ATOM | 1953 | CA | PRO A | 252 | 0 | 24.293 | 5.637 | 13.755 | 1.00 | 20.06 |
| ATOM | 1954 | C | PRO A | 252 | 0 | 23.940 | 6.671 | 12.702 | 1.00 | 21.83 |
| ATOM | 1955 | O | PRO A | 252 | 0 | 22.973 | 7.424 | 12.940 | 1.00 | 22.51 |
| ATOM | 1956 | CB | PRO A | 252 | 0 | 23.417 | 4.367 | 13.647 | 1.00 | 19.98 |
| ATOM | 1957 | CG | PRO A | 252 | 0 | 23.288 | 3.997 | 15.096 | 1.00 | 19.94 |
| ATOM | 1958 | CD | PRO A | 252 | 0 | 23.223 | 5.289 | 15.902 | 1.00 | 19.68 |
| ATOM | 1959 | N | VAL A | 253 | 0 | 24.663 | 6.728 | 11.584 | 1.00 | 20.85 |
| ATOM | 1960 | CA | VAL A | 253 | 0 | 24.302 | 7.741 | 10.604 | 1.00 | 22.29 |
| ATOM | 1961 | C | VAL A | 253 | 0 | 22.897 | 7.414 | 10.108 | 1.00 | 23.02 |
| ATOM | 1962 | O | VAL A | 253 | 0 | 22.593 | 6.289 | 9.753 | 1.00 | 21.37 |
| ATOM | 1963 | CB | VAL A | 253 | 0 | 25.298 | 8.065 | 9.494 | 1.00 | 23.22 |
| ATOM | 1964 | CG1 | VAL A | 253 | 0 | 26.696 | 7.582 | 9.827 | 1.00 | 22.25 |
| ATOM | 1965 | CG2 | VAL A | 253 | 0 | 24.859 | 7.680 | 8.101 | 1.00 | 22.26 |
| ATOM | 1966 | N | ASP A | 254 | 0 | 22.012 | 8.422 | 10.159 | 1.00 | 24.32 |
| ATOM | 1967 | CA | ASP A | 254 | 0 | 20.613 | 8.176 | 9.786 | 1.00 | 22.09 |
| ATOM | 1968 | C | ASP A | 254 | 0 | 19.782 | 9.448 | 9.821 | 1.00 | 20.71 |
| ATOM | 1969 | O | ASP A | 254 | 0 | 20.365 | 10.481 | 10.099 | 1.00 | 18.92 |
| ATOM | 1970 | CB | ASP A | 254 | 0 | 20.048 | 7.211 | 10.830 | 1.00 | 23.39 |
| ATOM | 1971 | CG | ASP A | 254 | 0 | 18.964 | 6.331 | 10.251 | 1.00 | 24.43 |
| ATOM | 1972 | QD1 | ASP A | 254 | 0 | 18.355 | 6.663 | 9.239 | 1.00 | 23.21 |
| ATOM | 1973 | OD2 | ASP A | 254 | 0 | 18.736 | 5.244 | 10.816 | 1.00 | 28.26 |
| ATOM | 1974 | N | ASN A | 255 | 0 | 18.485 | 9.338 | 9.496 | 1.00 | 18.97 |
| ATOM | 1975 | CA | ASN A | 255 | 0 | 17.583 | 10.479 | 9.599 | 1.00 | 17.69 |
| ATOM | 1976 | C | ASN A | 255 | 0 | 16.785 | 10.335 | 10.889 | 1.00 | 17.64 |
| ATOM | 1977 | O | ASN A | 255 | 0 | 16.390 | 9.204 | 11.249 | 1.00 | 17.75 |
| ATOM | 1978 | CB | ASN A | 255 | 0 | 16.663 | 10.554 | 8.386 | 1.00 | 17.19 |
| ATOM | 1979 | CG | ASN A | 255 | 0 | 17.467 | 10.882 | 7.143 | 1.00 | 17.33 |
| ATOM | 1980 | OD1 | ASN A | 255 | 0 | 17.891 | 12.023 | 6.932 | 1.00 | 18.05 |

APPENDIX 1-continued

```
ATOM   1981  ND2  ASN A  255  0   17.649   9.913   6.263  1.00  15.98
ATOM   1982  N    TYR A  256  0   16.657  11.403  11.684  1.00  14.89
ATOM   1983  CA   TYR A  256  0   15.983  11.364  12.961  1.00  12.56
ATOM   1984  C    TYR A  256  0   14.966  12.520  12.991  1.00  15.02
ATOM   1985  O    TYR A  256  0   15.208  13.637  12.509  1.00  14.49
ATOM   1986  CB   TYR A  256  0   16.867  11.479  14.216  1.00  14.85
ATOM   1987  CG   TYR A  256  0   17.883  10.349  14.316  1.00  13.96
ATOM   1988  CD1  TYR A  256  0   19.030  10.427  13.529  1.00  13.97
ATOM   1989  CD2  TYR A  256  0   17.712   9.245  15.129  1.00  14.62
ATOM   1990  CE1  TYR A  256  0   19.986   9.422  13.534  1.00  13.83
ATOM   1991  CE2  TYR A  256  0   18.667   8.224  15.170  1.00  15.31
ATOM   1992  CZ   TYR A  256  0   19.795   8.336  14.346  1.00  15.90
ATOM   1993  OH   TYR A  256  0   20.763   7.341  14.337  1.00  17.15
ATOM   1994  N    TRP A  257  0   13.801  12.198  13.564  1.00  13.58
ATOM   1995  CA   TRP A  257  0   12.742  13.196  13.657  1.00  14.21
ATOM   1996  C    TRP A  257  0   13.041  14.198  14.769  1.00  12.04
ATOM   1997  O    TRP A  257  0   13.382  13.811  15.878  1.00  10.46
ATOM   1998  CB   TRP A  257  0   11.363  12.592  13.988  1.00  12.49
ATOM   1999  CG   TRP A  257  0   10.648  11.906  12.865  1.00  13.06
ATOM   2000  CD1  TRP A  257  0   10.315  10.568  12.879  1.00  12.86
ATOM   2001  CD2  TRP A  257  0   10.161  12.437  11.633  1.00  12.33
ATOM   2002  NE1  TRP A  257  0    9.640  10.267  11.720  1.00  13.75
ATOM   2003  CE2  TRP A  257  0    9.530  11.388  10.940  1.00  13.78
ATOM   2004  CE3  TRP A  257  0   10.173  13.691  11.035  1.00  14.13
ATOM   2005  CZ2  TRP A  257  0    8.940  11.538   9.681  1.00  13.24
ATOM   2006  CZ3  TRP A  257  0    9.590  13.868   9.786  1.00  14.34
ATOM   2007  CH2  TRP A  257  0    8.963  12.789   9.127  1.00  13.64
ATOM   2008  N    ILE A  258  0   12.790  15.463  14.454  1.00  12.29
ATOM   2009  CA   ILE A  258  0   12.886  16.498  15.508  1.00  12.44
ATOM   2010  C    ILE A  258  0   11.391  16.840  15.769  1.00  12.40
ATOM   2011  O    ILE A  258  0   10.629  17.039  14.812  1.00  12.43
ATOM   2012  CB   ILE A  258  0   13.617  17.777  15.048  1.00  13.32
ATOM   2013  CG1  ILE A  258  0   15.107  17.477  14.854  1.00  14.52
ATOM   2014  CG2  ILE A  258  0   13.365  18.888  16.052  1.00  12.32
ATOM   2015  CD1  ILE A  258  0   15.839  18.474  13.994  1.00  14.35
ATOM   2016  N    ARG A  259  0   11.017  16.764  17.013  1.00  11.51
ATOM   2017  CA   ARG A  259  0    9.610  16.832  17.407  1.00  13.43
ATOM   2018  C    ARG A  259  0    9.254  18.019  18.274  1.00  12.74
ATOM   2019  O    ARG A  259  0    9.931  18.246  19.280  1.00  12.62
ATOM   2020  CB   ARG A  259  0    9.326  15.567  18.253  1.00  12.43
```

APPENDIX 1-continued

| ATOM | 2021 | CG  | ARG A | 259 | 0 |  9.308 | 14.290 | 17.414 | 1.00 | 15.81 |
|------|------|-----|-------|-----|---|--------|--------|--------|------|-------|
| ATOM | 2022 | CD  | ARG A | 259 | 0 |  8.910 | 13.054 | 18.244 | 1.00 | 16.58 |
| ATOM | 2023 | NE  | ARG A | 259 | 0 |  9.204 | 11.818 | 17.528 | 1.00 | 16.91 |
| ATOM | 2024 | CZ  | ARG A | 259 | 0 |  8.475 | 11.187 | 16.616 | 1.00 | 18.43 |
| ATOM | 2025 | NH1 | ARG A | 259 | 0 |  7.285 | 11.657 | 16.239 | 1.00 | 19.39 |
| ATOM | 2026 | NH2 | ARG A | 259 | 0 |  8.907 | 10.070 | 16.045 | 1.00 | 17.95 |
| ATOM | 2027 | N   | ALA A | 260 | 0 |  8.226 | 18.764 | 17.884 | 1.00 | 13.12 |
| ATOM | 2028 | CA  | ALA A | 260 | 0 |  7.768 | 19.882 | 18.727 | 1.00 | 12.65 |
| ATOM | 2029 | C   | ALA A | 260 | 0 |  6.237 | 19.763 | 18.802 | 1.00 | 14.47 |
| ATOM | 2030 | O   | ALA A | 260 | 0 |  5.545 | 20.140 | 17.868 | 1.00 | 14.73 |
| ATOM | 2031 | CB  | ALA A | 260 | 0 |  8.281 | 21.188 | 18.165 | 1.00 |  9.58 |
| ATOM | 2032 | N   | GLN A | 261 | 0 |  5.690 | 19.225 | 19.870 | 1.00 | 14.78 |
| ATOM | 2033 | CA  | GLN A | 261 | 0 |  4.272 | 19.004 | 20.060 | 1.00 | 16.99 |
| ATOM | 2034 | C   | GLN A | 261 | 0 |  3.606 | 20.154 | 20.803 | 1.00 | 15.01 |
| ATOM | 2035 | O   | GLN A | 261 | 0 |  3.914 | 20.389 | 21.961 | 1.00 | 13.86 |
| ATOM | 2036 | CB  | GLN A | 261 | 0 |  4.118 | 17.747 | 20.924 | 1.00 | 20.94 |
| ATOM | 2037 | CG  | GLN A | 261 | 0 |  2.717 | 17.131 | 20.940 | 1.00 | 27.53 |
| ATOM | 2038 | CD  | GLN A | 261 | 0 |  2.721 | 15.991 | 21.947 | 1.00 | 29.63 |
| ATOM | 2039 | OE1 | GLN A | 261 | 0 |  3.152 | 14.887 | 21.682 | 1.00 | 31.60 |
| ATOM | 2040 | NE2 | GLN A | 261 | 0 |  2.331 | 16.255 | 23.188 | 1.00 | 34.91 |
| ATOM | 2041 | N   | PRO A | 262 | 0 |  2.663 | 20.820 | 20.167 | 1.00 | 14.60 |
| ATOM | 2042 | CA  | PRO A | 262 | 0 |  1.974 | 21.969 | 20.739 | 1.00 | 15.72 |
| ATOM | 2043 | C   | PRO A | 262 | 0 |  0.921 | 21.568 | 21.757 | 1.00 | 16.25 |
| ATOM | 2044 | O   | PRO A | 262 | 0 |  0.498 | 20.409 | 21.814 | 1.00 | 15.61 |
| ATOM | 2045 | CB  | PRO A | 262 | 0 |  1.401 | 22.752 | 19.539 | 1.00 | 13.88 |
| ATOM | 2046 | CG  | PRO A | 262 | 0 |  1.168 | 21.608 | 18.563 | 1.00 | 13.62 |
| ATOM | 2047 | CD  | PRO A | 262 | 0 |  2.257 | 20.570 | 18.772 | 1.00 | 13.23 |
| ATOM | 2048 | N   | ASN A | 263 | 0 |  0.570 | 22.481 | 22.665 | 1.00 | 17.25 |
| ATOM | 2049 | CA  | ASN A | 263 | 0 | -0.471 | 22.203 | 23.648 | 1.00 | 17.50 |
| ATOM | 2050 | C   | ASN A | 263 | 0 | -1.834 | 22.460 | 22.981 | 1.00 | 18.43 |
| ATOM | 2051 | O   | ASN A | 263 | 0 | -2.810 | 22.121 | 23.608 | 1.00 | 19.35 |
| ATOM | 2052 | CB  | ASN A | 263 | 0 | -0.422 | 22.990 | 24.954 | 1.00 | 16.12 |
| ATOM | 2053 | CG  | ASN A | 263 | 0 | -0.333 | 24.493 | 24.728 | 1.00 | 16.97 |
| ATOM | 2054 | OD1 | ASN A | 263 | 0 |  0.236 | 25.002 | 23.751 | 1.00 | 15.54 |
| ATOM | 2055 | ND2 | ASN A | 263 | 0 | -0.905 | 25.269 | 25.653 | 1.00 | 16.31 |
| ATOM | 2056 | N   | LYS A | 264 | 0 | -1.947 | 23.055 | 21.818 | 1.00 | 20.51 |
| ATOM | 2057 | CA  | LYS A | 264 | 0 | -3.256 | 23.208 | 21.180 | 1.00 | 24.76 |
| ATOM | 2058 | C   | LYS A | 264 | 0 | -3.055 | 23.395 | 19.683 | 1.00 | 23.64 |
| ATOM | 2059 | O   | LYS A | 264 | 0 | -1.909 | 23.572 | 19.267 | 1.00 | 24.23 |

APPENDIX 1-continued

| | | | | | | | | | | |
|---|---|---|---|---|---|---|---|---|---|---|
| ATOM | 2060 | CB | LYS | A | 264 | 0 | -4.038 | 24.393 | 21.775 | 1.00 25.87 |
| ATOM | 2061 | CG | LYS | A | 264 | 0 | -3.266 | 25.702 | 21.602 | 1.00 28.62 |
| ATOM | 2062 | CD | LYS | A | 264 | 0 | -3.579 | 26.624 | 22.772 | 1.00 30.65 |
| ATOM | 2063 | CE | LYS | A | 264 | 0 | -4.114 | 27.960 | 22.283 | 1.00 32.62 |
| ATOM | 2064 | NZ | LYS | A | 264 | 0 | -4.593 | 28.753 | 23.459 | 1.00 34.39 |
| ATOM | 2065 | N | GLY | A | 265 | 0 | -4.112 | 23.386 | 18.892 | 1.00 22.60 |
| ATOM | 2066 | CA | GLY | A | 265 | 0 | -3.959 | 23.591 | 17.452 | 1.00 22.98 |
| ATOM | 2067 | C | GLY | A | 265 | 0 | -5.190 | 23.002 | 16.758 | 1.00 23.95 |
| ATOM | 2068 | O | GLY | A | 265 | 0 | -5.904 | 22.202 | 17.362 | 1.00 22.64 |
| ATOM | 2069 | N | ARG | A | 266 | 0 | -5.398 | 23.434 | 15.537 | 1.00 24.60 |
| ATOM | 2070 | CA | ARG | A | 266 | 0 | -6.527 | 23.051 | 14.734 | 1.00 26.24 |
| ATOM | 2071 | C | ARG | A | 266 | 0 | -6.412 | 21.605 | 14.272 | 1.00 27.29 |
| ATOM | 2072 | O | ARG | A | 266 | 0 | -5.329 | 21.074 | 14.015 | 1.00 25.41 |
| ATOM | 2073 | CB | ARG | A | 266 | 0 | -6.628 | 23.903 | 13.469 | 1.00 30.71 |
| ATOM | 2074 | CG | ARG | A | 266 | 0 | -7.065 | 25.334 | 13.563 | 1.00 35.66 |
| ATOM | 2075 | CD | ARG | A | 266 | 0 | -8.161 | 25.673 | 12.539 | 1.00 40.48 |
| ATOM | 2076 | NE | ARG | A | 266 | 0 | -9.379 | 25.957 | 13.286 | 1.00 45.08 |
| ATOM | 2077 | CZ | ARG | A | 266 | 0 | -10.551 | 25.334 | 13.319 | 1.00 47.09 |
| ATOM | 2078 | NH1 | ARG | A | 266 | 0 | -10.921 | 24.294 | 12.577 | 1.00 48.10 |
| ATOM | 2079 | NH2 | ARG | A | 266 | 0 | -11.452 | 25.828 | 14.165 | 1.00 47.80 |
| ATOM | 2080 | N | ASN | A | 267 | 0 | -7.586 | 20.983 | 14.141 | 1.00 25.17 |
| ATOM | 2081 | CA | ASN | A | 267 | 0 | -7.727 | 19.669 | 13.602 | 1.00 23.96 |
| ATOM | 2082 | C | ASN | A | 267 | 0 | -6.859 | 18.625 | 14.244 | 1.00 22.35 |
| ATOM | 2083 | O | ASN | A | 267 | 0 | -6.306 | 17.864 | 13.448 | 1.00 23.57 |
| ATOM | 2084 | CB | ASN | A | 267 | 0 | -7.390 | 19.695 | 12.098 | 1.00 26.46 |
| ATOM | 2085 | CG | ASN | A | 267 | 0 | -8.461 | 20.426 | 11.309 | 1.00 29.21 |
| ATOM | 2086 | OD1 | ASN | A | 267 | 0 | -8.190 | 21.226 | 10.405 | 1.00 30.18 |
| ATOM | 2087 | ND2 | ASN | A | 267 | 0 | -9.681 | 20.075 | 11.701 | 1.00 28.77 |
| ATOM | 2088 | N | GLY | A | 268 | 0 | -6.706 | 18.594 | 15.550 | 1.00 21.85 |
| ATOM | 2089 | CA | GLY | A | 268 | 0 | -5.890 | 17.533 | 16.121 | 1.00 22.47 |
| ATOM | 2090 | C | GLY | A | 268 | 0 | -4.383 | 17.760 | 16.118 | 1.00 23.29 |
| ATOM | 2091 | O | GLY | A | 268 | 0 | -3.652 | 16.898 | 16.632 | 1.00 23.28 |
| ATOM | 2092 | N | LEU | A | 269 | 0 | -3.880 | 18.901 | 15.676 | 1.00 22.69 |
| ATOM | 2093 | CA | LEU | A | 269 | 0 | -2.454 | 19.222 | 15.684 | 1.00 22.62 |
| ATOM | 2094 | C | LEU | A | 269 | 0 | -1.753 | 18.890 | 16.990 | 1.00 23.26 |
| ATOM | 2095 | O | LEU | A | 269 | 0 | -0.650 | 18.335 | 17.035 | 1.00 23.42 |
| ATOM | 2096 | CB | LEU | A | 269 | 0 | -2.311 | 20.713 | 15.472 | 1.00 22.28 |
| ATOM | 2097 | CG | LEU | A | 269 | 0 | -1.183 | 21.414 | 14.745 | 1.00 23.42 |
| ATOM | 2098 | CD1 | LEU | A | 269 | 0 | -0.508 | 22.380 | 15.682 | 1.00 19.64 |
| ATOM | 2099 | CD2 | LEU | A | 269 | 0 | -0.213 | 20.492 | 14.009 | 1.00 21.26 |

APPENDIX 1-continued

| ATOM | 2100 | N   | ALA | A | 270 | 0 | -2.371 | 19.199 | 18.135 | 1.00 | 21.51 |
| ATOM | 2101 | CA  | ALA | A | 270 | 0 | -1.784 | 18.899 | 19.419 | 1.00 | 22.26 |
| ATOM | 2102 | C   | ALA | A | 270 | 0 | -1.612 | 17.415 | 19.680 | 1.00 | 23.22 |
| ATOM | 2103 | O   | ALA | A | 270 | 0 | -0.898 | 17.077 | 20.637 | 1.00 | 21.81 |
| ATOM | 2104 | CB  | ALA | A | 270 | 0 | -2.632 | 19.518 | 20.542 | 1.00 | 21.06 |
| ATOM | 2105 | N   | GLY | A | 271 | 0 | -2.337 | 16.521 | 18.996 | 1.00 | 23.75 |
| ATOM | 2106 | CA  | GLY | A | 271 | 0 | -2.190 | 15.125 | 19.372 | 1.00 | 24.98 |
| ATOM | 2107 | C   | GLY | A | 271 | 0 | -1.507 | 14.267 | 18.328 | 1.00 | 26.07 |
| ATOM | 2108 | O   | GLY | A | 271 | 0 | -1.501 | 13.045 | 18.523 | 1.00 | 26.26 |
| ATOM | 2109 | N   | THR | A | 272 | 0 | -0.906 | 14.825 | 17.278 | 1.00 | 26.48 |
| ATOM | 2110 | CA  | THR | A | 272 | 0 | -0.327 | 13.901 | 16.294 | 1.00 | 25.27 |
| ATOM | 2111 | C   | THR | A | 272 | 0 |  0.986 | 14.362 | 15.701 | 1.00 | 25.58 |
| ATOM | 2112 | O   | THR | A | 272 | 0 |  1.216 | 15.567 | 15.701 | 1.00 | 24.46 |
| ATOM | 2113 | CB  | THR | A | 272 | 0 | -1.380 | 13.759 | 15.164 | 1.00 | 24.40 |
| ATOM | 2114 | OG1 | THR | A | 272 | 0 | -0.931 | 12.737 | 14.275 | 1.00 | 26.32 |
| ATOM | 2115 | CG2 | TRR | A | 272 | 0 | -1.575 | 15.022 | 14.347 | 1.00 | 22.50 |
| ATOM | 2116 | N   | PHE | A | 273 | 0 |  1.714 | 13.443 | 15.062 | 1.00 | 24.01 |
| ATOM | 2117 | CA  | PHE | A | 273 | 0 |  2.897 | 13.755 | 14.271 | 1.00 | 23.99 |
| ATOM | 2118 | C   | PHE | A | 273 | 0 |  2.663 | 13.201 | 12.858 | 1.00 | 24.84 |
| ATOM | 2119 | O   | PHE | A | 273 | 0 |  3.534 | 13.207 | 11.987 | 1.00 | 24.73 |
| ATOM | 2120 | CB  | PHE | A | 273 | 0 |  4.175 | 13.094 | 14.812 | 1.00 | 22.16 |
| ATOM | 2121 | CG  | PHE | A | 273 | 0 |  4.550 | 13.676 | 16.153 | 1.00 | 21.84 |
| ATOM | 2122 | CD1 | PHE | A | 273 | 0 |  4.190 | 13.037 | 17.327 | 1.00 | 20.67 |
| ATOM | 2123 | CD2 | PHE | A | 273 | 0 |  5.221 | 14.881 | 16.216 | 1.00 | 20.98 |
| ATOM | 2124 | CE1 | PHE | A | 273 | 0 |  4.538 | 13.574 | 18.554 | 1.00 | 21.75 |
| ATOM | 2125 | CE2 | PHE | A | 273 | 0 |  5.559 | 15.428 | 17.440 | 1.00 | 21.65 |
| ATOM | 2126 | CZ  | PHE | A | 273 | 0 |  5.216 | 14.787 | 18.616 | 1.00 | 22.38 |
| ATOM | 2127 | N   | ALA | A | 274 | 0 |  1.440 | 12.718 | 12.647 | 1.00 | 24.38 |
| ATOM | 2128 | CA  | ALA | A | 274 | 0 |  1.094 | 12.053 | 11.397 | 1.00 | 24.29 |
| ATOM | 2129 | C   | ALA | A | 274 | 0 |  1.399 | 12.920 | 10.194 | 1.00 | 24.15 |
| ATOM | 2130 | O   | ALA | A | 274 | 0 |  0.990 | 14.078 | 10.161 | 1.00 | 23.07 |
| ATOM | 2131 | CB  | ALA | A | 274 | 0 | -0.385 | 11.681 | 11.387 | 1.00 | 23.53 |
| ATOM | 2132 | N   | ASN | A | 275 | 0 |  2.075 | 12.355 |  9.204 | 1.00 | 23.41 |
| ATOM | 2133 | CA  | ASN | A | 275 | 0 |  2.389 | 13.068 |  7.987 | 1.00 | 24.88 |
| ATOM | 2134 | C   | ASN | A | 275 | 0 |  3.498 | 14.093 |  8.191 | 1.00 | 22.73 |
| ATOM | 2135 | O   | ASN | A | 275 | 0 |  3.708 | 14.947 |  7.337 | 1.00 | 21.57 |
| ATOM | 2136 | CB  | ASN | A | 275 | 0 |  1.138 | 13.806 |  7.516 | 1.00 | 30.04 |
| ATOM | 2137 | CG  | ASN | A | 275 | 0 |  0.194 | 13.070 |  6.633 | 1.00 | 35.28 |
| ATOM | 2138 | OD1 | ASN | A | 275 | 0 | -0.458 | 12.071 |  6.985 | 1.00 | 36.92 |

APPENDIX 1-continued

```
ATOM   2139  ND2  ASN A  275  0     0.156  13.655   5.427  1.00  37.87
ATOM   2140  N    GLY A  276  0     4.185  14.083   9.322  1.00  22.10
ATOM   2141  CA   GLY A  276  0     5.278  15.025   9.503  1.00  20.95
ATOM   2142  C    GLY A  276  0     4.801  16.392   9.962  1.00  19.61
ATOM   2143  O    GLY A  276  0     5.587  17.325   9.816  1.00  19.96
ATOM   2144  N    VAL A  277  0     3.600  16.504  10.540  1.00  16.82
ATOM   2145  CA   VAL A  277  0     3.207  17.796  11.107  1.00  15.06
ATOM   2146  C    VAL A  277  0     4.033  17.942  12.379  1.00  13.80
ATOM   2147  O    VAL A  277  0     4.454  16.912  12.926  1.00  13.80
ATOM   2148  CB   VAL A  277  0     1.676  17.849  11.397  1.00  14.37
ATOM   2149  CG1  VAL A  277  0     0.882  17.824  10.099  1.00  13.37
ATOM   2150  CG2  VAL A  277  0     1.213  16.763  12.330  1.00  11.77
ATOM   2151  N    ASN A  278  0     4.307  19.100  12.936  1.00  14.25
ATOM   2152  CA   ASN A  278  0     5.026  19.262  14.209  1.00  13.80
ATOM   2153  C    ASN A  278  0     6.443  18.640  14.208  1.00  13.80
ATOM   2154  O    ASN A  278  0     7.020  18.228  15.229  1.00  11.81
ATOM   2155  CB   ASN A  278  0     4.216  18.607  15.312  1.00  14.24
ATOM   2156  CG   ASN A  278  0     2.890  19.288  15.659  1.00  15.35
ATOM   2157  OD1  ASN A  278  0     1.952  18.531  16.009  1.00  14.81
ATOM   2158  ND2  ASN A  278  0     2.821  20.591  15.593  1.00  10.69
ATOM   2159  N    SER A  279  0     7.044  18.595  13.025  1.00  12.68
ATOM   2160  CA   SER A  279  0     8.296  17.892  12.860  1.00  15.48
ATOM   2161  C    SER A  279  0     9.323  18.571  11.964  1.00  15.07
ATOM   2162  O    SER A  279  0     8.995  19.309  11.044  1.00  12.20
ATOM   2163  CB   SER A  279  0     7.976  16.549  12.122  1.00  14.76
ATOM   2164  OG   SER A  279  0     7.268  15.722  13.054  1.00  19.57
ATOM   2165  N    ALA A  280  0    10.570  18.152  12.229  1.00  15.67
ATOM   2166  CA   ALA A  280  0    11.664  18.548  11.327  1.00  16.75
ATOM   2167  C    ALA A  280  0    12.620  17.341  11.287  1.00  15.83
ATOM   2168  O    ALA A  280  0    12.438  16.346  11.997  1.00  15.55
ATOM   2169  CB   ALA A  280  0    12.363  19.828  11.745  1.00  16.40
ATOM   2170  N    ILE A  281  0    13.669  17.478  10.485  1.00  14.79
ATOM   2171  CA   ILE A  281  0    14.569  16.346  10.257  1.00  15.55
ATOM   2172  C    ILE A  281  0    16.002  16.610  10.699  1.00  15.92
ATOM   2173  O    ILE A  281  0    16.649  17.577  10.284  1.00  14.96
ATOM   2174  CB   ILE A  281  0    14.557  16.013   8.735  1.00  16.44
ATOM   2175  CG1  ILE A  281  0    13.147  15.573   8.275  1.00  16.42
ATOM   2176  CG2  ILE A  281  0    15.615  14.959   8.421  1.00  15.71
ATOM   2177  CD1  ILE A  281  0    12.981  15.376   6.771  1.00  14.22
ATOM   2178  N    LEU A  282  0    16.505  15.698  11.515  1.00  16.76
```

APPENDIX 1-continued

| ATOM | 2179 | CA  | LEU A | 282 | 0 | 17.920 | 15.736 | 11.912 | 1.00 | 15.82 |
|------|------|-----|-------|-----|---|--------|--------|--------|------|-------|
| ATOM | 2180 | C   | LEU A | 282 | 0 | 18.655 | 14.747 | 10.990 | 1.00 | 16.16 |
| ATOM | 2181 | O   | LEU A | 282 | 0 | 18.409 | 13.530 | 11.034 | 1.00 | 16.41 |
| ATOM | 2182 | CB  | LEU A | 282 | 0 | 18.129 | 15.400 | 13.379 | 1.00 | 14.54 |
| ATOM | 2183 | CG  | LEU A | 282 | 0 | 19.632 | 15.346 | 13.773 | 1.00 | 16.00 |
| ATOM | 2184 | CD1 | LEU A | 282 | 0 | 20.100 | 16.767 | 14.052 | 1.00 | 16.10 |
| ATOM | 2185 | CD2 | LEU A | 282 | 0 | 19.865 | 14.469 | 14.970 | 1.00 | 13.21 |
| ATOM | 2186 | N   | ARG A | 283 | 0 | 19.490 | 15.254 | 10.100 | 1.00 | 15.20 |
| ATOM | 2187 | CA  | ARG A | 283 | 0 | 20.160 | 14.377 | 9.141  | 1.00 | 16.98 |
| ATOM | 2188 | C   | ARG A | 283 | 0 | 21.683 | 14.326 | 9.279  | 1.00 | 17.31 |
| ATOM | 2189 | O   | ARG A | 283 | 0 | 22.398 | 15.330 | 9.203  | 1.00 | 17.82 |
| ATOM | 2190 | CB  | ARG A | 283 | 0 | 19.844 | 14.861 | 7.736  | 1.00 | 17.30 |
| ATOM | 2191 | CG  | ARG A | 283 | 0 | 20.417 | 13.978 | 6.641  | 1.00 | 19.94 |
| ATOM | 2192 | CD  | ARG A | 283 | 0 | 19.860 | 14.446 | 5.301  | 1.00 | 20.04 |
| ATOM | 2193 | NE  | ARG A | 283 | 0 | 18.474 | 14.010 | 5.208  | 1.00 | 21.56 |
| ATOM | 2194 | CZ  | ARG A | 283 | 0 | 17.479 | 14.530 | 4.505  | 1.00 | 21.81 |
| ATOM | 2195 | NH1 | ARG A | 283 | 0 | 16.287 | 13.922 | 4.564  | 1.00 | 21.52 |
| ATOM | 2196 | NH2 | ARG A | 283 | 0 | 17.653 | 15.634 | 3.797  | 1.00 | 21.84 |
| ATOM | 2197 | N   | TYR A | 284 | 0 | 22.163 | 13.136 | 9.567  | 1.00 | 16.79 |
| ATOM | 2198 | CA  | TYR A | 284 | 0 | 23.581 | 12.821 | 9.620  | 1.00 | 16.35 |
| ATOM | 2199 | C   | TYR A | 284 | 0 | 24.155 | 12.787 | 8.198  | 1.00 | 16.52 |
| ATOM | 2200 | O   | TYR A | 284 | 0 | 23.556 | 12.226 | 7.271  | 1.00 | 16.33 |
| ATOM | 2201 | CB  | TYR A | 284 | 0 | 23.730 | 11.444 | 10.252 | 1.00 | 16.51 |
| ATOM | 2202 | CG  | TYR A | 284 | 0 | 23.727 | 11.460 | 11.755 | 1.00 | 17.09 |
| ATOM | 2203 | CD1 | TYR A | 284 | 0 | 24.910 | 11.178 | 12.437 | 1.00 | 17.37 |
| ATOM | 2204 | CD2 | TYR A | 284 | 0 | 22.601 | 11.753 | 12.504 | 1.00 | 17.15 |
| ATOM | 2205 | CE1 | TYR A | 284 | 0 | 24.937 | 11.163 | 13.817 | 1.00 | 17.64 |
| ATOM | 2206 | CE2 | TYR A | 284 | 0 | 22.623 | 11.770 | 13.892 | 1.00 | 15.66 |
| ATOM | 2207 | CZ  | TYR A | 284 | 0 | 23.796 | 11.476 | 14.542 | 1.00 | 15.99 |
| ATOM | 2208 | OH  | TYR A | 284 | 0 | 23.873 | 11.448 | 15.919 | 1.00 | 14.03 |
| ATOM | 2209 | N   | ALA A | 285 | 0 | 25.276 | 13.463 | 7.992  | 1.00 | 17.42 |
| ATOM | 2210 | CA  | ALA A | 285 | 0 | 25.950 | 13.461 | 6.692  | 1.00 | 19.35 |
| ATOM | 2211 | C   | ALA A | 285 | 0 | 26.186 | 11.994 | 6.328  | 1.00 | 19.20 |
| ATOM | 2212 | O   | ALA A | 285 | 0 | 26.692 | 11.237 | 7.146  | 1.00 | 17.18 |
| ATOM | 2213 | CB  | ALA A | 285 | 0 | 27.293 | 14.194 | 6.770  | 1.00 | 19.86 |
| ATOM | 2214 | N   | GLY A | 286 | 0 | 25.724 | 11.614 | 5.153  | 1.00 | 20.01 |
| ATOM | 2215 | CA  | GLY A | 286 | 0 | 25.851 | 10.224 | 4.747  | 1.00 | 21.88 |
| ATOM | 2216 | C   | GLY A | 286 | 0 | 24.507 | 9.510  | 4.754  | 1.00 | 22.87 |
| ATOM | 2217 | O   | GLY A | 286 | 0 | 24.406 | 8.418  | 4.197  | 1.00 | 23.06 |

APPENDIX 1-continued

| | | | | | | | | | | |
|---|---|---|---|---|---|---|---|---|---|---|
| ATOM | 2218 | N | ALA | A | 287 | 0 | 23.504 | 10.076 | 5.423 | 1.00 22.81 |
| ATOM | 2219 | CA | ALA | A | 287 | 0 | 22.176 | 9.449 | 5.364 | 1.00 21.50 |
| ATOM | 2220 | C | ALA | A | 287 | 0 | 21.482 | 9.880 | 4.079 | 1.00 20.58 |
| ATOM | 2221 | O | ALA | A | 287 | 0 | 21.647 | 11.032 | 3.629 | 1.00 19.44 |
| ATOM | 2222 | CB | ALA | A | 287 | 0 | 21.340 | 9.890 | 6.562 | 1.00 21.34 |
| ATOM | 2223 | N | ALA | A | 288 | 0 | 20.632 | 9.041 | 3.523 | 1.00 21.20 |
| ATOM | 2224 | CA | ALA | A | 288 | 0 | 19.899 | 9.450 | 2.310 | 1.00 23.46 |
| ATOM | 2225 | C | ALA | A | 288 | 0 | 18.965 | 10.629 | 2.513 | 1.00 24.70 |
| ATOM | 2226 | O | ALA | A | 288 | 0 | 18.494 | 10.929 | 3.621 | 1.00 25.30 |
| ATOM | 2227 | CB | ALA | A | 288 | 0 | 19.012 | 8.298 | 1.827 | 1.00 24.84 |
| ATOM | 2228 | N | ASN | A | 289 | 0 | 18.638 | 11.300 | 1.411 | 1.00 25.98 |
| ATOM | 2229 | CA | ASN | A | 289 | 0 | 17.674 | 12.398 | 1.439 | 1.00 27.16 |
| ATOM | 2230 | C | ASN | A | 289 | 0 | 16.303 | 11.707 | 1.505 | 1.00 27.36 |
| ATOM | 2231 | O | ASN | A | 289 | 0 | 15.761 | 11.330 | 0.477 | 1.00 27.56 |
| ATOM | 2232 | CB | ASN | A | 289 | 0 | 17.784 | 13.250 | 0.189 | 1.00 29.01 |
| ATOM | 2233 | CG | ASN | A | 289 | 0 | 18.808 | 14.364 | 0.299 | 1.00 30.44 |
| ATOM | 2234 | OD1 | ASN | A | 289 | 0 | 20.005 | 14.168 | 0.545 | 1.00 30.40 |
| ATOM | 2235 | ND2 | ASN | A | 289 | 0 | 18.340 | 15.591 | 0.121 | 1.00 31.98 |
| ATOM | 2236 | N | ALA | A | 290 | 0 | 15.837 | 11.426 | 2.703 | 1.00 25.22 |
| ATOM | 2237 | CA | ALA | A | 290 | 0 | 14.600 | 10.727 | 2.955 | 1.00 25.09 |
| ATOM | 2238 | C | ALA | A | 290 | 0 | 14.087 | 11.057 | 4.363 | 1.00 22.98 |
| ATOM | 2239 | O | ALA | A | 290 | 0 | 14.830 | 11.555 | 5.205 | 1.00 22.02 |
| ATOM | 2240 | CB | ALA | A | 290 | 0 | 14.764 | 9.210 | 2.823 | 1.00 24.89 |
| ATOM | 2241 | N | ASP | A | 291 | 0 | 12.822 | 10.718 | 4.597 | 1.00 21.88 |
| ATOM | 2242 | CA | ASP | A | 291 | 0 | 12.223 | 10.985 | 5.907 | 1.00 21.71 |
| ATOM | 2243 | C | ASP | A | 291 | 0 | 12.724 | 9.965 | 6.916 | 1.00 18.93 |
| ATOM | 2244 | O | ASP | A | 291 | 0 | 12.911 | 8.814 | 6.596 | 1.00 19.66 |
| ATOM | 2245 | CB | ASP | A | 291 | 0 | 10.695 | 10.862 | 5.834 | 1.00 22.63 |
| ATOM | 2246 | CG | ASP | A | 291 | 0 | 10.088 | 12.005 | 5.076 | 1.00 25.41 |
| ATOM | 2247 | OD1 | ASP | A | 291 | 0 | 10.781 | 12.988 | 4.735 | 1.00 27.11 |
| ATOM | 2248 | OD2 | ASP | A | 291 | 0 | 8.885 | 11.932 | 4.812 | 1.00 27.47 |
| ATOM | 2249 | N | PRO | A | 292 | 0 | 12.863 | 10.362 | 8.164 | 1.00 16.14 |
| ATOM | 2250 | CA | PRO | A | 292 | 0 | 13.229 | 9.473 | 9.230 | 1.00 15.27 |
| ATOM | 2251 | C | PRO | A | 292 | 0 | 12.087 | 8.484 | 9.389 | 1.00 19.40 |
| ATOM | 2252 | O | PRO | A | 292 | 0 | 10.925 | 8.785 | 9.063 | 1.00 20.36 |
| ATOM | 2253 | CB | PRO | A | 292 | 0 | 13.257 | 10.335 | 10.511 | 1.00 14.68 |
| ATOM | 2254 | CG | PRO | A | 292 | 0 | 13.291 | 11.739 | 9.941 | 1.00 14.39 |
| ATOM | 2255 | CD | PRO | A | 292 | 0 | 12.606 | 11.735 | 8.593 | 1.00 14.02 |
| ATOM | 2256 | N | THR | A | 293 | 0 | 12.357 | 7.361 | 10.024 | 1.00 19.91 |
| ATOM | 2257 | CA | THR | A | 293 | 0 | 11.360 | 6.379 | 10.373 | 1.00 20.62 |

APPENDIX 1-continued

```
ATOM   2258 C    THR A 293  0    11.589   6.055 11.847 1.00 20.83
ATOM   2259 O    THR A 293  0    11.323   4.943 12.287 1.00 23.91
ATOM   2260 CB   THR A 293  0    11.556   5.088  9.557 1.00 23.41
ATOM   2261 OG1  THR A 293  0    12.874   4.577  9.836 1.00 24.50
ATOM   2262 CG2  THR A 293  0    11.438   5.341  8.058 1.00 23.72
ATOM   2263 N    THR A 294  0    12.172   6.958 12.624 1.00 19.30
ATOM   2264 CA   THR A 294  0    12.440   6.634 14.017 1.00 19.42
ATOM   2265 C    THR A 294  0    11.214   6.896 14.878 1.00 20.66
ATOM   2266 O    THR A 294  0    10.240   7.485 14.411 1.00 19.89
ATOM   2267 CB   THR A 294  0    13.565   7.548 14.553 1.00 19.28
ATOM   2268 OG1  THR A 294  0    13.174   8.889 14.251 1.00 17.55
ATOM   2269 CG2  THR A 294  0    14.860   7.214 13.822 1.00 19.27
ATOM   2270 N    SER A 295  0    11.359   6.576 16.159 1.00 23.85
ATOM   2271 CA   SER A 295  0    10.274   6.851 17.095 1.00 27.18
ATOM   2272 C    SER A 295  0    10.781   7.484 18.375 1.00 27.92
ATOM   2273 O    SER A 295  0    11.900   7.292 18.844 1.00 27.09
ATOM   2274 CB   SER A 295  0     9.513   5.546 17.367 1.00 28.92
ATOM   2275 OG   SER A 295  0    10.389   4.761 18.160 1.00 33.04
ATOM   2276 N    ALA A 296  0     9.930   8.331 18.965 1.00 30.04
ATOM   2277 CA   ALA A 296  0    10.295   9.003 20.207 1.00 29.82
ATOM   2278 C    ALA A 296  0    10.552   8.011 21.327 1.00 30.83
ATOM   2279 O    ALA A 296  0    10.114   6.861 21.328 1.00 30.67
ATOM   2280 CB   ALA A 296  0     9.187   9.968 20.599 1.00 30.16
ATOM   2281 N    ASN A 297  0    11.286   8.489 22.328 1.00 31.65
ATOM   2282 CA   ASN A 297  0    11.543   7.750 23.549 1.00 32.16
ATOM   2283 C    ASN A 297  0    10.200   7.650 24.285 1.00 32.80
ATOM   2284 O    ASN A 297  0     9.492   8.616 24.565 1.00 31.30
ATOM   2285 CB   ASN A 297  0    12.522   8.497 24.443 1.00 33.07
ATOM   2286 CG   ASN A 297  0    12.869   7.742 25.706 1.00 35.21
ATOM   2287 OD1  ASN A 297  0    12.116   6.965 26.284 1.00 35.45
ATOM   2288 ND2  ASN A 297  0    14.106   7.982 26.162 1.00 37.10
ATOM   2289 N    PRO A 298  0     9.865   6.430 24.647 1.00 33.40
ATOM   2290 CA   PRO A 298  0     8.626   6.116 25.331 1.00 33.89
ATOM   2291 C    PRO A 298  0     8.580   6.690 26.732 1.00 32.60
ATOM   2292 O    PRO A 298  0     7.522   7.155 27.173 1.00 32.72
ATOM   2293 CB   PRO A 298  0     8.505   4.576 25.358 1.00 35.13
ATOM   2294 CG   PRO A 298  0     9.932   4.147 25.128 1.00 34.52
ATOM   2295 CD   PRO A 298  0    10.630   5.222 24.323 1.00 34.10
ATOM   2296 N    ASN A 299  0     9.689   6.721 27.461 1.00 29.60
```

APPENDIX 1-continued

| ATOM | 2297 | CA | ASN | A | 299 | 0 | 9.701 | 7.229 | 28.834 | 1.00 | 28.47 |
|---|---|---|---|---|---|---|---|---|---|---|---|
| ATOM | 2298 | C | ASN | A | 299 | 0 | 10.818 | 8.251 | 29.006 | 1.00 | 27.18 |
| ATOM | 2299 | O | ASN | A | 299 | 0 | 11.906 | 7.967 | 29.528 | 1.00 | 25.69 |
| ATOM | 2300 | CB | ASN | A | 299 | 0 | 9.964 | 6.017 | 29.747 | 1.00 | 29.50 |
| ATOM | 2301 | CG | ASN | A | 299 | 0 | 8.907 | 4.935 | 29.673 | 1.00 | 32.34 |
| ATOM | 2302 | OD1 | ASN | A | 299 | 0 | 9.090 | 3.873 | 29.075 | 1.00 | 33.50 |
| ATOM | 2303 | ND2 | ASN | A | 299 | 0 | 7.735 | 5.182 | 30.251 | 1.00 | 33.04 |
| ATOM | 2304 | N | PRO | A | 300 | 0 | 10.629 | 9.450 | 28.498 | 1.00 | 26.02 |
| ATOM | 2305 | CA | PRO | A | 300 | 0 | 11.668 | 10.486 | 28.498 | 1.00 | 23.99 |
| ATOM | 2306 | C | PRO | A | 300 | 0 | 11.987 | 11.054 | 29.860 | 1.00 | 21.16 |
| ATOM | 2307 | O | PRO | A | 300 | 0 | 11.051 | 11.174 | 30.649 | 1.00 | 20.81 |
| ATOM | 2308 | CB | PRO | A | 300 | 0 | 11.137 | 11.623 | 27.594 | 1.00 | 23.33 |
| ATOM | 2309 | CG | PRO | A | 300 | 0 | 9.645 | 11.422 | 27.729 | 1.00 | 24.68 |
| ATOM | 2310 | CD | PRO | A | 300 | 0 | 9.387 | 9.918 | 27.882 | 1.00 | 25.22 |
| ATOM | 2311 | N | ALA | A | 301 | 0 | 13.242 | 11.361 | 30.179 | 1.00 | 19.17 |
| ATOM | 2312 | CA | ALA | A | 301 | 0 | 13.538 | 12.139 | 31.410 | 1.00 | 17.57 |
| ATOM | 2313 | C | ALA | A | 301 | 0 | 13.159 | 13.588 | 31.084 | 1.00 | 16.53 |
| ATOM | 2314 | O | ALA | A | 301 | 0 | 13.613 | 14.235 | 30.131 | 1.00 | 16.24 |
| ATOM | 2315 | CB | ALA | A | 301 | 0 | 15.006 | 11.982 | 31.774 | 1.00 | 17.17 |
| ATOM | 2316 | N | GLN | A | 302 | 0 | 12.139 | 14.131 | 31.723 | 1.00 | 18.15 |
| ATOM | 2317 | CA | GLN | A | 302 | 0 | 11.580 | 15.446 | 31.441 | 1.00 | 19.34 |
| ATOM | 2318 | C | GLN | A | 302 | 0 | 12.335 | 16.580 | 32.124 | 1.00 | 19.16 |
| ATOM | 2319 | O | GLN | A | 302 | 0 | 12.577 | 16.444 | 33.324 | 1.00 | 19.07 |
| ATOM | 2320 | CB | GLN | A | 302 | 0 | 10.122 | 15.483 | 31.937 | 1.00 | 19.10 |
| ATOM | 2321 | CG | GLN | A | 302 | 0 | 9.304 | 16.666 | 31.478 | 1.00 | 20.55 |
| ATOM | 2322 | CD | GLN | A | 302 | 0 | 8.960 | 16.738 | 30.009 | 1.00 | 20.18 |
| ATOM | 2323 | OE1 | GLN | A | 302 | 0 | 8.843 | 15.721 | 29.331 | 1.00 | 22.29 |
| ATOM | 2324 | NE2 | GLN | A | 302 | 0 | 8.813 | 17.936 | 29.436 | 1.00 | 18.46 |
| ATOM | 2325 | N | LEU | A | 303 | 0 | 12.629 | 17.681 | 31.444 | 1.00 | 17.92 |
| ATOM | 2326 | CA | LEU | A | 303 | 0 | 13.241 | 18.824 | 32.139 | 1.00 | 17.32 |
| ATOM | 2327 | C | LEU | A | 303 | 0 | 12.316 | 19.357 | 33.232 | 1.00 | 17.65 |
| ATOM | 2328 | O | LEU | A | 303 | 0 | 11.140 | 19.664 | 33.021 | 1.00 | 17.55 |
| ATOM | 2329 | CB | LEU | A | 303 | 0 | 13.489 | 19.988 | 31.168 | 1.00 | 15.14 |
| ATOM | 2330 | CG | LEU | A | 303 | 0 | 13.919 | 21.317 | 31.797 | 1.00 | 16.94 |
| ATOM | 2331 | CD1 | LEU | A | 303 | 0 | 15.262 | 21.146 | 32.504 | 1.00 | 17.30 |
| ATOM | 2332 | CD2 | LEU | A | 303 | 0 | 13.988 | 22.432 | 30.764 | 1.00 | 12.82 |
| ATOM | 2333 | N | ASN | A | 304 | 0 | 12.868 | 19.580 | 34.399 | 1.00 | 17.34 |
| ATOM | 2334 | CA | ASN | A | 304 | 0 | 12.199 | 20.212 | 35.531 | 1.00 | 19.12 |
| ATOM | 2335 | C | ASA | A | 304 | 0 | 13.071 | 21.435 | 35.833 | 1.00 | 19.06 |
| ATOM | 2336 | O | ASN | A | 304 | 0 | 14.265 | 21.349 | 36.122 | 1.00 | 20.37 |

APPENDIX 1-continued

| ATOM | 2337 | CB  | ASN A | 304 | 0 | 12.073 | 19.244 | 36.704 | 1.00 | 22.16 |
|------|------|-----|-------|-----|---|--------|--------|--------|------|-------|
| ATOM | 2338 | CG  | ASN A | 304 | 0 | 11.748 | 19.900 | 38.024 | 1.00 | 25.02 |
| ATOM | 2339 | OD1 | ASN A | 304 | 0 | 11.506 | 21.111 | 38.146 | 1.00 | 26.72 |
| ATOM | 2340 | ND2 | ASN A | 304 | 0 | 11.766 | 19.133 | 39.114 | 1.00 | 25.99 |
| ATOM | 2341 | N   | GLU A | 305 | 0 | 12.541 | 22.629 | 35.662 | 1.00 | 17.64 |
| ATOM | 2342 | CA  | GLU A | 305 | 0 | 13.204 | 23.890 | 35.840 | 1.00 | 16.64 |
| ATOM | 2343 | C   | GLU A | 305 | 0 | 13.884 | 23.977 | 37.194 | 1.00 | 16.06 |
| ATOM | 2344 | O   | GLU A | 305 | 0 | 14.965 | 24.564 | 37.208 | 1.00 | 14.78 |
| ATOM | 2345 | CB  | GLU A | 305 | 0 | 12.286 | 25.085 | 35.567 | 1.00 | 15.91 |
| ATOM | 2346 | CG  | GLU A | 305 | 0 | 12.898 | 26.484 | 35.831 | 1.00 | 14.81 |
| ATOM | 2347 | CD  | GLU A | 305 | 0 | 11.794 | 27.546 | 35.666 | 1.00 | 15.72 |
| ATOM | 2348 | OE1 | GLU A | 305 | 0 | 11.584 | 28.026 | 34.527 | 1.00 | 14.63 |
| ATOM | 2349 | OE2 | GLU A | 305 | 0 | 11.154 | 27.861 | 36.685 | 1.00 | 13.05 |
| ATOM | 2350 | N   | ALA A | 306 | 0 | 13.416 | 23.432 | 38.298 | 1.00 | 15.83 |
| ATOM | 2351 | CA  | ALA A | 306 | 0 | 14.131 | 23.509 | 39.565 | 1.00 | 17.92 |
| ATOM | 2352 | C   | ALA A | 306 | 0 | 15.437 | 22.682 | 39.532 | 1.00 | 18.62 |
| ATOM | 2353 | O   | ALA A | 306 | 0 | 16.213 | 22.867 | 40.464 | 1.00 | 18.37 |
| ATOM | 2354 | CB  | ALA A | 306 | 0 | 13.283 | 22.993 | 40.711 | 1.00 | 16.23 |
| ATOM | 2355 | N   | ASP A | 307 | 0 | 15.721 | 21.860 | 38.523 | 1.00 | 18.04 |
| ATOM | 2356 | CA  | ASP A | 307 | 0 | 16.988 | 21.164 | 38.409 | 1.00 | 18.68 |
| ATOM | 2357 | C   | ASP A | 307 | 0 | 18.035 | 22.039 | 37.707 | 1.00 | 19.89 |
| ATOM | 2358 | O   | ASP A | 307 | 0 | 19.239 | 21.695 | 37.739 | 1.00 | 20.36 |
| ATOM | 2359 | CB  | ASP A | 307 | 0 | 16.904 | 19.863 | 37.592 | 1.00 | 17.64 |
| ATOM | 2360 | CG  | ASP A | 307 | 0 | 15.980 | 18.873 | 38.290 | 1.00 | 18.17 |
| ATOM | 2361 | OD1 | ASP A | 307 | 0 | 15.918 | 18.919 | 39.535 | 1.00 | 18.27 |
| ATOM | 2362 | OD2 | ASP A | 307 | 0 | 15.311 | 18.094 | 37.592 | 1.00 | 17.32 |
| ATOM | 2363 | N   | LEU A | 308 | 0 | 17.583 | 23.110 | 37.052 | 1.00 | 16.43 |
| ATOM | 2364 | CA  | LEU A | 308 | 0 | 18.581 | 23.962 | 36.377 | 1.00 | 16.80 |
| ATOM | 2365 | C   | LEU A | 308 | 0 | 19.327 | 24.827 | 37.384 | 1.00 | 16.94 |
| ATOM | 2366 | O   | LEU A | 308 | 0 | 18.784 | 25.320 | 38.380 | 1.00 | 17.28 |
| ATOM | 2367 | CB  | LEU A | 308 | 0 | 17.925 | 24.775 | 35.257 | 1.00 | 12.52 |
| ATOM | 2368 | CG  | LEU A | 308 | 0 | 17.436 | 23.936 | 34.073 | 1.00 | 12.15 |
| ATOM | 2369 | CD1 | LEU A | 308 | 0 | 16.692 | 24.834 | 33.101 | 1.00 | 11.67 |
| ATOM | 2370 | CD2 | LEU A | 308 | 0 | 18.547 | 23.186 | 33.341 | 1.00 | 12.23 |
| ATOM | 2371 | N   | HIS A | 309 | 0 | 20.640 | 24.968 | 37.243 | 1.00 | 18.01 |
| ATOM | 2372 | CA  | HIS A | 309 | 0 | 21.430 | 25.802 | 38.158 | 1.00 | 18.47 |
| ATOM | 2373 | C   | HIS A | 309 | 0 | 22.328 | 26.770 | 37.394 | 1.00 | 17.36 |
| ATOM | 2374 | O   | HIS A | 309 | 0 | 23.015 | 26.378 | 36.459 | 1.00 | 17.82 |
| ATOM | 2375 | CB  | HIS A | 309 | 0 | 22.267 | 24.997 | 39.140 | 1.00 | 18.51 |

APPENDIX 1-continued

| | | | | | | | | | | |
|---|---|---|---|---|---|---|---|---|---|---|
| ATOM | 2376 | CG | HIS | A | 309 | 0 | 21.470 | 24.052 | 39.965 | 1.00 20.71 |
| ATOM | 2377 | ND1 | HIS | A | 309 | 0 | 21.526 | 22.684 | 39.790 | 1.00 21.77 |
| ATOM | 2378 | CD2 | HIS | A | 309 | 0 | 20.578 | 24.285 | 40.956 | 1.00 22.07 |
| ATOM | 2379 | CE1 | HIS | A | 309 | 0 | 20.701 | 22.115 | 40.657 | 1.00 22.85 |
| ATOM | 2380 | NE2 | HIS | A | 309 | 0 | 20.120 | 23.059 | 41.377 | 1.00 22.67 |
| ATOM | 2381 | N | ALA | A | 310 | 0 | 22.352 | 28.005 | 37.837 | 1.00 17.27 |
| ATOM | 2382 | CA | ALA | A | 310 | 0 | 23.173 | 29.068 | 37.228 | 1.00 17.74 |
| ATOM | 2383 | C | ALA | A | 310 | 0 | 24.663 | 28.775 | 37.342 | 1.00 18.13 |
| ATOM | 2384 | O | ALA | A | 310 | 0 | 25.103 | 28.233 | 38.369 | 1.00 19.61 |
| ATOM | 2385 | CB | ALA | A | 310 | 0 | 22.869 | 30.356 | 37.985 | 1.00 16.92 |
| ATOM | 2386 | N | LEU | A | 311 | 0 | 25.427 | 29.021 | 36.304 | 1.00 19.30 |
| ATOM | 2387 | CA | LEU | A | 311 | 0 | 26.856 | 28.762 | 36.277 | 1.00 20.71 |
| ATOM | 2388 | C | LEU | A | 311 | 0 | 27.655 | 29.922 | 36.881 | 1.00 22.67 |
| ATOM | 2389 | O | LEU | A | 311 | 0 | 28.581 | 29.788 | 37.682 | 1.00 23.06 |
| ATOM | 2390 | CB | LEU | A | 311 | 0 | 27.305 | 28.591 | 34.817 | 1.00 20.57 |
| ATOM | 2391 | CG | LEU | A | 311 | 0 | 28.796 | 28.196 | 34.684 | 1.00 21.52 |
| ATOM | 2392 | CD1 | LEU | A | 311 | 0 | 28.993 | 26.783 | 35.229 | 1.00 20.80 |
| ATOM | 2393 | CD2 | LEU | A | 311 | 0 | 29.319 | 28.282 | 33.254 | 1.00 20.17 |
| ATOM | 2394 | N | ILE | A | 312 | 0 | 27.333 | 31.142 | 36.449 | 1.00 23.42 |
| ATOM | 2395 | CA | ILE | A | 312 | 0 | 28.092 | 32.311 | 36.899 | 1.00 24.86 |
| ATOM | 2396 | C | ILE | A | 312 | 0 | 27.337 | 33.157 | 37.914 | 1.00 26.54 |
| ATOM | 2397 | O | ILE | A | 312 | 0 | 26.154 | 33.467 | 37.739 | 1.00 25.31 |
| ATOM | 2398 | CB | ILE | A | 312 | 0 | 28.397 | 33.179 | 35.670 | 1.00 24.45 |
| ATOM | 2399 | CG1 | ILE | A | 312 | 0 | 28.998 | 32.330 | 34.576 | 1.00 25.60 |
| ATOM | 2400 | CG2 | ILE | A | 312 | 0 | 29.261 | 34.373 | 36.075 | 1.00 26.44 |
| ATOM | 2401 | CD1 | ILE | A | 312 | 0 | 30.462 | 32.026 | 34.512 | 1.00 24.51 |
| ATOM | 2402 | N | ASP | A | 313 | 0 | 28.008 | 33.523 | 39.003 | 1.00 28.70 |
| ATOM | 2403 | CA | ASP | A | 313 | 0 | 27.432 | 34.339 | 40.071 | 1.00 30.99 |
| ATOM | 2404 | C | ASP | A | 313 | 0 | 26.065 | 33.763 | 40.417 | 1.00 29.83 |
| ATOM | 2405 | O | ASP | A | 313 | 0 | 25.024 | 34.385 | 40.235 | 1.00 28.51 |
| ATOM | 2406 | CB | ASP | A | 313 | 0 | 27.266 | 35.777 | 39.576 | 1.00 35.88 |
| ATOM | 2407 | CG | ASP | A | 313 | 0 | 28.532 | 36.505 | 39.187 | 1.00 40.21 |
| ATOM | 2408 | OD1 | ASP | A | 313 | 0 | 29.577 | 36.243 | 39.847 | 1.00 42.99 |
| ATOM | 2409 | OD2 | ASP | A | 313 | 0 | 28.525 | 37.346 | 38.252 | 1.00 40.95 |
| ATOM | 2410 | N | PRO | A | 314 | 0 | 26.041 | 32.517 | 40.863 | 1.00 28.77 |
| ATOM | 2411 | CA | PRO | A | 314 | 0 | 24.841 | 31.743 | 41.074 | 1.00 27.80 |
| ATOM | 2412 | C | PRO | A | 314 | 0 | 23.865 | 32.198 | 42.137 | 1.00 26.49 |
| ATOM | 2413 | O | PRO | A | 314 | 0 | 22.671 | 31.857 | 42.032 | 1.00 27.17 |
| ATOM | 2414 | CB | PRO | A | 314 | 0 | 25.297 | 30.311 | 41.479 | 1.00 27.61 |
| ATOM | 2415 | CG | PRO | A | 314 | 0 | 26.711 | 30.573 | 41.929 | 1.00 29.37 |

APPENDIX 1-continued

```
ATOM   2416  CD   PRO A  314  0   27.248  31.726  41.111  1.00  28.10
ATOM   2417  N    ALA A  315  0   24.364  32.818  43.206  1.00  23.45
ATOM   2418  CA   ALA A  315  0   23.505  33.092  44.336  1.00  22.34
ATOM   2419  C    ALA A  315  0   22.414  34.111  44.008  1.00  22.46
ATOM   2420  O    ALA A  315  0   22.678  35.127  43.370  1.00  22.52
ATOM   2421  CB   ALA A  315  0   24.294  33.617  45.532  1.00  21.68
ATOM   2422  N    ALA A  316  0   21.226  33.838  44.534  1.00  20.85
ATOM   2423  CA   ALA A  316  0   20.133  34.805  44.422  1.00  20.78
ATOM   2424  C    ALA A  316  0   20.547  36.010  45.271  1.00  20.55
ATOM   2425  O    ALA A  316  0   21.143  35.846  46.333  1.00  21.47
ATOM   2426  CB   ALA A  316  0   18.897  34.166  45.043  1.00  18.32
ATOM   2427  N    PRO A  317  0   20.237  37.212  44.864  1.00  20.84
ATOM   2428  CA   PRO A  317  0   20.539  38.410  45.634  1.00  20.82
ATOM   2429  C    PRO A  317  0   19.766  38.449  46.945  1.00  20.96
ATOM   2430  O    PRO A  317  0   18.668  37.885  47.030  1.00  21.42
ATOM   2431  CB   PRO A  317  0   20.064  39.590  44.758  1.00  21.64
ATOM   2432  CG   PRO A  317  0   19.178  38.938  43.746  1.00  21.69
ATOM   2433  CD   PRO A  317  0   19.517  37.466  43.619  1.00  20.10
ATOM   2434  N    GLY A  318  0   20.269  39.080  47.988  1.00  20.69
ATOM   2435  CA   GLY A  318  0   19.533  39.282  49.225  1.00  21.68
ATOM   2436  C    GLY A  318  0   19.631  38.218  50.283  1.00  22.93
ATOM   2437  O    GLY A  318  0   20.344  37.221  50.101  1.00  23.87
ATOM   2438  N    ILE A  319  0   18.895  38.398  51.368  1.00  22.20
ATOM   2439  CA   ILE A  319  0   18.879  37.432  52.454  1.00  24.16
ATOM   2440  C    ILE A  319  0   18.169  36.189  51.956  1.00  25.28
ATOM   2441  O    ILE A  319  0   17.071  36.271  51.405  1.00  26.26
ATOM   2442  CB   ILE A  319  0   18.208  38.030  53.704  1.00  24.54
ATOM   2443  CG1  ILE A  319  0   19.075  39.176  54.213  1.00  25.08
ATOM   2444  CG2  ILE A  319  0   17.944  37.012  54.793  1.00  24.03
ATOM   2445  CD1  ILE A  319  0   18.262  40.183  55.006  1.00  27.56
ATOM   2446  N    PRO A  320  0   18.762  35.030  52.159  1.00  26.23
ATOM   2447  CA   PRO A  320  0   18.273  33.748  51.684  1.00  26.64
ATOM   2448  C    PRO A  320  0   17.105  33.172  52.453  1.00  26.74
ATOM   2449  O    PRO A  320  0   17.140  32.025  52.896  1.00  27.54
ATOM   2450  CB   PRO A  320  0   19.501  32.801  51.772  1.00  27.16
ATOM   2451  CG   PRO A  320  0   20.216  33.388  52.985  1.00  25.20
ATOM   2452  CD   PRO A  320  0   20.061  34.891  52.837  1.00  25.62
ATOM   2453  N    THR A  321  0   16.022  33.909  52.611  1.00  27.35
ATOM   2454  CA   THR A  321  0   14.820  33.550  53.329  1.00  28.07
```

APPENDIX 1-continued

| ATOM | 2455 | C   | THR | A | 321 | 0 | 13.632 | 34.190 | 52.603 | 1.00 | 27.48 |
|------|------|-----|-----|---|-----|---|--------|--------|--------|------|-------|
| ATOM | 2456 | O   | THR | A | 321 | 0 | 13.597 | 35.383 | 52.302 | 1.00 | 27.13 |
| ATOM | 2457 | CB  | THR | A | 321 | 0 | 14.824 | 34.085 | 54.780 | 1.00 | 29.87 |
| ATOM | 2458 | OG1 | THR | A | 321 | 0 | 15.957 | 33.582 | 55.511 | 1.00 | 31.85 |
| ATOM | 2459 | CG2 | THR | A | 321 | 0 | 13.548 | 33.687 | 55.507 | 1.00 | 31.06 |
| ATOM | 2460 | N   | PRO | A | 322 | 0 | 12.630 | 33.378 | 52.326 | 1.00 | 26.63 |
| ATOM | 2461 | CA  | PRO | A | 322 | 0 | 11.428 | 33.824 | 51.637 | 1.00 | 25.91 |
| ATOM | 2462 | C   | PRO | A | 322 | 0 | 10.892 | 35.072 | 52.313 | 1.00 | 25.37 |
| ATOM | 2463 | O   | PRO | A | 322 | 0 | 10.945 | 35.194 | 53.542 | 1.00 | 25.02 |
| ATOM | 2464 | CB  | PRO | A | 322 | 0 | 10.456 | 32.638 | 51.661 | 1.00 | 26.11 |
| ATOM | 2465 | CG  | PRO | A | 322 | 0 | 11.370 | 31.477 | 51.931 | 1.00 | 26.67 |
| ATOM | 2466 | CD  | PRO | A | 322 | 0 | 12.592 | 31.961 | 52.691 | 1.00 | 26.21 |
| ATOM | 2467 | N   | GLY | A | 323 | 0 | 10.432 | 36.075 | 51.573 | 1.00 | 24.30 |
| ATOM | 2468 | CA  | GLY | A | 323 | 0 |  9.943 | 37.288 | 52.197 | 1.00 | 24.13 |
| ATOM | 2469 | C   | GLY | A | 323 | 0 | 11.013 | 38.161 | 52.842 | 1.00 | 25.48 |
| ATOM | 2470 | O   | GLY | A | 323 | 0 | 10.603 | 39.128 | 53.512 | 1.00 | 25.28 |
| ATOM | 2471 | N   | ALA | A | 324 | 0 | 12.320 | 37.959 | 52.688 | 1.00 | 24.80 |
| ATOM | 2472 | CA  | ALA | A | 324 | 0 | 13.278 | 38.831 | 53.377 | 1.00 | 24.61 |
| ATOM | 2473 | C   | ALA | A | 324 | 0 | 14.034 | 39.773 | 52.451 | 1.00 | 23.92 |
| ATOM | 2474 | O   | ALA | A | 324 | 0 | 15.148 | 40.225 | 52.748 | 1.00 | 24.53 |
| ATOM | 2475 | CB  | ALA | A | 324 | 0 | 14.255 | 38.012 | 54.204 | 1.00 | 23.79 |
| ATOM | 2476 | N   | ALA | A | 325 | 0 | 13.423 | 40.081 | 51.315 | 1.00 | 22.22 |
| ATOM | 2477 | CA  | ALA | A | 325 | 0 | 14.033 | 40.985 | 50.341 | 1.00 | 20.42 |
| ATOM | 2478 | C   | ALA | A | 325 | 0 | 13.825 | 42.423 | 50.803 | 1.00 | 19.97 |
| ATOM | 2479 | O   | ALA | A | 325 | 0 | 12.987 | 42.648 | 51.677 | 1.00 | 18.14 |
| ATOM | 2480 | CB  | ALA | A | 325 | 0 | 13.272 | 40.763 | 49.018 | 1.00 | 19.40 |
| ATOM | 2481 | N   | ASP | A | 326 | 0 | 14.422 | 43.421 | 50.161 | 1.00 | 20.69 |
| ATOM | 2482 | CA  | ASP | A | 326 | 0 | 14.141 | 44.804 | 50.529 | 1.00 | 22.54 |
| ATOM | 2483 | C   | ASP | A | 326 | 0 | 12.702 | 45.158 | 50.220 | 1.00 | 22.83 |
| ATOM | 2484 | O   | ASP | A | 326 | 0 | 12.015 | 45.754 | 51.030 | 1.00 | 23.68 |
| ATOM | 2485 | CB  | ASP | A | 326 | 0 | 15.089 | 45.767 | 49.789 | 1.00 | 22.32 |
| ATOM | 2486 | CG  | ASP | A | 326 | 0 | 16.494 | 45.378 | 50.238 | 1.00 | 23.83 |
| ATOM | 2487 | OD1 | ASP | A | 326 | 0 | 16.650 | 45.284 | 51.475 | 1.00 | 24.78 |
| ATOM | 2488 | OD2 | ASP | A | 326 | 0 | 17.393 | 45.171 | 49.409 | 1.00 | 24.90 |
| ATOM | 2489 | N   | VAL | A | 327 | 0 | 12.254 | 44.821 | 49.026 | 1.00 | 24.29 |
| ATOM | 2490 | CA  | VAL | A | 327 | 0 | 10.914 | 45.064 | 48.503 | 1.00 | 23.57 |
| ATOM | 2491 | C   | VAL | A | 327 | 0 | 10.246 | 43.721 | 48.170 | 1.00 | 23.46 |
| ATOM | 2492 | O   | VAL | A | 327 | 0 | 10.785 | 42.933 | 47.386 | 1.00 | 22.62 |
| ATOM | 2493 | CB  | VAL | A | 327 | 0 | 10.946 | 45.898 | 47.220 | 1.00 | 24.70 |
| ATOM | 2494 | CG1 | VAL | A | 327 | 0 |  9.554 | 46.274 | 46.751 | 1.00 | 24.11 |

APPENDIX 1-continued

```
ATOM   2495 CG2 VAL A  327  0   11.773 47.173 47.420 1 00 26.30
ATOM   2496 N   ASN A  328  0    9.113 43.463 48.811 1.00 21.44
ATOM   2497 CA  ASN A  328  0    8.390 42.212 48.717 1.00 23.21
ATOM   2498 C   ASN A  328  0    6.986 42.410 48.158 1.00 23.12
ATOM   2499 O   ASN A  328  0    6.140 43.030 48.799 1.00 22.76
ATOM   2500 CB  ASN A  328  0    8.223 41.603 50.121 1.00 23.09
ATOM   2501 CG  ASN A  328  0    9.569 41.204 50.693 1.00 24.61
ATOM   2502 OD1 ASN A  328  0   10.181 40.188 50.295 1.00 25.87
ATOM   2503 ND2 ASN A  328  0   10.017 42.029 51.617 1.00 21.47
ATOM   2504 N   LEU A  329  0    6.776 42.000 46.923 1.00 23.14
ATOM   2505 CA  LEU A  329  0    5.497 42.179 46.268 1.00 24.23
ATOM   2506 C   LEU A  329  0    4.859 40.822 45.953 1.00 25.21
ATOM   2507 O   LEU A  329  0    5.489 39.876 45.469 1.00 24.20
ATOM   2508 CB  LEU A  329  0    5.622 42.963 44.948 1.00 24.33
ATOM   2509 CG  LEU A  329  0    6.369 44.279 45.082 1.00 26.30
ATOM   2510 CD1 LEU A  329  0    6.778 44.884 43.757 1.00 26.24
ATOM   2511 CD2 LEU A  329  0    5.550 45.249 45.913 1.00 27.07
ATOM   2512 N   ARG A  330  0    3.562 40.806 46.204 1.00 25.13
ATOM   2513 CA  ARG A  330  0    2.740 39.641 45.899 1.00 27.48
ATOM   2514 C   ARG A  330  0    1.628 40.116 44.965 1.00 27.52
ATOM   2515 O   ARG A  330  0    0.988 41.132 45.257 1.00 27.17
ATOM   2516 CB  ARG A  330  0    2.200 39.017 47.166 1.00 29.82
ATOM   2517 CG  ARG A  330  0    1.351 37.794 46.932 1.00 33.18
ATOM   2518 CD  ARG A  330  0    0.880 37.251 48.284 1.00 37.06
ATOM   2519 NE  ARG A  330  0    0.305 35.914 48.038 1.00 40.34
ATOM   2520 CZ  ARG A  330  0    1.009 34.803 48.298 1.00 40.82
ATOM   2521 NH1 ARG A  330  0    2.229 34.903 48.812 1.00 40.36
ATOM   2522 NH2 ARG A  330  0    0.415 33.642 48.040 1.00 41.33
ATOM   2523 N   PHE A  331  0    1.507 39.481 43.795 1.00 25.88
ATOM   2524 CA  PHE A  331  0    0.475 39.937 42.855 1.00 25.87
ATOM   2525 C   PHE A  331  0   -0.657 38.919 42.779 1.00 25.94
ATOM   2526 O   PHE A  331  0   -0.441 37.697 42.824 1.00 24.61
ATOM   2527 CB  PHE A  331  0    1.102 40.269 41.511 1.00 25.94
ATOM   2528 CG  PHE A  331  0    1.884 41.565 41.496 1.00 28.66
ATOM   2529 CD1 PHE A  331  0    1.282 42.782 41.759 1.00 28.04
ATOM   2530 CD2 PHE A  331  0    3.246 41.569 41.214 1.00 29.71
ATOM   2531 CE1 PHE A  331  0    1.988 43.963 41.744 1.00 29.21
ATOM   2532 CE2 PHE A  331  0    3.975 42.753 41.181 1.00 30.61
ATOM   2533 CZ  PHE A  331  0    3.348 43.965 41.453 1.00 30.66
```

APPENDIX 1-continued

| | | | | | | | | | | |
|---|---|---|---|---|---|---|---|---|---|---|
| ATOM | 2534 | N | GLN | A | 332 | 0 | -1.873 | 39.446 | 42.676 | 1.00 25.58 |
| ATOM | 2535 | CA | GLN | A | 332 | 0 | -3.085 | 38.628 | 42.608 | 1.00 26.60 |
| ATOM | 2536 | C | GLN | A | 332 | 0 | -3.672 | 38.698 | 41.203 | 1.00 23.61 |
| ATOM | 2537 | O | GLN | A | 332 | 0 | -4.136 | 39.739 | 40.755 | 1.00 21.73 |
| ATOM | 2538 | CB | GLN | A | 332 | 0 | -4.110 | 39.094 | 43.630 | 1.00 30.32 |
| ATOM | 2539 | CG | GLN | A | 332 | 0 | -5.412 | 38.299 | 43.642 | 1.00 35.72 |
| ATOM | 2540 | CD | GLN | A | 332 | 0 | -5.199 | 36.961 | 44.325 | 1.00 39.98 |
| ATOM | 2541 | OE1 | GLN | A | 332 | 0 | -5.859 | 35.961 | 44.007 | 1.00 42.32 |
| ATOM | 2542 | NE2 | GLN | A | 332 | 0 | -4.257 | 36.915 | 45.270 | 1.00 42.27 |
| ATOM | 2543 | N | LEU | A | 333 | 0 | -3.612 | 37.576 | 40.504 | 1.00 23.60 |
| ATOM | 2544 | CA | LEU | A | 333 | 0 | -4.105 | 37.565 | 39.118 | 1.00 26.25 |
| ATOM | 2545 | C | LEU | A | 333 | 0 | -5.627 | 37.373 | 39.123 | 1.00 26.55 |
| ATOM | 2546 | O | LEU | A | 333 | 0 | -6.107 | 36.655 | 39.998 | 1.00 25.70 |
| ATOM | 2547 | CB | LEU | A | 333 | 0 | -3.424 | 36.465 | 38.304 | 1.00 25.25 |
| ATOM | 2548 | CG | LEU | A | 333 | 0 | -1.919 | 36.608 | 38.052 | 1.00 25.72 |
| ATOM | 2549 | CD1 | LEU | A | 333 | 0 | -1.431 | 35.565 | 37.067 | 1.00 23.66 |
| ATOM | 2550 | CD2 | LEU | A | 333 | 0 | -1.551 | 38.000 | 37.558 | 1.00 25.25 |
| ATOM | 2551 | N | GLY | A | 334 | 0 | -6.327 | 37.976 | 38.188 | 1.00 27.85 |
| ATOM | 2552 | CA | GLY | A | 334 | 0 | -7.770 | 37.782 | 38.118 | 1.00 29.96 |
| ATOM | 2553 | C | GLY | A | 334 | 0 | -8.253 | 37.802 | 36.672 | 1.00 32.36 |
| ATOM | 2554 | O | GLY | A | 334 | 0 | -7.559 | 38.175 | 35.719 | 1.00 30.74 |
| ATOM | 2555 | N | PHE | A | 335 | 0 | -9.502 | 37.377 | 36.544 | 1.00 34.76 |
| ATOM | 2556 | CA | PHE | A | 335 | 0 | -10.181 | 37.360 | 35.260 | 1.00 38.54 |
| ATOM | 2557 | C | PHE | A | 335 | 0 | -11.625 | 37.806 | 35.514 | 1.00 41.05 |
| ATOM | 2558 | O | PHE | A | 335 | 0 | -12.443 | 37.028 | 36.021 | 1.00 41.53 |
| ATOM | 2559 | CB | PHE | A | 335 | 0 | -10.183 | 36.003 | 34.586 | 1.00 39.00 |
| ATOM | 2560 | CG | PHE | A | 335 | 0 | -10.772 | 36.105 | 33.197 | 1.00 40.61 |
| ATOM | 2561 | CD1 | PHE | A | 335 | 0 | -10.052 | 36.686 | 32.175 | 1.00 40.45 |
| ATOM | 2562 | CD2 | PHE | A | 335 | 0 | -12.045 | 35.614 | 32.942 | 1.00 41.39 |
| ATOM | 2563 | CE1 | PHE | A | 335 | 0 | -10.580 | 36.778 | 30.901 | 1.00 40.81 |
| ATOM | 2564 | CE2 | PHE | A | 335 | 0 | -12.588 | 35.697 | 31.671 | 1.00 41.51 |
| ATOM | 2565 | CZ | PHE | A | 335 | 0 | -11.849 | 36.281 | 30.652 | 1.00 41.87 |
| ATOM | 2566 | N | SER | A | 336 | 0 | -11.861 | 39.075 | 35.193 | 1.00 42.39 |
| ATOM | 2567 | CA | SER | A | 336 | 0 | -13.203 | 39.582 | 35.445 | 1.00 44.12 |
| ATOM | 2568 | C | SER | A | 336 | 0 | -13.704 | 40.525 | 34.370 | 1.00 44.31 |
| ATOM | 2569 | O | SER | A | 336 | 0 | -13.028 | 41.440 | 33.903 | 1.00 44.49 |
| ATOM | 2570 | CB | SER | A | 336 | 0 | -13.214 | 40.206 | 36.842 | 1.00 45.46 |
| ATOM | 2571 | OG | SER | A | 336 | 0 | -13.727 | 39.233 | 37.758 | 1.00 47.11 |
| ATOM | 2572 | N | GLY | A | 337 | 0 | -14.963 | 40.267 | 33.983 | 1.00 44.12 |
| ATOM | 2573 | CA | GLY | A | 337 | 0 | -15.630 | 41.067 | 32.959 | 1.00 41.89 |

APPENDIX 1-continued

| ATOM | 2574 | C | GLY | A | 337 | 0 | -14.963 | 40.920 | 31.608 | 1.00 | 40.08 |
| ATOM | 2575 | O | GLY | A | 337 | 0 | -14.712 | 41.891 | 30.888 | 1.00 | 41.35 |
| ATOM | 2576 | N | GLY | A | 338 | 0 | -14.583 | 39.699 | 31.263 | 1.00 | 39.12 |
| ATOM | 2577 | CA | GLY | A | 338 | 0 | -13.899 | 39.364 | 30.034 | 1.00 | 36.11 |
| ATOM | 2578 | C | GLY | A | 338 | 0 | -12.503 | 39.970 | 29.929 | 1 00 | 34.97 |
| ATOM | 2579 | O | GLY | A | 338 | 0 | -12.005 | 40.116 | 28.806 | 1.00 | 33.64 |
| ATOM | 2580 | N | ARG | A | 339 | 0 | -11.885 | 40.355 | 31.048 | 1.00 | 33.21 |
| ATOM | 2581 | CA | ARG | A | 339 | 0 | -10.538 | 40.916 | 30.982 | 1.00 | 32.04 |
| ATOM | 2582 | C | ARG | A | 339 | 0 | -9.724 | 40.397 | 32.164 | 1.00 | 29.23 |
| ATOM | 2583 | O | ARG | A | 339 | 0 | -10.260 | 40.053 | 33.210 | 1.00 | 26.38 |
| ATOM | 2584 | CB | ARG | A | 339 | 0 | -10.495 | 42.419 | 30.845 | 1.00 | 36.52 |
| ATOM | 2585 | CG | ARG | A | 339 | 0 | -11.291 | 43.281 | 31.790 | 1.00 | 42.08 |
| ATOM | 2586 | CD | ARG | A | 339 | 0 | -11.895 | 44.502 | 31.127 | 1.00 | 45.03 |
| ATOM | 2587 | NE | ARG | A | 339 | 0 | -11.046 | 45.380 | 30.351 | 1.00 | 47.77 |
| ATOM | 2588 | CZ | ARG | A | 339 | 0 | -10.635 | 46.616 | 30.664 | 1.00 | 49.55 |
| ATOM | 2589 | NH1 | ARG | A | 339 | 0 | -10.935 | 47.242 | 31.799 | 1.00 | 49.60 |
| ATOM | 2590 | NH2 | ARG | A | 339 | 0 | -9.862 | 47.295 | 29.805 | 1.00 | 49.96 |
| ATOM | 2591 | N | PHE | A | 340 | 0 | -8.425 | 40.181 | 31.900 | 1.00 | 25.50 |
| ATOM | 2592 | CA | PHE | A | 340 | 0 | -7.526 | 39.713 | 32.938 | 1.00 | 22.68 |
| ATOM | 2593 | C | PHE | A | 340 | 0 | -7.171 | 40.945 | 33.774 | 1.00 | 22.15 |
| ATOM | 2594 | O | PHE | A | 340 | 0 | -7.069 | 42.069 | 33.266 | 1.00 | 21.26 |
| ATOM | 2595 | CB | PHE | A | 340 | 0 | -6.210 | 39.135 | 32.397 | 1.00 | 22.39 |
| ATOM | 2596 | CG | PHE | A | 340 | 0 | -6.333 | 37.792 | 31.736 | 1.00 | 20.74 |
| ATOM | 2597 | CD1 | PHE | A | 340 | 0 | -6.338 | 37.710 | 30.357 | 1.00 | 20.97 |
| ATOM | 2598 | CD2 | PHE | A | 340 | 0 | -6.448 | 36.644 | 32.468 | 1.00 | 21.19 |
| ATOM | 2599 | CE1 | PHE | A | 340 | 0 | -6.449 | 36.488 | 29.721 | 1.00 | 21.61 |
| ATOM | 2600 | CE2 | PHE | A | 340 | 0 | -6.585 | 35.408 | 31.826 | 1.00 | 22.99 |
| ATOM | 2601 | CZ | PHE | A | 340 | 0 | -6.578 | 35.334 | 30.444 | 1.00 | 19.90 |
| ATOM | 2602 | N | THR | A | 341 | 0 | -7.000 | 40.736 | 35.069 | 1.00 | 20.76 |
| ATOM | 2603 | CA | THR | A | 341 | 0 | -6.605 | 41.879 | 35.889 | 1.00 | 21.55 |
| ATOM | 2604 | C | THR | A | 341 | 0 | -5.400 | 41.509 | 36.759 | 1.00 | 21.00 |
| ATOM | 2605 | O | THR | A | 341 | 0 | -5.236 | 40.329 | 37.089 | 1.00 | 20.70 |
| ATOM | 2606 | CB | THR | A | 341 | 0 | -7.757 | 42.255 | 36.853 | 1.00 | 21.12 |
| ATOM | 2607 | OG1 | THR | A | 341 | 0 | -8.014 | 41.102 | 37.668 | 1.00 | 21.26 |
| ATOM | 2608 | CG2 | THR | A | 341 | 0 | -9.050 | 42.630 | 36.150 | 1.00 | 21.74 |
| ATOM | 2609 | N | ILE | A | 342 | 0 | -4.750 | 42.529 | 37.308 | 1.00 | 20.28 |
| ATOM | 2610 | CA | ILE | A | 342 | 0 | -3.739 | 42.273 | 38.333 | 1.00 | 20.34 |
| ATOM | 2611 | C | ILE | A | 342 | 0 | -4.026 | 43.212 | 39.496 | 1.00 | 18.92 |
| ATOM | 2612 | O | ILE | A | 342 | 0 | -4.004 | 44.437 | 39.327 | 1.00 | 16.42 |

APPENDIX 1-continued

| ATOM | 2613 | CB  | ILE | A | 342 | 0 | -2.306 | 42.439 | 37.820 | 1.00 | 21.04 |
| ATOM | 2614 | CG1 | ILE | A | 342 | 0 | -1.337 | 42.721 | 38.988 | 1.00 | 21.39 |
| ATOM | 2615 | CG2 | ILE | A | 342 | 0 | -2.250 | 43.540 | 36.800 | 1.00 | 24.57 |
| ATOM | 2616 | CD1 | ILE | A | 342 | 0 | -0.260 | 41.661 | 38.949 | 1.00 | 24.53 |
| ATOM | 2617 | N   | ASN | A | 343 | 0 | -4.282 | 42.601 | 40.650 | 1.00 | 17.77 |
| ATOM | 2618 | CA  | ASN | A | 343 | 0 | -4.702 | 43.413 | 41.782 | 1.00 | 21.51 |
| ATOM | 2619 | C   | ASN | A | 343 | 0 | -5.881 | 44.287 | 41.394 | 1.00 | 21.43 |
| ATOM | 2620 | O   | ASN | A | 343 | 0 | -5.903 | 45.495 | 41.598 | 1.00 | 20.26 |
| ATOM | 2621 | CB  | ASN | A | 343 | 0 | -3.513 | 44.231 | 42.356 | 1.00 | 22.34 |
| ATOM | 2622 | CG  | ASN | A | 343 | 0 | -2.685 | 43.190 | 43.073 | 1.00 | 25.38 |
| ATOM | 2623 | OD1 | ASN | A | 343 | 0 | -2.075 | 42.218 | 42.598 | 1.00 | 26.90 |
| ATOM | 2624 | ND2 | ASN | A | 343 | 0 | -2.652 | 43.238 | 44.425 | 1.00 | 25.34 |
| ATOM | 2625 | N   | GLY | A | 344 | 0 | -6.875 | 43.703 | 40.730 | 1.00 | 23.77 |
| ATOM | 2626 | CA  | GLY | A | 344 | 0 | -8.078 | 44.406 | 40.324 | 1.00 | 25.28 |
| ATOM | 2627 | C   | GLY | A | 344 | 0 | -7.954 | 45.280 | 39.111 | 1.00 | 26.82 |
| ATOM | 2628 | O   | GLY | A | 344 | 0 | -9.029 | 45.728 | 38.672 | 1.00 | 29.56 |
| ATOM | 2629 | N   | THR | A | 345 | 0 | -6.798 | 45.561 | 38.527 | 1.00 | 26.28 |
| ATOM | 2630 | CA  | THR | A | 345 | 0 | -6.766 | 46.440 | 37.366 | 1.00 | 25.48 |
| ATOM | 2631 | C   | THR | A | 345 | 0 | -6.343 | 45.703 | 36.109 | 1.00 | 26.49 |
| ATOM | 2632 | O   | THR | A | 345 | 0 | -5.385 | 44.925 | 36.122 | 1.00 | 28.22 |
| ATOM | 2633 | CB  | THR | A | 345 | 0 | -5.829 | 47.648 | 37.589 | 1.00 | 26.17 |
| ATOM | 2634 | OG1 | THR | A | 345 | 0 | -6.191 | 48.334 | 38.788 | 1.00 | 25.32 |
| ATOM | 2635 | CG2 | THR | A | 345 | 0 | -5.867 | 48.677 | 36.462 | 1.00 | 24.83 |
| ATOM | 2636 | N   | ALA | A | 346 | 0 | -7.017 | 46.012 | 35.008 | 1.00 | 24.80 |
| ATOM | 2637 | CA  | ALA | A | 346 | 0 | -6.768 | 45.491 | 33.688 | 1.00 | 23.82 |
| ATOM | 2638 | C   | ALA | A | 346 | 0 | -5.862 | 46.511 | 32.997 | 1.00 | 23.77 |
| ATOM | 2639 | O   | ALA | A | 346 | 0 | -6.098 | 47.711 | 33.088 | 1.00 | 22.93 |
| ATOM | 2640 | CB  | ALA | A | 346 | 0 | -8.031 | 45.353 | 32.841 | 1.00 | 24.13 |
| ATOM | 2641 | N   | TYR | A | 347 | 0 | -4.793 | 46.023 | 32.392 | 1.00 | 22.69 |
| ATOM | 2642 | CA  | TYR | A | 347 | 0 | -3.862 | 46.949 | 31.792 | 1.00 | 22.75 |
| ATOM | 2643 | C   | TYR | A | 347 | 0 | -4.483 | 47.532 | 30.527 | 1.00 | 23.42 |
| ATOM | 2644 | O   | TYR | A | 347 | 0 | -4.954 | 46.753 | 29.709 | 1.00 | 22.19 |
| ATOM | 2645 | CB  | TYR | A | 347 | 0 | -2.521 | 46.274 | 31.455 | 1.00 | 21.25 |
| ATOM | 2646 | CG  | TYR | A | 347 | 0 | -1.584 | 47.221 | 30.732 | 1.00 | 18.93 |
| ATOM | 2647 | CD1 | TYR | A | 347 | 0 | -0.819 | 48.137 | 31.442 | 1.00 | 18.17 |
| ATOM | 2648 | CD2 | TYR | A | 347 | 0 | -1.473 | 47.176 | 29.353 | 1.00 | 19.30 |
| ATOM | 2649 | CE1 | TYR | A | 347 | 0 |  0.034 | 49.003 | 30.763 | 1.00 | 18.37 |
| ATOM | 2650 | CE2 | TYR | A | 347 | 0 | -0.650 | 48.063 | 28.664 | 1.00 | 18.40 |
| ATOM | 2651 | CZ  | TYR | A | 347 | 0 |  0.102 | 48.962 | 29.394 | 1.00 | 18.99 |
| ATOM | 2652 | OH  | TYR | A | 347 | 0 |  0.947 | 49.802 | 28.706 | 1.00 | 19.65 |

APPENDIX 1-continued

| ATOM | 2653 | N | GLU A | 348 | 0 | -4.378 | 48.833 | 30.359 | 1.00 | 25.22 |
|---|---|---|---|---|---|---|---|---|---|---|
| ATOM | 2654 | CA | GLU A | 348 | 0 | -4.769 | 49.453 | 29.098 | 1.00 | 28.77 |
| ATOM | 2655 | C | GLU A | 348 | 0 | -3.659 | 50.470 | 28.805 | 1.00 | 27.38 |
| ATOM | 2656 | O | GLU A | 348 | 0 | -3.297 | 51.229 | 29.704 | 1.00 | 28.49 |
| ATOM | 2657 | CB | GLU A | 348 | 0 | -6.114 | 50.134 | 29.110 | 1.00 | 32.95 |
| ATOM | 2658 | CG | GLU A | 348 | 0 | -7.391 | 49.302 | 29.072 | 1.00 | 39.29 |
| ATOM | 2659 | CD | GLU A | 348 | 0 | -8.562 | 50.170 | 29.559 | 1.00 | 43.20 |
| ATOM | 2660 | OE1 | GLU A | 348 | 0 | -8.825 | 51.211 | 28.900 | 1.00 | 45.31 |
| ATOM | 2661 | 0E2 | GLU A | 348 | 0 | -9.175 | 49.855 | 30.601 | 1.00 | 44.11 |
| ATOM | 2662 | N | SER A | 349 | 0 | -3.168 | 50.541 | 27.621 | 1.00 | 25.73 |
| ATOM | 2663 | CA | SER A | 349 | 0 | -2.080 | 51.410 | 27.201 | 1.00 | 28.25 |
| ATOM | 2664 | C | SER A | 349 | 0 | -2.401 | 52.887 | 27.194 | 1.00 | 28.71 |
| ATOM | 2665 | O | SER A | 349 | 0 | -3.279 | 53.399 | 26.526 | 1.00 | 29.13 |
| ATOM | 2666 | CB | SER A | 349 | 0 | -1.743 | 50.818 | 25.838 | 1.00 | 28.54 |
| ATOM | 2667 | OG | SER A | 349 | 0 | -0.850 | 51.499 | 25.026 | 1.00 | 33.31 |
| ATOM | 2668 | N | PRO A | 350 | 0 | -1.623 | 53.700 | 27.898 | 1.00 | 29.56 |
| ATOM | 2669 | CA | PRO A | 350 | 0 | -1.770 | 55.145 | 27.997 | 1.00 | 28.53 |
| ATOM | 2670 | C | PRO A | 350 | 0 | -1.480 | 55.825 | 26.679 | 1.00 | 28.01 |
| ATOM | 2671 | O | PRO A | 350 | 0 | -0.787 | 55.217 | 25.856 | 1.00 | 26.93 |
| ATOM | 2672 | CB | PRO A | 350 | 0 | -0.752 | 55.632 | 29.063 | 1.00 | 27.91 |
| ATOM | 2673 | CG | PRO A | 350 | 0 | 0.309 | 54.560 | 28.863 | 1.00 | 28.03 |
| ATOM | 2674 | CD | PRO A | 350 | 0 | -0.461 | 53.245 | 28.688 | 1.00 | 28.76 |
| ATOM | 2675 | N | SER A | 351 | 0 | -1.951 | 57.066 | 26.485 | 1.00 | 28.89 |
| ATOM | 2676 | CA | SER A | 351 | 0 | -1.630 | 57.718 | 25.206 | 1.00 | 29.67 |
| ATOM | 2677 | C | SER A | 351 | 0 | -0.213 | 58.287 | 25.257 | 1.00 | 27.67 |
| ATOM | 2678 | O | SER A | 351 | 0 | 0.320 | 58.524 | 24.177 | 1.00 | 28.18 |
| ATOM | 2679 | CB | SER A | 351 | 0 | -2.566 | 58.860 | 24.790 | 1.00 | 31.71 |
| ATOM | 2680 | OG | SER A | 351 | 0 | -2.793 | 59.679 | 25.938 | 1.00 | 34.19 |
| ATOM | 2681 | N | VAL A | 352 | 0 | 0.316 | 58.529 | 26.449 | 1.00 | 25.32 |
| ATOM | 2682 | CA | VAL A | 352 | 0 | 1.703 | 58.997 | 26.534 | 1.00 | 25.27 |
| ATOM | 2683 | C | VAL A | 352 | 0 | 2.503 | 57.872 | 27.211 | 1.00 | 23.63 |
| ATOM | 2684 | O | VAL A | 352 | 0 | 2.181 | 57.493 | 28.323 | 1.00 | 23.26 |
| ATOM | 2685 | CB | VAL A | 352 | 0 | 1.934 | 60.300 | 27.303 | 1.00 | 24.91 |
| ATOM | 2686 | CG1 | VAL A | 352 | 0 | 1.129 | 61.436 | 26.658 | 1.00 | 24.41 |
| ATOM | 2687 | CG2 | VAL A | 352 | 0 | 3.424 | 60.635 | 27.281 | 1.00 | 23.35 |
| ATOM | 2688 | N | PRO A | 353 | 0 | 3.498 | 57.375 | 26.510 | 1.00 | 22.39 |
| ATOM | 2689 | CA | PRO A | 353 | 0 | 4.342 | 56.300 | 26.983 | 1.00 | 21.86 |
| ATOM | 2690 | C | PRO A | 353 | 0 | 4.978 | 56.699 | 28.300 | 1.00 | 20.91 |
| ATOM | 2691 | O | PRO A | 353 | 0 | 5.393 | 57.852 | 28.483 | 1.00 | 21.91 |

APPENDIX 1-continued

| ATOM | 2692 | CB  | PRO A | 353 | 0 | 5.417  | 56.054 | 25.916 | 1.00 | 23.95 |
| ATOM | 2693 | CG  | PRO A | 353 | 0 | 5.181  | 57.123 | 24.878 | 1.00 | 23.79 |
| ATOM | 2694 | CD  | PRO A | 353 | 0 | 3.882  | 57.848 | 25.180 | 1.00 | 23.03 |
| ATOM | 2695 | N   | THR A | 354 | 0 | 5.043  | 55.778 | 29.234 | 1.00 | 18.66 |
| ATOM | 2696 | CA  | THR A | 354 | 0 | 5.646  | 56.015 | 30.530 | 1.00 | 18.05 |
| ATOM | 2697 | C   | THR A | 354 | 0 | 6.981  | 56.739 | 30.478 | 1.00 | 18.33 |
| ATOM | 2698 | O   | THR A | 354 | 0 | 7.168  | 57.630 | 31.319 | 1.00 | 19.46 |
| ATOM | 2699 | CB  | THR A | 354 | 0 | 5.871  | 54.661 | 31.242 | 1.00 | 17.10 |
| ATOM | 2700 | OG1 | THR A | 354 | 0 | 4.903  | 53.710 | 30.797 | 1.00 | 17.24 |
| ATOM | 2701 | CG2 | THR A | 354 | 0 | 5.772  | 54.852 | 32.741 | 1.00 | 16.43 |
| ATOM | 2702 | N   | LEU A | 355 | 0 | 7.940  | 56.380 | 29.618 | 1.00 | 17.49 |
| ATOM | 2703 | CA  | LEU A | 355 | 0 | 9.215  | 57.076 | 29.604 | 1.00 | 18.84 |
| ATOM | 2704 | C   | LEU A | 355 | 0 | 9.013  | 58.579 | 29.284 | 1.00 | 19.80 |
| ATOM | 2705 | O   | LEU A | 355 | 0 | 9.722  | 59.417 | 29.849 | 1.00 | 17.13 |
| ATOM | 2706 | CB  | LEU A | 355 | 0 | 10.200 | 56.498 | 28.622 | 1.00 | 17.89 |
| ATOM | 2707 | CG  | LEU A | 355 | 0 | 11.703 | 56.488 | 28.819 | 1.00 | 18.66 |
| ATOM | 2708 | CD1 | LEU A | 355 | 0 | 12.436 | 56.851 | 27.547 | 1.00 | 18.37 |
| ATOM | 2709 | CD2 | LEU A | 355 | 0 | 12.199 | 57.204 | 30.056 | 1.00 | 16.79 |
| ATOM | 2710 | N   | LEU A | 356 | 0 | 8.134  | 58.883 | 28.328 | 1.00 | 20.48 |
| ATOM | 2711 | CA  | LEU A | 356 | 0 | 7.812  | 60.274 | 27.993 | 1.00 | 21.62 |
| ATOM | 2712 | C   | LEU A | 356 | 0 | 7.085  | 60.932 | 29.163 | 1.00 | 21.28 |
| ATOM | 2713 | O   | LEU A | 356 | 0 | 7.497  | 62.042 | 29.506 | 1.00 | 22.01 |
| ATOM | 2714 | CB  | LEU A | 356 | 0 | 7.028  | 60.474 | 26.700 | 1.00 | 22.08 |
| ATOM | 2715 | CG  | LEU A | 356 | 0 | 6.850  | 61.939 | 26.239 | 1.00 | 23.98 |
| ATOM | 2716 | CD1 | LEU A | 356 | 0 | 8.157  | 62.709 | 26.207 | 1.00 | 23.11 |
| ATOM | 2717 | CD2 | LEU A | 356 | 0 | 6.191  | 61.985 | 24.864 | 1.00 | 24.74 |
| ATOM | 2718 | N   | GLN A | 357 | 0 | 6.219  | 60.267 | 29.922 | 1.00 | 21.37 |
| ATOM | 2719 | CA  | GLN A | 357 | 0 | 5.669  | 60.893 | 31.120 | 1.00 | 21.87 |
| ATOM | 2720 | C   | GLN A | 357 | 0 | 6.759  | 61.254 | 32.128 | 1.00 | 24.12 |
| ATOM | 2721 | O   | GLN A | 357 | 0 | 6.674  | 62.277 | 32.811 | 1.00 | 24.92 |
| ATOM | 2722 | CB  | GLN A | 357 | 0 | 4.636  | 60.015 | 31.822 | 1.00 | 20.63 |
| ATOM | 2723 | CG  | GLN A | 357 | 0 | 3.447  | 59.674 | 30.906 | 1.00 | 19.17 |
| ATOM | 2724 | CD  | GLN A | 357 | 0 | 2.547  | 58.643 | 31.540 | 1.00 | 18.85 |
| ATOM | 2725 | OE1 | GLN A | 357 | 0 | 2.162  | 58.748 | 32.713 | 1.00 | 19.06 |
| ATOM | 2726 | NE2 | GLN A | 357 | 0 | 2.262  | 57.600 | 30.742 | 1.00 | 18.49 |
| ATOM | 2727 | N   | ILE A | 358 | 0 | 7.735  | 60.371 | 32.346 | 1.00 | 25.66 |
| ATOM | 2728 | CA  | ILE A | 358 | 0 | 8.822  | 60.651 | 33.263 | 1.00 | 26.19 |
| ATOM | 2729 | C   | ILE A | 358 | 0 | 9.699  | 61.800 | 32.762 | 1.00 | 27.66 |
| ATOM | 2730 | O   | ILE A | 358 | 0 | 9.940  | 62.725 | 33.551 | 1.00 | 26.65 |
| ATOM | 2731 | CB  | ILE A | 358 | 0 | 9.692  | 59.420 | 33.578 | 1.00 | 24.79 |

APPENDIX 1-continued

```
ATOM   2732  CG1  ILE A   358  0     8.807  58.395  34.304  1.00  24.09
ATOM   2733  CG2  ILE A   358  0    10.865  59.841  34.451  1.00  23.78
ATOM   2734  CD1  ILE A   358  0     9.251  56.954  34.234  1.00  23.34
ATOM   2735  N    MET A   359  0    10.054  61.844  31.486  1.00  29.63
ATOM   2736  CA   MET A   359  0    10.893  62.910  30.965  1.00  33.02
ATOM   2737  C    MET A   359  0    10.174  64.260  31.027  1.00  34.46
ATOM   2738  O    MET A   359  0    10.801  65.324  31.026  1.00  33.77
ATOM   2739  CB   MET A   359  0    11.346  62.664  29.537  1.00  35.67
ATOM   2740  CG   MET A   359  0    12.065  61.403  29.138  1.00  40.75
ATOM   2741  SD   MET A   359  0    13.764  61.153  29.671  1.00  44.90
ATOM   2742  CE   MET A   359  0    14.594  62.592  29.007  1.00  44.24
ATOM   2743  N    SER A   360  0     8.835  64.238  31.070  1.00  33.43
ATOM   2744  CA   SER A   360  0     8.024  65.430  31.088  1.00  32.92
ATOM   2745  C    SER A   360  0     7.761  65.995  32.474  1.00  33.24
ATOM   2746  O    SER A   360  0     6.989  66.966  32.556  1.00  34.08
ATOM   2747  CB   SER A   360  0     6.678  65.134  30.393  1.00  31.34
ATOM   2748  OG   SER A   360  0     6.928  65.109  28.996  1.00  31.06
ATOM   2749  N    GLY A   361  0     8.288  65.360  33.517  1.00  32.06
ATOM   2750  CA   GLY A   361  0     8.072  65.868  34.847  1.00  31.80
ATOM   2751  C    GLY A   361  0     7.487  64.955  35.880  1.00  32.48
ATOM   2752  O    GLY A   361  0     7.420  65.377  37.043  1.00  33.20
ATOM   2753  N    ALA A   362  0     6.991  63.769  35.535  1.00  33.69
ATOM   2754  CA   ALA A   362  0     6.406  62.926  36.601  1.00  35.10
ATOM   2755  C    ALA A   362  0     7.475  62.615  37.650  1.00  34.45
ATOM   2756  O    ALA A   362  0     8.598  62.306  37.286  1.00  33.60
ATOM   2757  CB   ALA A   362  0     5.789  61.658  36.043  1.00  34.88
ATOM   2758  N    GLN A   363  0     7.146  62.676  38.920  1.00  36.22
ATOM   2759  CA   GLN A   363  0     8.083  62.458  40.007  1.00  37.87
ATOM   2760  C    GLN A   363  0     7.776  61.189  40.787  1.00  37.20
ATOM   2761  O    GLN A   363  0     8.620  60.777  41.587  1.00  36.79
ATOM   2762  CB   GLN A   363  0     8.012  63.619  41.022  1.00  40.41
ATOM   2763  CG   GLN A   363  0     8.986  64.740  40.721  1.00  44.07
ATOM   2764  CD   GLN A   363  0     8.586  66.154  41.092  1.00  45.77
ATOM   2765  OE1  GLN A   363  0     7.697  66.473  41.901  1.00  46.53
ATOM   2766  NE2  GLN A   363  0     9.294  67.089  40.435  1.00  46.12
ATOM   2767  N    SER A   364  0     6.579  60.632  40.610  1.00  35.74
ATOM   2768  CA   SER A   364  0     6.249  59.434  41.381  1.00  34.54
ATOM   2769  C    SER A   364  0     5.225  58.588  40.653  1.00  34.32
ATOM   2770  O    SER A   364  0     4.605  59.037  39.692  1.00  33.71
```

APPENDIX 1-continued

| | | | | | | | | | | |
|---|---|---|---|---|---|---|---|---|---|---|
| ATOM | 2771 | CB | SER | A | 364 | 0 | 5.774 | 59.835 | 42.769 | 1.00 35.68 |
| ATOM | 2772 | OG | SER | A | 364 | 0 | 4.396 | 60.095 | 42.928 | 1.00 35.86 |
| ATOM | 2773 | N | ALA | A | 365 | 0 | 5.015 | 57.372 | 41.146 | 1.00 33.95 |
| ATOM | 2774 | CA | ALA | A | 365 | 0 | 4.017 | 56.486 | 40.564 | 1.00 34.62 |
| ATOM | 2775 | C | ALA | A | 365 | 0 | 2.637 | 57.148 | 40.560 | 1.00 34.46 |
| ATOM | 2776 | O | ALA | A | 365 | 0 | 1.906 | 56.995 | 39.582 | 1.00 34.37 |
| ATOM | 2777 | CB | ALA | A | 365 | 0 | 3.963 | 55.155 | 41.301 | 1.00 33.51 |
| ATOM | 2778 | N | ASN | A | 366 | 0 | 2.261 | 57.916 | 41.571 | 1.00 34.45 |
| ATOM | 2779 | CA | ASN | A | 366 | 0 | 1.003 | 58.619 | 41.632 | 1.00 36.37 |
| ATOM | 2780 | C | ASN | A | 366 | 0 | 0.708 | 59.524 | 40.447 | 1.00 35.60 |
| ATOM | 2781 | O | ASN | A | 366 | 0 | -0.462 | 59.719 | 40.131 | 1.00 36.50 |
| ATOM | 2782 | CB | ASN | A | 366 | 0 | 0.904 | 59.464 | 42.918 | 1.00 38.72 |
| ATOM | 2783 | CG | ASN | A | 366 | 0 | 0.794 | 58.558 | 44.126 | 1.00 41.08 |
| ATOM | 2784 | OD1 | ASN | A | 366 | 0 | 0.863 | 58.966 | 45.284 | 1.00 43.39 |
| ATOM | 2785 | ND2 | ASN | A | 366 | 0 | 0.646 | 57.256 | 43.914 | 1.00 42.72 |
| ATOM | 2786 | N | ASP | A | 367 | 0 | 1.694 | 60.046 | 39.752 | 1.00 34.06 |
| ATOM | 2787 | CA | ASP | A | 367 | 0 | 1.571 | 60.899 | 38.610 | 1.00 33.37 |
| ATOM | 2788 | C | ASP | A | 367 | 0 | 1.566 | 60.122 | 37.293 | 1.00 32.09 |
| ATOM | 2789 | O | ASP | A | 367 | 0 | 1.430 | 60.762 | 36.247 | 1.00 31.74 |
| ATOM | 2790 | CB | ASP | A | 367 | 0 | 2.768 | 61.841 | 38.483 | 1.00 35.96 |
| ATOM | 2791 | CG | ASP | A | 367 | 0 | 3.048 | 62.818 | 39.602 | 1.00 37.69 |
| ATOM | 2792 | OD1 | ASP | A | 367 | 0 | 2.123 | 63.209 | 40.336 | 1.00 37.23 |
| ATOM | 2793 | 0D2 | ASP | A | 367 | 0 | 4.258 | 63.194 | 39.705 | 1.00 39.62 |
| ATOM | 2794 | N | LEU | A | 368 | 0 | 1.791 | 58.814 | 37.371 | 1.00 30.39 |
| ATOM | 2795 | CA | LEU | A | 368 | 0 | 1.897 | 58.055 | 36.123 | 1.00 28.74 |
| ATOM | 2796 | C | LEU | A | 368 | 0 | 0.586 | 57.386 | 35.745 | 1.00 28.85 |
| ATOM | 2797 | O | LEU | A | 368 | 0 | -0.214 | 56.947 | 36.555 | 1.00 28.17 |
| ATOM | 2798 | CB | LEU | A | 368 | 0 | 3.043 | 57.046 | 36.194 | 1.00 26.94 |
| ATOM | 2799 | CG | LEU | A | 368 | 0 | 4.436 | 57.668 | 36.422 | 1.00 27.05 |
| ATOM | 2800 | CD1 | LEU | A | 368 | 0 | 5.455 | 56.581 | 36.765 | 1.00 25.41 |
| ATOM | 2801 | CD2 | LEU | A | 368 | 0 | 4.882 | 58.499 | 35.236 | 1.00 24.44 |
| ATOM | 2802 | N | LEU | A | 369 | 0 | 0.392 | 57.332 | 34.446 | 1.00 28.81 |
| ATOM | 2803 | CA | LEU | A | 369 | 0 | -0.753 | 56.671 | 33.834 | 1.00 29.65 |
| ATOM | 2804 | C | LEU | A | 369 | 0 | -0.238 | 55.398 | 33.162 | 1.00 28.29 |
| ATOM | 2805 | O | LEU | A | 369 | 0 | 0.875 | 55.356 | 32.660 | 1.00 25.59 |
| ATOM | 2806 | CB | LEU | A | 369 | 0 | -1.333 | 57.668 | 32.821 | 1.00 30.27 |
| ATOM | 2807 | CG | LEU | A | 369 | 0 | -1.800 | 58.998 | 33.456 | 1.00 32.06 |
| ATOM | 2808 | CD1 | LEU | A | 369 | 0 | -2.220 | 59.979 | 32.370 | 1.00 31.87 |
| ATOM | 2809 | CD2 | LEU | A | 369 | 0 | -2.932 | 58.787 | 34.455 | 1.00 30.89 |
| ATOM | 2810 | N | PRO | A | 370 | 0 | -1.054 | 54.361 | 33.157 | 1.00 27.87 |

APPENDIX 1-continued

```
ATOM   2811  CA   PRO A  370  0    -2.396  54.379  33.688  1.00  26.71
ATOM   2812  C    PRO A  370  0    -2.513  54.112  35.169  1.00  26.73
ATOM   2813  O    PRO A  370  0    -1.872  53.184  35.668  1.00  26.55
ATOM   2814  CB   PRO A  370  0    -3.126  53.222  32.958  1.00  27.28
ATOM   2815  CG   PRO A  370  0    -2.003  52.317  32.557  1.00  27.38
ATOM   2816  CD   PRO A  370  0    -0.720  53.102  32.482  1.00  27.24
ATOM   2817  N    ALA A  371  0    -3.414  54.810  35.870  1.00  26.16
ATOM   2818  CA   ALA A  371  0    -3.581  54.556  37.302  1.00  25.73
ATOM   2819  C    ALA A  371  0    -3.892  53.103  37.616  1.00  24.59
ATOM   2820  O    ALA A  371  0    -4.758  52.533  36.946  1.00  25.05
ATOM   2821  CB   ALA A  371  0    -4.718  55.394  37.903  1.00  26.42
ATOM   2822  N    GLY A  372  0    -3.261  52.524  38.625  1.00  22.47
ATOM   2823  CA   GLY A  372  0    -3.519  51.187  39.087  1.00  21.06
ATOM   2824  C    GLY A  372  0    -2.691  50.096  38.427  1.00  23.01
ATOM   2825  O    GLY A  372  0    -2.758  48.928  38.831  1.00  23.85
ATOM   2826  N    SER A  373  0    -1.910  50.428  37.421  1.00  23.30
ATOM   2827  CA   SER A  373  0    -1.054  49.459  36.736  1.00  24.36
ATOM   2828  C    SER A  373  0     0.429  49.746  36.919  1.00  24.76
ATOM   2829  O    SER A  373  0     1.257  49.103  36.270  1.00  25.75
ATOM   2830  CB   SER A  373  0    -1.371  49.584  35.233  1.00  23.25
ATOM   2831  OG   SER A  373  0    -2.638  49.014  34.952  1.00  23.80
ATOM   2832  N    VAL A  374  0     0.779  50.799  37.657  1.00  23.87
ATOM   2833  CA   VAL A  374  0     2.176  51.255  37.706  1.00  22.95
ATOM   2834  C    VAL A  374  0     2.739  51.109  39.105  1.00  21.72
ATOM   2835  O    VAL A  374  0     2.093  51.518  40.059  1.00  21.03
ATOM   2836  CB   VAL A  374  0     2.317  52.687  37.169  1.00  23.05
ATOM   2837  CG1  VAL A  374  0     3.720  53.273  37.323  1.00  24.13
ATOM   2838  CG2  VAL A  374  0     1.945  52.771  35.698  1.00  21.58
ATOM   2839  N    TYR A  375  0     3.862  50.402  39.246  1.00  20.52
ATOM   2840  CA   TYR A  375  0     4.445  50.184  40.573  1.00  22.02
ATOM   2841  C    TYR A  375  0     5.873  50.743  40.549  1.00  22.56
ATOM   2842  O    TYR A  375  0     6.665  50.524  39.639  1.00  21.82
ATOM   2843  CB   TYR A  375  0     4.467  48.729  41.067  1.00  21.98
ATOM   2844  CG   TYR A  375  0     3.042  48.217  41.226  1.00  24.04
ATOM   2845  CD1  TYR A  375  0     2.398  48.261  42.445  1.00  23.57
ATOM   2846  CD2  TYR A  375  0     2.339  47.760  40.115  1.00  24.92
ATOM   2847  CE1  TYR A  375  0     1.100  47.831  42.575  1.00  25.65
ATOM   2848  CE2  TYR A  375  0     1.034  47.327  40.220  1.00  25.89
ATOM   2849  CZ   TYR A  375  0     0.429  47.352  41.464  1.00  26.65
```

APPENDIX 1-continued

| ATOM | 2850 | OH | TYR A | 375 | 0 | -0.869 | 46.916 | 41.593 | 1.00 | 27.26 |
|------|------|----|----|-----|---|--------|--------|--------|------|-------|
| ATOM | 2851 | N | GLU A | 376 | 0 | 6.130 | 51.563 | 41.546 | 1.00 | 22.36 |
| ATOM | 2852 | CA | GLU A | 376 | 0 | 7.403 | 52.214 | 41.718 | 1.00 | 23.62 |
| ATOM | 2853 | C | GLU A | 376 | 0 | 8.411 | 51.289 | 42.387 | 1.00 | 22.40 |
| ATOM | 2854 | O | GLU A | 376 | 0 | 8.062 | 50.578 | 43.324 | 1.00 | 21.88 |
| ATOM | 2855 | CB | GLU A | 376 | 0 | 7.211 | 53.465 | 42.614 | 1.00 | 25.13 |
| ATOM | 2856 | CG | GLU A | 376 | 0 | 8.500 | 54.255 | 42.720 | 1.00 | 27.91 |
| ATOM | 2857 | CD | GLU A | 376 | 0 | 8.376 | 55.725 | 43.046 | 1.00 | 29.20 |
| ATOM | 2858 | OE1 | GLU A | 376 | 0 | 7.247 | 56.268 | 43.109 | 1.00 | 30.01 |
| ATOM | 2859 | OE2 | GLU A | 376 | 0 | 9.458 | 56.336 | 43.219 | 1.00 | 28.05 |
| ATOM | 2860 | N | LEU A | 377 | 0 | 9.669 | 51.353 | 41.954 | 1.00 | 21.23 |
| ATOM | 2861 | CA | LEU A | 377 | 0 | 10.705 | 50.535 | 42.626 | 1.00 | 19.95 |
| ATOM | 2862 | C | LEU A | 377 | 0 | 11.838 | 51.478 | 42.982 | 1.00 | 20.30 |
| ATOM | 2863 | O | LEU A | 377 | 0 | 12.220 | 52.350 | 42.197 | 1.00 | 20.12 |
| ATOM | 2864 | CB | LEU A | 377 | 0 | 11.129 | 49.419 | 41.692 | 1.00 | 20.77 |
| ATOM | 2865 | CG | LEU A | 377 | 0 | 10.668 | 47.964 | 41.818 | 1.00 | 20.49 |
| ATOM | 2866 | CD1 | LEU A | 377 | 0 | 9.439 | 47.739 | 42.629 | 1.00 | 17.77 |
| ATOM | 2867 | CD2 | LEU A | 377 | 0 | 10.617 | 47.242 | 40.483 | 1.00 | 19.28 |
| ATOM | 2868 | N | PRO A | 378 | 0 | 12.407 | 51.334 | 44.162 | 1.00 | 19.69 |
| ATOM | 2869 | CA | PRO A | 378 | 0 | 13.523 | 52.117 | 44.631 | 1.00 | 19.91 |
| ATOM | 2870 | C | PRO A | 378 | 0 | 14.797 | 51.650 | 43.937 | 1.00 | 19.81 |
| ATOM | 2871 | O | PRO A | 378 | 0 | 14.795 | 50.645 | 43.241 | 1.00 | 17.74 |
| ATOM | 2872 | CB | PRO A | 378 | 0 | 13.611 | 51.893 | 46.157 | 1.00 | 20.21 |
| ATOM | 2873 | CG | PRO A | 378 | 0 | 12.957 | 50.546 | 46.291 | 1.00 | 20.73 |
| ATOM | 2874 | CD | PRO A | 378 | 0 | 12.050 | 50.292 | 45.114 | 1.00 | 19.74 |
| ATOM | 2875 | N | ARG A | 379 | 0 | 15.877 | 52.410 | 44.059 | 1.00 | 19.68 |
| ATOM | 2876 | CA | ARG A | 379 | 0 | 17.172 | 52.135 | 43.449 | 1.00 | 18.58 |
| ATOM | 2877 | C | ARG A | 379 | 0 | 18.027 | 51.129 | 44.193 | 1.00 | 18.68 |
| ATOM | 2878 | O | ARG A | 379 | 0 | 18.151 | 51.126 | 45.432 | 1.00 | 17.60 |
| ATOM | 2879 | CB | ARG A | 379 | 0 | 47.946 | 53.487 | 43.431 | 1.00 | 18.33 |
| ATOM | 2880 | CG | ARG A | 379 | 0 | 19.406 | 53.348 | 43.030 | 1.00 | 19.33 |
| ATOM | 2881 | CD | ARG A | 379 | 0 | 20.026 | 54.710 | 42.729 | 1.00 | 19.06 |
| ATOM | 2882 | NE | ARG A | 379 | 0 | 21.413 | 54.561 | 42.295 | 1.00 | 16.65 |
| ATOM | 2883 | CZ | ARG A | 379 | 0 | 21.794 | 54.681 | 41.031 | 1.00 | 15.60 |
| ATOM | 2884 | NR1 | ARG A | 379 | 0 | 20.964 | 54.904 | 40.038 | 1.00 | 14.29 |
| ATOM | 2885 | NH2 | ARG A | 379 | 0 | 23.096 | 54.505 | 40.783 | 1.00 | 17.29 |
| ATOM | 2886 | N | ASN A | 380 | 0 | 18.701 | 50.263 | 43.441 | 1.00 | 20.11 |
| ATOM | 2887 | CA | ASN A | 380 | 0 | 19.658 | 49.328 | 44.011 | 1.00 | 21.97 |
| ATOM | 2888 | C | ASN A | 380 | 0 | 19.129 | 48.604 | 45.227 | 1.00 | 22.44 |
| ATOM | 2889 | O | ASN A | 380 | 0 | 19.712 | 48.630 | 46.317 | 1.00 | 22.53 |

APPENDIX 1-continued

```
ATOM   2890  CB   ASN A  380  0   20.995 50.045 44.345 1.00 23.30
ATOM   2891  CG   ASN A  380  0   21.860 50.231 43.107 1.00 25.83
ATOM   2892  OD1  ASN A  380  0   22.636 51.186 42.877 1.00 27.14
ATOM   2893  ND2  ASN A  380  0   21.767 49.271 42.185 1.00 24.91
ATOM   2894  N    GLN A  381  0   17.974 47.936 45.097 1.00 21.39
ATOM   2895  CA   GLN A  381  0   17.468 47.162 46.220 1.00 20.88
ATOM   2896  C    GLN A  381  0   17.169 45.760 45.679 1.00 19.96
ATOM   2897  O    GLN A  381  0   17.000 45.635 44.471 1.00 19.90
ATOM   2898  CB   GLN A  381  0   16.219 47.722 46.871 1.00 22.84
ATOM   2899  CG   GLN A  381  0   16.326 49.172 47.318 1.00 27.28
ATOM   2900  CD   GLN A  381  0   16.065 49.297 48.792 1.00 30.24
ATOM   2901  QE1  GLN A  381  0   15.067 49.917 49.171 1.00 34.48
ATOM   2902  NE2  GLN A  381  0   16.929 48.742 49.611 1.00 30.80
ATOM   2903  N    VAL A  382  0   17.046 44.825 46.594 1.00 18.67
ATOM   2904  CA   VAL A  382  0   16.665 43.472 46.248 1.00 18.98
ATOM   2905  C    VAL A  382  0   15.139 43.327 46.212 1.00 19.75
ATOM   2906  O    VAL A  382  0   14.443 43.550 47.225 1.00 18.76
ATOM   2907  CB   VAL A  382  0   17.252 42.491 47.278 1.00 19.03
ATOM   2908  CG1  VAL A  382  0   16.811 41.065 46.960 1.00 18.87
ATOM   2909  CG2  VAL A  382  0   18.779 42.637 47.344 1.00 17.54
ATOM   2910  N    VAL A  383  0   14.601 42.954 45.046 1.00 17.58
ATOM   2911  CA   VAL A  383  0   13.151 42.715 45.037 1.00 17.76
ATOM   2912  C    VAL A  383  0   12.777 41.254 44.883 1.00 17.50
ATOM   2913  O    VAL A  383  0   13.348 40.472 44.153 1.00 16.42
ATOM   2914  CB   VAL A  383  0   12.306 43.626 44.145 1.00 17.69
ATOM   2915  CG1  VAL A  383  0   13.111 44.759 43.585 1.00 15.33
ATOM   2916  CG2  VAL A  383  0   11.400 43.009 43.126 1.00 17.79
ATOM   2917  N    GLU A  384  0   11.743 40.861 45.638 1.00 18.47
ATOM   2918  CA   GLU A  384  0   11.173 39.529 45.542 1.00 18.27
ATOM   2919  C    GLU A  384  0    9.711 39.683 45.096 1.00 18.94
ATOM   2920  O    GLU A  384  0    8.956 40.311 45.816 1.00 19.06
ATOM   2921  CB   GLU A  384  0   11.253 38.764 46.852 1.00 17.12
ATOM   2922  CG   GLU A  384  0   10.717 37.345 46.738 1.00 17.52
ATOM   2923  CD   GLU A  384  0   10.979 36.551 47.998 1.00 19.10
ATOM   2924  OET  GLU A  384  0   12.101 36.050 48.218 1.00 20.69
ATOM   2925  OE2  GLU A  384  0   10.018 36.405 48.773 1.00 21.22
ATOM   2926  N    LEU A  385  0    9.326 39.182 43.948 1.00 19.78
ATOM   2927  CA   LEU A  385  0    7.966 39.153 43.463 1.00 21.07
ATOM   2928  C    LEU A  385  0    7.391 37.738 43.591 1.00 20.91
```

APPENDIX 1-continued

| ATOM | 2929 | O | LEU A | 385 | 0 | 8.043 | 36.790 | 43.113 | 1.00 | 21.40 |
|---|---|---|---|---|---|---|---|---|---|---|
| ATOM | 2930 | CB | LEU A | 385 | 0 | 7.881 | 39.466 | 41.959 | 1.00 | 20.92 |
| ATOM | 2931 | CG | LEU A | 385 | 0 | 8.393 | 40.795 | 41.457 | 1.00 | 23.75 |
| ATOM | 2932 | CD1 | LEU A | 385 | 0 | 8.118 | 40.984 | 39.962 | 1.00 | 23.01 |
| ATOM | 2933 | CD2 | LEU A | 385 | 0 | 7.827 | 41.977 | 42.244 | 1.00 | 22.40 |
| ATOM | 2934 | N | VAL A | 386 | 0 | 6.182 | 37.574 | 44.099 | 1.00 | 20.91 |
| ATOM | 2935 | CA | VAL A | 386 | 0 | 5.510 | 36.274 | 44.189 | 1.00 | 19.03 |
| ATOM | 2936 | C | VAL A | 386 | 0 | 4.228 | 36.334 | 43.356 | 1.00 | 21.11 |
| ATOM | 2937 | O | VAL A | 386 | 0 | 3.465 | 37.326 | 43.516 | 1.00 | 20.56 |
| ATOM | 2938 | CB | VAL A | 386 | 0 | 5.159 | 35.967 | 45.654 | 1.00 | 20.91 |
| ATOM | 2939 | CGT | VAL A | 356 | 0 | 4.518 | 34.575 | 45.739 | 1.00 | 20.40 |
| ATOM | 2940 | CG2 | VAL A | 386 | 0 | 6.321 | 36.044 | 46.625 | 1.00 | 19.89 |
| ATOM | 2941 | N | VAL A | 387 | 0 | 4.011 | 35.469 | 42.358 | 1.00 | 20.02 |
| ATOM | 2942 | CA | VAL A | 387 | 0 | 2.817 | 35.515 | 41.491 | 1.00 | 20.83 |
| ATOM | 2943 | C | VAL A | 387 | 0 | 2.119 | 34.152 | 41.385 | 1.00 | 21.15 |
| ATOM | 2944 | O | VAL A | 387 | 0 | 2.369 | 33.285 | 40.528 | 1.00 | 19.97 |
| ATOM | 2945 | CB | VAL A | 387 | 0 | 3.163 | 36.076 | 40.104 | 1.00 | 20.91 |
| ATOM | 2946 | CG1 | VAL A | 387 | 0 | 1.917 | 36.472 | 39.297 | 1.00 | 22.49 |
| ATOM | 2947 | CG2 | VAL A | 387 | 0 | 3.9s9 | 37.393 | 40.171 | 1.00 | 22.24 |
| ATOM | 2948 | N | PRO A | 388 | 0 | 1.262 | 33.832 | 42.358 | 1.00 | 20.55 |
| ATOM | 2949 | CA | PRO A | 388 | 0 | 0.570 | 32.548 | 42.483 | 1.00 | 20.93 |
| ATOM | 2950 | C | PRO A | 388 | 0 | -0.271 | 32.226 | 41.264 | 1.00 | 20.76 |
| ATOM | 2951 | O | PRO A | 388 | 0 | -0.928 | 33.118 | 40.715 | 1.00 | 19.53 |
| ATOM | 2952 | CB | PRO A | 388 | 0 | -0.310 | 32.559 | 43.757 | 1.00 | 20.54 |
| ATOM | 2953 | CG | PRO A | 388 | 0 | 0.280 | 33.766 | 44.482 | 1.00 | 21.86 |
| ATOM | 2954 | CD | PRO A | 388 | 0 | 0.841 | 34.707 | 43.438 | 1.00 | 20.83 |
| ATOM | 2955 | N | ALA A | 389 | 0 | -0.160 | 30.986 | 40.807 | 1.00 | 21.68 |
| ATOM | 2956 | CA | ALA A | 389 | 0 | -0.983 | 30.617 | 39.640 | 1.00 | 24.20 |
| ATOM | 2957 | C | ALA A | 389 | 0 | -2.394 | 30.320 | 40.148 | 1.00 | 25.02 |
| ATOM | 2958 | O | ALA A | 389 | 0 | -2.619 | 30.162 | 41.350 | 1.00 | 24.19 |
| ATOM | 2959 | CB | ALA A | 389 | 0 | -0.383 | 29.403 | 38.968 | 1.00 | 23.67 |
| ATOM | 2960 | N | GLY A | 390 | 0 | -3.309 | 30.143 | 39.222 | 1.00 | 28.43 |
| ATOM | 2961 | CA | GLY A | 390 | 0 | -4.713 | 29.811 | 39.539 | 1.00 | 28.47 |
| ATOM | 2962 | C | GLY A | 390 | 0 | -5.624 | 30.325 | 38.431 | 1.00 | 28.63 |
| ATOM | 2963 | O | GLY A | 390 | 0 | -6.512 | 29.630 | 37.937 | 1.00 | 31.26 |
| ATOM | 2964 | N | VAL A | 391 | 0 | -5.402 | 31.531 | 37.961 | 1.00 | 27.11 |
| ATOM | 2965 | CA | VAL A | 391 | 0 | -6.234 | 32.164 | 36.962 | 1.00 | 26.51 |
| ATOM | 2966 | C | VAL A | 391 | 0 | -6.246 | 31.377 | 35.666 | 1.00 | 29.59 |
| ATOM | 2967 | O | VAL A | 391 | 0 | -5.274 | 30.775 | 35.181 | 1.00 | 30.61 |
| ATOM | 2968 | CB | VAL A | 391 | 0 | -5.835 | 33.634 | 36.788 | 1.00 | 25.83 |

APPENDIX 1-continued

```
ATOM   2969 CG1  VAL A  391  0   -4.584  33.787  35.937  1.00  24.18
ATOM   2970 CG2  VAL A  391  0   -7.017  34.419  36.219  1.00  24.11
ATOM   2971 N    LEU A  392  0   -7.439  31.392  35.058  1.00  30.83
ATOM   2972 CA   LEU A  392  0   -7.705  30.604  33.867  1.00  30.29
ATOM   2973 C    LEU A  392  0   -6.809  31.004  32.710  1.00  27.38
ATOM   2974 O    LEU A  392  0   -6.316  32.113  32.665  1.00  24.62
ATOM   2975 CB   LEU A  392  0   -9.173  30.726  33.436  1.00  32.58
ATOM   2976 CG   LEU A  392  0   -9.711  32.126  33.189  1.00  33.97
ATOM   2977 CD1  LEU A  392  0   -9.411  32.626  31.786  1.00  34.78
ATOM   2978 CD2  LEU A  392  0  -11.225  32.122  33.463  1.00  36.03
ATOM   2919 N    GLY A  393  0   -6.725  30.074  31.754  1.00  26.24
ATOM   2980 CA   GLY A  393  0   -5.936  30.302  30.554  1.00  25.54
ATOM   2981 C    GLY A  393  0   -4.458  29.994  30.710  1.00  25.81
ATOM   2982 O    GLY A  393  0   -3.686  30.361  29.820  1.00  26.67
ATOM   2983 N    GLY A  394  0   -4.033  29.379  31.803  1.00  25.84
ATOM   2984 CA   GLY A  394  0   -2.615  29.112  32.035  1.00  25.94
ATOM   2985 C    GLY A  394  0   -2.140  27.844  31.348  1.00  26.00
ATOM   2986 O    GLY A  394  0   -2.884  27.193  30.625  1.00  25.18
ATOM   2987 N    PRO A  395  0   -0.860  27.527  31.517  1.00  24.26
ATOM   2988 CA   PRO A  395  0    0.051  28.258  32.364  1.00  21.79
ATOM   2989 C    PRO A  395  0    0.517  29.518  31.660  1.00  19.29
ATOM   2990 O    PRO A  395  0    0.704  29.597  30.445  1.00  17.41
ATOM   2991 CB   PRO A  395  0    1.159  27.279  32.794  1.00  22.52
ATOM   2992 CG   PRO A  395  0    1.062  26.223  31.758  1.00  24.35
ATOM   2993 CD   PRO A  395  0   -0.241  26.312  30.973  1.00  24.87
ATOM   2994 N    HIS A  396  0    0.586  30.591  32.451  1.00  16.97
ATOM   2995 CA   HIS A  396  0    0.970  31.917  31.980  1.00  15.05
ATOM   2996 C    HIS A  396  0    2.477  32.137  32.186  1.00  15.41
ATOM   2997 O    HIS A  396  0    3.039  32.025  33.275  1.00  14.21
ATOM   2998 CB   HIS A  396  0    0.288  32.989  32.842  1.00  15.40
ATOM   2999 CG   HIS A  396  0   -1.224  32.924  32.737  1.00  18.23
ATOM   3000 ND1  HIS A  396  0   -1.942  33.504  31.702  1.00  16.23
ATOM   3001 CD2  HIS A  396  0   -2.109  32.319  33.557  1.00  17.00
ATOM   3002 CE1  HIS A  396  0   -3.218  33.262  31.906  1.00  18.22
ATOM   3003 NE2  HIS A  396  0   -3.343  32.526  33.014  1.00  19.08
ATOM   3004 N    PRO A  397  0    3.143  32.403  31.090  1.00  14.69
ATOM   3005 CA   PRO A  397  0    4.593  32.617  31.080  1.00  16.91
ATOM   3006 C    PRO A  397  0    4.818  34.129  31.202  1.00  17.59
ATOM   3007 O    PRO A  397  0    4.524  34.843  30.235  1.00  17.59
```

APPENDIX 1-continued

| | | | | | | | | | | |
|---|---|---|---|---|---|---|---|---|---|---|
| ATOM | 3008 | CB | PRO | A | 397 | 0 | 5.076 | 32.040 | 29.757 | 1.00 16.63 |
| ATOM | 3009 | CG | PRO | A | 397 | 0 | 3.785 | 31.844 | 28.978 | 1.00 17.83 |
| ATOM | 3010 | CD | PRO | A | 397 | 0 | 2.620 | 32.464 | 29.736 | 1.00 14.36 |
| ATOM | 3011 | N | PHE | A | 398 | 0 | 5.242 | 34.590 | 32.377 | 1.00 16.39 |
| ATOM | 3012 | CA | PHE | A | 398 | 0 | 5.462 | 36.019 | 32.529 | 1.00 15.95 |
| ATOM | 3013 | C | PHE | A | 398 | 0 | 6.906 | 36.365 | 32.168 | 1.00 15.74 |
| ATOM | 3014 | O | PHE | A | 398 | 0 | 7.846 | 35.619 | 32.444 | 1.00 15.78 |
| ATOM | 3015 | CB | PHE | A | 398 | 0 | 5.173 | 36.455 | 33.963 | 1.00 17.20 |
| ATOM | 3016 | CG | PHE | A | 398 | 0 | 3.817 | 37.073 | 34.169 | 1.00 19.23 |
| ATOM | 3017 | CD1 | PHE | A | 398 | 0 | 2.673 | 36.299 | 34.005 | 1.00 19.58 |
| ATOM | 3018 | CD2 | PHE | A | 398 | 0 | 3.688 | 38.403 | 34.537 | 1.00 19.42 |
| ATOM | 3019 | CE1 | PHE | A | 398 | 0 | 1.409 | 36.832 | 34.198 | 1.00 19.83 |
| ATOM | 3020 | CE2 | PHE | A | 398 | 0 | 2.405 | 38.933 | 34.709 | 1.00 21.46 |
| ATOM | 3021 | CZ | PHE | A | 398 | 0 | 1.260 | 38.162 | 34.539 | 1.00 19.65 |
| ATOM | 3022 | N | HIS | A | 399 | 0 | 7.080 | 37.562 | 31.640 | 1.00 14.77 |
| ATOM | 3023 | CA | HIS | A | 399 | 0 | 8.374 | 38.089 | 31.333 | 1.00 14.75 |
| ATOM | 3024 | C | HIS | A | 399 | 0 | 8.580 | 39.496 | 31.872 | 1.00 17.67 |
| ATOM | 3025 | O | HIS | A | 399 | 0 | 7.635 | 40.308 | 31.925 | 1.00 18.29 |
| ATOM | 3026 | CB | HIS | A | 399 | 0 | 8.582 | 37.968 | 29.861 | 1.00 14.01 |
| ATOM | 3027 | CG | HIS | A | 399 | 0 | 8.747 | 39.105 | 28.962 | 1.00 16.26 |
| ATOM | 3028 | ND1 | HIS | A | 399 | 0 | 9.957 | 39.511 | 28.446 | 1.00 15.35 |
| ATOM | 3029 | CD2 | HIS | A | 399 | 0 | 7.788 | 39.903 | 28.386 | 1.00 17.58 |
| ATOM | 3030 | CE1 | HIS | A | 399 | 0 | 9.764 | 40.507 | 27.593 | 1.00 15.61 |
| ATOM | 3031 | NE2 | HIS | A | 399 | 0 | 8.457 | 40.770 | 27.548 | 1.00 17.52 |
| ATOM | 3032 | N | LEU | A | 400 | 0 | 9.837 | 39.771 | 32.201 | 1.00 15.57 |
| ATOM | 3033 | CA | LEU | A | 400 | 0 | 10.220 | 41.061 | 32.745 | 1.00 16.93 |
| ATOM | 3034 | C | LEU | A | 400 | 0 | 11.207 | 41.732 | 31.788 | 1.00 16.51 |
| ATOM | 3035 | O | LEU | A | 400 | 0 | 12.268 | 41.175 | 31.510 | 1.00 15.77 |
| ATOM | 3036 | CB | LEU | A | 400 | 0 | 10.913 | 40.825 | 34.084 | 1.00 18.17 |
| ATOM | 3037 | CG | LEU | A | 400 | 0 | 10.877 | 41.741 | 35.288 | 1.00 21.27 |
| ATOM | 3038 | CD1 | LEU | A | 400 | 0 | 12.130 | 41.638 | 36.151 | 1.00 19.27 |
| ATOM | 3039 | CD2 | LEU | A | 400 | 0 | 10.536 | 43.166 | 34.926 | 1.00 19.86 |
| ATOM | 3040 | N | HIS | A | 401 | 0 | 10.945 | 42.916 | 31.321 | 1.00 14.34 |
| ATOM | 3041 | CA | HIS | A | 401 | 0 | 11.830 | 43.707 | 30.508 | 1.00 16.06 |
| ATOM | 3042 | C | HIS | A | 401 | 0 | 12.924 | 44.300 | 31.428 | 1.00 16.15 |
| ATOM | 3043 | O | HIS | A | 401 | 0 | 12.644 | 44.543 | 32.600 | 1.00 13.61 |
| ATOM | 3044 | CB | HIS | A | 401 | 0 | 11.105 | 44.884 | 29.843 | 1.00 13.27 |
| ATOM | 3045 | CG | HIS | A | 401 | 0 | 10.184 | 44.441 | 28.751 | 1.00 14.50 |
| ATOM | 3046 | ND1 | HIS | A | 401 | 0 | 10.201 | 44.973 | 27.479 | 1.00 14.96 |
| ATOM | 3047 | CD2 | HIS | A | 401 | 0 | 9.202 | 43.492 | 28.750 | 1.00 12.35 |

APPENDIX 1-continued

```
ATOM   3048  CE1  HIS A  401  0    9.263  44.387  26.725  1.00  12.61
ATOM   3049  NE2  HIS A  401  0    8.677  43.507  27.492  1.00  12.41
ATOM   3050  N    GLY A  402  0   14.103  44.549  30.855  1.00  15.59
ATOM   3051  CA   GLY A  402  0   15.152  45.209  31.598  1.00  15.18
ATOM   3052  C    GLY A  402  0   16.009  44.351  32.510  1.00  15.96
ATOM   3053  O    GLY A  402  0   16.927  44.898  33.170  1.00  16.30
ATOM   3054  N    HIS A  403  0   15.618  43.147  32.893  1.00  12.96
ATOM   3055  CA   HIS A  403  0   16.282  42.337  33.873  1.00  15.00
ATOM   3056  C    HIS A  403  0   16.226  40.839  33.586  1.00  15.22
ATOM   3057  O    HIS A  403  0   15.253  40.381  32.971  1.00  16.16
ATOM   3058  CB   HIS A  403  0   15.525  42.478  35.227  1.00  14.13
ATOM   3059  CG   HIS A  403  0   15.571  43.829  35.827  1.00  16.69
ATOM   3060  ND1  HIS A  403  0   16.604  44.253  36.649  1.00  16.13
ATOM   3061  CD2  HIS A  403  0   14.744  44.911  35.659  1.00  15.50
ATOM   3062  CE1  HIS A  403  0   16.425  45.520  37.002  1.00  15.02
ATOM   3063  NE2  HIS A  403  0   15.285  45.905  36.430  1.00  16.15
ATOM   3064  N    ALA A  404  0   17.138  40.054  34.113  1.00  13.71
ATOM   3065  CA   ALA A  404  0   17.039  38.607  34.158  1.00  12.60
ATOM   3066  C    ALA A  404  0   16.771  38.370  35.649  1.00  12.31
ATOM   3067  O    ALA A  404  0   17.156  39.291  36.373  1.00  13.94
ATOM   3068  CB   ALA A  404  0   18.249  37.819  33.721  1.00  13.84
ATOM   3069  N    PHE A  405  0   16.085  37.356  36.126  1.00  12.21
ATOM   3070  CA   PHE A  405  0   15.813  37.235  37.559  1.00  11.64
ATOM   3071  C    PHE A  405  0   16.177  35.821  38.008  1.00  12.55
ATOM   3072  O    PHE A  405  0   16.196  34.883  37.201  1.00  12.23
ATOM   3073  CB   PHE A  405  0   14.325  37.487  37.907  1.00  11.82
ATOM   3074  CG   PHE A  405  0   13.382  36.893  36.879  1.00  11.75
ATOM   3075  CD1  PHE A  405  0   13.030  35.557  36.933  1.00  10.76
ATOM   3076  CD2  PHE A  405  0   12.917  37.663  35.824  1.00  11.55
ATOM   3077  CE1  PHE A  405  0   12.189  35.002  35.978  1.00  11.52
ATOM   3078  CE2  PHE A  405  0   12.087  37.112  34.862  1.00  13.32
ATOM   3079  CZ   PHE A  405  0   11.692  35.767  34.946  1.00  11.45
ATOM   3080  N    SER A  406  0   16.414  35.625  39.288  1.00  12.86
ATOM   3081  CA   SER A  406  0   16.660  34.286  39.796  1.00  13.43
ATOM   3082  C    SER A  406  0   15.276  33.712  40.130  1.00  13.49
ATOM   3083  O    SER A  406  0   14.518  34.375  40.847  1.00  10.13
ATOM   3084  CB   SER A  406  0   17.433  34.290  41.123  1.00  13.78
ATOM   3085  OG   SER A  406  0   18.708  34.834  40.938  1.00  16.72
ATOM   3086  N    VAL A  407  0   15.100  32.453  39.741  1.00  14.53
```

APPENDIX 1-continued

| | | | | | | | | | | |
|---|---|---|---|---|---|---|---|---|---|---|
| ATOM | 3087 | CA | VAL | A | 407 | 0 | 13.853 | 31.777 | 40.093 | 1.00 13.90 |
| ATOM | 3088 | C | VAL | A | 407 | 0 | 14.160 | 30.943 | 41.325 | 1.00 14.53 |
| ATOM | 3089 | O | VAL | A | 407 | 0 | 14.513 | 29.753 | 41.262 | 1.00 14.62 |
| ATOM | 3090 | CB | VAL | A | 407 | 0 | 13.333 | 30.903 | 38.941 | 1.00 16.43 |
| ATOM | 3091 | CG1 | VAL | A | 407 | 0 | 11.969 | 30.317 | 39.341 | 1.00 16.69 |
| ATOM | 3092 | CG2 | VAL | A | 407 | 0 | 13.272 | 31.682 | 37.626 | 1.00 14.90 |
| ATOM | 3093 | N | VAL | A | 408 | 0 | 13.971 | 31.544 | 42.485 | 1.00 14.32 |
| ATOM | 3094 | CA | VAL | A | 408 | 0 | 14.173 | 30.947 | 43.780 | 1.00 15.47 |
| ATOM | 3095 | C | VAL | A | 408 | 0 | 13.115 | 29.870 | 44.049 | 1.00 16.51 |
| ATOM | 3096 | O | VAL | A | 408 | 0 | 13.387 | 28.927 | 44.812 | 1.00 17.39 |
| ATOM | 3097 | CB | VAL | A | 408 | 0 | 14.280 | 31.967 | 44.932 | 1.00 15.75 |
| ATOM | 3098 | CG1 | VAL | A | 408 | 0 | 15.345 | 33.015 | 44.600 | 1.00 14.81 |
| ATOM | 3099 | CG2 | VAL | A | 408 | 0 | 12.952 | 32.693 | 45.189 | 1.00 15.99 |
| ATOM | 3100 | N | ARG | A | 409 | 0 | 11.972 | 29.940 | 43.387 | 1.00 16.28 |
| ATOM | 3101 | CA | ARG | A | 409 | 0 | 10.960 | 28.900 | 43.570 | 1.00 17.67 |
| ATOM | 3102 | C | ARG | A | 409 | 0 | 10.217 | 28.757 | 42.236 | 1.00 17.09 |
| ATOM | 3103 | O | ARG | A | 409 | 0 | 9.585 | 29.698 | 41.763 | 1.00 15.25 |
| ATOM | 3104 | CB | ARG | A | 409 | 0 | 9.993 | 29.143 | 44.718 | 1.00 17.87 |
| ATOM | 3105 | CG | ARG | A | 409 | 0 | 8.796 | 28.188 | 44.663 | 1.00 21.12 |
| ATOM | 3106 | CD | ARG | A | 409 | 0 | 8.008 | 28.181 | 45.945 | 1.00 22.10 |
| ATOM | 3107 | NE | ARG | A | 409 | 0 | 6.801 | 27.370 | 45.955 | 1.00 24.80 |
| ATOM | 3108 | CZ | ARG | A | 409 | 0 | 5.918 | 27.361 | 46.961 | 1.00 25.93 |
| ATOM | 3109 | NH1 | ARG | A | 409 | 0 | 4.859 | 26.569 | 46.877 | 1.00 27.14 |
| ATOM | 3110 | NH2 | ARG | A | 409 | 0 | 6.068 | 28.117 | 48.046 | 1.00 25.44 |
| ATOM | 3111 | N | SER | A | 410 | 0 | 10.366 | 27.576 | 41.668 | 1.00 16.33 |
| ATOM | 3112 | CA | SER | A | 410 | 0 | 9.802 | 27.245 | 40.373 | 1.00 18.33 |
| ATOM | 3113 | C | SER | A | 410 | 0 | 8.406 | 26.612 | 40.492 | 1.00 18.60 |
| ATOM | 3114 | O | SER | A | 410 | 0 | 7.941 | 26.223 | 41.566 | 1.00 16.94 |
| ATOM | 3115 | CB | SER | A | 410 | 0 | 10.724 | 26.199 | 39.705 | 1.00 19.51 |
| ATOM | 3116 | OG | SER | A | 410 | 0 | 11.718 | 26.865 | 38.933 | 1.00 20.28 |
| ATOM | 3117 | N | ALA | A | 411 | 0 | 7.754 | 26.551 | 39.343 | 1.00 18.19 |
| ATOM | 3118 | CA | ALA | A | 411 | 0 | 6.458 | 25.899 | 39.231 | 1.00 19.76 |
| ATOM | 3119 | C | ALA | A | 411 | 0 | 6.667 | 24.406 | 39.474 | 1.00 22.62 |
| ATOM | 3120 | O | ALA | A | 411 | 0 | 7.636 | 23.759 | 39.067 | 1.00 20.97 |
| ATOM | 3121 | CB | ALA | A | 411 | 0 | 5.873 | 26.075 | 37.841 | 1.00 17.13 |
| ATOM | 3122 | N | GLY | A | 412 | 0 | 5.710 | 23.856 | 40.229 | 1.00 26.30 |
| ATOM | 3123 | CA | GLY | A | 412 | 0 | 5.714 | 22.442 | 40.558 | 1.00 27.05 |
| ATOM | 3124 | C | GLY | A | 412 | 0 | 6.692 | 22.150 | 41.677 | 1.00 29.22 |
| ATOM | 3125 | O | GLY | A | 412 | 0 | 6.917 | 20.959 | 41.944 | 1.00 32.10 |
| ATOM | 3126 | N | SER | A | 413 | 0 | 7.293 | 23.139 | 42.322 | 1.00 28.66 |

APPENDIX 1-continued

| ATOM | 3127 | CA  | SER A | 413 | 0 | 8.223  | 22.871 | 43.400 | 1.00 | 28.58 |
|------|------|-----|-------|-----|---|--------|--------|--------|------|-------|
| ATOM | 3128 | C   | SER A | 413 | 0 | 7.757  | 23.600 | 44.642 | 1.00 | 29.64 |
| ATOM | 3129 | O   | SER A | 413 | 0 | 7.279  | 24.735 | 44.524 | 1.00 | 30.66 |
| ATOM | 3130 | CB  | SER A | 413 | 0 | 9.610  | 23.407 | 43.015 | 1.00 | 30.12 |
| ATOM | 3131 | OG  | SER A | 413 | 0 | 10.484 | 23.233 | 44.127 | 1.00 | 31.74 |
| ATOM | 3132 | N   | SER A | 414 | 0 | 7.902  | 23.031 | 45.819 | 1.00 | 29.19 |
| ATOM | 3133 | CA  | SER A | 414 | 0 | 7.523  | 23.753 | 47.033 | 1.00 | 30.71 |
| ATOM | 3134 | C   | SER A | 414 | 0 | 8.762  | 24.124 | 47.834 | 1.00 | 30.51 |
| ATOM | 3135 | O   | SER A | 414 | 0 | 8.746  | 24.453 | 49.017 | 1.00 | 31.90 |
| ATOM | 3136 | CB  | SER A | 414 | 0 | 6.612  | 22.832 | 47.853 | 1.00 | 31.10 |
| ATOM | 3137 | OG  | SER A | 414 | 0 | 7.438  | 21.764 | 48.299 | 1.00 | 34.24 |
| ATOM | 3138 | N   | THR A | 415 | 0 | 9.919  | 24.063 | 47.194 | 1.00 | 30.60 |
| ATOM | 3139 | CA  | THR A | 415 | 0 | 11.194 | 24.336 | 47.860 | 1.00 | 30.60 |
| ATOM | 3140 | C   | THR A | 415 | 0 | 11.819 | 25.614 | 47.291 | 1.00 | 27.71 |
| ATOM | 3141 | O   | THR A | 415 | 0 | 11.582 | 25.998 | 46.137 | 1.00 | 27.49 |
| ATOM | 3142 | CB  | THR A | 415 | 0 | 12.089 | 23.095 | 47.747 | 1.00 | 32.16 |
| ATOM | 3143 | OG1 | THR A | 415 | 0 | 13.411 | 23.441 | 47.285 | 1.00 | 35.60 |
| ATOM | 3144 | CG2 | THR A | 415 | 0 | 11.599 | 22.103 | 46.710 | 1.00 | 34.11 |
| ATOM | 3145 | N   | TYR A | 416 | 0 | 12.662 | 26.268 | 48.053 | 1.00 | 24.34 |
| ATOM | 3146 | CA  | TYR A | 416 | 0 | 13.288 | 27.513 | 47.621 | 1.00 | 25.69 |
| ATOM | 3147 | C   | TYR A | 416 | 0 | 14.782 | 27.297 | 47.392 | 1.00 | 24.69 |
| ATOM | 3148 | O   | TYR A | 416 | 0 | 15.364 | 26.603 | 48.211 | 1.00 | 25.96 |
| ATOM | 3149 | CB  | TYR A | 416 | 0 | 13.129 | 28.633 | 48.659 | 1.00 | 23.79 |
| ATOM | 3150 | CG  | TYR A | 416 | 0 | 11.690 | 29.091 | 48.794 | 1.00 | 24.53 |
| ATOM | 3151 | CD1 | TYR A | 416 | 0 | 10.789 | 28.387 | 49.596 | 1.00 | 24.14 |
| ATOM | 3152 | CD2 | TYR A | 416 | 0 | 11.230 | 30.219 | 48.131 | 1.00 | 23.99 |
| ATOM | 3153 | CE1 | TYR A | 416 | 0 | 9.474  | 28.799 | 49.713 | 1.00 | 23.70 |
| ATOM | 3154 | CE2 | TYR A | 416 | 0 | 9.922  | 30.641 | 48.248 | 1.00 | 23.96 |
| ATOM | 3155 | CZ  | TYR A | 416 | 0 | 9.050  | 29.929 | 49.054 | 1.00 | 23.73 |
| ATOM | 3156 | OH  | TYR A | 416 | 0 | 7.744  | 30.337 | 49.152 | 1.00 | 23.53 |
| ATOM | 3157 | N   | ASN A | 417 | 0 | 15.360 | 27.867 | 46.353 | 1.00 | 22.34 |
| ATOM | 3158 | CA  | ASN A | 417 | 0 | 16.810 | 27.702 | 46.223 | 1.00 | 20.83 |
| ATOM | 3159 | C   | ASN A | 417 | 0 | 17.425 | 29.089 | 46.092 | 1.00 | 20.43 |
| ATOM | 3160 | O   | ASN A | 417 | 0 | 17.247 | 29.761 | 45.082 | 1.00 | 20.00 |
| ATOM | 3161 | CB  | ASN A | 417 | 0 | 17.179 | 26.763 | 45.086 | 1.00 | 19.72 |
| ATOM | 3162 | CG  | ASN A | 417 | 0 | 18.660 | 26.716 | 44.758 | 1.00 | 19.50 |
| ATOM | 3163 | OD1 | ASN A | 417 | 0 | 19.485 | 27.313 | 45.465 | 1.00 | 20.18 |
| ATOM | 3164 | ND2 | ASN A | 417 | 0 | 18.981 | 26.043 | 43.660 | 1.00 | 17.21 |
| ATOM | 3165 | N   | PHE A | 418 | 0 | 18.153 | 29.508 | 47.119 | 1.00 | 20.79 |

APPENDIX 1-continued

```
ATOM   3166  CA   PHE A 418  0   18.831 30.797 47.049 1.00 20.77
ATOM   3167  C    PHE A 418  0   20.314 30.613 46.725 1.00 20.47
ATOM   3168  O    PHE A 418  0   20.973 31.618 46.517 1.00 19.47
ATOM   3169  CB   PHE A 418  0   18.764 31.542 48.384 1.00 20.52
ATOM   3170  CG   PHE A 418  0   17.332 31.821 48.753 1.00 22.19
ATOM   3171  CD1  PHE A 418  0   16.644 30.947 49.578 1.00 21.36
ATOM   3172  CD2  PHE A 418  0   16.697 32.951 48.244 1.00 21.95
ATOM   3173  CE1  PHE A 418  0   15.320 31.208 49.919 1.00 21.64
ATOM   3174  CE2  PHE A 418  0   15.386 33.198 48.599 1.00 22.81
ATOM   3175  CZ   PHE A 418  0   14.694 32.325 49.419 1.00 22.57
ATOM   3176  N    VAL A 419  0   20.816 29.380 46.732 1.00 19.72
ATOM   3177  CA   YAL A 419  0   22.272 29.235 46.564 1.00 19.96
ATOM   3178  C    VAL A 419  0   22.682 29.261 45.114 1.00 20.65
ATOM   3179  O    VAL A 419  0   23.634 29.875 44.671 1.00 21.02
ATOM   3180  CB   VAL A 419  0   22.708 27.888 47.200 1.00 21.81
ATOM   3181  CG1  VAL A 419  0   23.954 27.291 46.588 1.00 21.97
ATOM   3182  CG2  VAL A 419  0   22.885 28.098 48.713 1.00 21.55
ATOM   3183  N    ASN A 420  0   21.867 28.585 44.327 1.00 19.77
ATOM   3184  CA   ASN A 420  0   22.076 28.232 42.967 1.00 21.81
ATOM   3185  C    ASN A 420  0   21.028 28.263 41.891 1.00 20.21
ATOM   3186  O    ASN A 420  0   21.046 27.407 41.004 1.00 20.13
ATOM   3187  CB   ASN A 420  0   22.166 26.587 43.207 1.00 21.91
ATOM   3188  CG   ASN A 420  0   23.441 26.231 42.529 1.00 24.12
ATOM   3189  OD1  ASN A 420  0   23.933 25.113 42.403 1.00 26.75
ATOM   3190  ND2  ASN A 420  0   24.051 27.318 42.027 1.00 25.42
ATOM   3191  N    PRO A 421  0   19.987 29.034 42.038 1.00 20.27
ATOM   3192  CA   PRO A 421  0   18.808 28.951 41.183 1.00 17.57
ATOM   3193  C    PRO A 421  0   19.100 29.369 39.778 1.00 15.76
ATOM   3194  O    PRO A 421  0   19.907 30.281 39.586 1.00 15.13
ATOM   3195  CB   PRO A 421  0   17.769 29.850 41.894 1.00 19.52
ATOM   3196  CG   PRO A 421  0   18.674 30.863 42.589 1.00 19.88
ATOM   3197  CD   PRO A 421  0   19.847 30.057 43.095 1.00 20.45
ATOM   3198  N    VAL A 422  0   18.385 28.803 38.820 1.00 15.28
ATOM   3199  CA   VAL A 422  0   18.502 29.239 37.420 1.00 13.48
ATOM   3200  C    VAL A 422  0   18.157 30.721 37.397 1.00 14.53
ATOM   3201  O    VAL A 422  0   17.340 31.208 38.183 1.00 14.44
ATOM   3202  CB   VAL A 422  0   17.498 28.435 36.585 1.00 15.23
ATOM   3203  CG1  VAL A 422  0   16.032 28.747 36.937 1.00 13.85
ATOM   3204  CG2  VAL A 422  0   17.681 28.514 35.089 1.00 13.26
ATOM   3205  N    LYS A 423  0   18.691 31.447 36.451 1.00 15.35
```

APPENDIX 1-continued

```
ATOM   3206  CA   LYS A   423  0    18.366  32.831  36.189  1.00  17.23
ATOM   3207  C    LYS A   423  0    17.759  32.891  34.784  1.00  16.55
ATOM   3208  O    LYS A   423  0    18.284  32.189  33.909  1.00  16.92
ATOM   3209  CB   LYS A   423  0    19.627  33.681  36.174  1.00  19.33
ATOM   3210  CG   LYS A   423  0    20.118  33.985  37.565  1.00  24.09
ATOM   3211  CD   LYS A   423  0    21.065  35.206  37.466  1.00  27.32
ATOM   3212  CE   LYS A   423  0    22.470  34.596  37.263  1.00  28.78
ATOM   3213  NZ   LYS A   423  0    23.128  34.482  38.595  1.00  29.50
ATOM   3214  N    ARG A   424  0    16.630  33.570  34.617  1.00  15.85
ATOM   3215  CA   ARG A   424  0    16.016  33.592  33.294  1.00  16.20
ATOM   3216  C    ARG A   424  0    15.235  34.890  33.105  1.00  14.86
ATOM   3217  O    ARG A   424  0    15.354  35.771  33.959  1.00  14.64
ATOM   3218  CB   ARG A   424  0    15.158  32.367  32.994  1.00  16.11
ATOM   3219  CG   ARG A   424  0    14.036  31.864  33.849  1.00  14.06
ATOM   3220  CD   ARG A   424  0    13.447  30.506  33.427  1.00  11.65
ATOM   3221  NE   ARG A   424  0    13.422  30.395  31.961  1.00   9.03
ATOM   3222  CZ   ARG A   424  0    13.312  29.234  31.319  1.00  10.63
ATOM   3223  NH1  ARG A   424  0    13.185  28.133  32.082  1.00  11.02
ATOM   3224  NH2  ARG A   424  0    13.403  29.213  29.988  1.00   8.52
ATOM   3225  N    ASP A   425  0    14.519  34.975  31.995  1.00  13.83
ATOM   3226  CA   ASP A   425  0    13.751  36.209  31.752  1.00  15.00
ATOM   3227  C    ASP A   425  0    12.298  35.929  31.359  1.00  15.65
ATOM   3228  O    ASP A   425  0    11.474  36.850  31.271  1.00  15.11
ATOM   3229  CB   ASP A   425  0    14.499  37.130  30.797  1.00  12.96
ATOM   3230  CG   ASP A   425  0    14.609  36.652  29.371  1.00  14.32
ATOM   3231  OD1  ASP A   425  0    13.697  35.957  28.818  1.00  13.30
ATOM   3232  OD2  ASP A   425  0    15.632  37.003  28.729  1.00  13.76
ATOM   3233  N    VAL A   426  0    11.883  34.675  31.206  1.00  15.21
ATOM   3234  CA   VAL A   426  0    10.530  34.229  30.984  1.00  13.92
ATOM   3235  C    VAL A   426  0    10.247  33.000  31.865  1.00  13.98
ATOM   3236  O    VAL A   426  0    10.891  31.965  31.696  1.00  15.56
ATOM   3237  CB   VAL A   426  0    10.128  33.807  29.567  1.00  12.49
ATOM   3238  CG1  VAL A   426  0     8.629  33.473  29.531  1.00  13.99
ATOM   3239  CG2  VAL A   426  0    10.390  34.874  28.536  1.00  12.37
ATOM   3240  N    VAL A   427  0     9.274  33.090  32.766  1.00  12.82
ATOM   3241  CA   VAL A   427  0     8.979  31.969  33.639  1.00  12.27
ATOM   3242  C    VAL A   427  0     7.495  31.589  33.651  1.00  14.14
ATOM   3243  O    VAL A   427  0     6.594  32.426  33.682  1.00  14.10
ATOM   3244  CB   VAL A   427  0     9.458  32.315  35.056  1.00  11.46
```

APPENDIX 1-continued

| ATOM | 3245 | CG1 | VAL | A | 427 | 0 | 8.732 | 33.549 | 35.594 | 1.00 | 9.39 |
|------|------|-----|-----|---|-----|---|-------|--------|--------|------|------|
| ATOM | 3246 | CG2 | VAL | A | 427 | 0 | 9.353 | 31.116 | 35.982 | 1.00 | 10.53 |
| ATOM | 3247 | N | SER | A | 428 | 0 | 7.229 | 30.282 | 33.622 | 1.00 | 13.74 |
| ATOM | 3248 | CA | SER | A | 428 | 0 | 5.889 | 29.766 | 33.721 | 1.00 | 15.16 |
| ATOM | 3249 | C | SER | A | 428 | 0 | 5.445 | 29.878 | 35.171 | 1.00 | 15.48 |
| ATOM | 3250 | O | SER | A | 428 | 0 | 6.186 | 29.505 | 36.087 | 1 00 | 15.38 |
| ATOM | 3251 | CB | SER | A | 428 | 0 | 5.776 | 28.323 | 33.206 | 1.00 | 16.37 |
| ATOM | 3252 | OG | SER | A | 428 | 0 | 4.464 | 27.821 | 33.484 | 1.00 | 17.00 |
| ATOM | 3253 | N | LEU | A | 429 | 0 | 4.246 | 30.376 | 35.399 | 1 00 | 15.74 |
| ATOM | 3254 | CA | LEU | A | 429 | 0 | 3.686 | 30.489 | 36.744 | 1.00 | 15.73 |
| ATOM | 3255 | C | LEU | A | 429 | 0 | 3.035 | 29.184 | 37.198 | 1.00 | 16.41 |
| ATOM | 3256 | O | LEU | A | 429 | 0 | 2.741 | 29.041 | 38.390 | 1.00 | 15.74 |
| ATOM | 3257 | CB | LEU | A | 429 | 0 | 2.669 | 31.627 | 36.886 | 1.00 | 14.99 |
| ATOM | 3258 | CG | LEU | A | 429 | 0 | 3.155 | 33.027 | 36.540 | 1.00 | 16.60 |
| ATOM | 3259 | CD1 | LEU | A | 429 | 0 | 2.043 | 34.042 | 36.862 | 1.00 | 17.78 |
| ATOM | 3260 | CD2 | LEU | A | 429 | 0 | 4.438 | 33.386 | 37.281 | 1.00 | 16.26 |
| ATOM | 3261 | N | GLY | A | 430 | 0 | 2.913 | 28.218 | 36.295 | 1.00 | 17.70 |
| ATOM | 3262 | CA | GLY | A | 430 | 0 | 2.419 | 26.904 | 36.701 | 1.00 | 19.84 |
| ATOM | 3263 | C | GLY | A | 430 | 0 | 0.894 | 26.836 | 36.778 | 1.00 | 20.72 |
| ATOM | 3264 | O | GLY | A | 430 | 0 | 0.178 | 27.498 | 36.029 | 1.00 | 20.89 |
| ATOM | 3265 | N | VAL | A | 431 | 0 | 0.428 | 26.056 | 37.729 | 1.00 | 22.04 |
| ATOM | 3266 | CA | VAL | A | 431 | 0 | -0.956 | 25.713 | 37.966 | 1.00 | 22.61 |
| ATOM | 3267 | C | VAL | A | 431 | 0 | -1.337 | 26.028 | 39.409 | 1.00 | 23.06 |
| ATOM | 3268 | O | VAL | A | 431 | 0 | -0.476 | 26.392 | 40.218 | 1.00 | 22.42 |
| ATOM | 3269 | CB | VAL | A | 431 | 0 | -1.245 | 24.193 | 37.768 | 1.00 | 23.03 |
| ATOM | 3270 | CG1 | VAL | A | 431 | 0 | -0.795 | 23.672 | 36.416 | 1.00 | 22.74 |
| ATOM | 3271 | CG2 | VAL | A | 431 | 0 | -0.574 | 23.315 | 38.820 | 1.00 | 22.77 |
| ATOM | 3272 | N | THR | A | 432 | 0 | -2.615 | 25.835 | 39.704 | 1.00 | 23.88 |
| ATOM | 3273 | CA | THR | A | 432 | 0 | -3.168 | 26.067 | 41.041 | 1.00 | 24.T8 |
| ATOM | 3274 | C | THR | A | 432 | 0 | -2.324 | 25.401 | 42.092 | 1.00 | 23.94 |
| ATOM | 3275 | O | THR | A | 432 | 0 | -1.915 | 24.249 | 41.909 | 1.00 | 24.69 |
| ATOM | 3276 | CB | THR | A | 432 | 0 | -4.625 | 25.565 | 41.069 | 1.00 | 25.75 |
| ATOM | 3277 | OG1 | THR | A | 432 | 0 | -5.336 | 26.344 | 40.087 | 1.00 | 25.87 |
| ATOM | 3278 | CG2 | THR | A | 432 | 0 | -5.319 | 25.800 | 42.398 | 1.00 | 26.65 |
| ATOM | 3279 | N | GLY | A | 433 | 0 | -1.924 | 26.136 | 43.124 | 1.00 | 24.45 |
| ATOM | 3280 | CA | GLY | A | 433 | 0 | -1.035 | 25.589 | 44.159 | 1.00 | 22.27 |
| ATOM | 3281 | C | GLY | A | 433 | 0 | 0.394 | 26.120 | 43.983 | 1.00 | 23.26 |
| ATOM | 3282 | O | GLY | A | 433 | 0 | 1.103 | 26.212 | 45.000 | 1.00 | 23.30 |
| ATOM | 3283 | N | ASP | A | 434 | 0 | 0.833 | 26.481 | 42.776 | 1.00 | 21.12 |
| ATOM | 3284 | CA | ASP | A | 434 | 0 | 2.192 | 26.986 | 42.586 | 1.00 | 20.62 |

APPENDIX 1-continued

| ATOM | 3285 | C | ASP A | 434 | 0 | 2.360 | 28.408 | 43.126 | 1.00 | 22.36 |
|---|---|---|---|---|---|---|---|---|---|---|
| ATOM | 3286 | O | ASP A | 434 | 0 | 1.425 | 29.225 | 43.076 | 1.00 | 21.24 |
| ATOM | 3287 | CB | ASP A | 434 | 0 | 2.548 | 27.024 | 41.087 | 1.00 | 18.78 |
| ATOM | 3288 | CG | ASP A | 434 | 0 | 2.827 | 25.616 | 40.597 | 1.00 | 19.71 |
| ATOM | 3289 | OD1 | ASP A | 434 | 0 | 3.304 | 24.828 | 41.409 | 1.00 | 20.43 |
| ATOM | 3290 | 0D2 | ASP A | 434 | 0 | 2.596 | 25.242 | 39.432 | 1.00 | 21.58 |
| ATOM | 3291 | N | GLU A | 435 | 0 | 3.585 | 28.721 | 43.562 | 1.00 | 22.08 |
| ATOM | 3292 | CA | GLU A | 435 | 0 | 3.853 | 30.077 | 44.068 | 1.00 | 23.24 |
| ATOM | 3293 | C | GLU A | 435 | 0 | 5.244 | 30.512 | 43.612 | 1.00 | 20.24 |
| ATOM | 3294 | O | GLU A | 435 | 0 | 6.201 | 30.611 | 44.372 | 1.00 | 19.50 |
| ATOM | 3295 | CB | GLU A | 435 | 0 | 3.659 | 30.068 | 45.572 | 1.00 | 25.56 |
| ATOM | 3296 | CG | GLU A | 435 | 0 | 3.739 | 31.409 | 46.258 | 1.00 | 30.52 |
| ATOM | 3297 | CD | GLU A | 435 | 0 | 3.107 | 31.350 | 47.657 | 1.00 | 35.00 |
| ATOM | 3298 | OE1 | GLU A | 435 | 0 | 2.093 | 30.603 | 47.760 | 1.00 | 35.71 |
| ATOM | 3299 | OE2 | GLU A | 435 | 0 | 3.658 | 32.020 | 48.579 | 1.00 | 35.91 |
| ATOM | 3300 | N | VAL A | 436 | 0 | 5.344 | 30.690 | 42.297 | 1.00 | 17.80 |
| ATOM | 3301 | CA | VAL A | 436 | 0 | 6.564 | 31.083 | 41.640 | 1.00 | 15.30 |
| ATOM | 3302 | C | VAL A | 436 | 0 | 7.049 | 32.416 | 42.221 | 1.00 | 17.15 |
| ATOM | 3303 | O | VAL A | 436 | 0 | 6.326 | 33.402 | 42.275 | 1.00 | 17.48 |
| ATOM | 3304 | CB | VAL A | 436 | 0 | 6.360 | 31.219 | 40.129 | 1.00 | 14.63 |
| ATOM | 3305 | CG1 | VAL A | 436 | 0 | 7.463 | 32.009 | 39.454 | 1.00 | 10.79 |
| ATOM | 3306 | CG2 | VAL A | 436 | 0 | 6.238 | 29.806 | 39.536 | 1.00 | 14.13 |
| ATOM | 3307 | N | THR A | 437 | 0 | 8.290 | 32.391 | 42.691 | 1.00 | 16.51 |
| ATOM | 3308 | CA | THR A | 437 | 0 | 8.940 | 33.505 | 43.364 | 1.00 | 16.19 |
| ATOM | 3309 | C | THR A | 437 | 0 | 10.254 | 33.817 | 42.668 | 1.00 | 15.24 |
| ATOM | 3310 | O | THR A | 437 | 0 | 11.100 | 32.940 | 42.419 | 1.00 | 15.47 |
| ATOM | 3311 | CB | THR A | 437 | 0 | 9.190 | 33.067 | 44.827 | 1.00 | 14.95 |
| ATOM | 3312 | OG1 | THR A | 437 | 0 | 7.969 | 32.499 | 45.308 | 1.00 | 13.50 |
| ATOM | 3313 | CG2 | THR A | 437 | 0 | 9.599 | 34.232 | 45.697 | 1.00 | 13.41 |
| ATOM | 3314 | N | ILE A | 438 | 0 | 10.413 | 35.059 | 42.251 | 1.00 | 13.38 |
| ATOM | 3315 | CA | ILE A | 438 | 0 | 11.597 | 35.471 | 41.510 | 1.00 | 15.78 |
| ATOM | 3316 | C | ILE A | 438 | 0 | 12.292 | 36.590 | 42.264 | 1.00 | 15.86 |
| ATOM | 3317 | O | ILE A | 438 | 0 | 11.617 | 37.270 | 43.048 | 1.00 | 17.32 |
| ATOM | 3318 | CB | ILE A | 438 | 0 | 11.249 | 35.848 | 40.053 | 1.00 | 15.40 |
| ATOM | 3319 | CG1 | ILE A | 438 | 0 | 10.340 | 37.055 | 39.985 | 1.00 | 15.85 |
| ATOM | 3320 | CG2 | ILE A | 438 | 0 | 10.602 | 34.653 | 39.346 | 1.00 | 17.11 |
| ATOM | 3321 | CD1 | ILE A | 438 | 0 | 9.971 | 37.607 | 38.632 | 1.00 | 17.49 |
| ATOM | 3322 | N | ARG A | 439 | 0 | 13.599 | 36.789 | 42.055 | 1.00 | 16.02 |
| ATOM | 3323 | CA | ARG A | 439 | 0 | 14.315 | 37.896 | 42.671 | 1.00 | 13.90 |

APPENDIX 1-continued

```
ATOM   3324 C    ARG A  439  0    15.181 38.645 41.676 1.00 13.52
ATOM   3325 O    ARG A  439  0    15.748 38.056 40.762 1.00 14.74
ATOM   3326 CB   ARG A  439  0    15.193 37.501 43.850 1.00 15.15
ATOM   3327 CG   ARG A  439  0    14.457 37.235 45.147 1.00 14.83
ATOM   3328 CD   ARG A  439  0    15.367 37.337 46.355 1.00 14.08
ATOM   3329 NE   ARG A  439  0    14.613 37.000 47.566 1.00 17.06
ATOM   3330 CZ   ARG A  439  0    15.192 36.922 48.767 1.00 18.01
ATOM   3331 NH1  ARG A  439  0    16.487 37.176 48.908 1.00 17.76
ATOM   3332 NH2  ARG A  439  0    14.459 36.604 49.818 1.00 18.55
ATOM   3333 N    PHE A  440  0    15.314 39.957 41.853 1.00 14.44
ATOM   3334 CA   PHE A  440  0    16.204 40.737 40.993 1.00 15.97
ATOM   3335 C    PHE A  440  0    16.645 41.986 41.761 1.00 15.86
ATOM   3336 O    PHE A  440  0    16.113 42.313 42.801 1.00 15.79
ATOM   3337 CB   PHE A  440  0    15.638 41.081 39.620 1.00 15.17
ATOM   3338 CG   PHE A  440  0    14.416 41.948 39.647 1.00 16.95
ATOM   3339 CD1  PHE A  440  0    14.525 43.333 39.528 1.00 17.23
ATOM   3340 CD2  PHE A  440  0    13.158 41.377 39.798 1.00 16.35
ATOM   3341 CE1  PHE A  440  0    13.397 44.152 39;566 1.00 17.07
ATOM   3342 CE2  PHE A  440  0    12.026 42.180 39.841 1.00 17.12
ATOM   3343 CZ   PHE A  440  0    12.144 43.575 39.719 1.00 18.30
ATOM   3344 N    VAL A  441  0    17.676 42.648 41.268 1.00 16.10
ATOM   3345 CA   VAL A  441  0    18.172 43.874 41.879 1.00 16.29
ATOM   3346 C    VAL A  441  0    17.776 45.035 40.972 1.00 14.00
ATOM   3347 O    VAL A  441  0    17.866 44.924 39.736 1.00 12.72
ATOM   3348 CB   VAL A  441  0    19.675 43.769 42.144 1.00 18.13
ATOM   3349 CG1  VAL A  441  0    20.195 45.040 42.794 1.00 18.53
ATOM   3350 CG2  VAL A  441  0    19.969 42.583 43.065 1.00 18.55
ATOM   3351 N    THR A  442  0    17.328 46.125 41.579 1.00 11.73
ATOM   3352 CA   THR A  442  0    16.905 47.291 40.800 1.00 13.02
ATOM   3353 C    THR A  442  0    18.055 48.208 40.432 1.00 14.83
ATOM   3354 O    THR A  442  0    18.218 49.323 40.947 1.00 15.17
ATOM   3355 CB   THR A  442  0    15.840 48.127 41.558 1.00 14.62
ATOM   3356 OG1  THR A  442  0    16.314 48.463 42.864 1.00 14.34
ATOM   3357 CG2  THR A  442  0    14.552 47.299 41.727 1.00 13.82
ATOM   3358 N    ASP A  443  0    18.S18 47.764 39.437 1.00 15.48
ATOM   3359 CA   ASP A  443  0    20.004 48.449 38.964 1.00 16.57
ATOM   3360 C    ASP A  443  0    19.807 49.010 37.569 1.00 15.38
ATOM   3361 O    ASP A  443  0    20.788 49.208 36.858 1.00 15.57
ATOM   3362 CB   ASP A  443  0    21.133 47.391 38.962 1.00 19.75
ATOM   3363 CG   ASP A  443  0    20.877 46.264 37.990 1.00 22.78
```

APPENDIX 1-continued

| | | | | | | | | | |
|---|---|---|---|---|---|---|---|---|---|
| ATOM | 3364 | OD1 | ASP | A | 443 | 0 | 21.711 45.353 37.789 | 1.00 | 25.70 |
| ATOM | 3365 | OD2 | ASP | A | 443 | 0 | 19.836 46.161 37.313 | 1.00 | 23.88 |
| ATOM | 3366 | N | ASN | A | 444 | 0 | 18.593 49.278 37.144 | 1.00 | 13.71 |
| ATOM | 3367 | CA | ASN | A | 444 | 0 | 18.388 49.721 35.752 | 1.00 | 15.87 |
| ATOM | 3368 | C | ASN | A | 444 | 0 | 17.245 50.728 35.702 | 1.00 | 17.00 |
| ATOM | 3369 | O | ASN | A | 444 | 0 | 16.052 50.419 35.614 | 1.00 | 16.83 |
| ATOM | 3370 | CB | ASN | A | 444 | 0 | 18.198 48.453 34.930 | 1.00 | 15.78 |
| ATOM | 3371 | CG | ASN | A | 444 | 0 | 18.225 48.675 33.442 | 1.00 | 18.49 |
| ATOM | 3372 | OD1 | ASN | A | 444 | 0 | 18.505 49.809 33.047 | 1.00 | 19.42 |
| ATOM | 3373 | ND2 | ASN | A | 444 | 0 | 17.925 47.689 32.588 | 1.00 | 15.91 |
| ATOM | 3374 | N | PRO | A | 445 | 0 | 17.598 52.003 35.890 | 1.00 | 17.59 |
| ATOM | 3375 | CA | PRO | A | 445 | 0 | 16.683 53.137 35.938 | 1.00 | 16.56 |
| ATOM | 3376 | C | PRO | A | 445 | 0 | 15.788 53.217 34.721 | 1.00 | 16.99 |
| ATOM | 3377 | O | PRO | A | 445 | 0 | 16.293 53.246 33.594 | 1.00 | 17.02 |
| ATOM | 3378 | CB | PRO | A | 445 | 0 | 17.552 54.418 35.951 | 1.00 | 18.28 |
| ATOM | 3379 | CG | PRO | A | 445 | 0 | 18.870 53.871 36.474 | 1.00 | 18.09 |
| ATOM | 3380 | CD | PRO | A | 445 | 0 | 19.002 52.409 36.084 | 1.00 | 16.05 |
| ATOM | 3381 | N | GLY | A | 446 | 0 | 14.462 53.194 34.918 | 1.00 | 17.16 |
| ATOM | 3382 | CA | GLY | A | 446 | 0 | 13.560 53.281 33.743 | 1.00 | 15.84 |
| ATOM | 3383 | C | GLY | A | 446 | 0 | 12.297 52.453 33.984 | 1.00 | 14.24 |
| ATOM | 3384 | O | GLY | A | 446 | 0 | 12.192 51.797 35.005 | 1.00 | 12.22 |
| ATOM | 3385 | N | PRO | A | 447 | 0 | 11.285 52.697 33.181 | 1.00 | 15.53 |
| ATOM | 3386 | CA | PRO | A | 447 | 0 | 9.999 52.048 33.195 | 1.00 | 15.24 |
| ATOM | 3387 | C | PRO | A | 447 | 0 | 10.101 50.737 32.401 | 1.00 | 13.82 |
| ATOM | 3388 | O | PRO | A | 447 | 0 | 10.514 50.733 31.240 | 1.00 | 13.85 |
| ATOM | 3389 | CB | PRO | A | 447 | 0 | 9.013 52.976 32.473 | 1.00 | 16.21 |
| ATOM | 3390 | CG | PRO | A | 447 | 0 | 9.933 53.729 31.554 | 1.00 | 16.19 |
| ATOM | 3391 | CD | PRO | A | 447 | 0 | 11.347 53.707 32.096 | 1.00 | 17.15 |
| ATOM | 3392 | N | TRP | A | 448 | 0 | 9.787 49.623 33.021 | 1.00 | 11.83 |
| ATOM | 3393 | CA | TRP | A | 448 | 0 | 9.898 48.317 32.371 | 1.00 | 14.30 |
| ATOM | 3394 | C | TRP | A | 448 | 0 | 8.610 47.493 32.427 | 1.00 | 13.12 |
| ATOM | 3395 | O | TRP | A | 448 | 0 | 8.013 47.355 33.502 | 1.00 | 11.63 |
| ATOM | 3396 | CB | TRP | A | 448 | 0 | 10.985 47.483 33.095 | 1.00 | 13.17 |
| ATOM | 3391 | CG | TRP | A | 448 | 0 | 12.321 48.160 33.124 | 1.00 | 14.54 |
| ATOM | 3398 | CD1 | TRP | A | 448 | 0 | 12.897 48.728 34.239 | 1.00 | 14.19 |
| ATOM | 3399 | CD2 | TRP | A | 448 | 0 | 13.211 48.382 32.029 | 1.00 | 14.38 |
| ATOM | 3400 | NE1 | TRP | A | 448 | 0 | 14.083 49.290 33.873 | 1.00 | 15.02 |
| ATOM | 3401 | CE2 | TRP | A | 448 | 0 | 14.308 49.095 32.527 | 1.00 | 14.41 |
| ATOM | 3402 | CE3 | TRP | A | 448 | 0 | 13.193 48.053 30.672 | 1.00 | 15.39 |

APPENDIX 1-continued

```
ATOM   3403  CZ2  TRP A  448  0    15.388  49.467  31.729  1.00  14.57
ATOM   3404  CZ3  TRP A  448  0    14.250  48.446  29.867  1 00  14.92
ATOM   3405  CH2  TRP A  448  0    15.355  49.135  30.399  1.00  14.93
ATOM   3406  N    PHE A  449  0     8.231  46.884  31.315  1.00  14.03
ATOM   3407  CA   PHE A  449  0     7.023  46.039  31.297  1.00  13.60
ATOM   3408  C    PHE A  449  0     7.231  44.712  32.016  1.00  15.32
ATOM   3409  O    PHE A  449  0     8.312  44.093  31.993  1.00  13.66
ATOM   3410  CB   PHE A  449  0     6.627  45.773  29.845  1.00  16.19
ATOM   3411  CG   PHE A  449  0     5.221  46.033  29.380  1.00  18.26
ATOM   3412  CD1  PHE A  449  0     4.165  46.288  30.226  1.00  17.95
ATOM   3413  CD2  PHE A  449  0     4.962  46.027  28.011  1.00  20.73
ATOM   3414  CE1  PHE A  449  0     2.899  46.565  29.745  1.00  18.55
ATOM   3415  CE2  PHE A  449  0     3.701  46.293  27.503  1.00  20.13
ATOM   3416  CZ   PHE A  449  0     2.664  46.543  28.387  1.00  18.59
ATOM   3417  N    PHE A  450  0     6.195  44.245  32.715  1.00  12.79
ATOM   3418  CA   PHE A  450  0     6.119  42.963  33.359  1.00  14.38
ATOM   3419  C    PHE A  450  0     4.775  42.323  32.952  1.00  15.45
ATOM   3420  O    PHE A  450  0     3.743  42.812  33.423  1.00  15.30
ATOM   3421  CB   PHE A  450  0     6.186  43.041  34.879  1.00  15.06
ATOM   3422  CG   PHE A  450  0     6.210  41.693  35.555  1.00  15.95
ATOM   3423  CD1  PHE A  450  0     7.157  40.734  35.204  1.00  16.36
ATOM   3424  CD2  PHE A  450  0     5.325  41.398  36.570  1.00  15.45
ATOM   3425  CE1  PHE A  450  0     7.222  39.518  35.855  1.00  13.87
ATOM   3426  CE2  PHE A  450  0     5.386  40.187  37.224  1.00  16.10
ATOM   3427  CZ   PHE A  450  0     6.317  39.236  36.854  1.00  15.90
ATOM   3428  N    HIS A  451  0     4.737  41.301  32.122  1.00  15.54
ATOM   3429  CA   HIS A  451  0     3.443  40.841  31.610  1.00  16.24
ATOM   3430  C    HIS A  451  0     3.461  39.426  31.073  1.00  16.95
ATOM   3431  O    HIS A  451  0     4.526  38.860  30.812  1.00  17.42
ATOM   3432  CB   HIS A  451  0     2.996  41.743  30.435  1.00  14.01
ATOM   3433  CG   HIS A  451  0     3.921  41.696  29.281  1.00  16.98
ATOM   3434  ND1  HIS A  451  0     3.791  40.844  28.201  1.00  18.14
ATOM   3435  CD2  HIS A  451  0     5.058  42.435  29.046  1.00  17.88
ATOM   3436  CE1  HIS A  451  0     4.759  41.060  27.337  1.00  17.83
ATOM   3437  NE2  HIS A  451  0     5.554  42.011  27.842  1.00  18.98
ATOM   3438  N    CYS A  452  0     2.261  38.863  30.951  1.00  16.78
ATOM   3439  CA   CYS A  452  0     2.167  37.537  30.388  1.00  16.34
ATOM   3440  C    CYS A  452  0     2.604  37.623  28.924  1.00  14.77
ATOM   3441  O    CYS A  452  0     2.167  38.514  28.188  1.00  13.61
ATOM   3442  CB   CYS A  452  0     0.727  36.983  30.451  1.00  18.22
```

APPENDIX 1-continued

| ATOM | 3443 | SG  | CYS A | 452 | 0 |  0.701 | 35.325 | 29.692 | 1.00 | 19.80 |
| --- | --- | --- | --- | --- | --- | --- | --- | --- | --- | --- |
| ATOM | 3444 | N   | HIS A | 453 | 0 |  3.388 | 36.640 | 28.474 | 1.00 | 13.29 |
| ATOM | 3445 | CA  | HIS A | 453 | 0 |  3.867 | 36.716 | 27.100 | 1.00 | 13.19 |
| ATOM | 3446 | C   | HIS A | 453 | 0 |  2.983 | 35.987 | 26.099 | 1.00 | 13.47 |
| ATOM | 3447 | O   | HIS A | 453 | 0 |  3.296 | 35.974 | 24.906 | 1.00 | 11.93 |
| ATOM | 3448 | CB  | HIS A | 453 | 0 |  5.314 | 36.251 | 27.033 | 1.00 | 13.98 |
| ATOM | 3449 | CG  | HIS A | 453 | 0 |  6.124 | 36.860 | 25.945 | 1.00 | 11.89 |
| ATOM | 3450 | ND1 | HIS A | 453 | 0 |  5.835 | 36.763 | 24.612 | 1.00 | 10.68 |
| ATOM | 3451 | CD2 | HIS A | 453 | 0 |  7.270 | 37.594 | 26.072 | 1.00 | 12.71 |
| ATOM | 3452 | CE1 | HIS A | 453 | 0 |  6.776 | 37.418 | 23.923 | 1.00 | 12.37 |
| ATOM | 3453 | NE2 | HIS A | 453 | 0 |  7.663 | 37.930 | 24.793 | 1 00 | 13.20 |
| ATOM | 3454 | N   | ILE A | 454 | 0 |  1.860 | 35.429 | 26.549 | 1.00 | 15.35 |
| ATOM | 3455 | CA  | ILE A | 454 | 0 |  0.849 | 34.937 | 25.600 | 1.00 | 15.85 |
| ATOM | 3456 | C   | ILE A | 454 | 0 |  0.214 | 36.238 | 25.089 | 1.00 | 18.65 |
| ATOM | 3457 | O   | ILE A | 454 | 0 | -0.452 | 36.997 | 25.824 | 1.00 | 17.92 |
| ATOM | 3458 | CB  | ILE A | 454 | 0 | -0.156 | 34.001 | 26.280 | 1.00 | 16.46 |
| ATOM | 3459 | CG1 | ILE A | 454 | 0 |  0.456 | 32.598 | 26.512 | 1.00 | 15.26 |
| ATOM | 3460 | CG2 | ILE A | 454 | 0 | -1.402 | 33.898 | 25.419 | 1.00 | 14.21 |
| ATOM | 3461 | CD  | ILE A | 454 | 0 | -0.249 | 31.804 | 27.592 | 1.00 | 16.26 |
| ATOM | 3462 | N   | GLU A | 455 | 0 |  0.448 | 36.607 | 23.832 | 1.00 | 21.02 |
| ATOM | 3463 | CA  | GLU A | 455 | 0 | -0.024 | 37.856 | 23.289 | 1.00 | 23.78 |
| ATOM | 3464 | C   | GLU A | 455 | 0 | -1.526 | 38.042 | 23.422 | 1.00 | 24.40 |
| ATOM | 3465 | O   | GLU A | 455 | 0 | -1.953 | 39.161 | 23.700 | 1.00 | 24.30 |
| ATOM | 3466 | CB  | GLU A | 455 | 0 |  0.399 | 38.090 | 21.830 | 1.00 | 27.20 |
| ATOM | 3467 | CG  | GLU A | 455 | 0 |  0.602 | 39.599 | 21.595 | 1.00 | 33.86 |
| ATOM | 3468 | CD  | GLU A | 455 | 0 |  1.783 | 40.205 | 22.309 | 1.00 | 37.49 |
| ATOM | 3469 | OE1 | GLU A | 455 | 0 |  2.311 | 39.657 | 23.320 | 1.00 | 41.51 |
| ATOM | 3470 | 0E2 | GLU A | 455 | 0 |  2.303 | 41.284 | 21.907 | 1.00 | 41.22 |
| ATOM | 3471 | N   | PHE A | 456 | 0 | -2.347 | 37.005 | 23.334 | 1.00 | 23.97 |
| ATOM | 3472 | CA  | PHE A | 456 | 0 | -3.775 | 37.163 | 23.516 | 1.00 | 24.68 |
| ATOM | 3473 | C   | PHE A | 456 | 0 | -4.084 | 37.533 | 24.959 | 1.00 | 25.11 |
| ATOM | 3474 | O   | PHE A | 456 | 0 | -5.181 | 38.092 | 25.170 | 1.00 | 27.37 |
| ATOM | 3475 | CB  | PHE A | 456 | 0 | -4.552 | 35.919 | 23.023 | 1.00 | 24.76 |
| ATOM | 3476 | CG  | PHE A | 456 | 0 | -4.098 | 35.614 | 21.606 | 1.00 | 24.98 |
| ATOM | 3477 | CD1 | PHE A | 456 | 0 | -4.392 | 36.500 | 20.590 | 1.00 | 24.98 |
| ATOM | 3478 | CD2 | PHE A | 456 | 0 | -3.331 | 34.506 | 21.320 | 1.00 | 24.42 |
| ATOM | 3479 | CE1 | PHE A | 456 | 0 | -3.988 | 36.292 | 19.291 | 1.00 | 25.44 |
| ATOM | 3480 | CE2 | PHE A | 456 | 0 | -2.913 | 34.293 | 20.015 | 1.00 | 26.40 |
| ATOM | 3481 | CZ  | PHE A | 456 | 0 | -3.226 | 35.171 | 18.997 | 1.00 | 25.10 |

APPENDIX 1-continued

| | | | | | | | | | | |
|---|---|---|---|---|---|---|---|---|---|---|
| ATOM | 3482 | N | HIS | A | 457 | 0 | -3.205 | 37.294 | 25.922 | 1.00 22.35 |
| ATOM | 3483 | CA | HIS | A | 457 | 0 | -3.508 | 37.682 | 27.291 | 1.00 22.55 |
| ATOM | 3484 | C | HIS | A | 457 | 0 | -3.053 | 39.121 | 27.561 | 1.00 23.81 |
| ATOM | 3485 | O | HIS | A | 457 | 0 | -3.756 | 39.832 | 28.262 | 1.00 21.33 |
| ATOM | 3486 | CB | HIS | A | 457 | 0 | -2.912 | 36.766 | 28.336 | 1.00 20.96 |
| ATOM | 3487 | CG | HIS | A | 457 | 0 | -3.345 | 35.346 | 28.201 | 1.00 22.51 |
| ATOM | 3488 | ND1 | HIS | A | 457 | 0 | -2.745 | 34.329 | 28.905 | 1.00 21.40 |
| ATOM | 3489 | CD2 | HIS | A | 457 | 0 | -4.291 | 34.771 | 27.404 | 1.00 22.50 |
| ATOM | 3490 | CE1 | HIS | A | 457 | 0 | -3.320 | 33.184 | 28.575 | 1.00 22.51 |
| ATOM | 3491 | NE2 | HIS | A | 457 | 0 | -4.237 | 33.428 | 27.666 | 1.00 23.19 |
| ATOM | 3492 | N | LEU | A | 458 | 0 | -1.876 | 39.481 | 27.028 | 1.00 23.74 |
| ATOM | 3493 | CA | LEU | A | 458 | 0 | -1.357 | 40.817 | 27.125 | 1.00 24.76 |
| ATOM | 3494 | C | LEU | A | 458 | 0 | -2.411 | 41.828 | 26.616 | 1.00 26.52 |
| ATOM | 3495 | O | LEU | A | 458 | 0 | -2.757 | 42.751 | 27.351 | 1.00 25.18 |
| ATOM | 3496 | CB | LEU | A | 458 | 0 | -0.108 | 40.986 | 26.252 | 1.00 23.81 |
| ATOM | 3497 | CG | LEU | A | 458 | 0 | 0.898 | 42.062 | 26.624 | 1.00 24.09 |
| ATOM | 3498 | CD1 | LEU | A | 458 | 0 | 1.619 | 42.606 | 25.390 | 1.00 24.28 |
| ATOM | 3499 | CD2 | LEU | A | 458 | 0 | 0.351 | 43.195 | 27.462 | 1.00 23.72 |
| ATOM | 3500 | N | MET | A | 459 | 0 | -2.896 | 41.611 | 25.388 | 1.00 28.19 |
| ATOM | 3501 | CA | MET | A | 459 | 0 | -3.914 | 42.458 | 24.785 | 1.00 31.98 |
| ATOM | 3502 | C | MET | A | 459 | 0 | -5.207 | 42.436 | 25.603 | 1.00 29.95 |
| ATOM | 3503 | O | MET | A | 459 | 0 | -5.886 | 43.439 | 25.520 | 1.00 29.10 |
| ATOM | 3504 | CB | MET | A | 459 | 0 | -4.148 | 42.226 | 23.284 | 1.00 35.99 |
| ATOM | 3505 | CG | MET | A | 459 | 0 | -5.056 | 41.103 | 22.852 | 1.00 42.66 |
| ATOM | 3506 | SD | MET | A | 459 | 0 | -5.296 | 40.817 | 21.069 | 1.00 49.28 |
| ATOM | 3507 | CE | MET | A | 459 | 0 | -6.238 | 39.291 | 21.119 | 1.00 47.39 |
| ATOM | 3508 | N | ASN | A | 460 | 0 | -5.523 | 41.486 | 26.464 | 1.00 29.07 |
| ATOM | 3509 | CA | ASN | A | 460 | 0 | -6.706 | 41.539 | 27.296 | 1.00 29.41 |
| ATOM | 3510 | C | ASN | A | 460 | 0 | -6.407 | 41.908 | 28.746 | 1.00 28.46 |
| ATOM | 3511 | O | ASN | A | 460 | 0 | -7.183 | 41.577 | 29.645 | 1.00 26.89 |
| ATOM | 3512 | CB | ASN | A | 460 | 0 | -7.537 | 40.253 | 27.210 | 1.00 31.34 |
| ATOM | 3513 | CG | ASN | A | 460 | 0 | -8.325 | 40.243 | 25.900 | 1.00 33.82 |
| ATOM | 3514 | OD1 | ASN | A | 460 | 0 | -7.909 | 39.609 | 24.926 | 1.00 34.29 |
| ATOM | 3515 | ND2 | ASN | A | 460 | 0 | -9.437 | 40.971 | 25.861 | 1.00 34.55 |
| ATOM | 3516 | N | GLY | A | 461 | 0 | -5.320 | 42.655 | 28.981 | 1.00 26.30 |
| ATOM | 3517 | CA | GLY | A | 461 | 0 | -5.020 | 43.198 | 30.268 | 1.00 24.99 |
| ATOM | 3518 | C | GLY | A | 461 | 0 | -4.043 | 42.601 | 31.235 | 1.00 24.75 |
| ATOM | 3519 | O | GLY | A | 461 | 0 | -3.879 | 43.228 | 32.304 | 1.00 22.69 |
| ATOM | 3520 | N | LEU | A | 462 | 0 | -3.375 | 41.478 | 30.914 | 1.00 22.85 |
| ATOM | 3521 | CA | LEU | A | 462 | 0 | -2.478 | 40.872 | 31.913 | 1.00 22.10 |

APPENDIX 1-continued

```
ATOM   3522  C    LEU A  462  0   -1.071  41.485  31.890  1.00  21.56
ATOM   3523  O    LEU A  462  0   -0.116  40.876  31.415  1.00  20.28
ATOM   3524  CB   LEU A  462  0   -2.477  39.376  31.669  1.00  20.03
ATOM   3525  CG   LEU A  462  0   -2.010  38.393  32.720  1.00  20.40
ATOM   3526  CD1  LEU A  462  0   -2.603  38.608  34.093  1.00  20.35
ATOM   3527  CD2  LEU A  462  0   -2.385  36.983  32.229  1.00  21.01
ATOM   3528  N    ALA A  463  0   -0.908  42.695  32.408  1.00  20.00
ATOM   3529  CA   ALA A  463  0    0.350  43.432  32.381  1.00  20.74
ATOM   3530  C    ALA A  463  0    0.398  44.511  33.481  1.00  21.85
ATOM   3531  O    ALA A  463  0   -0.667  44.965  33.934  1.00  22.85
ATOM   3532  CB   ALA A  463  0    0.559  44.179  31.060  1.00  15.13
ATOM   3533  N    ILE A  464  0    1.605  44.810  33.950  1.00  19.91
ATOM   3534  CA   ILE A  464  0    1.852  45.905  34.850  1.00  19.81
ATOM   3535  C    ILE A  464  0    3.180  46.579  34.434  1.00  19.41
ATOM   3536  O    ILE A  464  0    3.938  46.003  33.660  1.00  18.24
ATOM   3537  CB   ILE A  464  0    1.910  45.678  36.347  1.00  19.13
ATOM   3538  CG1  ILE A  464  0    2.867  44.546  36.697  1.00  19.39
ATOM   3539  CG2  ILE A  464  0    0.520  45.455  36.924  1.00  18.48
ATOM   3540  CD1  ILE A  464  0    3.205  44.549  38.179  1.00  21.00
ATOM   3541  N    VAL A  465  0    3.380  47.791  34.924  1.00  18.95
ATOM   3542  CA   VAL A  465  0    4.579  48.570  34.637  1.00  18.36
ATOM   3543  C    VAL A  465  0    5.327  48.928  35.931  1.00  18.07
ATOM   3544  O    VAL A  465  0    4.787  49.424  36.931  1.00  15.19
ATOM   3545  CB   VAL A  465  0    4.329  49.913  33.918  1.00  19.73
ATOM   3546  CG1  VAL A  465  0    5.659  50.605  33.602  1.00  18.34
ATOM   3547  CG2  VAL A  465  0    3.522  49.766  32.629  1.00  18.74
ATOM   3548  N    PHE A  466  0    6.649  48.655  35.879  1.00  17.55
ATOM   3549  CA   PHE A  466  0    7.499  49.051  37.013  1.00  14.72
ATOM   3550  C    PHE A  466  0    8.251  50.344  36.653  1.00  12.68
ATOM   3551  O    PHE A  466  0    9.007  50.420  35.679  1.00  12.23
ATOM   3552  CB   PHE A  466  0    8.484  47.978  37.381  1.00  15.19
ATOM   3553  CG   PHE A  466  0    7.962  46.770  38.080  1.00  15.90
ATOM   3554  CD1  PHE A  466  0    7.328  46.856  39.299  1.00  16.23
ATOM   3555  CD2  PHE A  466  0    8.153  45.533  37.492  1.00  16.23
ATOM   3556  CE1  PHE A  466  0    6.861  45.720  39.936  1.00  15.97
ATOM   3557  CE2  PHE A  466  0    7.665  44.389  38.133  1.00  18.27
ATOM   3558  CZ   PHE A  466  0    7.018  44.480  39.352  1.00  16.74
ATOM   3559  N    ALA A  467  0    8.045  51.361  37.443  1.00  10.60
ATOM   3560  CA   ALA A  467  0    8.788  52.648  37.194  1.00  12.27
```

APPENDIX 1-continued

```
ATOM   3561  C    ALA A  467  0    10.007 52.526 38.111 1.00 12.02
ATOM   3562  O    ALA A  467  0     9.905 52.728 39.325 1.00 12.43
ATOM   3563  CB   ALA A  467  0     7.845 53.790 37.501 1.00 10.50
ATOM   3564  N    GLU A  468  0    11.126 51.989 37.625 1.00 12.62
ATOM   3565  CA   GLU A  468  0    12.263 51.683 38.515 1.00 14.63
ATOM   3566  C    GLU A  468  0    13.195 52.883 38.685 1.00 13.91
ATOM   3567  O    GLU A  468  0    13.631 53.369 37.651 1.00 13.05
ATOM   3568  CB   GLU A  468  0    13.049 50.546 37.843 1.00 14.51
ATOM   3569  CG   GLU A  468  0    14.256 50.035 38.629 1.00 16.84
ATOM   3570  CD   GLU A  468  0    14.805 48.779 37.975 1.00 17.96
ATOM   3571  OE1  GLU A  468  0    15.985 48.479 38.124 1.00 16.98
ATOM   3572  0E2  GLU A  468  0    14.086 48.043 37.260 1.00 18.42
ATOM   3573  N    ASP A  469  0    13.546 53.286 39.886 1.00 15.17
ATOM   3574  CA   ASP A  469  0    14.491 54.371 40.116 1.00 16.85
ATOM   3575  C    ASP A  469  0    14.134 55.630 39.333 1.00 16.33
ATOM   3576  O    ASP A  469  0    14.851 56.046 38.437 1.00 16.59
ATOM   3577  CB   ASP A  469  0    15.899 53.920 39.748 1.00 19.86
ATOM   3578  CG   ASP A  469  0    17.040 54.766 40.289 1.00 21.40
ATOM   3579  OD1  ASP A  469  0    16.811 55.793 40.943 1.00 22.21
ATOM   3580  OD2  ASP A  469  0    18.216 54.403 40.069 1.00 22.21
ATOM   3581  N    MET A  470  0    13.007 56.246 39.635 1.00 16.12
ATOM   3582  CA   MET A  470  0    12.522 57.373 38.853 1.00 18.77
ATOM   3583  C    MET A  470  0    13.451 58.576 38.950 1.00 16.31
ATOM   3584  O    MET A  470  0    13.591 59.208 37.925 1.00 13.55
ATOM   3585  CB   MET A  470  0    11.116 57.847 39.302 1.00 20.06
ATOM   3586  CG   MET A  470  0    10.041 56.941 38.684 1.00 23.99
ATOM   3587  SD   MET A  470  0     8.375 57.337 39.283 1.00 26.08
ATOM   3588  CE   MET A  470  0     8.030 58.581 38.020 1.00 24.40
ATOM   3589  N    ALA A  471  0    14.046 58.793 40.117 1.00 14.69
ATOM   3590  CA   ALA A  471  0    14.953 59.906 40.287 1.00 16.97
ATOM   3591  C    ALA A  471  0    16.141 59.864 39.335 1.00 18.79
ATOM   3592  O    ALA A  471  0    16.602 60.956 38.945 1.00 21.08
ATOM   3593  CB   ALA A  471  0    15.471 59.927 41.728 1.00 17.62
ATOM   3594  N    ASN A  472  0    16.623 58.695 38.912 1.00 17.28
ATOM   3595  CA   ASN A  472  0    17.788 58.675 38.015 1.00 16.56
ATOM   3596  C    ASN A  472  0    17.457 58.355 36.572 1 00 16.99
ATOM   3597  O    ASN A  472  0    18.407 58.143 35.795 1.00 18.74
ATOM   3598  CB   ASN A  472  0    18.811 57.645 38.548 1.00 14.60
ATOM   3599  CG   ASN A  472  0    19.417 58.132 39.887 1.00 14.00
ATOM   3600  OD1  ASN A  472  0    18.895 57.830 40.967 1.00 12.71
```

APPENDIX 1-continued

```
ATOM   3601 ND2 ASN A  472  0   20.468 58.916 39.775 1.00 10.80
ATOM   3602 N   THR A  473  0   16.174 58.284 36.239 1.00 14.26
ATOM   3603 CA  THR A  473  0   15.789 57.885 34.882 1.00 15.82
ATOM   3604 C   THR A  473  0   16.150 58.891 33.812 1.00 16.81
ATOM   3605 O   THR A  473  0   16.599 58.455 32.746 1.00 15.89
ATOM   3606 CB  THR A  473  0   14.267 57.576 34.826 1.00 16.10
ATOM   3607 OG1 THR A  473  0   14.001 56.416 35.609 1.00 15.41
ATOM   3608 CG2 THR A  473  0   13.750 57.337 33.427 1.00 15.24
ATOM   3609 N   VAL A  474  0   16.000 60.195 34.081 1.00 18.57
ATOM   3610 CA  VAL A  474  0   16.355 61.192 33.050 1.00 21.06
ATOM   3611 C   VAL A  474  0   17.859 61.209 32.817 1.00 19.12
ATOM   3612 O   VAL A  474  0   18.339 61.234 31.688 1.00 19.95
ATOM   3613 CB  VAL A  474  0   15.860 62.616 33.424 1.00 22.91
ATOM   3614 CG1 VAL A  474  0   16.467 63.702 32.538 1.00 23.06
ATOM   3615 CG2 VAL A  474  0   14.346 62.721 33.334 1.00 23.04
ATOM   3616 N   ASP A  475  0   18.647 61.175 33.886 1.00 19.20
ATOM   3617 CA  ASP A  475  0   20.109 61.168 33.741 1.00 18.98
ATOM   3618 C   ASP A  475  0   20.578 59.899 33.047 1.00 17.52
ATOM   3619 O   ASP A  475  0   21.386 60.028 32.130 1.00 18.31
ATOM   3620 CB  ASP A  475  0   20.780 61.273 35.119 1.00 20.27
ATOM   3621 CG  ASP A  475  0   22.283 61.075 35.107 1.00 20.18
ATOM   3622 OD1 ASP A  475  0   22.950 61.889 34.431 1.00 21.73
ATOM   3623 OD2 ASP A  475  0   22.798 60.139 35.750 1.00 18.03
ATOM   3624 N   ALA A  476  0   20.062 58.725 33.392 1.00 18.26
ATOM   3625 CA  ALA A  476  0   20.539 57.486 32.793 1.00 18.93
ATOM   3626 C   ALA A  476  0   20.165 57.269 31.343 1.00 20.62
ATOM   3627 O   ALA A  476  0   20.845 56.502 30.661 1.00 22.64
ATOM   3628 CB  ALA A  476  0   19.966 56.298 33.551 1.00 18.48
ATOM   3629 N   ASN A  477  0   19.047 57.787 30.858 1.00 22.66
ATOM   3630 CA  ASN A  477  0   18.605 57.512 29.491 1.00 25.22
ATOM   3631 C   ASN A  477  0   18.578 58.782 28.683 1.00 28.55
ATOM   3632 O   ASN A  477  0   17.969 59.755 29.143 1.00 30.20
ATOM   3633 CB  ASN A  477  0   17.172 56.948 29.560 1.00 24.22
ATOM   3634 CG  ASN A  477  0   17.114 55.666 30.380 1.00 23.73
ATOM   3635 OD1 ASN A  477  0   16.747 55.672 31.570 1.00 21.33
ATOM   3636 ND2 ASN A  477  0   17.512 54.575 29.736 1.00 20.87
ATOM   3637 N   ASN A  478  0   19.208 58.878 27.514 1.00 31.69
ATOM   3638 CA  ASN A  478  0   19.036 60.131 26.776 1.00 33.61
ATOM   3639 C   ASN A  478  0   18.758 59.770 25.331 1.00 32.22
```

APPENDIX 1-continued

```
ATOM   3640 O    ASN A  478 0   19.602 59.478 24.508 1.00 32.16
ATOM   3641 CB   ASN A  478 0   20.086 61.194 27.017 1.00 38.57
ATOM   3642 CG   ASN A  478 0   21.426 60.602 27.370 1.00 40.94
ATOM   3643 OD1  ASN A  478 0   21.928 59.903 26.484 1.00 44.60
ATOM   3644 ND2  ASN A  478 0   21.866 60.861 28.578 1.00 41.32
ATOM   3645 N    PRO A  479 0   17.461 59.733 25.075 1.00 32.37
ATOM   3646 CA   PRO A  479 0   16.890 59.381 23.790 1.00 31.84
ATOM   3647 C    PRO A  479 0   17.268 60.448 22.776 1.00 32.35
ATOM   3648 O    PRO A  479 0   17.422 61.609 23.136 1.00 32.66
ATOM   3649 CB   PRO A  479 0   15.364 59.385 23.931 1.00 31.68
ATOM   3659 CG   PRO A  479 0   15.126 59.724 25.373 1.00 31.69
ATOM   3651 CD   PRO A  479 0   16.416 60.071 26.064 1.00 32.23
ATOM   3652 N    PRO A  480 0   17.399 60.036 21.537 1.00 31.62
ATOM   3653 CA   PRO A  480 0   17.670 60.939 20.422 1.00 30.72
ATOM   3654 C    PRO A  480 0   16.452 61.827 20.225 1.00 30.37
ATOM   3655 O    PRO A  480 0   15.362 61.525 20.733 1.00 29.47
ATOM   3656 CB   PRO A  480 0   17.935 60.035 19.203 1.00 29.87
ATOM   3657 CG   PRO A  480 0   17.111 58.811 19.590 1.00 30.44
ATOM   3658 CD   PRO A  480 0   17.161 58.657 21.093 1.00 30.35
ATOM   3659 N    VAL A  481 0   16.559 62.906 19.458 1.00 31.72
ATOM   3660 CA   VAL A  481 0   15.398 63.788 19.268 1.00 30.68
ATOM   3661 C    VAL A  481 0   14.335 63.090 18.446 1.00 29.51
ATOM   3662 O    VAL A  481 0   13.134 63.284 18.648 1.00 27.97
ATOM   3663 CB   VAL A  481 0   15.818 65.132 18.648 1.00 33.04
ATOM   3664 CG1  VAL A  481 0   16.126 65.010 17.161 1.00 31.91
ATOM   3665 CG2  VAL A  481 0   14.717 66.171 18.907 1.00 33.32
ATOM   3666 N    GLU A  482 0   14.746 62.167 17.562 1.00 28.90
ATOM   3667 CA   GLU A  482 0   13.755 61.402 16.803 1.00 29.62
ATOM   3668 C    GLU A  482 0   12.839 60.565 17.691 1.00 28.33
ATOM   3669 O    GLU A  482 0   11.704 60.287 17.280 1.00 28.36
ATOM   3670 CB   GLU A  482 0   14.449 60.498 15.788 1.00 30.63
ATOM   3671 CG   GLU A  482 0   15.143 61.256 14.666 1.00 32.78
ATOM   3672 CD   GLU A  482 0   16.522 61.784 14.990 1.00 34.96
ATOM   3673 OE1  GLU A  482 0   17.021 61.746 16.141 1.00 34.62
ATOM   3674 OE2  GLU A  482 0   17.170 62.297 14.033 1.00 37.13
ATOM   3675 N    TRP A  483 0   13.311 60.124 18.857 1.00 25.91
ATOM   3676 CA   TRP A  483 0   12.496 59.280 19.711 1.00 25.49
ATOM   3677 C    TRP A  483 0   11.224 60.011 20.125 1.00 26.47
ATOM   3678 O    TRP A  483 0   10.155 59.405 20.116 1.00 26.95
ATOM   3679 CB   TRP A  483 0   13.216 58.807 20.974 1.00 21.98
```

APPENDIX 1-continued

```
ATOM  3680 CG   TRP A  483 0   12.376 58.144 22.013 1.00 21.49
ATOM  3681 CD1  TRP A  483 0   11.960 56.827 22.003 1.00 20.81
ATOM  3682 CD2  TRP A  483 0   11.818 58.730 23.194 1.00 20.14
ATOM  3683 NE1  TRP A  483 0   11.187 56.575 23.143 1.00 20.29
ATOM  3684 CE2  TRP A  483 0   11.097 57.736 23.868 1.00 20.29
ATOM  3685 CE3  TRP A  483 0   11.875 60.006 23.754 1.00 21.32
ATOM  3686 CZ2  TRP A  483 0   10.422 57.973 25.062 1.00 20.89
ATOM  3687 CZ3  TRP A  483 0   11.217 60.248 24.946 1.00 20.78
ATOM  3688 CH2  TRP A  483 0   10.495 59.227 25.596 1.00 21.44
ATOM  3689 N    ALA A  484 0   11.342 61.261 20.560 1.00 28.59
ATOM  3690 CA   ALA A  484 0   10.165 62.003 21.029 1.00 30.73
ATOM  3691 C    ALA A  484 0    9.226 62.350 19.869 1.00 30.42
ATOM  3692 O    ALA A  484 0    8.024 62.337 20.071 1.00 31.34
ATOM  3693 CB   ALA A  484 0   10.583 63.244 21.806 1.00 31.05
ATOM  3694 N    GLN A  485 0    9.702 62.488 18.653 1.00 30.79
ATOM  3695 CA   GLN A  485 0    8.927 62.742 17.466 1.00 33.16
ATOM  3696 C    GLN A  485 0    8.026 61.608 17.017 1.00 32.81
ATOM  3697 O    GLN A  485 0    7.044 61.847 16.302 1.00 32.74
ATOM  3698 CB   GLN A  485 0    9.859 63.113 16.290 1.00 34.56
ATOM  3699 CG   GLN A  485 0   10.631 64.361 16.686 1.00 39.67
ATOM  3700 CD   GLN A  485 0   11.559 64.919 15.640 1.00 42.86
ATOM  3701 OE1  GLN A  485 0   11.528 66.145 15.434 1.00 45.48
ATOM  3702 NE2  GLN A  485 0   12.375 64.103 14.982 1.00 44.07
ATOM  3703 N    LEU A  486 0    8.328 60.380 17.443 1.00 30.46
ATOM  3704 CA   LEU A  486 0    7.500 59.231 17.095 1.00 27.76
ATOM  3705 C    LEU A  486 0    6.051 59.510 17.509 1.00 28.23
ATOM  3706 O    LEU A  486 0    5.100 59.331 16.752 1.00 26.71
ATOM  3707 CB   LEU A  486 0    8.043 58.034 17.838 1.00 25.03
ATOM  3708 CG   LEU A  486 0    8.988 57.012 17.226 1.00 24.18
ATOM  3709 CD1  LEU A  486 0    9.780 57.416 16.011 1.00 21.41
ATOM  3710 CD2  LEU A  486 0    9.864 56.464 18.342 1.00 23.28
ATOM  3711 N    CYS A  487 0    5.870 59.974 18.739 1.00 28.05
ATOM  3712 CA   CYS A  487 0    4.560 60.263 19.279 1.00 30.77
ATOM  3713 C    CYS A  487 0    3.823 61.350 18.499 1.00 33.19
ATOM  3714 O    CYS A  487 0    2.627 61.170 18.263 1.00 33.69
ATOM  3715 CB   CYS A  487 0    4.643 60.637 20.752 1.00 27.94
ATOM  3716 SG   CYS A  487 0    5.214 59.280 21.781 1.00 27.23
ATOM  3717 N    GLU A  488 0    4.543 62.373 18.064 1.00 35.80
ATOM  3718 CA   GLU A  488 0    3.871 63.458 17.334 1.00 39.12
```

APPENDIX 1-continued

| | | | | | | | | | | |
|---|---|---|---|---|---|---|---|---|---|---|
| ATOM | 3719 | C | GLU | A | 488 | 0 | 3.384 | 62.928 | 15.995 | 1.00 37.78 |
| ATOM | 3720 | O | GLU | A | 488 | 0 | 2.186 | 63.025 | 15.711 | 1.00 37.61 |
| ATOM | 3721 | CB | GLU | A | 488 | 0 | 4.737 | 64.697 | 17.257 | 1.00 42.04 |
| ATOM | 3722 | CG | GLU | A | 488 | 0 | 5.667 | 64.822 | 16.064 | 1.00 47.75 |
| ATOM | 3723 | CD | GLU | A | 488 | 0 | 5.634 | 66.239 | 15.500 | 1.00 51.36 |
| ATOM | 3724 | OE1 | GLU | A | 488 | 0 | 5.501 | 66.422 | 14.266 | 1.00 52.66 |
| ATOM | 3725 | OE2 | GLU | A | 488 | 0 | 5.743 | 67.154 | 16.358 | 1.00 53.40 |
| ATOM | 3726 | N | ILE | A | 489 | 0 | 4.263 | 62.253 | 15.267 | 1.00 36.63 |
| ATOM | 3727 | CA | ILE | A | 489 | 0 | 3.906 | 61.647 | 14.004 | 1.00 36.74 |
| ATOM | 3728 | C | ILE | A | 489 | 0 | 2.754 | 60.662 | 14.113 | 1.00 36.98 |
| ATOM | 3729 | O | ILE | A | 489 | 0 | 1.847 | 60.664 | 13.276 | 1 00 38.60 |
| ATOM | 3730 | CB | ILE | A | 489 | 0 | 5.089 | 60.903 | 13.361 | 1.00 36.57 |
| ATOM | 3731 | CG1 | ILE | A | 489 | 0 | 6.267 | 61.853 | 13.148 | 1.00 36.46 |
| ATOM | 3732 | CG2 | ILE | A | 489 | 0 | 4.651 | 60.305 | 12.030 | 1.00 36.90 |
| ATOM | 3733 | CD1 | ILE | A | 489 | 0 | 7.535 | 61.194 | 12.654 | 1.00 35.62 |
| ATOM | 3734 | N | TYR | A | 490 | 0 | 2.758 | 59.808 | 15.105 | 1.00 36.22 |
| ATOM | 3735 | CA | TYR | A | 490 | 0 | 1.771 | 58.765 | 15.298 | 1.00 35.95 |
| ATOM | 3736 | C | TYR | A | 490 | 0 | 0.413 | 59.314 | 15.692 | 1.00 37.83 |
| ATOM | 3737 | O | TYR | A | 490 | 0 | -0.581 | 58.816 | 15.165 | 1.00 39.24 |
| ATOM | 3738 | CB | TYR | A | 490 | 0 | 2.206 | 57.817 | 16.409 | 1.00 32.47 |
| ATOM | 3739 | CG | TYR | A | 490 | 0 | 1.314 | 56.641 | 16.663 | 1.00 30.55 |
| ATOM | 3740 | CD1 | TYR | A | 490 | 0 | 1.176 | 55.623 | 15.726 | 1.00 29.96 |
| ATOM | 3741 | CD2 | TYR | A | 490 | 0 | 0.610 | 56.536 | 17.849 | 1.00 29.79 |
| ATOM | 3742 | CE1 | TYR | A | 490 | 0 | 0.378 | 54.528 | 15.975 | 1.00 29.51 |
| ATOM | 3743 | CE2 | TYR | A | 490 | 0 | -0.192 | 55.441 | 18.114 | 1.00 29.64 |
| ATOM | 3744 | CZ | TYR | A | 490 | 0 | -0.288 | 54.445 | 17.171 | 1.00 29.51 |
| ATOM | 3745 | OH | TYR | A | 490 | 0 | -1.101 | 53.363 | 17.437 | 1.00 32.06 |
| ATOM | 3746 | N | ASP | A | 491 | 0 | 0.369 | 60.302 | 16.564 | 1.00 40.86 |
| ATOM | 3747 | CA | ASP | A | 491 | 0 | -0.909 | 60.887 | 16.963 | 1.00 43.97 |
| ATOM | 3748 | C | ASP | A | 491 | 0 | -1.586 | 61.633 | 15.811 | 1.00 45.30 |
| ATOM | 3749 | O | ASP | A | 491 | 0 | -2.809 | 61.752 | 15.820 | 1.00 45.60 |
| ATOM | 3750 | CB | ASP | A | 491 | 0 | -0.764 | 61.800 | 18.170 | 1.00 44.67 |
| ATOM | 3751 | CG | ASP | A | 491 | 0 | -0.441 | 61.101 | 19.475 | 1.00 45.90 |
| ATOM | 3752 | OD1 | ASP | A | 491 | 0 | 0.149 | 61.761 | 20.364 | 1.00 46.32 |
| ATOM | 3753 | OD2 | ASP | A | 491 | 0 | -0.763 | 59.911 | 19.669 | 1.00 46.04 |
| ATOM | 3754 | N | ASP | A | 492 | 0 | -0.871 | 62.107 | 14.817 | 1.00 46.75 |
| ATOM | 3755 | CA | ASP | A | 492 | 0 | -1.323 | 62.804 | 13.653 | 1.00 48.98 |
| ATOM | 3756 | C | ASP | A | 492 | 0 | -1.702 | 61.936 | 12.460 | 1.00 49.48 |
| ATOM | 3757 | O | ASP | A | 492 | 0 | -2.002 | 62.458 | 11.378 | 1.00 50.24 |
| ATOM | 3758 | CB | ASP | A | 492 | 0 | -0.155 | 63.649 | 13.107 | 1.00 51.54 |

APPENDIX 1-continued

```
ATOM   3759  CG   ASP A   492  0   -0.168 65.081 13.587 1.00 53.57
ATOM   3760  OD1  ASP A   492  0   -0.886 65.375 14.570 1.00 54.07
ATOM   3761  OD2  ASP A   492  0    0.576 65.857 12.939 1.00 55.04
ATOM   3762  N    LEU A   493  0   -1.554 60.630 12.584 1.00 49.01
ATOM   3763  CA   LEU A   493  0   -1.896 59.732 11.483 1.00 47.63
ATOM   3764  C    LEU A   493  0   -3.377 59.872 11.137 1.00 47.61
ATOM   3765  O    LEU A   493  0   -4.209 60.018 12.027 1.00 47.02
ATOM   3766  CB   LEU A   493  0   -1.661 58.296 11.940 1.00 46.08
ATOM   3767  CG   LEU A   493  0   -0.485 57.463 11.464 1.00 45.24
ATOM   3768  CD1  LEU A   493  0    0.616 58.224 10.756 1.00 43.57
ATOM   3769  CD2  LEU A   493  0    0.075 56.710 12.669 1.00 44.62
ATOM   3770  N    PRO A   494  0   -3.694 59.763  9.866 1.00 48.01
ATOM   3771  CA   PRO A   494  0   -5.049 59.734  9.353 1.00 49.11
ATOM   3772  C    PRO A   494  0   -5.617 58.339  9.570 1.00 51.21
ATOM   3773  O    PRO A   494  0   -4.919 57.325  9.495 1.00 50.61
ATOM   3774  CB   PRO A   494  0   -4.938 59.995  7.843 1.00 48.94
ATOM   3775  CG   PRO A   494  0   -3.559 59.463  7.544 1.00 48.47
ATOM   3776  CD   PRO A   494  0   -2.714 59.538  8.797 1.00 48.22
ATOM   3777  N    PRO A   495  0   -6.915 58.238  9.796 1.00 53.24
ATOM   3778  CA   PRO A   495  0   -7.630 57.006 10.055 1.00 53.93
ATOM   3779  C    PRO A   495  0   -7.404 55.890  9.058 1.00 54.84
ATOM   3780  O    PRO A   495  0   -7.348 54.705  9.423 1.00 55.08
ATOM   3781  CB   PRO A   495  0   -9.126 57.362 10.146 1.00 54.40
ATOM   3782  CG   PRO A   495  0   -9.090 58.848 10.391 1.00 54.17
ATOM   3783  CD   PRO A   495  0   -7.787 59.420  9.895 1.00 53.58
ATOM   3784  N    GLU A   496  0   -7.190 56.198  7.784 1.00 55.36
ATOM   3785  CA   GLU A   496  0   -6.936 55.187  6.763 1.00 55.83
ATOM   3786  C    GLU A   496  0   -5.582 54.521  6.971 1.00 54.09
ATOM   3787  O    GLU A   496  0   -5.345 53.406  6.505 1.00 53.29
ATOM   3788  CB   GLU A   496  0   -7.091 55.805  5.378 1.00 57.96
ATOM   3789  CG   GLU A   496  0   -6.030 55.604  4.339 1.00 61.30
ATOM   3790  CD   GLU A   496  0   -6.448 54.984  3.025 1.00 63.68
ATOM   3791  OE1  GLU A   496  0   -7.449 55.411  2.388 1.00 65.15
ATOM   3792  OE2  GLU A   496  0   -5.747 54.034  2.586 1.00 64.91
ATOM   3793  N    ALA A   497  0   -4.665 55.217  7.630 1.00 52.35
ATOM   3794  CA   ALA A   497  0   -3.326 54.738  7.886 1.00 50.83
ATOM   3795  C    ALA A   497  0   -3.245 53.626  8.924 1.00 49.08
ATOM   3796  O    ALA A   497  0   -2.361 52.773  8.794 1.00 47.61
ATOM   3797  CB   ALA A   497  0   -2.443 55.910  8.317 1.00 51.23
```

APPENDIX 1-continued

| ATOM | 3798 | N   | THR | A | 498 | 0 | -4.113  | 53.630 | 9.926  | 1.00 | 48.01 |
|------|------|-----|-----|---|-----|---|---------|--------|--------|------|-------|
| ATOM | 3799 | CA  | THR | A | 498 | 0 | -4.086  | 52.617 | 10.964 | 1.00 | 48.73 |
| ATOM | 3800 | C   | THR | A | 498 | 0 | -5.271  | 51.656 | 10.938 | 1.00 | 48.99 |
| ATOM | 3801 | O   | THR | A | 498 | 0 | -5.425  | 50.852 | 11.862 | 1.00 | 47.81 |
| ATOM | 3802 | CB  | THR | A | 498 | 0 | -4.055  | 53.223 | 12.388 | 1.00 | 49.04 |
| ATOM | 3803 | OG1 | THR | A | 498 | 0 | -5.315  | 53.816 | 12.752 | 1.00 | 47.95 |
| ATOM | 3804 | CG2 | THR | A | 498 | 0 | -2.919  | 54.223 | 12.514 | 1.00 | 48.94 |
| ATOM | 3805 | N   | SER | A | 499 | 0 | -6.101  | 51.756 | 9.911  | 1.00 | 49.78 |
| ATOM | 3806 | CA  | SER | A | 499 | 0 | -7.307  | 50.933 | 9.814  | 1.00 | 51.20 |
| ATOM | 3807 | C   | SER | A | 499 | 0 | -7.048  | 49.470 | 9.494  | 1.00 | 49.98 |
| ATOM | 3808 | O   | SER | A | 499 | 0 | -6.257  | 49.143 | 8.617  | 1.00 | 48.80 |
| ATOM | 3809 | CB  | SER | A | 499 | 0 | -8.223  | 51.606 | 8.800  | 1.00 | 52.62 |
| ATOM | 3810 | OG  | SER | A | 499 | 0 | -8.428  | 50.827 | 7.596  | 1.00 | 55.22 |
| ATOM | 3811 | N   | ILE | A | 500 | 0 | -7.706  | 48.585 | 10.230 | 1.00 | 50.08 |
| ATOM | 3812 | CA  | ILE | A | 500 | 0 | -7.563  | 47.151 | 10.077 | 1.00 | 51.25 |
| ATOM | 3813 | C   | ILE | A | 500 | 0 | -8.642  | 46.518 | 9.207  | 1.00 | 53.08 |
| ATOM | 3814 | O   | ILE | A | 500 | 0 | -9.785  | 46.351 | 9.639  | 1.00 | 54.00 |
| ATOM | 3815 | CB  | ILE | A | 500 | 0 | -7.631  | 46.428 | 11.436 | 1.00 | 50.61 |
| ATOM | 3816 | CG1 | ILE | A | 500 | 0 | -6.475  | 46.866 | 12.336 | 1.00 | 50.22 |
| ATOM | 3817 | CG2 | ILE | A | 500 | 0 | -7.619  | 44.907 | 11.302 | 1.00 | 50.34 |
| ATOM | 3818 | CD1 | ILE | A | 500 | 0 | -6.806  | 46.617 | 13.800 | 1.00 | 50.52 |
| ATOM | 3819 | N   | GLN | A | 501 | 0 | -8.263  | 46.074 | 8.024  | 1.00 | 54.35 |
| ATOM | 3820 | CA  | GLN | A | 501 | 0 | -9.177  | 45.360 | 7.129  | 1.00 | 55.14 |
| ATOM | 3821 | C   | GLN | A | 501 | 0 | -9.298  | 43.904 | 7.564  | 1.00 | 55.85 |
| ATOM | 3822 | O   | GLN | A | 501 | 0 | -8.335  | 43.130 | 7.556  | 1.00 | 55.59 |
| ATOM | 3823 | CB  | GLN | A | 501 | 0 | -8.594  | 45.485 | 5.732  | 1.00 | 55.56 |
| ATOM | 3824 | CG  | GLN | A | 501 | 0 | -9.262  | 44.736 | 4.604  | 1.00 | 56.32 |
| ATOM | 3825 | CD  | GLN | A | 501 | 0 | -8.874  | 45.369 | 3.271  | 1.00 | 57.46 |
| ATOM | 3826 | OE1 | GLN | A | 501 | 0 | -8.480  | 44.667 | 2.336  | 1.00 | 57.35 |
| ATOM | 3827 | NE2 | GLN | A | 501 | 0 | -8.998  | 46.697 | 3.219  | 1.00 | 57.61 |
| ATOM | 3828 | N   | THR | A | 502 | 0 | -10.493 | 43.506 | 7.968  | 1.00 | 57.08 |
| ATOM | 3829 | CA  | THR | A | 502 | 0 | -10.788 | 42.146 | 8.401  | 1.00 | 58.28 |
| ATOM | 3830 | C   | THR | A | 502 | 0 | -10.966 | 41.205 | 7.216  | 1.00 | 58.80 |
| ATOM | 3831 | O   | THR | A | 502 | 0 | -11.199 | 41.604 | 6.074  | 1.00 | 58.71 |
| ATOM | 3832 | CB  | THR | A | 502 | 0 | -12.046 | 42.109 | 9.293  | 1.00 | 58.99 |
| ATOM | 3833 | OG1 | THR | A | 502 | 0 | -11.794 | 42.909 | 10.464 | 1.00 | 59.62 |
| ATOM | 3834 | CG2 | THR | A | 502 | 0 | -12.421 | 40.707 | 9.749  | 1.00 | 58.74 |
| ATOM | 3835 | N   | VAL | A | 503 | 0 | -10.746 | 39.922 | 7.471  | 1.00 | 59.20 |
| ATOM | 3836 | CA  | VAL | A | 503 | 0 | -10.904 | 38.877 | 6.468  | 1.00 | 60.27 |
| ATOM | 3837 | C   | VAL | A | 503 | 0 | -11.687 | 37.736 | 7.119  | 1.00 | 61.11 |

APPENDIX 1-continued

| ATOM | 3838 | O | VAL A | 503 | 0 | -11.606 | 37.563 | 8.341 | 1.00 | 61.03 |
| ATOM | 3839 | CB | VAL A | 503 | 0 | -9.589 | 38.430 | 5.823 | 1.00 | 59.97 |
| ATOM | 3840 | CG1 | VAL A | 503 | 0 | -8.337 | 38.964 | 6.507 | 1.00 | 59.65 |
| ATOM | 3841 | CG2 | VAL A | 503 | 0 | -9.467 | 36.914 | 5.722 | 1.00 | 59.97 |
| ATOM | 3842 | N | VAL A | 504 | 0 | -12.478 | 37.002 | 6.341 | 1.00 | 61.77 |
| ATOM | 3843 | CA | VAL A | 504 | 0 | -13.203 | 35.863 | 6.911 | 1.00 | 62.40 |
| ATOM | 3844 | C | VAL A | 504 | 0 | -12.673 | 34.579 | 6.259 | 1 00 | 62.99 |
| ATOM | 3845 | O | VAL A | 504 | 0 | -11.811 | 33.894 | 6.803 | 1.00 | 63.13 |
| ATOM | 3846 | CB | VAL A | 504 | 0 | -14.730 | 35.882 | 6.756 | 1.00 | 62.39 |
| ATOM | 3847 | CG1 | VAL A | 504 | 0 | -15.392 | 36.931 | 7.635 | 1.00 | 61.89 |
| ATOM | 3848 | CG2 | VAL A | 504 | 0 | -15.127 | 36.068 | 5.297 | 1.00 | 62.17 |
| ATOM | 3849 | C1 | NAG A | 800 | 0 | -2.401 | 42.835 | 45.802 | 1.00 | 30.44 |
| ATOM | 3850 | C2 | NAG A | 800 | 0 | -1.327 | 43.232 | 46.780 | 1.00 | 31.80 |
| ATOM | 3851 | N2 | NAG A | 800 | 0 | -0.119 | 43.561 | 45.983 | 1.00 | 31.37 |
| ATOM | 3852 | C7 | NAG A | 800 | 0 | 0.179 | 44.844 | 45.683 | 1.00 | 32.37 |
| ATOM | 3853 | O7 | NAG A | 800 | 0 | -0.549 | 45.688 | 45.982 | 1.00 | 34.61 |
| ATOM | 3854 | C8 | NAG A | 800 | 0 | 1.457 | 45.094 | 44.983 | 1.00 | 31.67 |
| ATOM | 3855 | C3 | NAG A | 800 | 0 | -1.015 | 42.187 | 47.801 | 1.00 | 32.94 |
| ATOM | 3856 | O3 | NAG A | 800 | 0 | -0.264 | 42.838 | 48.796 | 1.00 | 34.46 |
| ATOM | 3857 | C4 | NAG A | 800 | 0 | -2.351 | 41.662 | 48.377 | 1.00 | 34.05 |
| ATOM | 3858 | O4 | NAG A | 800 | 0 | -2.097 | 40.644 | 49.344 | 1.00 | 35.62 |
| ATOM | 3859 | C5 | NAG A | 800 | 0 | -3.128 | 41.025 | 47.202 | 1.00 | 35.11 |
| ATOM | 3860 | O5 | NAG A | 800 | 0 | -3.466 | 42.046 | 46.295 | 1.00 | 33.06 |
| ATOM | 3861 | C6 | NAG A | 800 | 0 | -4.444 | 40.420 | 47.673 | 1.00 | 36.66 |
| ATOM | 3862 | O6 | NAG A | 800 | 0 | -5.199 | 41.411 | 48.288 | 1.00 | 39.73 |
| ATOM | 3863 | C1 | GLC A | 900 | 0 | -8.957 | 50.280 | 6.333 | 1.00 | 58.53 |
| ATOM | 3864 | C2 | GLC A | 900 | 0 | -8.500 | 49.605 | 5.037 | 1.00 | 59.25 |
| ATOM | 3865 | C3 | GLC A | 900 | 0 | -7.806 | 50.686 | 4.219 | 1.00 | 59.71 |
| ATOM | 3866 | C4 | GLC A | 900 | 0 | -8.691 | 51.905 | 3.987 | 1.00 | 60.13 |
| ATOM | 3867 | C5 | GLC A | 900 | 0 | -9.595 | 52.289 | 5.142 | 1.00 | 59.22 |
| ATOM | 3868 | O5 | GLC A | 900 | 0 | -10.004 | 51.177 | 5.937 | 1.00 | 59.71 |
| ATOM | 3869 | CU | IUM B | 1 | 0 | -1.332 | 34.401 | 30.132 | 1.00 | 29.47 |
| ATOM | 3870 | CU | IUM B | 2 | 0 | 7.297 | 42.245 | 26.618 | 1.00 | 27.01 |
| ATOM | 3871 | CU | IUM B | 3 | 0 | 9.569 | 38.786 | 23.923 | 1.00 | 21.38 |
| ATOM | 3872 | O | IUM B | 5 | 0 | 7.445 | 40.703 | 25.162 | 1.00 | 26.99 |
| ATOM | 3873 | OWO | WAT W | 1 | 0 | 19.509 | 36.893 | 30.054 | 1.00 | 13.07 |
| ATOM | 3874 | OWO | WAT W | 2 | 0 | 24.726 | 29.672 | 16.651 | 1.00 | 7.67 |
| ATOM | 3875 | OWO | WAT W | 3 | 0 | 15.295 | 17.988 | 35.061 | 1.00 | 8.65 |
| ATOM | 3876 | OWO | WAT W | 4 | 0 | 6.481 | 28.311 | 23.427 | 1.00 | 8.00 |

APPENDIX 1-continued

```
ATOM   3877  OWO  WAT  W    5  0    14.921  45.178  24.306  1.00  17.04
ATOM   3878  OWO  WAT  W    6  0    14.413  44.401  28.162  1.00  10.12
ATOM   3879  OWO  WAT  W    7  0     9.967  21.576   9.620  1.00  11.43
ATOM   3880  OWO  WAT  W    8  0    10.088  28.675  13.038  1.00   9.27
ATOM   3881  OWO  WAT  W    9  0     9.808  47.902  28.959  1.00  12.71
ATOM   3882  OWO  WAT  W   10  0    21.976  23.052  35.604  1.00  11.72
ATOM   3883  OWO  WAT  W   11  0    10.862  25.744  29.928  1.00  10.21
ATOM   3884  OWO  WAT  W   12  0    26.087  32.996  23.097  1.00  14.21
ATOM   3885  OWO  WAT  W   13  0    22.256  58.745  37.931  1.00  17.85
ATOM   3886  OWO  WAT  W   14  0    -0.104  29.831  35.249  1.00  16.36
ATOM   3887  OWO  WAT  W   15  0    18.153  61.857  36.641  1.00  14.38
ATOM   3888  OWO  WAT  W   16  0     9.426  38.431   9.161  1.00  15.35
ATOM   3889  OWO  WAT  W   17  0     7.639  24.371   3.713  1.00  22.18
ATOM   3890  OWO  WAT  W   18  0    27.977  11.643   9.481  1.00  19.22
ATOM   3891  OWO  WAT  W   19  0     3.140  21.028  24.695  1.00  11.12
ATOM   3892  OWO  WAT  W   20  0     9.847  20.701  30.902  1.00  16.16
ATOM   3893  OWO  WAT  W   21  0    -1.517  29.009  43.180  1.00  27.18
ATOM   3894  OWO  WAT  W   22  0     3.497  29.138  26.088  1.00  17.22
ATOM   3895  OWO  WAT  W   23  0    20.614  32.765  40.433  1.00  17.63
ATOM   3896  OWO  WAT  W   24  0    19.098  51.778  39.452  1.00  22.33
ATOM   3897  OWO  WAT  W   25  0     0.977  21.396   5.064  1.00  18.54
ATOM   3898  OWO  WAT  W   26  0     8.546  16.150  21.761  1.00  16.40
ATOM   3899  OWO  WAT  W   27  0     6.102  19.858  10.350  1.00  17.79
ATOM   3900  OWO  WAT  W   28  0    11.702  55.189  41.955  1.00  18.92
ATOM   3901  OWO  WAT  W   29  0     3.360  42.251  18.209  1.00  16.26
ATOM   3902  OWO  WAT  W   30  0     6.232  14.672  22.473  1.00  24.49
ATOM   3903  OWO  WAT  W   31  0    16.729  26.542  39.731  1.00  15.28
ATOM   3904  OWO  WAT  W   32  0     2.834  30.640  40.601  1.00  18.11
ATOM   3905  OWO  WAT  W   33  0    21.893  42.837  27.884  1.00  15.08
ATOM   3906  OWO  WAT  W   34  0     1.581  28.193  27.914  1.00  17.77
ATOM   3907  OWO  WAT  W   35  0    -3.503  21.749  11.578  1.00  15.32
ATOM   3908  OWO  WAT  W   36  0     7.131  33.344  11.786  1.00  18.18
ATOM   3909  OWO  WAT  W   37  0    17.312  38.603  29.961  1.00  14.75
ATOM   3910  OWO  WAT  W   38  0    -6.705  40.723  39.909  1.00  23.49
ATOM   3911  OWO  WAT  W   39  0     9.010  31.121  11.736  1.00  19.99
ATOM   3912  OWO  WAT  W   40  0     9.376  28.353  33.076  1.00  16.22
ATOM   3913  OWO  WAT  W   41  0    30.104  29.895  20.857  1.00  25.77
ATOM   3914  OWO  WAT  W   42  0    -6.950  33.663  21.335  1.00  26.62
ATOM   3915  OWO  WAT  W   43  0     8.541  27.867  36.827  1.00  12.80
ATOM   3916  OWO  WAT  W   44  0     3.590  21.651  11.893  1.00  14.46
```

APPENDIX 1-continued

| ATOM | 3917 | OWO | WAT | W | 45 | 0 | 23.290 | 21.665 | 37.787 | 1.00 | 28.75 |
|------|------|-----|-----|---|----|---|--------|--------|--------|------|-------|
| ATOM | 3918 | OWO | WAT | W | 46 | 0 | 22.724 | 11.873 | 22.270 | 1.00 | 23.07 |
| ATOM | 3919 | OWO | WAT | W | 47 | 0 | -1.090 | 42.001 | 12.877 | 1.00 | 19.33 |
| ATOM | 3920 | OWO | WAT | W | 48 | 0 | 14.091 | 27.298 | 40.583 | 1.00 | 18.51 |
| ATOM | 3921 | OWO | WAT | W | 49 | 0 | 2.336 | 52.026 | 29.983 | 1.00 | 25.66 |
| ATOM | 3922 | OWO | WAT | W | 50 | 0 | 15.475 | 14.450 | 22.853 | 1.00 | 20.37 |
| ATOM | 3923 | OWO | WAT | W | 51 | 0 | 25.945 | 26.568 | 40.287 | 1.00 | 24.49 |
| ATOM | 3924 | OWO | WAT | W | 52 | 0 | 19.545 | 41.598 | 35.087 | 1.00 | 20.70 |
| ATOM | 3925 | OWO | WAT | W | 53 | 0 | -3.802 | 47.942 | 9.638 | 1.00 | 29.98 |
| ATOM | 3926 | OWO | WAT | W | 54 | 0 | -7.478 | 41.160 | 9.585 | 1.00 | 24.26 |
| ATOM | 3927 | OWO | WAT | W | 55 | 0 | -2.938 | 29.733 | 36.048 | 1.00 | 22.93 |
| ATOM | 3928 | OWO | WAT | W | 56 | 0 | 29.051 | 32.114 | 22.680 | 1.00 | 22.50 |
| ATOM | 3929 | OWO | WAT | W | 57 | 0 | 0.360 | 29.505 | 5.595 | 1.00 | 17.78 |
| ATOM | 3930 | OWO | WAT | W | 58 | 0 | 8.583 | 57.422 | 21.440 | 1.00 | 21.90 |
| ATOM | 3931 | OWO | WAT | W | 59 | 0 | 25.151 | 31.947 | 34.812 | 1.00 | 22.13 |
| ATOM | 3932 | OWO | WAT | W | 60 | 0 | 25.133 | 62.204 | 32.968 | 1.00 | 25.75 |
| ATOM | 3933 | OWO | WAT | W | 61 | 0 | 14.909 | 40.770 | 30.294 | 1.00 | 17.25 |
| ATOM | 3934 | OWO | WAT | W | 62 | 0 | 20.825 | 30.520 | 34.676 | 1.00 | 16.18 |
| ATOM | 3935 | OWO | WAT | W | 63 | 0 | 5.509 | 26.744 | 43.167 | 1.00 | 30.12 |
| ATOM | 3936 | OWO | WAT | W | 64 | 0 | 5.280 | 57.279 | 14.627 | 1.00 | 22.66 |
| ATOM | 3937 | OWO | WAT | W | 65 | 0 | 2.944 | 53.436 | 32.359 | 1.00 | 22.97 |
| ATOM | 3938 | OWO | WAT | W | 66 | 0 | 11.266 | 43.508 | 3.407 | 1.00 | 20.01 |
| ATOM | 3939 | OWO | WAT | W | 67 | 0 | 21.535 | 45.549 | 26.563 | 1.00 | 24.47 |
| ATOM | 3940 | OWO | WAT | W | 68 | 0 | 0.412 | 33.358 | 11.837 | 1.00 | 19.89 |
| ATOM | 3941 | OWO | WAT | W | 69 | 0 | 26.466 | 32.305 | 25.785 | 1.00 | 20.19 |
| ATOM | 3942 | OWO | WAT | W | 70 | 0 | 0.910 | 45.068 | 7.829 | 1.00 | 22.05 |
| ATOM | 3943 | OWO | WAT | W | 71 | 0 | -2.060 | 46.506 | 39.381 | 1.00 | 23.49 |
| ATOM | 3944 | OWO | WAT | W | 72 | 0 | 20.236 | 56.718 | 25.851 | 1.00 | 23.74 |
| ATOM | 3945 | OWO | WAT | W | 73 | 0 | 3.253 | 23.017 | 38.254 | 1.00 | 24.83 |
| ATOM | 3946 | OWO | WAT | W | 74 | 0 | 9.653 | 22.835 | 35.143 | 1.00 | 25.79 |
| ATOM | 3947 | OWO | WAT | W | 75 | 0 | 16.877 | 52.904 | 47.331 | 1.00 | 24.42 |
| ATOM | 3948 | OWO | WAT | W | 76 | 0 | 14.293 | 22.021 | 3.993 | 1.00 | 32.28 |
| ATOM | 3949 | OWO | WAT | W | 77 | 0 | -5.287 | 19.835 | 18.528 | 1.00 | 24.65 |
| ATOM | 3950 | OWO | WAT | W | 78 | 0 | 8.414 | 38.317 | 49.069 | 1.00 | 28.77 |
| ATOM | 3951 | OWO | WAT | W | 79 | 0 | 7.070 | 32.466 | 47.926 | 1.00 | 21.83 |
| ATOM | 3952 | OWO | WAT | W | 80 | 0 | -0.452 | 28.307 | 25.779 | 1.00 | 16.58 |
| ATOM | 3953 | OWO | WAT | W | 81 | 0 | 14.774 | 15.006 | 34.455 | 1.00 | 25.63 |
| ATOM | 3954 | OWO | WAT | W | 82 | 0 | 11.515 | 54.942 | 35.962 | 1.00 | 14.20 |
| ATOM | 3955 | OWO | WAT | W | 83 | 0 | 25.643 | 33.451 | 32.105 | 1.00 | 30.31 |

APPENDIX 1-continued

```
ATOM   3956  OWO  WAT W   84  0   11.869  12.221  20.394  1.00  31.37
ATOM   3957  OWO  WAT W   85  0   11.653  51.587  22.411  1.00  16.48
ATOM   3958  OWO  WAT W   86  0   17.334  40.837  51.079  1.00  30.26
ATOM   3959  OWO  WAT W   87  0    4.355  25.208  34.030  1.00  32.26
ATOM   3960  OWO  WAT W   88  0   18.816  52.360  32.512  1.00  21.19
ATOM   3961  OWO  WAT W   89  0   -2.704  46.518  35.364  1.00  21.99
ATOM   3962  OWO  WAT W   90  0   18.793  27.893  49.481  1.00  24.52
ATOM   3963  OWO  WAT W   91  0   22.459  46.584  28.898  1.00  18.99
ATOM   3964  OWO  WAT W   92  0    7.958  34.422  49.370  1.00  26.14
ATOM   3965  OWO  WAT W   93  0   23.972  16.246   6.806  1.00  24.35
ATOM   3966  OWO  WAT W   94  0    1.340  49.185  26.307  1.00  31.64
ATOM   3967  OWO  WAT W   95  0   -1.830  35.291  12.266  1.00  27.28
ATOM   3968  OWO  WAT W   96  0   20.460  17.486   3.589  1.00  33.51
ATOM   3969  OWO  WAT W   97  0   15.177   6.964   9.868  1.00  24.40
ATOM   3970  OWO  WAT W   98  0   18.616  57.927  43.922  1.00  30.76
ATOM   3971  OWO  WAT W   99  0   10.562  32.112   9.972  1.00  28.90
ATOM   3972  OWO  WAT W  100  0    1.630  61.363  10.878  1.00  33.92
ATOM   3973  OWO  WAT W  101  0   -4.939  49.989  33.211  1.00  29.73
ATOM   3974  OWO  WAT W  102  0   19.385  44.813  34.546  1.00  23.52
ATOM   3975  OWO  WAT W  103  0   19.055  43.063  37.581  1.00  30.59
ATOM   3976  OWO  WAT W  105  0   28.703  33.555  27.406  1.00  32.92
ATOM   3977  OWO  WAT W  106  0   28.835  19.646  10.759  1.00  40.44
ATOM   3978  OWO  WAT W  107  0   22.047  22.465   9.758  1.00  29.98
ATOM   3979  OWO  WAT W  108  0   14.689  61.032  36.346  1.00  30.63
ATOM   3980  OWO  WAT W  109  0   16.998  24.042   9.318  1.00  23.90
ATOM   3981  OWO  WAT W  110  0   13.472  30.533  11.848  1.00  34.83
ATOM   3982  OWO  WAT W  111  0   -2.175  35.601  41.496  1.00  28.55
ATOM   3983  OWO  WAT W  112  0    1.528  17.373  -1.396  1.00  38.21
ATOM   3984  OWO  WAT W  113  0   -2.856  29.748  19.681  1.00  30.55
ATOM   3985  OWO  WAT W  114  0    2.377  42.810  47.971  1.00  26.87
ATOM   3986  OWO  WAT W  115  0   10.947  12.820  33.745  1.00  31.60
ATOM   3987  OWO  WAT W  116  0    9.807  58.194  12.442  1.00  29.63
ATOM   3988  OWO  WAT W  117  0   18.488  62.559  29.470  1.00  45.83
ATOM   3989  OWO  WAT W  118  0   11.708  61.566  40.940  1.00  37.19
ATOM   3990  OWO  WAT W  119  0  -10.101  22.257  15.091  1.00  30.48
ATOM   3991  OWO  WAT W  120  0   -1.930  15.913   7.386  1.00  36.63
ATOM   3992  OWO  WAT W  121  0   23.988  43.686  29.319  1.00  32.15
ATOM   3993  OWO  WAT W  122  0    7.354  57.153  12.809  1.00  28.10
ATOM   3994  OWO  WAT W  123  0   24.207  22.101  11.958  1.00  32.83
ATOM   3995  OWO  WAT W  124  0   -1.268  15.083   9.738  1.00  32.53
```

APPENDIX 1-continued

```
ATOM   3996  OWO  WAT  W  125  0    19.363   5.047  13.812  1.00  34.57
ATOM   3997  OWO  WAT  W  126  0     4.799  41.145  23.688  1.00  28.33
ATOM   3998  OWO  WAT  W  127  0    15.975  23.287   5.889  1.00  30.95
ATOM   3999  OWO  WAT  W  128  0     3.698  38.582  -2.369  1.00  36.84
ATOM   4000  OWO  WAT  W  129  0    -2.601  49.124  11.710  1.00  28.91
ATOM   4001  OWO  WAT  W  130  0    15.779  56.598  43.285  1.00  27.76
ATOM   4002  OWO  WAT  W  131  0    26.306  32.724  13.233  1.00  37.94
ATOM   4003  OWO  WAT  W  132  0     3.610  46.947  23.991  1.00  35.49
ATOM   4004  OWO  WAT  W  133  0    18.354  11.929  29.348  1.00  33.88
ATOM   4005  OWO  WAT  W  134  0    13.966  41.517  27.765  1.00  18.02
ATOM   4006  OWO  WAT  W  135  0    23.545  49.080  27.785  1.00  25.21
ATOM   4007  OWO  WAT  W  136  0    16.876  25.082  41.791  1.00  28.71
ATOM   4008  OWO  WAT  W  137  0    15.439  54.809  45.527  1.00  35.30
ATOM   4009  OWO  WAT  W  138  0    11.733  25.676  43.264  1.00  38.24
ATOM   4010  OWO  WAT  W  139  0     9.795  34.460  11.898  1.00  31.61
ATOM   4011  OWO  WAT  W  140  0    13.328  57.569  42.356  1.00  30.66
ATOM   4012  OWO  WAT  W  141  0    14.146   7.869  20.604  1.00  35.72
ATOM   4013  OWO  WAT  W  142  0    23.330  12.948   3.922  1.00  29.83
ATOM   4014  OWO  WAT  W  143  0    16.607  10.575  24.347  1.00  36.47
ATOM   4015  OWO  WAT  W  144  0     8.509  25.546  35.012  1.00  35.43
ATOM   4016  OWO  WAT  W  145  0    12.597  44.457   1.450  1.00  39.54
ATOM   4017  OWO  WAT  W  146  0    21.680  51.509  39.154  1.00  40.08
ATOM   4018  OWO  WAT  W  147  0    -0.702  52.593  39.700  1.00  29.62
ATOM   4019  OWO  WAT  W  148  0    23.269  14.719  22.589  1.00  30.24
ATOM   4020  OWO  WAT  W  149  0    27.149  22.972  41.846  1.00  35.00
ATOM   4021  OWO  WAT  W  150  0     2.854   9.792   8.923  1.00  46.35
ATOM   4022  OWO  WAT  W  151  0    24.831  15.672  24.889  1.00  29.22
ATOM   4023  OWO  WAT  W  152  0    24.965  51.606  19.113  1.00  32.19
ATOM   4024  OWO  WAT  W  153  0    -4.611  25.034  37.817  1.00  46.51
ATOM   4025  OWO  WAT  W  154  0    12.225  39.382  28.864  1.00  25.42
ATOM   4026  OWO  WAT  W  155  0    18.332  22.341  43.180  1.00  36.18
ATOM   4027  OWO  WAT  W  156  0    36.467  20.701  17.144  1.00  44.13
ATOM   4028  OWO  WAT  W  157  0    -4.903  47.901  40.886  1.00  33.97
ATOM   4029  OWO  WAT  W  158  0    12.979  13.955   3.208  1.00  33.60
ATOM   4030  OWO  WAT  W  159  0    32.383  12.693  24.743  1.00  30.25
ATOM   4031  OWO  WAT  W  160  0    30.796  26.296  14.368  1.00  44.37
ATOM   4032  OWO  WAT  W  161  0    19.332  37.280  40.057  1.00  31.54
ATOM   4033  OWO  WAT  W  162  0    17.625  20.028  41.642  1.00  45.88
ATOM   4034  OWO  WAT  W  163  0    19.917  56.115  46.103  1.00  40.37
```

APPENDIX 1-continued

```
ATOM   4035  OWO  WAT  W  164  0   -4.743  14.204  16.748  1.00  40.86
ATOM   4036  OWO  WAT  W  165  0    0.738  46.912  21.790  1.00  38.56
ATOM   4037  OWO  WAT  W  166  0   22.648  62.277  30.976  1.00  24.37
ATOM   4038  OWO  WAT  W  167  0   -4.322  45.754  26.894  1.00  48.97
ATOM   4039  OWO  WAT  W  168  0   -2.386  24.601   0.665  1.00  32.57
ATOM   4040  OWO  WAT  W  169  0   -0.459  41.618  35.838  1.00  35.25
ATOM   4041  OWO  WAT  W  170  0   26.659   4.722  11.434  1.00  41.25
ATOM   4042  OWO  WAT  W  171  0   13.720  11.379  22.121  1.00  39.59
ATOM   4043  OWO  WAT  W  172  0   15.266   7.451   6.576  1.00  41.71
ATOM   4044  OWO  WAT  W  173  0    0.134  17.450   6.165  1.00  42.12
ATOM   4045  OWO  WAT  W  174  0   38.646  32.884  25.247  1.00  41.80
ATOM   4046  OWO  WAT  W  175  0   10.591  17.398   3.251  1.00  29.37
ATOM   4047  OWO  WAT  W  176  0   22.444  49.424  25.264  1.00  19.51
ATOM   4048  OWO  WAT  W  177  0    0.429  23.224  28.598  1.00  33.54
ATOM   4049  OWO  WAT  W  178  0   -2.302  27.278  34.780  1.00  44.76
ATOM   4050  OWO  WAT  W  179  0    2.054  25.866  16.462  1.00  34.29
ATOM   4051  OWO  WAT  W  180  0   30.277  18.006  25.789  1.00  42.28
ATOM   4052  OWO  WAT  W  181  0    2.316  18.424  27.884  1.00  47.39
ATOM   4053  OWO  WAT  W  182  0   19.401  41.164  39.560  1.00  39.68
ATOM   4054  OWO  WAT  W  183  0   23.742  10.982  24.879  1.00  43.32
ATOM   4055  OWO  WAT  W  184  O    3.926  24.450  44.251  1.00  48.95
ATOM   4056  OWO  WAT  W  185  0   25.186  21.211  40.951  1.00  39.05
ATOM   4057  OWO  WAT  W  186  0   20.353  34.816  48.799  1.00  34.08
ATOM   4058  OWO  WAT  W  187  0   35.782  22.476  21.693  1.00  40.04
ATOM   4059  OWO  WAT  W  188  0   27.256  23.617  12.235  1.00  40.85
ATOM   4060  OWO  WAT  W  189  0    6.777  12.502  12.641  1.00  53.37
ATOM   4061  OWO  WAT  W  190  0   -4.663  38.998   4.159  1.00  39.85
ATOM   4062  OWO  WAT  W  191  0   24.398  52.064  24.607  1.00  45.51
ATOM   4063  OWO  WAT  W  192  0    1.808  15.541   4.832  1.00  41.06
ATOM   4064  OWO  WAT  W  193  0    5.341  36.359   7.569  1.00  39.36
ATOM   4065  OWO  WAT  W  194  0   32.192  38.650  21.799  1.00  37.18
ATOM   4066  OWO  WAT  W  195  0  -10.782  36.616  38.705  1.00  50.35
ATOM   4067  OWO  WAT  W  196  0    4.119  64.116  32.946  1.00  34.51
ATOM   4068  OWO  WAT  W  197  0   19.427  22.772   5.898  1.00  37.94
ATOM   4069  OWO  WAT  W  198  0   -4.671  33.476   1.652  1.00  43.38
ATOM   4070  OWO  WAT  W  199  0   -8.983  23.757  17.693  1.00  57.10
ATOM   4071  OWO  WAT  W  200  0   -6.735  22.473  20.432  1.00  38.49
ATOM   4072  OWO  WAT  W  201  0   -6.954  26.746  37.309  1.00  55.48
ATOM   4073  OWO  WAT  W  202  0   23.418  38.662  33.700  1.00  42.20
ATOM   4074  OWO  WAT  W  203  0    9.004  24.070  36.971  1.00  40.06
```

APPENDIX 1-continued

```
ATOM   4075  OWO  WAT  W  204  0   18.890  42.920  51.502  1.00  46.29
ATOM   4076  OWO  WAT  W  205  0   13.301  18.514   3.624  1.00  42.17
ATOM   4077  OWO  WAT  W  206  0   31.189  12.995  19.645  1.00  51.92
ATOM   4078  OWO  WAT  W  207  0   15.589  57.456  13.738  1.00  38.96
ATOM   4079  OWO  WAT  W  208  0   -3.389  12.961  12.738  1.00  46.99
ATOM   4080  OWO  WAT  W  209  0    9.321  30.475   6.320  1.00  49.75
ATOM   4081  OWO  WAT  W  210  0    1.680  61.379  33.738  1.00  37.48
ATOM   4082  OWO  WAT  W  211  0   -3.811  36.417   3.807  1.00  46.01
ATOM   4083  OWO  WAT  W  212  0   17.087  46.902   3.830  1.00  45.12
ATOM   4084  OWO  WAT  W  213  0   23.702  22.325  43.022  1.00  36.14
ATOM   4085  OWO  WAT  W  214  0   10.849  60.003  14.389  1.00  32.05
ATOM   4086  OWO  WAT  W  215  0   34.001  25.493  20.855  1.00  40.75
ATOM   4087  OWO  WAT  W  216  0   27.422  37.093  28.951  1.00  42.33
ATOM   4088  OWO  WAT  W  217  0    2.471  63.256  35.173  1.00  48.36
ATOM   4089  OWO  WAT  W  218  0   -0.973  59.086  28.720  1.00  53.14
ATOM   4090  OWO  WAT  W  219  0   28.841   9.287   6.463  1.00  39.02
ATOM   4091  OWO  WAT  W  220  0   -5.593  21.802   9.619  1.00  44.21
ATOM   4092  OWO  WAT  W  221  0   22.109  15.521   1.696  1.00  38.33
ATOM   4093  OWO  WAT  W  222  0   13.029  32.860  12.233  1.00  37.63
ATOM   4094  OWO  WAT  W  223  0   11.840  33.823   3.800  1.00  42.20
ATOM   4095  OWO  WAT  W  224  0    8.476  42.976  -0.104  1.00  40.23
ATOM   4096  OWO  WAT  W  225  0    6.607   9.754  13.906  1.00  41.30
ATOM   4097  OWO  WAT  W  226  0   22.513  32.613  49.067  1.00  47.26
ATOM   4098  OWO  WAT  W  227  0   13.790   4.924  16.718  1.00  38.05
ATOM   4099  OWO  WAT  W  228  0    4.578  46.381   2.146  1.00  38.90
ATOM   4100  OWO  WAT  W  229  0   -0.178  18.054  23.533  1.00  43.42
ATOM   4101  OWO  WAT  W  230  0   -5.146  34.010   4.766  1.00  38.90
ATOM   4102  OWO  WAT  W  231  0   20.232  28.890  51.507  1.00  44.95
ATOM   4103  OWO  WAT  W  232  0   16.083  32.879  10.309  1.00  45.29
ATOM   4104  OWO  WAT  W  233  0   22.111  51.333  10.599  1.00  34.03
ATOM   4105  OWO  WAT  W  234  0    3.247  15.790  28.046  1.00  50.25
ATOM   4106  OWO  WAT  W  235  0    5.547  11.598   9.674  1.00  56.39
ATOM   4107  OWO  WAT  W  236  0   -1.085  18.297  -2.265  1.00  45.26
ATOM   4108  OWO  WAT  W  237  0   30.994  12.013  22.690  1.00  50.37
ATOM   4109  OWO  WAT  W  238  0   24.691  33.260  27.819  1.00  37.65
ATOM   4110  OWO  WAT  W  239  0   18.911  40.770   5.815  1.00  44.15
ATOM   4111  OWO  WAT  W  240  0   21.532  53.033  33.280  1.00  31.23
ATOM   4112  OWO  WAT  W  241  0   19.745  46.029   4.364  1.00  46.38
ATOM   4113  OWO  WAT  W  242  0   27.516  16.526  25.474  1.00  51.75
```

APPENDIX 1-continued

```
ATOM   4114  OWO  WAT W 243  0    34.171 19.604  8.423 1.00 55.79
ATOM   4115  OWO  WAT W 244  0    23.870 53.512 11.474 1.00 42.01
ATOM   4116  OWO  WAT W 245  0    14.492 23.842 44.882 1.00 52.25
ATOM   4117  OWO  WAT W 246  0    -3.070 63.260 33.189 1.00 40.77
ATOM   4118  OWO  WAT W 247  0    22.185 55.701 37.353 1.00 39.52
ATOM   4119  OWO  WAT W 248  0    14.144 26.239 42.825 1.00 42.50
ATOM   4120  OWO  WAT W 249  0    25.026 36.545 35.213 1.00 58.19
ATOM   4121  OWO  WAT W 250  0    27.072 34.293 43.895 1.00 46.58
ATOM   4122  OWO  WAT W 251  0    11.742  7.192  4.856 1.00 42.78
ATOM   4123  OWO  WAT W 252  0     0.730 46.405 24.947 1.00 39.31
ATOM   4124  OWO  WAT W 253  0    28.346 34.036 30.808 1.00 43.10
ATOM   4125  OWO  WAT W 254  0    -3.838 40.281  1.903 1.00 38.67
ATOM   4126  OWO  WAT W 255  0     6.837 35.163 51.935 1.00 58.57
ATOM   4127  OWO  WAT W 256  0    19.740 62.853 17.880 1.00 52.39
ATOM   4128  OWO  WAT W 258  0    -0.994 41.755 22.088 1.00 69.57
ATOM   4129  OWO  WAT W 259  0     1.221 10.473 15.458 1.00 54.80
ATOM   4130  OWO  WAT W 260  0    23.445 55.367 31.430 1.00 48.90
ATOM   4131  OWO  WAT W 261  0    23.757 57.854 34.657 1.00 37.69
ATOM   4132  OWO  WAT W 262  0     8.508 19.111 34.572 1.00 55.52
ATOM   4133  OWO  WAT W 263  0    22.806 22.381  3.611 1.00 64.20
ATOM   4134  OWO  WAT W 264  0     0.398 22.602 42.625 1.00 58.86
ATOM   4135  OWO  WAT W 265  0     4.195 52.287 43.465 1.00 36.84
ATOM   4136  OWO  WAT W 266  0    20.211  6.536  4.911 1.00 39.34
ATOM   4137  OWO  WAT W 267  0    14.680 16.117  2.803 1.00 45.76
ATOM   4138  OWO  WAT W 268  0    14.938 25.582  6.850 1.00 41.01
ATOM   4139  OWO  WAT W 269  0     7.763  7.940 31.891 1.00 71.30
ATOM   4140  OWO  WAT W 270  0    -3.459 33.491 39.400 1.00 40.80
ATOM   4141  OWO  WAT W 271  0    23.154 22.897  6.985 1.00 48.25
ATOM   4142  OWO  WAT W 272  0    34.916 25.555 28.092 1.00 52.63
ATOM   4143  OWO  WAT W 273  0     8.332 45.481 50.776 1.00 47.23
ATOM   4144  OWO  WAT W 274  0    -3.441 57.643 28.775 1.00 49.70
ATOM   4145  OWO  WAT W 275  0    23.213 40.573 47.561 1.00 56.02
ATOM   4146  OWO  WAT W 276  0     5.421 55.179 45.172 1.00 52.70
ATOM   4147  OWO  WAT W 277  0    -3.012 21.908 40.933 1.00 41.69
ATOM   4148  OWO  WAT W 278  0    26.328 53.637 17.905 1.00 37.80
ATOM   4149  OWO  WAT W 279  0     9.740 58.922 43.485 1.00 52.06
ATOM   4150  OWO  WAT W 280  0    23.545 15.660  4.258 1.00 41.55
ATOM   4151  OWO  WAT W 281  0    22.652 31.154 51.246 1.00 58.65
ATOM   4152  OWO  WAT W 282  0    22.192 51.135  8.251 1.00 44.76
ATOM   4153  OWO  WAT W 283  0    -6.046 22.886 24.288 1.00 52.40
```

APPENDIX 1-continued

```
ATOM   4154  OWO  WAT  W  284  0   19.949  45.276  49.516  1.00  54.58
ATOM   4155  OWO  WAT  W  285  0    7.388  22.308  32.108  1.00  43.62
ATOM   4156  OWO  WAT  W  286  0   15.080  50.452   2.795  1.00  52.20
ATOM   4157  QWO  WAT  W  287  0    1.016  62.235  30.878  1.00  56.81
ATOM   4158  OWO  WAT  W  288  0   23.803  52.570  27.699  1.00  56.22
ATOM   4159  OWO  WAT  W  289  0  -10.525  31.623  13.870  1.00  47.21
ATOM   4160  OWO  WAT  W  290  0    1.599  55.502  24.567  1.00  44.50
ATOM   4161  OWO  WAT  W  291  0  -15.671  37.251  14.660  1.00  83.62
ATOM   4162  OWO  WAT  W  292  0    7.231   7.950  17.754  1.00  50.61
ATOM   4163  OWO  WAT  W  293  0   -4.009  34.057  42.492  1.00  78.48
ATOM   4164  OWO  WAT  W  294  0   21.004  58.371  18.690  1.00  61.15
ATOM   4165  OWO  WAT  W  295  0   16.405  48.869  52.211  1.00  53.17
ATOM   4166  OWO  WAT  W  296  0    7.329  31.202   1.964  1.00  38.86
ATOM   4167  OWO  WAT  W  297  0    9.518  53.886   5.467  1.00  41.62
ATOM   4168  OWO  WAT  W  298  0   10.398  48.995   0.335  1.00  49.64
ATOM   4169  OWO  WAT  W  299  0    9.889  15.077   3.774  1.00  42.28
ATOM   4170  OWO  WAT  W  300  0   15.854  56.731  10.934  1.00  44.02
```

What is claimed is:

1. A method of constructing a variant of a parent Coprinus-like laccase, which variant has laccase activity and improved storage stability as compared to said parent laccase, said method comprising i) comparing the three-dimensional structure of the Coprinus laccase of SEQ ID NO:1 depicted in the Appendix 1 with the structure of the Coprinus-like laccase, ii) identifying a part of the Coprinus-like laccase structure which is different from the Coprinus laccase structure and responsible for differences in the storage stability of the Coprinus and Coprinus-like laccase, iii) modifying the part of the Coprinus-like laccase identified in ii) whereby a Coprinus-like laccase variant is obtained, which has an improved storage stability compared to the parent Coprinus-like laccase, and optionally, iv) testing the resulting Coprinus-like laccase variant with respect to storage stability.

2. The method according to claim 1, wherein, in step iii), the part of the Coprinus-like laccase is modified to correspond to the structure of the Coprinus laccase.

3. The method according to claim 1, wherein, in step iii), the modification is accomplished by:

(a) deleting one or more amino acid residues of the part of the Coprinus-like laccase to be modified;

(b) replacing one or more amino acid residues of the part of the Coprinus-like laccase to be modified with the amino acid residues occupying corresponding positions in the Coprinus laccase; or (c) inserting one or more amino acid residues present in the Coprinus laccase into a corresponding position in the Coprinus-like laccase.

4. The method according to claim 1, wherein the Coprinus-like laccase is selected from the group consisting of *Polyporus pinsitus* laccase, *Phlebia radiata* laccase, *Rhizoctonia solani* laccase, *Scytalidium thermophilum* laccase and *Myceliophthora thermophila* laccase.

* * * * *